US011466328B2

(12) United States Patent
Mongan et al.

(10) Patent No.: US 11,466,328 B2
(45) Date of Patent: Oct. 11, 2022

(54) COMPOSITIONS AND METHODS FOR ASSESSING IMMUNE RESPONSE

(71) Applicant: LIFE TECHNOLOGIES CORPORATION, Carlsbad, CA (US)

(72) Inventors: Ann Mongan, San Francisco, CA (US); Alex Atkins, San Francisco, CA (US)

(73) Assignee: Life Technologies Corporation, Carlsbad, CA (US)

( * ) Notice: Subject to any disclaimer, the term of this patent is extended or adjusted under 35 U.S.C. 154(b) by 486 days.

(21) Appl. No.: 16/335,553

(22) PCT Filed: Sep. 22, 2017

(86) PCT No.: PCT/US2017/053077
§ 371 (c)(1),
(2) Date: Aug. 12, 2019

(87) PCT Pub. No.: WO2018/057971
PCT Pub. Date: Mar. 29, 2018

(65) Prior Publication Data
US 2019/0360053 A1   Nov. 28, 2019

Related U.S. Application Data

(60) Provisional application No. 62/419,091, filed on Nov. 8, 2016, provisional application No. 62/398,756, filed on Sep. 23, 2016.

(51) Int. Cl.
*C12Q 1/6886* (2018.01)
(52) U.S. Cl.
CPC ..... *C12Q 1/6886* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2006/0008807 A1* | 1/2006 | O'Hara | C12N 15/1003 435/6.14 |
| 2013/0210665 A1* | 8/2013 | Sanchez | C12N 15/1072 435/7.1 |
| 2014/0141436 A1* | 5/2014 | Erlich | C12Q 1/6881 435/6.12 |
| 2016/0257993 A1* | 9/2016 | Fu | C12Q 1/6844 |

FOREIGN PATENT DOCUMENTS

| | | |
|---|---|---|
| EP | 3516078 A1 | 7/2019 |
| WO | WO-2009003905 A2 | 1/2009 |
| WO | WO-2014055561 A1 | 4/2014 |
| WO | WO-2015120382 A1 | 8/2015 |
| WO | WO-2016118915 A1 | 7/2016 |
| WO | WO-2016172126 A2 | 10/2016 |
| WO | WO-2018057971 A1 | 3/2018 |

OTHER PUBLICATIONS

Gogas H., et al., "Evaluation of six CTLA-4 polymorphisms in high-risk melanoma patients receiving adjuvant interferon therapy in the He13A/98 multicenter trial," Journal of Translational Medicine, Biomed Central, vol. 8, No. 1, Nov. 3, 2010 (Nov. 3, 2010), p. 108, XP021078846, ISSN: 1479-5876, DOI:10.1186/1479-5876-8-108.

International Search Report and Written Opinion for Application No. PCT/US2017/053077, dated Dec. 1, 2017, 13 pages.

Otte M., et al., "MAGE-A Gene Expression Pattern in Primary Breast Cancer," Cancer Research, AACR—American Association for Cancer Research, US, vol. 61, No. 18, Sep. 15, 2001 (Sep. 15, 2001), pp. 6682-6687, XP002277597, ISSN: 0008-5472.

Jiang Y et al., "Development of a clinically feasible molecular assay to predict recurrence of stage II colon cancer", The Journal of Molecular Diagnostics, American Society for Investigative Pathology, US, vol. 10, No. 4, Jul. 1, 2008 (Jul. 1, 2008), pp. 346-354, XP002567042, ISSN: 1525-1578, DOI: 10.2353/JMOLDX.2008.080011 [retrieved on Jun. 13, 2008].

* cited by examiner

*Primary Examiner* — Katherine D Salmon
(74) *Attorney, Agent, or Firm* — Klarquist Sparkman, LLP

(57) ABSTRACT

The present invention provides methods and compositions that are useful for assessing gene expression for tumor immune response profile of a sample. In particular, a target-specific primer panel is provided that allows for selective amplification of immune response target sequences in a sample. In one aspect, the invention relates to target-specific primers useful for selective amplification of one or more target sequences associated with immune response. In some aspects, amplified target sequences obtained using the disclosed methods, and compositions can be used in various processes including nucleic acid sequencing and used to detect the presence of genetic variants and/or expression levels of one or more targeted sequences associated with immune response.

8 Claims, 9 Drawing Sheets

Specification includes a Sequence Listing.

Figure 1. Repeatability of Immune Response Assay
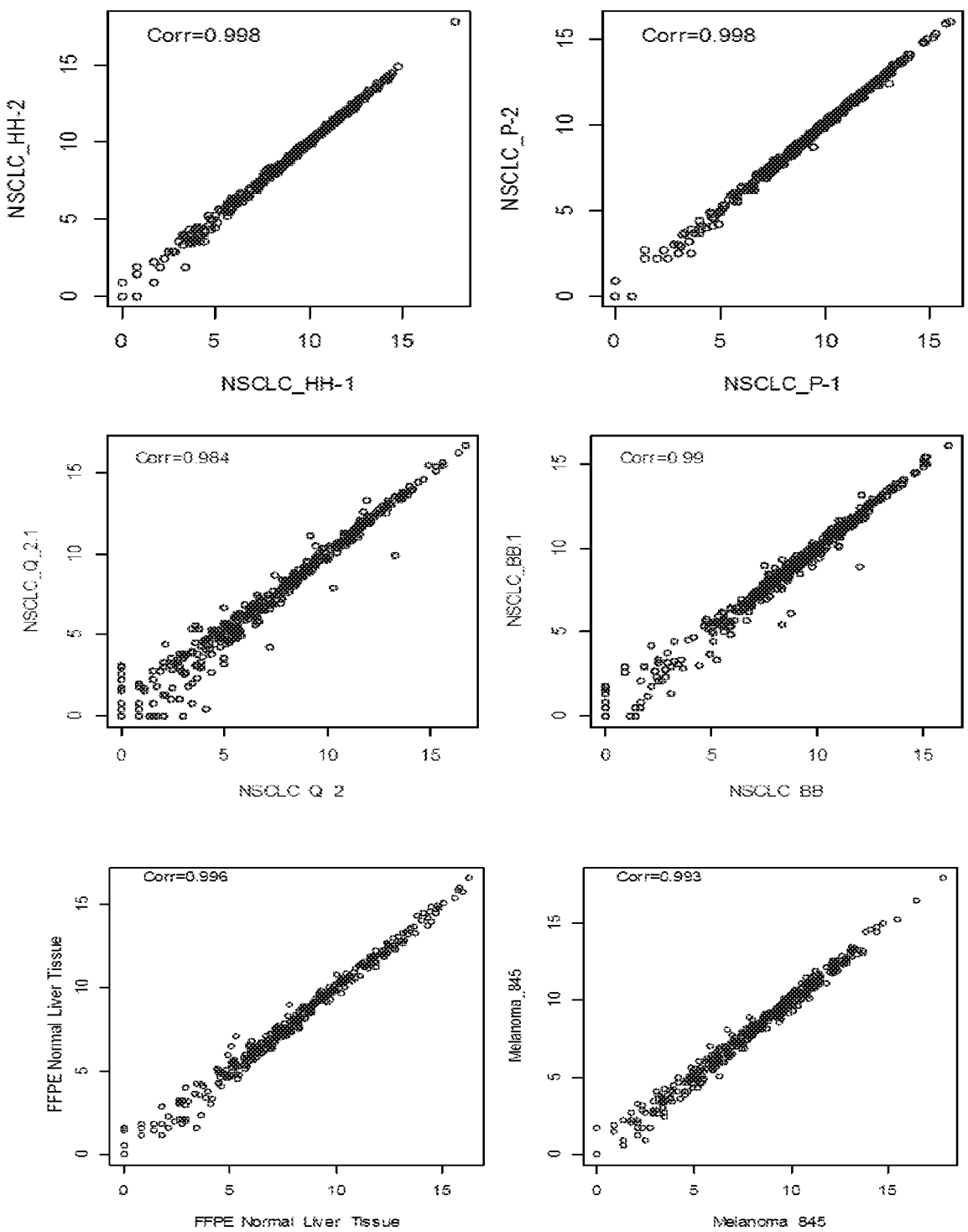

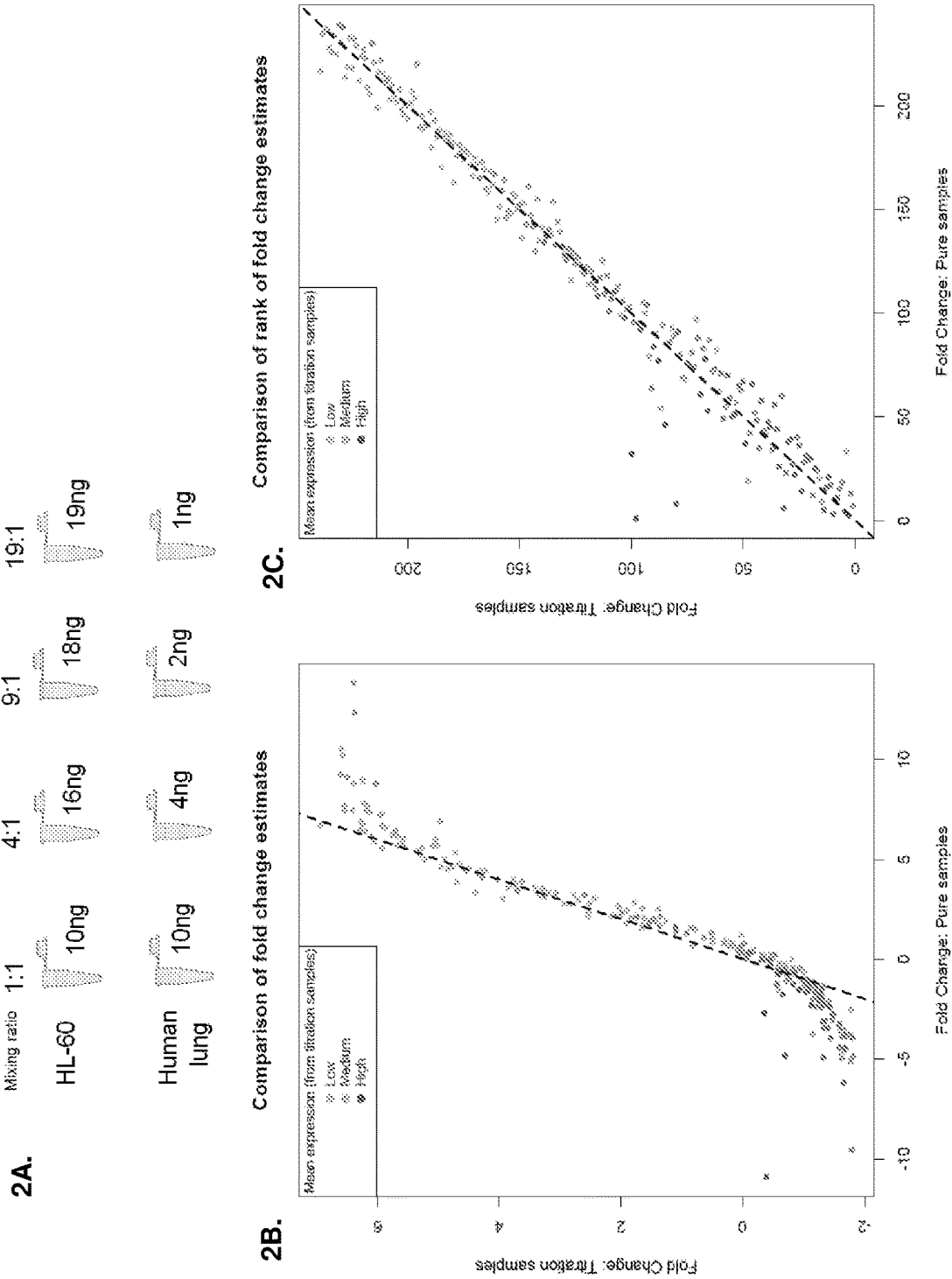
Figure 2. Limit of fold-change detection and dynamic range of Immune Response Research Assay

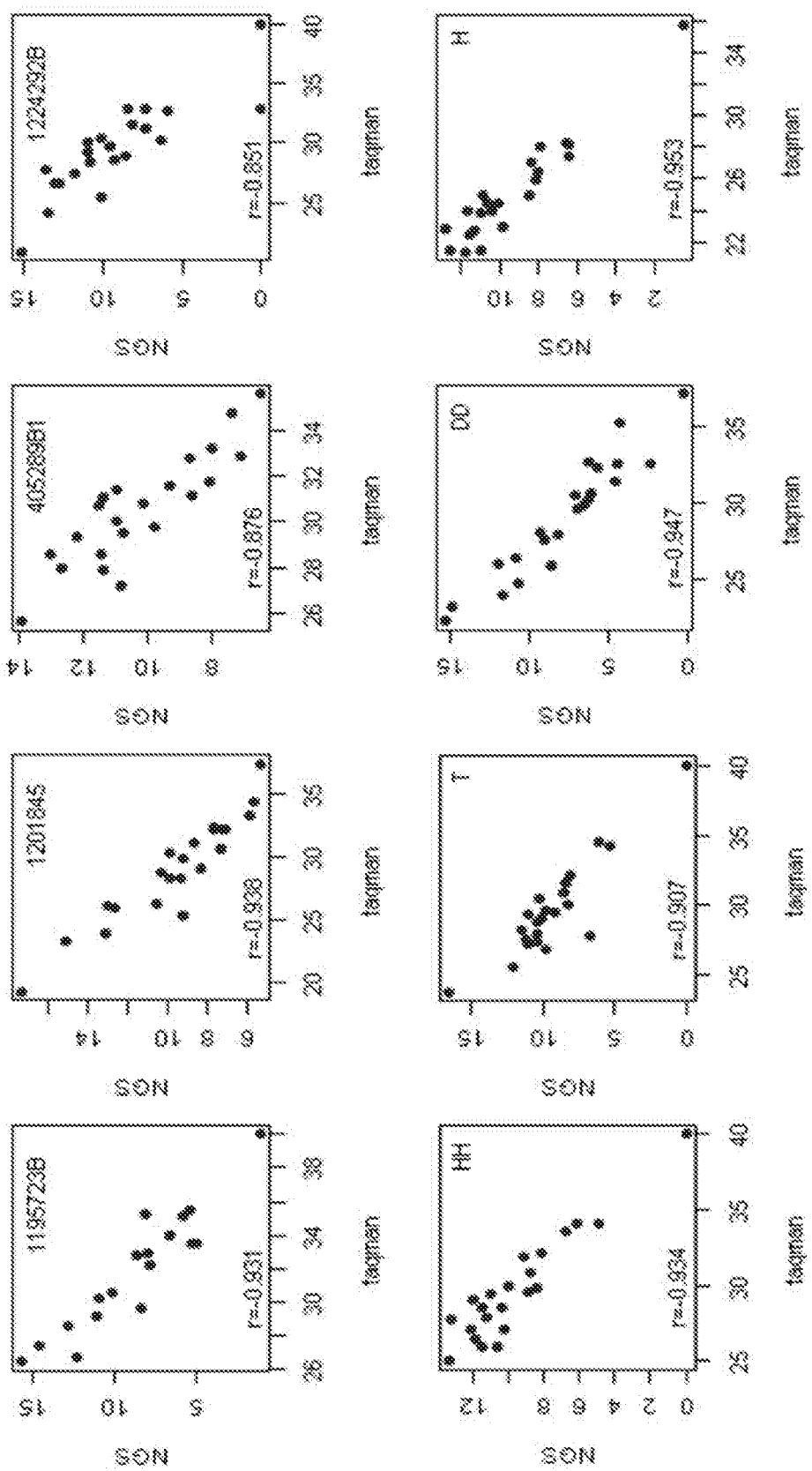
Figure 3. High correlations between quantitative RT-PCR and NGS results Figure 4. Correlations between NSCLC fresh frozen and FFPE samples.
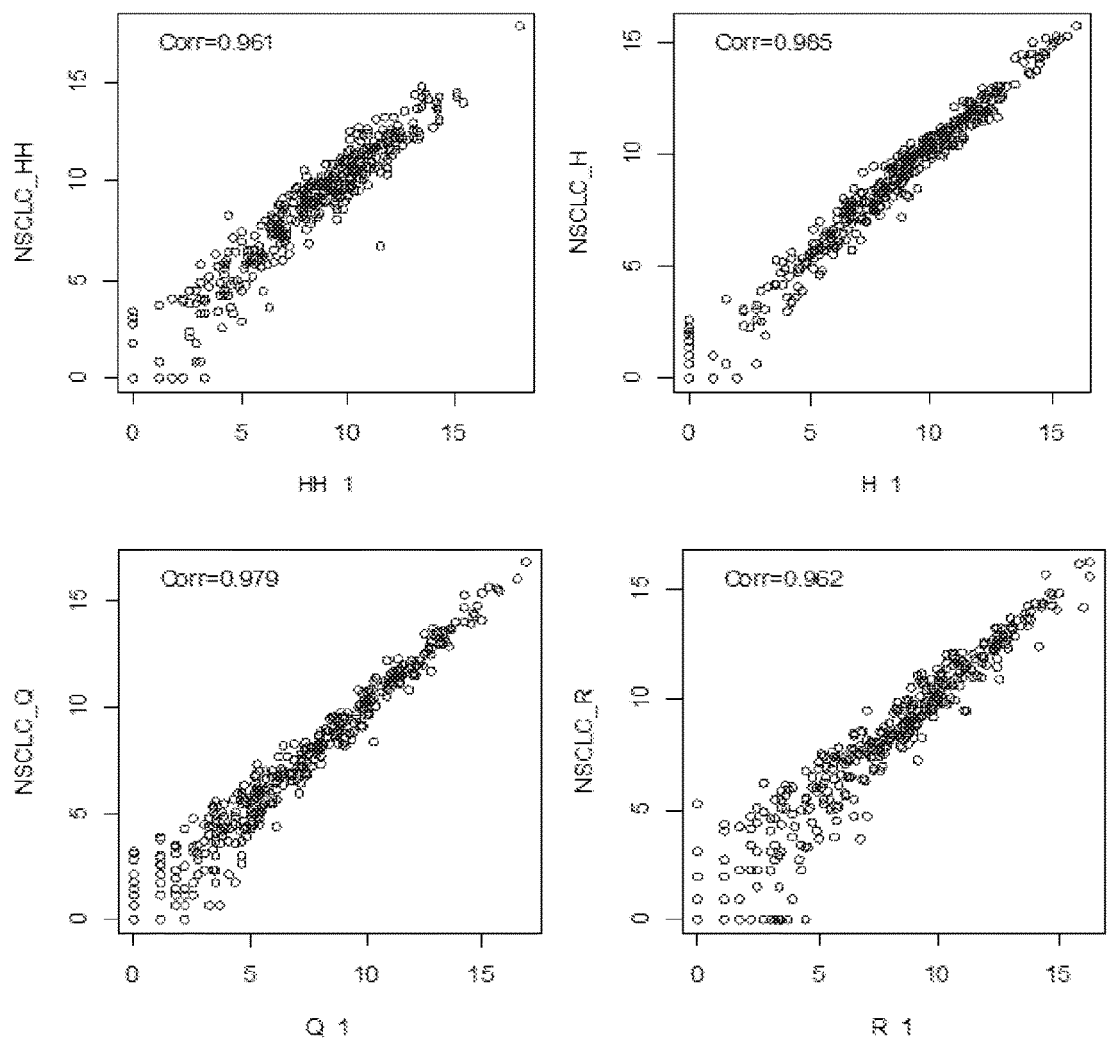

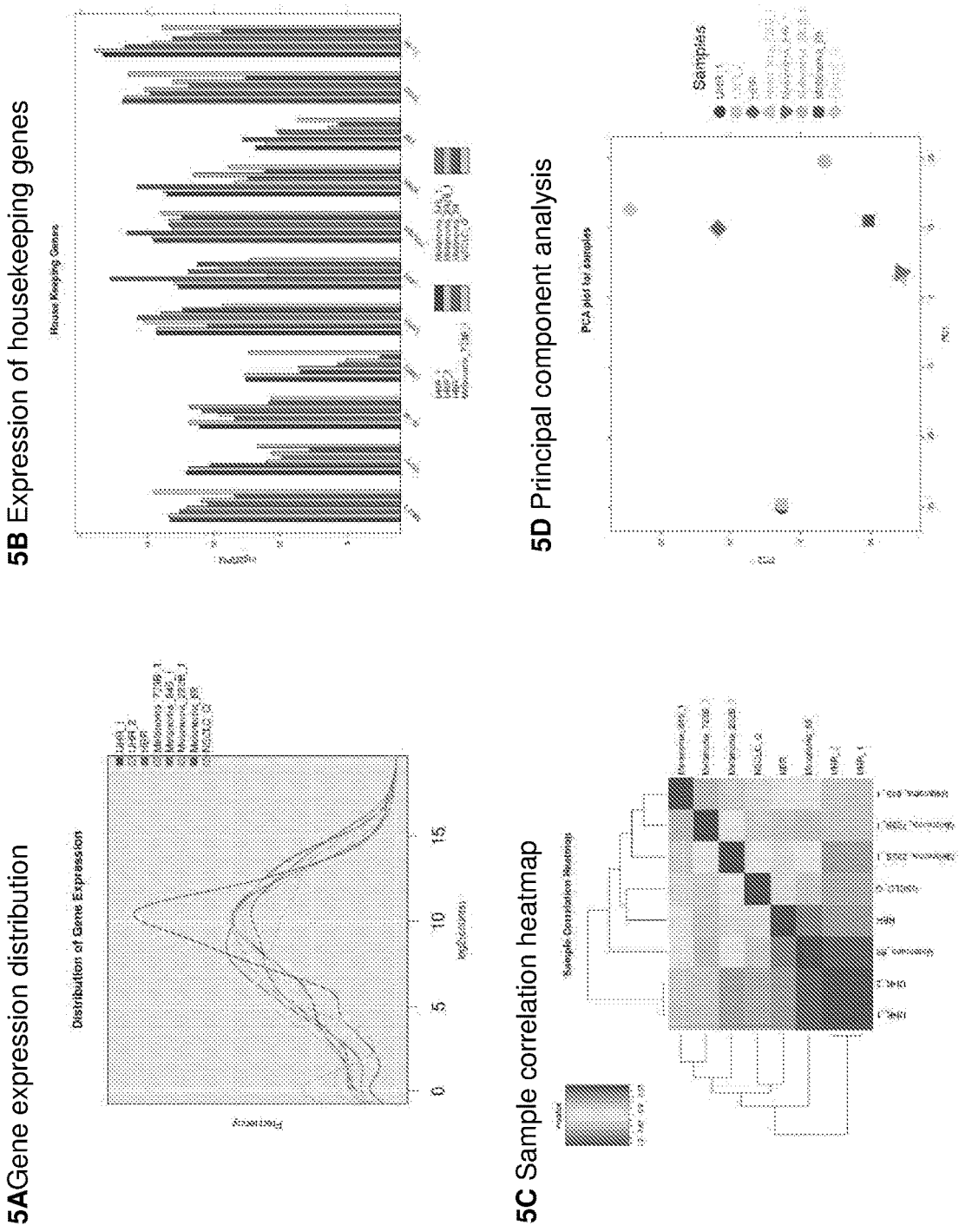
Figure 5. Immune Response Assay Results

Figure 6: Immune Response Assay Sample Correlations
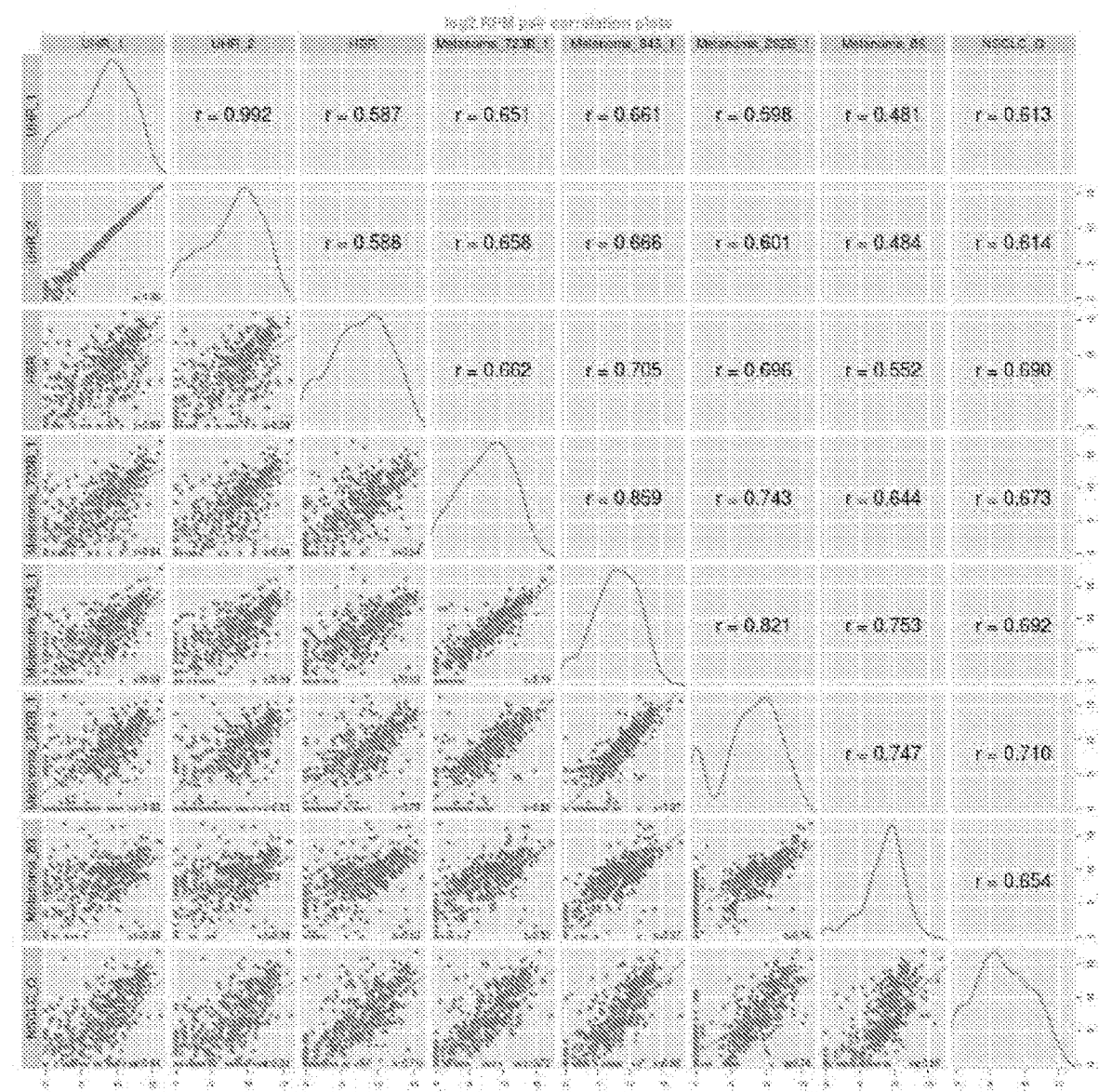

Figure 7: Immune Response Assay Heatmap

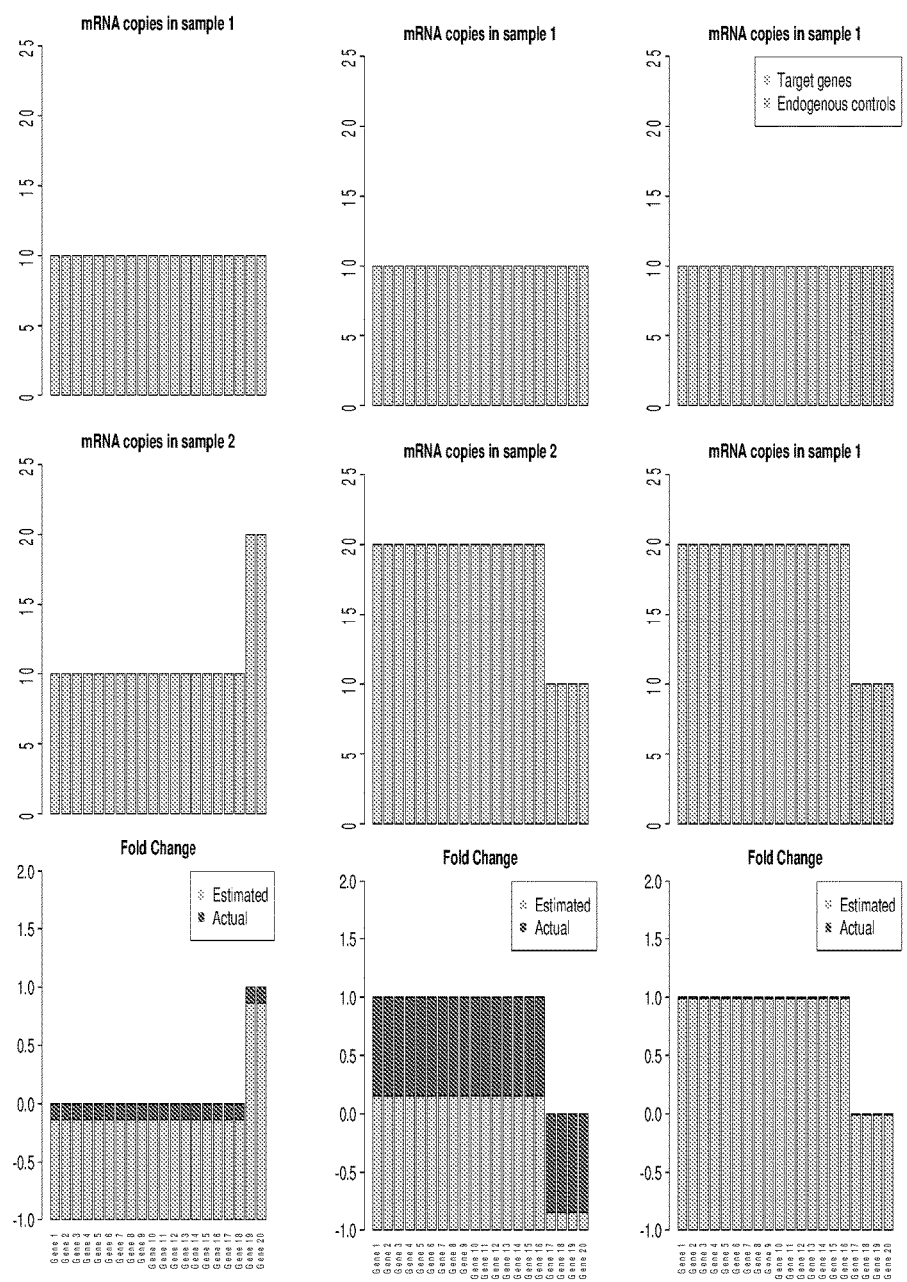
Figure 8. Fold change estimates can be biased on targeted expression panels

Figure 9: Acurate Expression Fold Change Estimates
9A
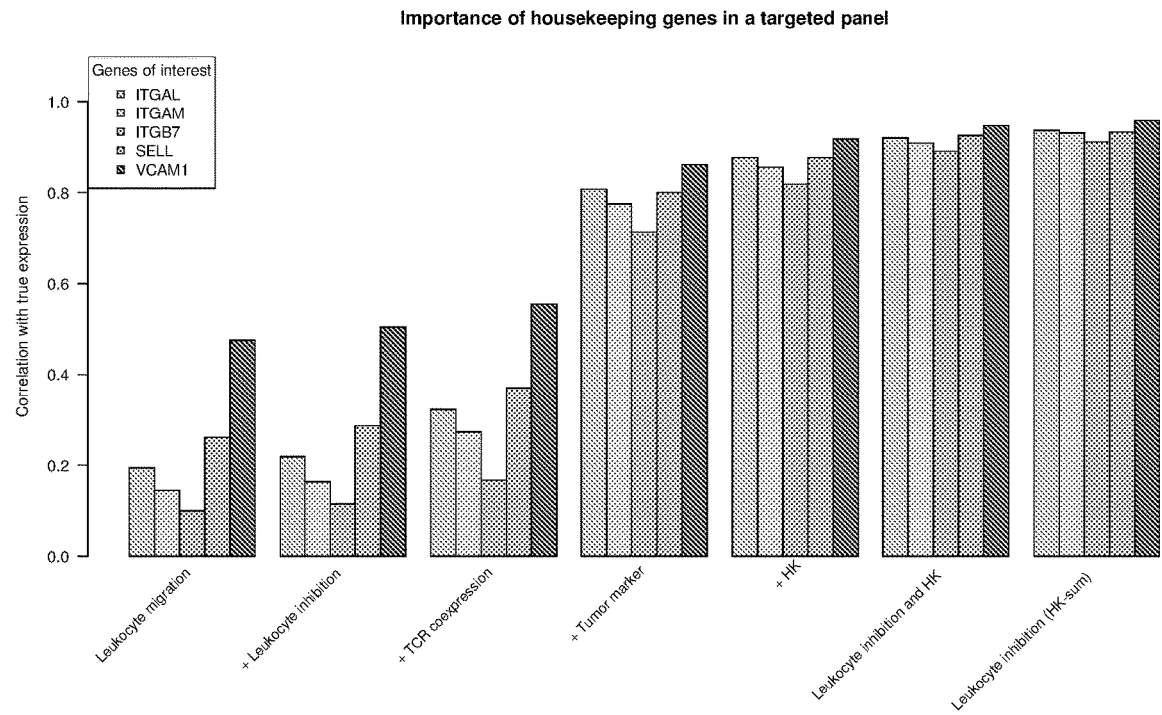
9B
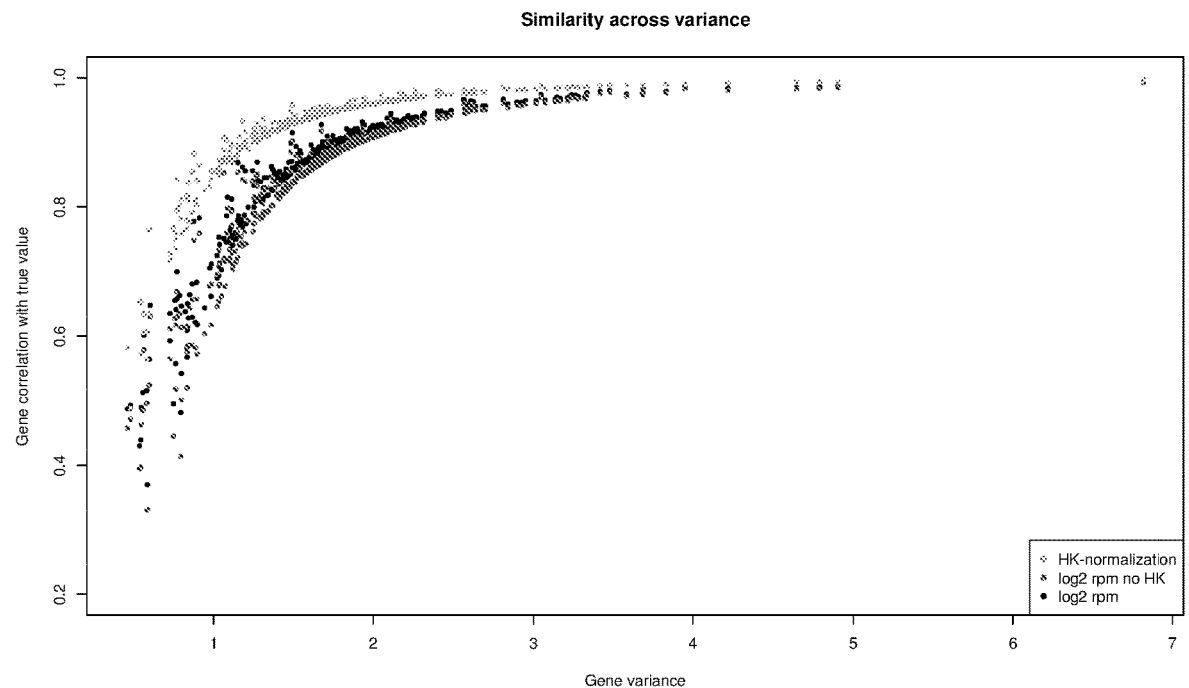

SEQUENCE LISTING

```
<160> NUMBER OF SEQ ID NOS: 1194

<210> SEQ ID NO 1
<211> LENGTH: 108
<212> TYPE: DNA
<213> ORGANISM: Artificial Sequence
<220> FEATURE:
<223> OTHER INFORMATION: synthetic sequence

<400> SEQUENCE: 1
cccgactcct gctgcattaa tgttactgtg ggctgtggga ttaatttcaa cgagaaggcg      60
atccataagg agggctgtgt ggagaagatt gggggctggc tgaggaaa               108

<210> SEQ ID NO 2
<211> LENGTH: 108
<212> TYPE: DNA
<213> ORGANISM: Artificial Sequence
<220> FEATURE:
<223> OTHER INFORMATION: synthetic sequence

<400> SEQUENCE: 2
gttcctgtcc tgtgtgctgt aatgaatgtg gtcttcatca ccattttaat catagctctc      60
attgccttat cagtgggcca atacaattgt ccaggccaat acacattc                108

<210> SEQ ID NO 3
<211> LENGTH: 102
<212> TYPE: DNA
<213> ORGANISM: Artificial Sequence
<220> FEATURE:
<223> OTHER INFORMATION: synthetic sequence
```

<400> SEQUENCE: 3
taagaaaatc atcgaaaaga tgctgaacag tgacaaatcc aactgaccag aagggaggag    60
gaagctcact ggtggctgtt cctgaaggag gccctgccct ta                      102

<210> SEQ ID NO 4
<211> LENGTH: 104
<212> TYPE: DNA
<213> ORGANISM: Artificial Sequence
<220> FEATURE:
<223> OTHER INFORMATION: synthetic sequence

<400> SEQUENCE: 4
cggcatctct gtgcttctca gaaatccagc ctgcttcagc ttcaaaacac agatgaactg    60
gattttatga gctccagtca acaattttac tggattggac tctc                    104

<210> SEQ ID NO 5
<211> LENGTH: 108
<212> TYPE: DNA
<213> ORGANISM: Artificial Sequence
<220> FEATURE:
<223> OTHER INFORMATION: synthetic sequence

<400> SEQUENCE: 5
ctccagaaga ttttgtgatt caggcaaagg ctgactgtta cttcaccaac gggacagaaa    60
aggtgcagtt tgtggtcaga ttcatcttta acttggagga gtatgtac                108

<210> SEQ ID NO 6
<211> LENGTH: 99
<212> TYPE: DNA
<213> ORGANISM: Artificial Sequence
<220> FEATURE:
<223> OTHER INFORMATION: synthetic sequence

<400> SEQUENCE: 6
ggtgactcac agccggcaca gccatgaact acccgctaac gctggaaatg gacctcgaga    60
acctggagga cctgttctgg gaactggaca gattggaca                          99

<210> SEQ ID NO 7
<211> LENGTH: 108
<212> TYPE: DNA
<213> ORGANISM: Artificial Sequence
<220> FEATURE:
<223> OTHER INFORMATION: synthetic sequence

<400> SEQUENCE: 7
caaaggaggc gaggttctaa gccattcgct cctgctgctt cacaaaaagg aagatggaat    60
ttggtccact gatattttaa aggaccagaa agaacccaaa ataagac                 108

<210> SEQ ID NO 8
<211> LENGTH: 109
<212> TYPE: DNA
<213> ORGANISM: Artificial Sequence
<220> FEATURE:
<223> OTHER INFORMATION: synthetic sequence

<400> SEQUENCE: 8
ttgcctgacc caggccacac caaaacctac agttgtctgg tacagaaacc agatgctcat    60
ctcagaggac tcacggttcg aggtcttcaa gaatgggacc ttgcgcatc               109

<210> SEQ ID NO 9
<211> LENGTH: 108

```
<212> TYPE: DNA
<213> ORGANISM: Artificial Sequence
<220> FEATURE:
<223> OTHER INFORMATION: synthetic sequence

<400> SEQUENCE: 9
gtcactggct gcaacaggac cacagtcaag acgatcatag tcactgagct aagtccagta    60
gtagcaaagc cccaaatcaa agccagcaag accacagtca caggagat               108

<210> SEQ ID NO 10
<211> LENGTH: 101
<212> TYPE: DNA
<213> ORGANISM: Artificial Sequence
<220> FEATURE:
<223> OTHER INFORMATION: synthetic sequence

<400> SEQUENCE: 10
ccaagggact atccacctac aatccttgaa agaccttaaa caatttgccc caagcccttc    60
ctgcgagaaa attgaaatca ttgctacact gaagaatgga g                      101

<210> SEQ ID NO 11
<211> LENGTH: 110
<212> TYPE: DNA
<213> ORGANISM: Artificial Sequence
<220> FEATURE:
<223> OTHER INFORMATION: synthetic sequence

<400> SEQUENCE: 11
caacgtgtca ggctgcagtg ccatcgagaa gacccagagg atgctgagcg gattctgccc    60
gcacaaggtc tcagctgggc agttttccag cttgcatgtc cgagacacca              110

<210> SEQ ID NO 12
<211> LENGTH: 102
<212> TYPE: DNA
<213> ORGANISM: Artificial Sequence
<220> FEATURE:
<223> OTHER INFORMATION: synthetic sequence

<400> SEQUENCE: 12 tgagggtgt ggacgtcgtg gtgggaggac actccaacac atttctttac acaggcaatc     60
caccttccaa agaggtgcct gctgggaagt acccattcat ag                     102

<210> SEQ ID NO 13
<211> LENGTH: 105
<212> TYPE: DNA
<213> ORGANISM: Artificial Sequence
<220> FEATURE:
<223> OTHER INFORMATION: synthetic sequence

<400> SEQUENCE: 13
cagatgtgac aagccgaggc ggtgagccgg gcaggaggaa ggagcctccc tcagggtttc    60
gggaaccaga tctctcacca ggaaagactg atacagaacg atcga                  105

<210> SEQ ID NO 14
<211> LENGTH: 109
<212> TYPE: DNA
<213> ORGANISM: Artificial Sequence
<220> FEATURE:
<223> OTHER INFORMATION: synthetic sequence

<400> SEQUENCE: 14
tgatgtgttg ctgtgtgagc aggaggtggt agcagatgag acaccagcag tccaggctgt    60
```

```
tcttcgagct gacaccaagc gattgaagct gctggaagag gagcggcgg              109
```

```
<210> SEQ ID NO 15
<211> LENGTH: 109
<212> TYPE: DNA
<213> ORGANISM: Artificial Sequence
<220> FEATURE:
<223> OTHER INFORMATION: synthetic sequence

<400> SEQUENCE: 15
tccagcggga catgttcacc ctggaggaca cgctgctagg ctaccttgct gatgacctca    60
catggtgtgg tgaattcaac acttccaaaa taaactatca atcttgccc              109
```

```
<210> SEQ ID NO 16
<211> LENGTH: 110
<212> TYPE: DNA
<213> ORGANISM: Artificial Sequence
<220> FEATURE:
<223> OTHER INFORMATION: synthetic sequence

<400> SEQUENCE: 16
ctttcagttg agcttgggga ctgcagctgt ggggagattt cagtgcattg cctcccctgg    60
gtgctcttca tcttggattt gaaagttgag agcagcatgt tttgcccact             110
```

```
<210> SEQ ID NO 17
<211> LENGTH: 95
<212> TYPE: DNA
<213> ORGANISM: Artificial Sequence
<220> FEATURE:
<223> OTHER INFORMATION: synthetic sequence

<400> SEQUENCE: 17
gggaatttcc atgccgtcta cagggatgac ctgaagaaat tgctagagac cgagtgtcct    60
cagtatatca ggaaaaaggg tgcagacgtc tggtt                              95
```

```
<210> SEQ ID NO 18
<211> LENGTH: 109
<212> TYPE: DNA
<213> ORGANISM: Artificial Sequence
<220> FEATURE:
<223> OTHER INFORMATION: synthetic sequence

<400> SEQUENCE: 18
gcagctgctt agacgctgga ttttttcgg gtagtggaaa accagcagcc tcccgcgacg    60
atgcccctca acgttagctt caccaacagg aactatgacc tcgactacg              109
```

```
<210> SEQ ID NO 19
<211> LENGTH: 109
<212> TYPE: DNA
<213> ORGANISM: Artificial Sequence
<220> FEATURE:
<223> OTHER INFORMATION: synthetic sequence

<400> SEQUENCE: 19
ggaggtggag caggccctga ctccagcact gtcgccatgt gctgtcagca gcactctccc    60
cgactggcac atcccagtgg aagttgtgcc ggacagcacc agtgatctg              109
```

```
<210> SEQ ID NO 20
<211> LENGTH: 106
<212> TYPE: DNA
<213> ORGANISM: Artificial Sequence
<220> FEATURE:
<223> OTHER INFORMATION: synthetic sequence
```

<400> SEQUENCE: 20
gctgtggcgc ttcaagcaac tgaggcaggc ccctacggcg ccaacatgga agacagcgtc    60
tgctgccgtg attacgtccg ttaccgtctg ccctgcgcg tggtga                   106

<210> SEQ ID NO 21
<211> LENGTH: 107
<212> TYPE: DNA
<213> ORGANISM: Artificial Sequence
<220> FEATURE:
<223> OTHER INFORMATION: synthetic sequence

<400> SEQUENCE: 21
agcccagcga cccagtcagg atttaagttt acctcaaaaa tggaagattt taacatggag    60
agtgacagct ttgaagattt ctggaaaggt gaagatctta gtaatta                 107

<210> SEQ ID NO 22
<211> LENGTH: 101
<212> TYPE: DNA
<213> ORGANISM: Artificial Sequence
<220> FEATURE:
<223> OTHER INFORMATION: synthetic sequence

<400> SEQUENCE: 22
acagcaacca tgagtacaaa tggtgatgat catcaggtca aggatagtct ggagcaattg    60
agatgtcact ttacatggga gttatccatt gatgacgatg a                       101

<210> SEQ ID NO 23
<211> LENGTH: 100
<212> TYPE: DNA
<213> ORGANISM: Artificial Sequence
<220> FEATURE:
<223> OTHER INFORMATION: synthetic sequence

<400> SEQUENCE: 23
gcagctgcct gaaccgagcc ctgccgaaca gctgagaatt gcactgcaac catgagtgag    60
aacaataaga attccttgga gagcagccta cggcaactaa                         100

<210> SEQ ID NO 24
<211> LENGTH: 108
<212> TYPE: DNA
<213> ORGANISM: Artificial Sequence
<220> FEATURE:
<223> OTHER INFORMATION: synthetic sequence

<400> SEQUENCE: 24
tgggtgaggc ggttcagcca tgaggctggc tgtgcttttc tcggggggccc tgctggggct   60 actggcagcc cagggacag ggaatgactg tcctcacaaa aaatcagc                 108

<210> SEQ ID NO 25
<211> LENGTH: 107
<212> TYPE: DNA
<213> ORGANISM: Artificial Sequence
<220> FEATURE:
<223> OTHER INFORMATION: synthetic sequence

<400> SEQUENCE: 25
tcactgggga ttctgagctt tggctactcc agtttcccac gacacgatgt tccctttcta    60
cagctgctgg aggactggac tgctactact actcctggct gtggcag                 107

<210> SEQ ID NO 26

```
<211> LENGTH: 102
<212> TYPE: DNA
<213> ORGANISM: Artificial Sequence
<220> FEATURE:
<223> OTHER INFORMATION: synthetic sequence

<400> SEQUENCE: 26
aacaggttct tggagtgctg agacagcacc tgggtacat aaagatatt tccggaaaat      60 aaaaaatctc atttcagcat ttcagaagcc agatcaaggc at                      102

<210> SEQ ID NO 27
<211> LENGTH: 108
<212> TYPE: DNA
<213> ORGANISM: Artificial Sequence
<220> FEATURE:
<223> OTHER INFORMATION: synthetic sequence

<400> SEQUENCE: 27
ggcgtgaggc caagctggac cactgcaggc gtgtctccct gcgggtgctg agtgagcgcc    60
tcctgcacaa gagcatccag aacagcctgc ttggacacag ctcggtgg                108

<210> SEQ ID NO 28
<211> LENGTH: 101
<212> TYPE: DNA
<213> ORGANISM: Artificial Sequence
<220> FEATURE:
<223> OTHER INFORMATION: synthetic sequence

<400> SEQUENCE: 28
tttctccctg gacttggaag cagatggaca acccctcaca ccagatgagt acctgacata    60
ctccctgaag ctgaagaaag gtaccagtca aaaagatgaa a                       101

<210> SEQ ID NO 29
<211> LENGTH: 108
<212> TYPE: DNA
<213> ORGANISM: Artificial Sequence
<220> FEATURE:
<223> OTHER INFORMATION: synthetic sequence

<400> SEQUENCE: 29
ccaagaagaa agtgaacatc atggatcaga acaacagcct gccaccttac gctcagggct    60
tggcctcccc tcagggtgcc atgactcccg aatccctat ctttagtc                 108

<210> SEQ ID NO 30
<211> LENGTH: 108
<212> TYPE: DNA
<213> ORGANISM: Artificial Sequence
<220> FEATURE:
<223> OTHER INFORMATION: synthetic sequence

<400> SEQUENCE: 30
ggggcctgga agtgcccgct gagaaaggga gaagacagca gaggggttgc cgaggcaacc    60
tccaagtccc agatcatgtc tctgtggggt ctggtctcca agatgccc                108

<210> SEQ ID NO 31
<211> LENGTH: 106
<212> TYPE: DNA
<213> ORGANISM: Artificial Sequence
<220> FEATURE:
<223> OTHER INFORMATION: synthetic sequence

<400> SEQUENCE: 31
atcctacagc gcgtcatcga ctacattctc gacctgcagg tagtcctggc cgagccagcc    60
```
cctggacccc ctgatggccc ccaccttccc atccagacag ccgagc                    106

<210> SEQ ID NO 32
<211> LENGTH: 108
<212> TYPE: DNA
<213> ORGANISM: Artificial Sequence
<220> FEATURE:
<223> OTHER INFORMATION: synthetic sequence

<400> SEQUENCE: 32
aagatacctg tagctttgct catccactat caacagaacc aggcatcatg cggcaaacgc    60
gcaatcatct tggagacgag acagcacagg ctgttctgtg ccgacccg                 108

<210> SEQ ID NO 33
<211> LENGTH: 107
<212> TYPE: DNA
<213> ORGANISM: Artificial Sequence
<220> FEATURE:
<223> OTHER INFORMATION: synthetic sequence

<400> SEQUENCE: 33
ttgccctgaa acttagctgt gctgggatta ttctccttgt cttggttgtt actgggttga    60
gtgtttcagt gacatcctta atacagaaat catcaataga aaaatgc                  107

<210> SEQ ID NO 34
<211> LENGTH: 92
<212> TYPE: DNA
<213> ORGANISM: Artificial Sequence
<220> FEATURE:
<223> OTHER INFORMATION: synthetic sequence

<400> SEQUENCE: 34
acaatttacc gaatataaga aggagaaagg tttcatcctc acttcccaaa aggaggatga    60
aatcatgaag gtgcagaaca actcagtcat ca                                  92

<210> SEQ ID NO 35
<211> LENGTH: 105
<212> TYPE: DNA
<213> ORGANISM: Artificial Sequence
<220> FEATURE:
<223> OTHER INFORMATION: synthetic sequence

<400> SEQUENCE: 35
ccaagacagc cacgaagatc ctaccaaaat gaagcgcttc ctcttcctcc tactcaccat    60
cagcctcctg gttatggtac agatacaaac tggactctca ggaca                    105

<210> SEQ ID NO 36
<211> LENGTH: 104
<212> TYPE: DNA
<213> ORGANISM: Artificial Sequence
<220> FEATURE:
<223> OTHER INFORMATION: synthetic sequence

<400> SEQUENCE: 36
tccaccacat cctccactgg acacccatcc caaatcagtc tgaaagtacc tgctatgaag    60
tggcgctcct gaggtatgga atagagtcct ggaactccat ctcc                     104

<210> SEQ ID NO 37
<211> LENGTH: 108
<212> TYPE: DNA
<213> ORGANISM: Artificial Sequence
<220> FEATURE:

<223> OTHER INFORMATION: synthetic sequence

<400> SEQUENCE: 37
tgattaaagc accagagtgt aatggccctc agagcagggc tggtcctggg gttccacacc    60
ctgatgaccc tcctgagccc gcaggaggca ggggccacca aggctgac                108

<210> SEQ ID NO 38
<211> LENGTH: 107
<212> TYPE: DNA
<213> ORGANISM: Artificial Sequence
<220> FEATURE:
<223> OTHER INFORMATION: synthetic sequence

<400> SEQUENCE: 38
gtggaaatcc taaggaactt ttacttcatt aacagactta caggttacct ccgaaactga    60
agatctccta gcctgtgcct ctgggactgg acaattgctt caagcat                 107

<210> SEQ ID NO 39
<211> LENGTH: 108
<212> TYPE: DNA
<213> ORGANISM: Artificial Sequence
<220> FEATURE:
<223> OTHER INFORMATION: synthetic sequence

<400> SEQUENCE: 39
cgttccccta caagaaactc tccccgggtg aacaagatg gattatcaag tgtcaagtcc    60
aatctatgac atcaattatt atacatcgga gccctgccaa aaaatcaa                108

<210> SEQ ID NO 40
<211> LENGTH: 107
<212> TYPE: DNA
<213> ORGANISM: Artificial Sequence
<220> FEATURE:
<223> OTHER INFORMATION: synthetic sequence

<400> SEQUENCE: 40
gtgtggatta tcctgcatca gcttcaatgt cttaatggtt cataagcgaa gccatactgg    60
tgaacgccca ttccagtgta atcagtgtgg ggcatctttt actcaga                 107

<210> SEQ ID NO 41
<211> LENGTH: 109
<212> TYPE: DNA
<213> ORGANISM: Artificial Sequence
<220> FEATURE:
<223> OTHER INFORMATION: synthetic sequence

<400> SEQUENCE: 41
agtgctgagt tggcagtttt cttctgtcac caaaagaggt ctcaatgtgg accagctgaa    60
catgttggga gagaagcttc ttggtcctaa cgccagcccc gatggtctc               109

<210> SEQ ID NO 42
<211> LENGTH: 109
<212> TYPE: DNA
<213> ORGANISM: Artificial Sequence
<220> FEATURE:
<223> OTHER INFORMATION: synthetic sequence

<400> SEQUENCE: 42
gcaggttcca gatgccaccc ttggaggaag gacttgaaga gttgcatgcc tcccacatcc    60
caactgccaa ccctggacac tgcattacag acccgccatc cctgggccc               109

```
<210> SEQ ID NO 43
<211> LENGTH: 104
<212> TYPE: DNA
<213> ORGANISM: Artificial Sequence
<220> FEATURE:
<223> OTHER INFORMATION: synthetic sequence

<400> SEQUENCE: 43
ctgagtgaca aggaattggt ttcagatgat gaagaaagag gaacgggctt ggaagaaaat      60
aatcaagaag agcaaagcat ggattcaaac ttaggtgaag cagc                     104

<210> SEQ ID NO 44
<211> LENGTH: 106
<212> TYPE: DNA
<213> ORGANISM: Artificial Sequence
<220> FEATURE:
<223> OTHER INFORMATION: synthetic sequence

<400> SEQUENCE: 44
ggccctgatc tgtgaggcca gcggggagg ggccttcctg gtgctgcccc tgggcaagac       60
tggacgtgtg gacaagaatg cgcccacggt ctgtggccac acagcc                   106

<210> SEQ ID NO 45
<211> LENGTH: 111
<212> TYPE: DNA
<213> ORGANISM: Artificial Sequence
<220> FEATURE:
<223> OTHER INFORMATION: synthetic sequence

<400> SEQUENCE: 45
tttgggaaac taaagctcac aaacaacaag ggggcgtcca acaatgtgac ccagatgatt      60
gtgctccagt ccctccataa gtaccagccc cggctgcata tcgttgaggt g             111

<210> SEQ ID NO 46
<211> LENGTH: 106
<212> TYPE: DNA
<213> ORGANISM: Artificial Sequence
<220> FEATURE:
<223> OTHER INFORMATION: synthetic sequence

<400> SEQUENCE: 46
ctcacccaac ctactaacaa taattgaaat gcagaaggga gactgtgcac tctatgcctc      60
gagctttaaa ggctatatag aaaactgttc aactccaaat acgtac                   106

<210> SEQ ID NO 47
<211> LENGTH: 105
<212> TYPE: DNA
<213> ORGANISM: Artificial Sequence
<220> FEATURE:
<223> OTHER INFORMATION: synthetic sequence

<400> SEQUENCE: 47
gcatctctgc tggtgttcat cagaacagac accatggcag agcatgatta ccatgaagac      60
tatgggttca gcagtttcaa tgacagcagc caggaggagc atcaa                    105

<210> SEQ ID NO 48
<211> LENGTH: 105
<212> TYPE: DNA
<213> ORGANISM: Artificial Sequence
<220> FEATURE:
<223> OTHER INFORMATION: synthetic sequence

<400> SEQUENCE: 48
tatctagtac ttactttaac aaaaaatgat cttgacaaag caaataaaga caaagccaac      60
cgatactttt ctccaaattt taaggtgaag ctgtacttca caaaa                    105

<210> SEQ ID NO 49
<211> LENGTH: 106
```
ccagagtgga cagaagccca gagacttgac tgctggagag gtggtcaagt gtccctcaag    60
gtcagtaatg atgggcctac actgattggt gcaaatgcct ccttct                 106

<210> SEQ ID NO 50
<211> LENGTH: 106
<212> TYPE: DNA
<213> ORGANISM: Artificial Sequence
<220> FEATURE:
<223> OTHER INFORMATION: synthetic sequence

<400> SEQUENCE: 50
agcaccaacc tgctctgtct gccaaatcac atgcaagcca gtgtgagcag gagctatctc    60
caatccttgg gcttttctgc cagtgacctt gtcatttcca cctgga                 106

<210> SEQ ID NO 51
<211> LENGTH: 99
<212> TYPE: DNA
<213> ORGANISM: Artificial Sequence
<220> FEATURE:
<223> OTHER INFORMATION: synthetic sequence

<400> SEQUENCE: 51
cttcaagaca acttttaaa catgagtaga tctatgactt ctcaaagccg ggtcatgaat     60
gtccataaaa tgctaggcat tcctatttcc aatattttg                          99

<210> SEQ ID NO 52
<211> LENGTH: 109
<212> TYPE: DNA
<213> ORGANISM: Artificial Sequence
<220> FEATURE:
<223> OTHER INFORMATION: synthetic sequence

<400> SEQUENCE: 52
catggaagtg cccacctatc tcaacttcaa gtccatgaac cacatgaatt acctccccag    60
ccaggaggat atgcctcata accagttcat caagatgatg atcatctttt              109

<210> SEQ ID NO 53
<211> LENGTH: 104
<212> TYPE: DNA
<213> ORGANISM: Artificial Sequence
<220> FEATURE:
<223> OTHER INFORMATION: synthetic sequence

<400> SEQUENCE: 53
gtcacagtct cagactcggg gctttaccgc tgctacttgc aggccagcgc aggagaaaac    60
gaaaccttcg tgatgagatt gactgtagcc gagggtaaaa ccga                   104

<210> SEQ ID NO 54
<211> LENGTH: 105
<212> TYPE: DNA
<213> ORGANISM: Artificial Sequence
<220> FEATURE:
<223> OTHER INFORMATION: synthetic sequence

<400> SEQUENCE: 54
ctcagcttta aaggggaag tgccctagaa gaaaagaga ataaaatatt ggtcaaagaa      60
actggttact tttttatata tggtcaggtt ttatatactg ataag                  105

<210> SEQ ID NO 55
<211> LENGTH: 105
<212> TYPE: DNA

```
<213> ORGANISM: Artificial Sequence
<220> FEATURE:
<223> OTHER INFORMATION: synthetic sequence

<400> SEQUENCE: 55
tattacttct gcaacctatc aattttttgat cctcctcctt ttaaagtaac tcttacagga    60
ggatatttgc atatttatga atcacaactt tgttgccagc tgaag                    105

<210> SEQ ID NO 56
<211> LENGTH: 106
<212> TYPE: DNA
<213> ORGANISM: Artificial Sequence
<220> FEATURE:
<223> OTHER INFORMATION: synthetic sequence

<400> SEQUENCE: 56
ctgggcctgc tgacagcgtg caggatgctg ttggaacccg gcagaggctg ctgtgccctg    60
gccatcctgc tggcaattgt ggacatccag tctggtggat gcatta                   106

<210> SEQ ID NO 57
<211> LENGTH: 108
<212> TYPE: DNA
<213> ORGANISM: Artificial Sequence
<220> FEATURE:
<223> OTHER INFORMATION: synthetic sequence

<400> SEQUENCE: 57
gaatcatagc accgtgacag tggaggaggc caaggccgag aaggagacgg agctgtcatt    60
gcaaaaggag cagctgcagc tcaagatcat tgagattgag gatgaagc                 108

<210> SEQ ID NO 58
<211> LENGTH: 98
<212> TYPE: DNA
<213> ORGANISM: Artificial Sequence
<220> FEATURE:
<223> OTHER INFORMATION: synthetic sequence

<400> SEQUENCE: 58
ccagcccctg atcatttcgc ctaaaagagc aaggactaga gttcctgacc tccaggccag    60
tccctgatcc ctgacctaat gttatcgcgg aatgatga                            98

<210> SEQ ID NO 59
<211> LENGTH: 104
<212> TYPE: DNA
<213> ORGANISM: Artificial Sequence
<220> FEATURE:
<223> OTHER INFORMATION: synthetic sequence

<400> SEQUENCE: 59
gcctgctgtc gctgaaggcc gacgtgctgg gggatgacgg ctccctgctg ttcgagtacc    60
tgcccagagg ggcccactcg ctgtccctga atgagttcac ggtg                     104

<210> SEQ ID NO 60
<211> LENGTH: 108
<212> TYPE: DNA
<213> ORGANISM: Artificial Sequence
<220> FEATURE:
<223> OTHER INFORMATION: synthetic sequence

<400> SEQUENCE: 60
ggcagcggca gctccactca gccagtaccc agatacgctg ggaaccttcc ccagccatgg    60
cttccctggg gcagatcctc ttctggagca taattagcat catcatta                 108
```

<210> SEQ ID NO 61
<211> LENGTH: 103
<212> TYPE: DNA
<213> ORGANISM: Artificial Sequence
<220> FEATURE:
<223> OTHER INFORMATION: synthetic sequence

<400> SEQUENCE: 61
aagatacttc tgcacgtcac attcaaatcc catcgtgttc ctgcttcagg ggaccttagg      60
gattgtcatc aaccagggac ttcgggggaa atctggagca ttt                       103

<210> SEQ ID NO 62
<211> LENGTH: 108
<212> TYPE: DNA
<213> ORGANISM: Artificial Sequence
<220> FEATURE:
<223> OTHER INFORMATION: synthetic sequence

<400> SEQUENCE: 62
caccagatag cagctttatt cacagtgaca gtccctaagg aactgtacat aatagagcat      60
ggcagcaatg tgaccctgga atgcaacttt gacactggaa gtcatgtg                  108

<210> SEQ ID NO 63
<211> LENGTH: 110
<212> TYPE: DNA
<213> ORGANISM: Artificial Sequence
<220> FEATURE:
<223> OTHER INFORMATION: synthetic sequence

<400> SEQUENCE: 63
tggccagatc tttagaccag acaactttgt atttggtcag tctggggcag gtaacaactg      60
ggccaaaggc cactacacag agggcgccga gctggttgat tctgtcctgg                110

<210> SEQ ID NO 64
<211> LENGTH: 107
<212> TYPE: DNA
<213> ORGANISM: Artificial Sequence
<220> FEATURE:
<223> OTHER INFORMATION: synthetic sequence

<400> SEQUENCE: 64
tgaccctgca tggtgtgcgg tgccctcctg cctcaggccg cgaagaagga tctaagggct      60
tggcttgttt gaaagaacca caccccgaaa gtaacatctt tggagaa                   107

<210> SEQ ID NO 65
<211> LENGTH: 98
<212> TYPE: DNA
<213> ORGANISM: Artificial Sequence
<220> FEATURE:
<223> OTHER INFORMATION: synthetic sequence

<400> SEQUENCE: 65
tgtgatggcc ttcctgctct ctggtgctgc tcctctgaag attcaagctt atttcaatga     60
gactgcagac ctgccatgcc aatttgcaaa ctctcaaa                             98

<210> SEQ ID NO 66
<211> LENGTH: 111
<212> TYPE: DNA
<213> ORGANISM: Artificial Sequence
<220> FEATURE:
<223> OTHER INFORMATION: synthetic sequence

<400> SEQUENCE: 66
tcccaggcat aatgaatgat gaaaaattta acctgaagtt ggtcatcaaa ccagccaagg    60
tcacccctgc accgactcgg cagagagact tcactgcagc ctttccaagg a             111

<210> SEQ ID NO 67
<211> LENGTH: 106
<212> TYPE: DNA
<213> ORGANISM: Artificial Sequence
<220> FEATURE:
<223> OTHER INFORMATION: synthetic sequence

<400> SEQUENCE: 67
gagaagagtc ggaagaggtg tggcggcatc ctagtgagaa aggactttgt gctgacagct    60
gctcactgcc agggaagctc cataaatgtc accttggggg cccaca                   106

<210> SEQ ID NO 68
<211> LENGTH: 107
<212> TYPE: DNA
<213> ORGANISM: Artificial Sequence
<220> FEATURE:
<223> OTHER INFORMATION: synthetic sequence

<400> SEQUENCE: 68
gcgagagcct gaagagttgg accagttgta cctggatgac gtaaatgaaa taatacgaaa    60
tgacctctcc agcacgagca cccactccta gttgccacat tggagca                  107

<210> SEQ ID NO 69
<211> LENGTH: 107
<212> TYPE: DNA
<213> ORGANISM: Artificial Sequence
<220> FEATURE:
<223> OTHER INFORMATION: synthetic sequence

<400> SEQUENCE: 69
ctgcatgatc gtcgggagcc ccgagctgac cttcgggaag ggaactcagc tgagtgtggt    60
tgatttcctt cccaccactg cccagcccac caagaagtcc accctca                  107

<210> SEQ ID NO 70
<211> LENGTH: 104
<212> TYPE: DNA
<213> ORGANISM: Artificial Sequence
<220> FEATURE:
<223> OTHER INFORMATION: synthetic sequence

<400> SEQUENCE: 70
ggcacctgca cacctggatc caggataacg gaggctggga tgcctttgtg gaactgtacg    60
gccccagcat gcggcctctg tttgatttct cctggctgtc tctg                     104

<210> SEQ ID NO 71
<211> LENGTH: 100
<212> TYPE: DNA
<213> ORGANISM: Artificial Sequence
<220> FEATURE:
<223> OTHER INFORMATION: synthetic sequence

<400> SEQUENCE: 71
ggcgaccatg caggagtcgc tgcgggtgaa gcagctggcc gaagagcaga agcgtcggga    60
gagggagcag cacatcgcag agtgcatggc caagatgcca                          100

<210> SEQ ID NO 72
<211> LENGTH: 111

```
<212> TYPE: DNA
<213> ORGANISM: Artificial Sequence
<220> FEATURE:
<223> OTHER INFORMATION: synthetic sequence

<400> SEQUENCE: 72
cggcgccgaa agaactaaaa ttccagatgg caaactcaat gaatggcaga aaccctggtg       60
gtcgaggagg aaatccccga aaaggtcgaa ttttgggtat tattgatgct a               111

<210> SEQ ID NO 73
<211> LENGTH: 100
<212> TYPE: DNA
<213> ORGANISM: Artificial Sequence
<220> FEATURE:
<223> OTHER INFORMATION: synthetic sequence

<400> SEQUENCE: 73
gacacagcaa gaaaggaggc attcacggaa gcccggggtg cccgaagagg agttaaaaaa       60
gtcatggtta ttgtgacaga tggagagtct catgacaatc                            100

<210> SEQ ID NO 74
<211> LENGTH: 104
<212> TYPE: DNA
<213> ORGANISM: Artificial Sequence
<220> FEATURE:
<223> OTHER INFORMATION: synthetic sequence

<400> SEQUENCE: 74
gtccccggcc tgtggtcaaa tcgggagaca agcccagcct ttcggcgaga tacgtctaac       60
cctgtgcaac agccactaca ttacttcaaa ctgagatcct tcct                       104

<210> SEQ ID NO 75
<211> LENGTH: 98
<212> TYPE: DNA
<213> ORGANISM: Artificial Sequence
<220> FEATURE:
<223> OTHER INFORMATION: synthetic sequence

<400> SEQUENCE: 75
tggggactgc tcacgttcat catggtgcct ggctgccagg cagagctctg tgacgatgac       60
ccgccagaga tcccacacgc cacattcaaa gccatggc                              98

<210> SEQ ID NO 76
<211> LENGTH: 100
<212> TYPE: DNA
<213> ORGANISM: Artificial Sequence
<220> FEATURE:
<223> OTHER INFORMATION: synthetic sequence

<400> SEQUENCE: 76
ccacacttcc gtgattatct gcgtgcattt tggacaaagc ttccaaccag gatacgggaa       60
gaagaaatgg ctggtgatct ttcagcaggt ttcttcatgg                            100

<210> SEQ ID NO 77
<211> LENGTH: 95
<212> TYPE: DNA
<213> ORGANISM: Artificial Sequence
<220> FEATURE:
<223> OTHER INFORMATION: synthetic sequence

<400> SEQUENCE: 77
caacaggctc gtccaaacct gcgggtgacc agctgcccgc ggctctgtgg accagcagtg       60
cggtgctggg actgctgctc ctggccttgc ccacc                                 95

<210> SEQ ID NO 78
<211> LENGTH: 110
<212> TYPE: DNA
<213> ORGANISM: Artificial Sequence
```

<210> SEQ ID NO 79
<211> LENGTH: 107
<212> TYPE: DNA
<213> ORGANISM: Artificial Sequence
<220> FEATURE:
<223> OTHER INFORMATION: synthetic sequence

<400> SEQUENCE: 79
gcagacagcg accaaaaagc caggggggca ttcaacccca tgtttctaga actctgttcc      60
tgctgctgct gttggcagcc tcagcctggg gggtcaccct gagcccc                  107

<210> SEQ ID NO 80
<211> LENGTH: 109
<212> TYPE: DNA
<213> ORGANISM: Artificial Sequence
<220> FEATURE:
<223> OTHER INFORMATION: synthetic sequence

<400> SEQUENCE: 80
tcttcgacga tcggagcttg gtgctgacct atgtgtttac catcctcaac tgcctgcagg      60
gcgccttcct ctacctgctg cactgcctgc tcaacaagaa ggttcggga              109

<210> SEQ ID NO 81
<211> LENGTH: 102
<212> TYPE: DNA
<213> ORGANISM: Artificial Sequence
<220> FEATURE:
<223> OTHER INFORMATION: synthetic sequence

<400> SEQUENCE: 81
ttgctgctca aggaaggggt ggatggcaac tttcttttaa gagacagcga gtcgatacca      60
ggagtcctgt gcctctgtgt ctcgtttaaa aatattgtct ac                       102

<210> SEQ ID NO 82
<211> LENGTH: 106
<212> TYPE: DNA
<213> ORGANISM: Artificial Sequence
<220> FEATURE:
<223> OTHER INFORMATION: synthetic sequence

<400> SEQUENCE: 82
tgaccgtgca ggttcttccc cagtgtgagt gccggtgccg ggaccagagc agagaccgca      60
gcctctgcca tggcaagggc ttcttggagt gcggcatctg caggtg                  106

<210> SEQ ID NO 83
<211> LENGTH: 108
<212> TYPE: DNA
<213> ORGANISM: Artificial Sequence
<220> FEATURE:
<223> OTHER INFORMATION: synthetic sequence

<400> SEQUENCE: 83
tccatatcag agctgtgatc ttgagagccc tctccttggc tttcctgctg agtctccgag      60
gagctggggc catcaaggcg gaccatgtgt caacttatgc cgcgtttg               108

<210> SEQ ID NO 84
<211> LENGTH: 109
<212> TYPE: DNA
<213> ORGANISM: Artificial Sequence
<220> FEATURE:
<223> OTHER INFORMATION: synthetic sequence

<400> SEQUENCE: 84

```
aggtccaagg tggaaaagca gctacaggtc atctcagtgc tccagtgggt cctgtccttc    60
cttgtactgg gagtggcctg cagtgccatc ctcatgtaca tattctgca              109

<210> SEQ ID NO 85
<211> LENGTH: 109
<212> TYPE: DNA
<213> ORGANISM: Artificial Sequence
<220> FEATURE:
<223> OTHER INFORMATION: synthetic sequence

<400> SEQUENCE: 85
catgccttgg tctccttgtc cttcctaaaa aaccttcgcc tcatcctagg agaggagcag    60
ctagaaggga attactcctt ctacgtcctc gacaaccaga acttgcagc               109

<210> SEQ ID NO 86
<211> LENGTH: 107
<212> TYPE: DNA
<213> ORGANISM: Artificial Sequence
<220> FEATURE:
<223> OTHER INFORMATION: synthetic sequence

<400> SEQUENCE: 86
tgctcaccct ggagaatgac cagagcctgt catttgaagc ccagaaggac ctgaacaaca    60
aggtgaagac actggtggaa ttcctcattg ataactgctt tgaaata                107

<210> SEQ ID NO 87
<211> LENGTH: 108
<212> TYPE: DNA
<213> ORGANISM: Artificial Sequence
<220> FEATURE:
<223> OTHER INFORMATION: synthetic sequence

<400> SEQUENCE: 87
aaggagctga aagcgcgcaa taccaagaag gagggtgacc tgatagctgc tcaggctcgg    60
ctgaaggacc tggaggctct gctgaactcc aaggaggccg cactgagc               108

<210> SEQ ID NO 88
<211> LENGTH: 108
<212> TYPE: DNA
<213> ORGANISM: Artificial Sequence
<220> FEATURE:
<223> OTHER INFORMATION: synthetic sequence

<400> SEQUENCE: 88
ctgaacaagt gtggcctgtt catgtgcatt gcggtcaacc tgtgtggaaa agccgggccc    60
ggggccaagg gcaaggacat ggaggagggc aaggccgcct tctcgaaa               108

<210> SEQ ID NO 89
<211> LENGTH: 108
<212> TYPE: DNA
<213> ORGANISM: Artificial Sequence
<220> FEATURE:
<223> OTHER INFORMATION: synthetic sequence

<400> SEQUENCE: 89 cagggagta cttctgcatc tatcacacct accctgatgg gacgtacact gggagaatct    60
tcctggaggt cctagaaagc tcagtggctg agcacggtgc caggttcc               108

<210> SEQ ID NO 90
<211> LENGTH: 104
<212> TYPE: DNA
```

```
<213> ORGANISM: Artificial Sequence
<220> FEATURE:
<223> OTHER INFORMATION: synthetic sequence

<400> SEQUENCE: 90
aagagcttcc tgcacaaagt aagccaccag cgcaacatga cagtgaagac cctgcatggc    60
ccagccatgg tcaagtactt gctgctgtcg atattggggc ttgc                    104

<210> SEQ ID NO 91
<211> LENGTH: 108
<212> TYPE: DNA
<213> ORGANISM: Artificial Sequence
<220> FEATURE:
<223> OTHER INFORMATION: synthetic sequence

<400> SEQUENCE: 91
ctgcagctgt gctcacacct ggaggaaacc tcaatggtca catcctcttt cctgtgtcaa    60
gaagcatcgt ccggggaggt gagaagaaga cagtcctccc tagaattg                108

<210> SEQ ID NO 92
<211> LENGTH: 100
<212> TYPE: DNA
<213> ORGANISM: Artificial Sequence
<220> FEATURE:
<223> OTHER INFORMATION: synthetic sequence

<400> SEQUENCE: 92
ggaaggcgct tttcaccgcg gccatcctgc aggcacagtt gccgattaca gaggcacaga    60
gctttggcct gctggatccc aaactctgct acctgctgga                         100

<210> SEQ ID NO 93
<211> LENGTH: 106
<212> TYPE: DNA
<213> ORGANISM: Artificial Sequence
<220> FEATURE:
<223> OTHER INFORMATION: synthetic sequence

<400> SEQUENCE: 93
ccagggctgc ggcacagagc tgcgagtcat gggattcagc accttggcac agctgaagca    60
gaggaacacg ctgaaggatg gtatcatcat gatccagacg ctgctg                  106

<210> SEQ ID NO 94
<211> LENGTH: 104
<212> TYPE: DNA
<213> ORGANISM: Artificial Sequence
<220> FEATURE:
<223> OTHER INFORMATION: synthetic sequence

<400> SEQUENCE: 94
caagctcatg tggacaagat gcccctgctg agctgccagt tcctgaaggg tcaccgggag    60
cagcgcctgg cccacctggt cctgagcttc ctcaccatgg gtta                    104

<210> SEQ ID NO 95
<211> LENGTH: 97
<212> TYPE: DNA
<213> ORGANISM: Artificial Sequence
<220> FEATURE:
<223> OTHER INFORMATION: synthetic sequence

<400> SEQUENCE: 95
ttcctgaaac ggctcgacag gaacctctgg ggcctggcgg gcttgaattc ctgtcctgtg    60
aaggaagcca accagagtac gttggaaaac ttcttgg                            97
```

<210> SEQ ID NO 96
<211> LENGTH: 105
<212> TYPE: DNA
<213> ORGANISM: Artificial Sequence
<220> FEATURE:
<223> OTHER INFORMATION: synthetic sequence

<400> SEQUENCE: 96
tcaggagctc cagggtcaga ggtcggatgt ctacagcgac ctcaacacac agaggccgta    60
ttacaaatga gcccgaatca tgacagtcag caacatgata cctgg                   105

<210> SEQ ID NO 97
<211> LENGTH: 107
<212> TYPE: DNA
<213> ORGANISM: Artificial Sequence
<220> FEATURE:
<223> OTHER INFORMATION: synthetic sequence

<400> SEQUENCE: 97
ggaactggga aattattttg ggtcttcttc ttaatcccat atctggacat ctggaacatc    60
catgggaaag aatcatgtga tgtacagctt tatataaaga gacaatc                 107

<210> SEQ ID NO 98
<211> LENGTH: 109
<212> TYPE: DNA
<213> ORGANISM: Artificial Sequence
<220> FEATURE:
<223> OTHER INFORMATION: synthetic sequence

<400> SEQUENCE: 98
gtgaaggagg gttggctgca caaacgaggg gagtacatca agacctggcg gccacgctac    60
ttcctcctca agaatgatgg caccttcatt ggctacaagg agcggccgc               109

<210> SEQ ID NO 99
<211> LENGTH: 104
<212> TYPE: DNA
<213> ORGANISM: Artificial Sequence
<220> FEATURE:
<223> OTHER INFORMATION: synthetic sequence

<400> SEQUENCE: 99
atctctgttg gctccatggg attgattatc agccttctct gtgtgtattt ctggctggaa    60
cggacgatgc cccgaattcc caccctgaag aacctagagg atct                    104

<210> SEQ ID NO 100
<211> LENGTH: 101
<212> TYPE: DNA
<213> ORGANISM: Artificial Sequence
<220> FEATURE:
<223> OTHER INFORMATION: synthetic sequence

<400> SEQUENCE: 100
tcttcctgcg ctgcatcgag tccaacatgc tgacagatat gaccctgcag ggcatcgagc    60
agatcagcaa ggtgtacatg cacttgccac agacagacaa c                       101

<210> SEQ ID NO 101
<211> LENGTH: 103
<212> TYPE: DNA
<213> ORGANISM: Artificial Sequence
<220> FEATURE:
<223> OTHER INFORMATION: synthetic sequence

```
<400> SEQUENCE: 101
gttctaagaa cctgcttggg agccgtgacc tccaaagctc tgtgaccttg gacctggccc      60
tcgaccctgg ccgcctgagt ccccgtgcca ccttccagga aac                      103

<210> SEQ ID NO 102
<211> LENGTH: 107
<212> TYPE: DNA
<213> ORGANISM: Artificial Sequence
<220> FEATURE:
<223> OTHER INFORMATION: synthetic sequence

<400> SEQUENCE: 102
tgataagccc actctacagc tggagagtgt agatcccaaa aattacccaa agaagaagat      60
ggaaaagcga tttgtcttca acaagataga aatcaataac aagctgg                  107

<210> SEQ ID NO 103
<211> LENGTH: 104
<212> TYPE: DNA
<213> ORGANISM: Artificial Sequence
<220> FEATURE:
<223> OTHER INFORMATION: synthetic sequence

<400> SEQUENCE: 103
ggcagagaaa cacataaaga gctcagtgaa catccagatg gcccctccat ccctcaacgt      60
gaccaaggat ggagacagct acagcctgcg ctgggaaaca atga                    104

<210> SEQ ID NO 104
<211> LENGTH: 103
<212> TYPE: DNA
<213> ORGANISM: Artificial Sequence
<220> FEATURE:
<223> OTHER INFORMATION: synthetic sequence

<400> SEQUENCE: 104
ctgaatgttt aattaatcag gaatgtgaag aaattctaca gatttgctct actaagggga      60
tgatggcagg tgcagagaaa ttggtggaat gccttctcag atc                      103

<210> SEQ ID NO 105
<211> LENGTH: 107
<212> TYPE: DNA
<213> ORGANISM: Artificial Sequence
<220> FEATURE:
<223> OTHER INFORMATION: synthetic sequence

<400> SEQUENCE: 105
aaggaattgg agaattcttt aggttgtccc ctaaagattc tgaaaagag aatcagattc      60 ctgaagaggc aggaagcagt ggcttaggaa aagcaaagag aaaagca                  107

<210> SEQ ID NO 106
<211> LENGTH: 108
<212> TYPE: DNA
<213> ORGANISM: Artificial Sequence
<220> FEATURE:
<223> OTHER INFORMATION: synthetic sequence

<400> SEQUENCE: 106
tggtggtgcc gactacaagc gaattactgt gaaagtcaat gccccataca acaaaatcaa      60
ccaaagaatt tggttgtgg atccagtcac ctctgaacat gaactgac                  108

<210> SEQ ID NO 107
<211> LENGTH: 108
```

```
<212> TYPE: DNA
<213> ORGANISM: Artificial Sequence
<220> FEATURE:
<223> OTHER INFORMATION: synthetic sequence

<400> SEQUENCE: 107
agtgcgtgag tgaacagagc ctccagttgt cagcccacct gcaggtgaaa acaaccgatg    60
tccaacttca agcctttgat tttgaagatg accactttgg aaatgtgg              108

<210> SEQ ID NO 108
<211> LENGTH: 107
<212> TYPE: DNA
<213> ORGANISM: Artificial Sequence
<220> FEATURE:
<223> OTHER INFORMATION: synthetic sequence

<400> SEQUENCE: 108
ttatgcactc cgaagcagaa gaatccaagg aagtggccac agatgtcttt aattccaaaa    60
acctggccgt tcaggcacaa aagaagatct tgggtaaaat ggtgtcc                107

<210> SEQ ID NO 109
<211> LENGTH: 110
<212> TYPE: DNA
<213> ORGANISM: Artificial Sequence
<220> FEATURE:
<223> OTHER INFORMATION: synthetic sequence

<400> SEQUENCE: 109
gaagggcagg gcacaatgtc tcctccagag agagatggta cagtctctgg agcagcagct    60
ggtgctggag aaggagaagc tgagtgccat gcaggcccac ctggctggga             110

<210> SEQ ID NO 110
<211> LENGTH: 103
<212> TYPE: DNA
<213> ORGANISM: Artificial Sequence
<220> FEATURE:
<223> OTHER INFORMATION: synthetic sequence

<400> SEQUENCE: 110
gaccatgaat gcaaagcttc tgatggatcc taagaggcag atctttctag atcaaaacat    60
gctggcagtt attgatgagc tgatgcaggc cctgaatttc aac                    103

<210> SEQ ID NO 111
<211> LENGTH: 106
<212> TYPE: DNA
<213> ORGANISM: Artificial Sequence
<220> FEATURE:
<223> OTHER INFORMATION: synthetic sequence

<400> SEQUENCE: 111
atattttgtt cagtggtgtg cagacagaaa tttcaccaag ccgcaggatg gcgatgttat    60
agccccactc ataacacctc aaaaaaagga atggaacgac agtact                 106

<210> SEQ ID NO 112
<211> LENGTH: 106
<212> TYPE: DNA
<213> ORGANISM: Artificial Sequence
<220> FEATURE:
<223> OTHER INFORMATION: synthetic sequence

<400> SEQUENCE: 112
tctgcagcca tgagcagagg cgacaactgc acggatctac tcgcactggg aatcccctcc    60
```

| | |
|---|---|
| ataacccagg cctggggact gtgggtcctc ttagggctg tgacgc | 106 |

<210> SEQ ID NO 113
<211> LENGTH: 103
<212> TYPE: DNA
<213> ORGANISM: Artificial Sequence
<220> FEATURE:
<223> OTHER INFORMATION: synthetic sequence

<400> SEQUENCE: 113

| | |
|---|---|
| ctgggggctt gctgctgctg gtttactact ggagcaagaa tagaaaggcc aaggccaagc | 60 |
| ctgtgacacg aggagcgggt gctggcggca ggcaaagggg aca | 103 |

<210> SEQ ID NO 114
<211> LENGTH: 105
<212> TYPE: DNA
<213> ORGANISM: Artificial Sequence
<220> FEATURE:
<223> OTHER INFORMATION: synthetic sequence

<400> SEQUENCE: 114

| | |
|---|---|
| gccaatccct gggattccag gaggttttga gcgttgaggt tacactgcat gtggcagcaa | 60 |
| acttcagcgt gcccgtcgtc agcgccccc acagcccctc ccagg | 105 |

<210> SEQ ID NO 115
<211> LENGTH: 103
<212> TYPE: DNA
<213> ORGANISM: Artificial Sequence
<220> FEATURE:
<223> OTHER INFORMATION: synthetic sequence

<400> SEQUENCE: 115

| | |
|---|---|
| gaacatggaa gacttacatc gtcatatctt ctgggaacca gatgcaagta agctgaatga | 60 |
| gaattactgc cgaaatccag atgatgatgc tcatggaccc tgg | 103 |

<210> SEQ ID NO 116
<211> LENGTH: 101
<212> TYPE: DNA
<213> ORGANISM: Artificial Sequence
<220> FEATURE:
<223> OTHER INFORMATION: synthetic sequence

<400> SEQUENCE: 116

| | |
|---|---|
| aaaaatcatg gataaaaaca cactagggag tgatttgccc cggatcaaaa cggagattga | 60 |
| ggccttgaag aacctgagac atcagcatat atgtcaactc t | 101 |

<210> SEQ ID NO 117
<211> LENGTH: 1371
<212> TYPE: DNA
<213> ORGANISM: Artificial Sequence
<220> FEATURE:
<223> OTHER INFORMATION: synthetic sequence

<400> SEQUENCE: 117

| | |
|---|---|
| ttgagttcca catgcagagc agatgcgaca gctagaagtg agtagggccc agaccctggc | 60 |
| ccaggaagat ccactaaagg aggccatcct tccgccttct tctgcaggag tcaggatgga | 120 |
| aaggcagatg taaagtccct catggcgaaa tataacacgg ggggcaaccc gacagaggat | 180 |
| gtctcagtca atagccgacc cttcagagtc acagggccaa actcatcttc aggaatacaa | 240 |
| gcaagaaaga acttattcaa caaccaagga aatgccagcc ctcctgcagg acccagcaat | 300 |
| gtacctaagt ttgggtcccc aaagccacct gtggcagtca accttcttc tgaggaaaag | 360 |

```
cctgacaagg aacccaagcc cccgtttcta aagcccactg gagcaggcca aagattcgga      420
acaccagcca gcttgaccac cagagacccc gaggcgaaag tgggatttct gaaacctgta      480
ggccccaagc ccatcaactt gcccaaagaa gattccaaac ctacatttcc ctggcctcct      540
ggaaacaagc catctcttca cagtgtaaac caagaccatg acttaaagcc actaggcccg      600
aaatctgggc ctactcctcc aacctcagaa aatgaacaga agcaagcgtt tcccaaattg      660
actggggtta aagggaaatt tatgtcagca tcacaagatc ttgaacccaa gcccctcttc      720
cccaaacccg cctttggcca gaagccgccc ctaagtaccg agaactccca tgaagacgaa      780
agccccatga agaatgtgtc ttcatcaaaa gggtccccag ctcccctggg agtcaggtcc      840
aaaagcggcc ctttaaaacc agcaagggaa gactcagaaa ataaagacca tgcaggggag      900
atttcaagtt tgccctttcc tggagtggtt ttgaaacctg ctgcgagcag gggaggccca      960
ggtctctcca aaaatggtga agaaaaaaag gaagatagga agatagatgc tgctaagaac     1020
accttccaga gcaaaataaa tcaggaagag ttggcctcag ggactcctcc tgccaggttc     1080
cctaaggccc cttctaagct gacagtgggg gggccatggg gccaaagtca ggaaaaggaa     1140
aagggagaca agaattcagc caccccgaaa cagaagccat tgcctccctt gtttaccttg     1200
ggtccacctc caccaaaacc caacagacca ccaaatgttg acctgacgaa attccacaaa     1260
acctcttctg gaaacagtac tagcaaaggc cagacgtctt actcaacaac ttccctgcca     1320
ccacctccac catcccatcc ggccagccaa ccaccattgc cagcatctca c              1371
```

<210> SEQ ID NO 118
<211> LENGTH: 106
<212> TYPE: DNA
<213> ORGANISM: Artificial Sequence
<220> FEATURE:
<223> OTHER INFORMATION: synthetic sequence

<400> SEQUENCE: 118

```
tcctgcccgt gcctggccca ggagggcccc cagggtgacc tgttgaccaa aacacaggag       60
ctgggccgtg actacaggac ctgtctgacg atagtccaaa aactga                     106
```

<210> SEQ ID NO 119
<211> LENGTH: 107
<212> TYPE: DNA
<213> ORGANISM: Artificial Sequence
<220> FEATURE:
<223> OTHER INFORMATION: synthetic sequence

<400> SEQUENCE: 119

```
gccttttcac catgagtggg tgcccatttt taggaaacaa ctttggatat acttttaaaa       60
aactccccgt agaaggcagc gaagaagaca aatcacaaac tggtgtg                   107
```

<210> SEQ ID NO 120
<211> LENGTH: 458
<212> TYPE: DNA
<213> ORGANISM: Artificial Sequence
<220> FEATURE:
<223> OTHER INFORMATION: synthetic sequence

<400> SEQUENCE: 120

```
tcatcgacaa ggtgcggttc ctggagcagc agaacaaggt tctggacacc aagtggaccc       60
tgctgcagga gcagggcacc aagactgtga ggcagaacct ggagccgttg ttcgagcagt      120
acatcaacaa cctcaggagg cagctggaca gcatcgtggg ggaacggggc cgcctggact      180
```

| | |
|---|---|
| cagagctgag aaacatgcag gacctggtgg aagacttcaa gaacaagtat gaggatgaaa | 240 |
| tcaacaagcg taccactgct gagaatgagt ttgtgatgct gaagaaggat gtagatgctg | 300 |
| cctacatgaa caaggtggag ctggaggcca aggttgatgc actgatggat gagattaact | 360 |
| tcatgaagat gttctttgat gcggagctgt cccagatgca gacgcatgtc tctgacacct | 420 |
| cagtggtcct ctccatggac aacaaccgca acctggac | 458 |

<210> SEQ ID NO 121
<211> LENGTH: 108
<212> TYPE: DNA
<213> ORGANISM: Artificial Sequence
<220> FEATURE:
<223> OTHER INFORMATION: synthetic sequence

<400> SEQUENCE: 121

| | |
|---|---|
| tctgaggcgg agcaccagag agcctacctg gaagacacat gcgtggagtg gctccacaaa | 60 |
| tacctggaga aggggaagga gacgctgctt cacctggagc ccccaaag | 108 |

<210> SEQ ID NO 122
<211> LENGTH: 105
<212> TYPE: DNA
<213> ORGANISM: Artificial Sequence
<220> FEATURE:
<223> OTHER INFORMATION: synthetic sequence

<400> SEQUENCE: 122

| | |
|---|---|
| ctgctggaga atgtgctgtg tggcgtggcc tttggcctgg gtgtgctggg catcatcgtg | 60 |
| ggcattgttc tcatcatcta cttccggaag ccttgctcag gtgac | 105 |

<210> SEQ ID NO 123
<211> LENGTH: 111
<212> TYPE: DNA
<213> ORGANISM: Artificial Sequence
<220> FEATURE:
<223> OTHER INFORMATION: synthetic sequence

<400> SEQUENCE: 123

| | |
|---|---|
| atggtgaaaa atggcaacgg gaccgcgtgc ataatggcca acttctctgc tgccttctca | 60 |
| gtgaactacg acaccaagag tggccctaag aacatgacct tgacctgcc a | 111 |

<210> SEQ ID NO 124
<211> LENGTH: 95
<212> TYPE: DNA
<213> ORGANISM: Artificial Sequence
<220> FEATURE:
<223> OTHER INFORMATION: synthetic sequence

<400> SEQUENCE: 124

| | |
|---|---|
| ccctggccgt gccctgagtg accgtcgggc ttgcagggcc tgcgactgtc acccggttgg | 60 |
| tgctgctggc aagacctgca accagaccac aggcc | 95 |

<210> SEQ ID NO 125
<211> LENGTH: 103
<212> TYPE: DNA
<213> ORGANISM: Artificial Sequence
<220> FEATURE:
<223> OTHER INFORMATION: synthetic sequence

<400> SEQUENCE: 125

| | |
|---|---|
| agagcaatgg aaccattatc catgtgaaag ggaaacacct ttgtccaagt ccccctatttc | 60 |
| ccggaccttc taagcccttt tgggtgctgg tggtggttgg tgg | 103 |

<210> SEQ ID NO 126
<211> LENGTH: 101
<212> TYPE: DNA
<213> ORGANISM: Artificial Sequence
<220> FEATURE:
<223> OTHER INFORMATION: synthetic sequence

<400> SEQUENCE: 126
caattgttca aaagatgcaa atgatacact actgctgcag ctcacaaaca cctctgcata      60
ttacatgtac ctcctcctgc tcctcaagag tgtggtctat t                        101

<210> SEQ ID NO 127
<211> LENGTH: 103
<212> TYPE: DNA
<213> ORGANISM: Artificial Sequence
<220> FEATURE:
<223> OTHER INFORMATION: synthetic sequence

<400> SEQUENCE: 127
ggcccgagac ccccagcgct accttgtcat tcaggggat gaaagaatgc atttgccaag       60
tcctacagac tccaacttct accgtgccct gatggatgaa gaa                       103

<210> SEQ ID NO 128
<211> LENGTH: 106
<212> TYPE: DNA
<213> ORGANISM: Artificial Sequence
<220> FEATURE:
<223> OTHER INFORMATION: synthetic sequence

<400> SEQUENCE: 128
gcctcacaga ccttcctcag agccgctttc agaaaagcaa gctgcttctg gttgggccca      60
gacctgcctt gaggagcctg tagagttaaa aaatgaaccc cacgga                   106

<210> SEQ ID NO 129
<211> LENGTH: 104
<212> TYPE: DNA
<213> ORGANISM: Artificial Sequence
<220> FEATURE:
<223> OTHER INFORMATION: synthetic sequence

<400> SEQUENCE: 129
cggcctgacg tcggtggagg gaagcaggcg caggctccgt gaggaggcaa ggttctgagg      60
agacaggccc cggagcagca ctagctcctg cccacactcc tacc                     104

<210> SEQ ID NO 130
<211> LENGTH: 108
<212> TYPE: DNA
<213> ORGANISM: Artificial Sequence
<220> FEATURE:
<223> OTHER INFORMATION: synthetic sequence

<400> SEQUENCE: 130
cagccatgcc tcacagctcc gacagcagtg actccagctt cagccgctct cctcccctg       60 gcaaacagga ctcatctgat gatgtgagaa gagttcagag gagggaga                 108

<210> SEQ ID NO 131
<211> LENGTH: 108
<212> TYPE: DNA
<213> ORGANISM: Artificial Sequence
<220> FEATURE:
<223> OTHER INFORMATION: synthetic sequence

<400> SEQUENCE: 131
ggtctgagga acaattctgg ctggaggtgg gaagatggat cacctctaaa cttctcaagg    60
atttcttcta atagctttgt gcagacatgc ggtgccatca acaaaaat               108

<210> SEQ ID NO 132
<211> LENGTH: 100
<212> TYPE: DNA
<213> ORGANISM: Artificial Sequence
<220> FEATURE:
<223> OTHER INFORMATION: synthetic sequence

<400> SEQUENCE: 132
taagcgccta tgccagcatc agtttccaga agcagccaga ggaccgtcag tagctcaact    60
ggacatcaca gcagaatgaa gacctaaatg acctcagcaa                        100

<210> SEQ ID NO 133
<211> LENGTH: 106
<212> TYPE: DNA
<213> ORGANISM: Artificial Sequence
<220> FEATURE:
<223> OTHER INFORMATION: synthetic sequence

<400> SEQUENCE: 133
agggcaacag ttatactttc atcgacccca cgcagctgcc ttacaacgag aagtgggagt    60
tcccccggaa caacctgcag tttggtaaga ccctcggagc tggagc                 106

<210> SEQ ID NO 134
<211> LENGTH: 105
<212> TYPE: DNA
<213> ORGANISM: Artificial Sequence
<220> FEATURE:
<223> OTHER INFORMATION: synthetic sequence

<400> SEQUENCE: 134
ggcaacggaa cccagattta tgtaattgat ccagaaccgt gcccagattc tgacttcctc    60
ctctggatcc ttgcagcagt tagttcgggg ttgttttttt atagc                  105

<210> SEQ ID NO 135
<211> LENGTH: 100
<212> TYPE: DNA
<213> ORGANISM: Artificial Sequence
<220> FEATURE:
<223> OTHER INFORMATION: synthetic sequence

<400> SEQUENCE: 135
gatcatcctg gaagctgtgg ctcttttgct caatagttat gttgctattt ctttgctcct    60
tcagttggct aatctttatt tttctccaat tagagactgc                        100

<210> SEQ ID NO 136
<211> LENGTH: 107
<212> TYPE: DNA
<213> ORGANISM: Artificial Sequence
<220> FEATURE:
<223> OTHER INFORMATION: synthetic sequence

<400> SEQUENCE: 136
aaaaggcaac atcctgtcac aggccatgct ctggcaaaaa cccacagctc cggagcaagc    60
cccagccccg gcccggccat accagggcgt ccgtgtgaag gagccag                107

<210> SEQ ID NO 137
<211> LENGTH: 100

```
<212> TYPE: DNA
<213> ORGANISM: Artificial Sequence
<220> FEATURE:
<223> OTHER INFORMATION: synthetic sequence

<400> SEQUENCE: 137
ggtcctactt agtcttgaca gaaaaaccat ctgtgctggg gctttgattg caaaagactg      60
ggtgttgact gcagctcact gtaacttgaa caaaaggtcc                          100

<210> SEQ ID NO 138
<211> LENGTH: 106
<212> TYPE: DNA
<213> ORGANISM: Artificial Sequence
<220> FEATURE:
<223> OTHER INFORMATION: synthetic sequence

<400> SEQUENCE: 138
aagagtacct tgttccaatc ccaggtggaa tgaatggctg aattatgata tatacattcc     60
tgatcttcct cgtgctgctc gactttgcct ttccatttgc tctgtt                  106

<210> SEQ ID NO 139
<211> LENGTH: 106
<212> TYPE: DNA
<213> ORGANISM: Artificial Sequence
<220> FEATURE:
<223> OTHER INFORMATION: synthetic sequence

<400> SEQUENCE: 139
ctgaagacaa caggcgacca ctttgggaac ctgaagaaac tgtggtcatt gccttatatg     60
actaccaaac caatgatcct caggaactcg cactgcggcg caacga                  106

<210> SEQ ID NO 140
<211> LENGTH: 106
<212> TYPE: DNA
<213> ORGANISM: Artificial Sequence
<220> FEATURE:
<223> OTHER INFORMATION: synthetic sequence

<400> SEQUENCE: 140
cacattctca ggaactctcc ttctttgggt ctggctgaag ttgaggatct cttactctct     60
aggccacgga attaacccga gcaggcatgg aggcctctgc tctcac                  106

<210> SEQ ID NO 141
<211> LENGTH: 105
<212> TYPE: DNA
<213> ORGANISM: Artificial Sequence
<220> FEATURE:
<223> OTHER INFORMATION: synthetic sequence

<400> SEQUENCE: 141
aatgtgttcg tagaggtggt gctggcggac cccaaccact ggcgcttcca gggggggcaaa    60 tgggtgacct gtggcaaagc cgacaataac atgcagggca acaaa                   105

<210> SEQ ID NO 142
<211> LENGTH: 106
<212> TYPE: DNA
<213> ORGANISM: Artificial Sequence
<220> FEATURE:
<223> OTHER INFORMATION: synthetic sequence

<400> SEQUENCE: 142
gatcccagcc ccacctctga gcaaggtccc tctgcagcag aacttccagg acaaccaatt     60
```
ccagggaaag tggtatgtgg taggcctggc agggaatgca attctc        106

<210> SEQ ID NO 143
<211> LENGTH: 100
<212> TYPE: DNA
<213> ORGANISM: Artificial Sequence
<220> FEATURE:
<223> OTHER INFORMATION: synthetic sequence

<400> SEQUENCE: 143
gctcttggtg ctggctggtc tttctcactt ctgttcaggt gttatccacg tgaccaagga        60
agtgaaagaa gtggcaacgc tgtcctgtgg tcacaatgtt        100

<210> SEQ ID NO 144
<211> LENGTH: 100
<212> TYPE: DNA
<213> ORGANISM: Artificial Sequence
<220> FEATURE:
<223> OTHER INFORMATION: synthetic sequence

<400> SEQUENCE: 144
ctcggggaca tacaggtgca ctctgcagga cccggatggg cagagaaacc taagtggcaa        60
ggtgatcttg agagtgacag gatgccctgc acagcgtaaa        100

<210> SEQ ID NO 145
<211> LENGTH: 105
<212> TYPE: DNA
<213> ORGANISM: Artificial Sequence
<220> FEATURE:
<223> OTHER INFORMATION: synthetic sequence

<400> SEQUENCE: 145
ttatccctag acgcttcatt gatcgaattc aaatcttgcc ccgtgggaat ggttgtccaa        60
gaaaagaaat catagtctgg aagaagaaca agtcaattgt gtgtg        105

<210> SEQ ID NO 146
<211> LENGTH: 102
<212> TYPE: DNA
<213> ORGANISM: Artificial Sequence
<220> FEATURE:
<223> OTHER INFORMATION: synthetic sequence

<400> SEQUENCE: 146
ttggggaaag gaacgtgaaa ggcatgtttg aggtgctgga gcccttgcat gctatgatgg        60
aacggggccc ccagactctg aaggaaacat cctttaatca gg        102

<210> SEQ ID NO 147
<211> LENGTH: 107
<212> TYPE: DNA
<213> ORGANISM: Artificial Sequence
<220> FEATURE:
<223> OTHER INFORMATION: synthetic sequence

<400> SEQUENCE: 147
ccagcagtgg tcttgctctt actccttttg gttgaacaag cagcggccct gggagagcct        60
cagctctgct atatcctgga tgccatcctg tttctgtatg gaattgt        107

<210> SEQ ID NO 148
<211> LENGTH: 107
<212> TYPE: DNA
<213> ORGANISM: Artificial Sequence
<220> FEATURE:
<223> OTHER INFORMATION: synthetic sequence

<400> SEQUENCE: 148
caatcacact cagtttccac catctcggtc atcaggattg cctaatatac ctgtccagac    60
aatctccaga gctgctgcag aaaagctgtt tgggaatatg aaggag                  107

<210> SEQ ID NO 149
<211> LENGTH: 106
<212> TYPE: DNA
<213> ORGANISM: Artificial Sequence
<220> FEATURE:
<223> OTHER INFORMATION: synthetic sequence

<400> SEQUENCE: 149
tgtgccgggc ctacaatgct gacaaccgca cggtcttttt tgaaggcaaa tacggtggca    60
tggagctgtt ccgagccttg ggctgcagcg agctcatcag ctccat                  106

<210> SEQ ID NO 150
<211> LENGTH: 109
<212> TYPE: DNA
<213> ORGANISM: Artificial Sequence
<220> FEATURE:
<223> OTHER INFORMATION: synthetic sequence

<400> SEQUENCE: 150
ggcttctgcc cggaccaagg atacagtttg ttcctcgtgg cggcgcatga gttcggccac    60
gcgctgggct tagatcattc ctcagtgccg gaggcgctca tgtaccctta              109

<210> SEQ ID NO 151
<211> LENGTH: 103
<212> TYPE: DNA
<213> ORGANISM: Artificial Sequence
<220> FEATURE:
<223> OTHER INFORMATION: synthetic sequence

<400> SEQUENCE: 151
caacaagagc tgaccgaggc ccagaagggc tttcaggatg tggaggccca ggccgccacc    60
tgcaaccaca ctgtgatggc cctaatggct tccctggatg cag                     103

<210> SEQ ID NO 152
<211> LENGTH: 111
<212> TYPE: DNA
<213> ORGANISM: Artificial Sequence
<220> FEATURE:
<223> OTHER INFORMATION: synthetic sequence

<400> SEQUENCE: 152
ggctccttcg ccatcaagtc gctgcggaaa ctgacggacg atgagctgtt ccagtacctg    60
ctgcagctgg tgcaggtgct caagtacgag tcctacctgg actgcgagct g            111

<210> SEQ ID NO 153
<211> LENGTH: 111
<212> TYPE: DNA
<213> ORGANISM: Artificial Sequence
<220> FEATURE:
<223> OTHER INFORMATION: synthetic sequence

<400> SEQUENCE: 153
ggggatcatt gtggctgtgg tcactgggat tgctgtagcg gccattgttg ctgctgtagt    60
ggccttgatc tactgcagga aaaagcggat ttcagctctc ccaggatacc c             111

<210> SEQ ID NO 154

```
<211> LENGTH: 104
<212> TYPE: DNA
<213> ORGANISM: Artificial Sequence
<220> FEATURE:
<223> OTHER INFORMATION: synthetic sequence

<400> SEQUENCE: 154
ccaagtgcag ctggctggtg acgaaggccg gagctgggac cagcagctcc cactgggtat    60
ggtggtttct ctcagggagc ctcgtcatcg tcattgtttg ctcc                    104

<210> SEQ ID NO 155
<211> LENGTH: 109
<212> TYPE: DNA
<213> ORGANISM: Artificial Sequence
<220> FEATURE:
<223> OTHER INFORMATION: synthetic sequence

<400> SEQUENCE: 155
ttcgcccagc caagttgaag aacctaatct tgctggtgaa gcactggtac caccaggtgt    60
gcctacaggg gttgtggaag gagacgctgc ccccggtcta tgccctgga              109

<210> SEQ ID NO 156
<211> LENGTH: 104
<212> TYPE: DNA
<213> ORGANISM: Artificial Sequence
<220> FEATURE:
<223> OTHER INFORMATION: synthetic sequence

<400> SEQUENCE: 156
tgatttcact gcttcaggtg aggatgaact gagctttcac actggagatg ttttgaagat    60
tttaagtaac caagaggagt ggtttaaggc ggagcttggg agcc                   104

<210> SEQ ID NO 157
<211> LENGTH: 109
<212> TYPE: DNA
<213> ORGANISM: Artificial Sequence
<220> FEATURE:
<223> OTHER INFORMATION: synthetic sequence

<400> SEQUENCE: 157
acttcttaag gcgagcatca aaagccgggg aggttgatgt tgaacagcac actttagcca    60
agtatttgat ggagctgact ctcatcgact atgatatggt gcattatca             109

<210> SEQ ID NO 158
<211> LENGTH: 106
<212> TYPE: DNA
<213> ORGANISM: Artificial Sequence
<220> FEATURE:
<223> OTHER INFORMATION: synthetic sequence

<400> SEQUENCE: 158
tcctgggagt cttactgctc atcggctgtt ggtattgtag aagacgaaat ggatacagag    60
ccttgatgga taaaagtctt catgttggca ctcaatgtgc cttaac                 106

<210> SEQ ID NO 159
<211> LENGTH: 104
<212> TYPE: DNA
<213> ORGANISM: Artificial Sequence
<220> FEATURE:
<223> OTHER INFORMATION: synthetic sequence

<400> SEQUENCE: 159
cggcctgacg tcggtggagg gaagcaggcg caggctccgt gaggaggcaa ggttctgagg    60
```

```
agacaggccc cggagcagca ctagctcctg cccacactcc tacc              104
```

<210> SEQ ID NO 160
<211> LENGTH: 104
<212> TYPE: DNA
<213> ORGANISM: Artificial Sequence
<220> FEATURE:
<223> OTHER INFORMATION: synthetic sequence

<400> SEQUENCE: 160

```
aatggattct gtgcccacag taaggcaggc tgtaaaagaa ttgcaagtct acatatcacc   60
caagaataca gttatttctg tgaatccatc cacaaagctg caag                  104
```

<210> SEQ ID NO 161
<211> LENGTH: 100
<212> TYPE: DNA
<213> ORGANISM: Artificial Sequence
<220> FEATURE:
<223> OTHER INFORMATION: synthetic sequence

<400> SEQUENCE: 161

```
aatcgcagat ggagggactc ctgacatagc cagctgctgt gaaataatgg aagagcttac   60
aacctgcctt aaaaattacc gaaaaacctt aatacactgc                       100
```

<210> SEQ ID NO 162
<211> LENGTH: 107
<212> TYPE: DNA
<213> ORGANISM: Artificial Sequence
<220> FEATURE:
<223> OTHER INFORMATION: synthetic sequence

<400> SEQUENCE: 162

```
gacgggactc cagaaagacc atgccctctg ggatcacact gcccagaatc tccttcggat   60
gggcctggcc tttctagtcc tggtggctct agtgtggttc ctggttg              107
```

<210> SEQ ID NO 163
<211> LENGTH: 102
<212> TYPE: DNA
<213> ORGANISM: Artificial Sequence
<220> FEATURE:
<223> OTHER INFORMATION: synthetic sequence

<400> SEQUENCE: 163

```
cagttgagac tcagaacttg gaaggcctgc atcatgatgg ccaattctgc cataagccct   60
gtcctccagg tgaaaggaaa gctagggact gcacagtcaa tg                    102
```

<210> SEQ ID NO 164
<211> LENGTH: 107
<212> TYPE: DNA
<213> ORGANISM: Artificial Sequence
<220> FEATURE:
<223> OTHER INFORMATION: synthetic sequence

<400> SEQUENCE: 164

```
gtgcgaatct gacttacgcc attattacga cagtaccatt gagttgtgcg tggggaccc    60 agagattaaa aagacttcct ttaaggggga ctctggaggc cctcttg              107
```

<210> SEQ ID NO 165
<211> LENGTH: 103
<212> TYPE: DNA
<213> ORGANISM: Artificial Sequence
<220> FEATURE:

<223> OTHER INFORMATION: synthetic sequence

<400> SEQUENCE: 165

```
cttatcacag tgaagatgga gcaggccttt gcccgatact tgctggagca gactccagag    60
cagcaggcag ccattctgtc cctggtgtag agcctggggg acc                     103
```

<210> SEQ ID NO 166
<211> LENGTH: 106
<212> TYPE: DNA
<213> ORGANISM: Artificial Sequence
<220> FEATURE:
<223> OTHER INFORMATION: synthetic sequence

<400> SEQUENCE: 166

```
cgcctactcc gtgaagtcta gggacaggaa gatggttggc gacgtgaccg gggcccaggc    60
ctatgcctcc accgccaagt gcctgaacat ctgggccctg attctg                  106
```

<210> SEQ ID NO 167
<211> LENGTH: 110
<212> TYPE: DNA
<213> ORGANISM: Artificial Sequence
<220> FEATURE:
<223> OTHER INFORMATION: synthetic sequence

<400> SEQUENCE: 167

```
gaagggaaag ctgggggctc cccactgcac ttgccacctg agtcacattt tcagaagcct    60
ctggaaagtc gtgcacagcc caggagtgtt gagcaatttc ggtttcctct               110
```

<210> SEQ ID NO 168
<211> LENGTH: 107
<212> TYPE: DNA
<213> ORGANISM: Artificial Sequence
<220> FEATURE:
<223> OTHER INFORMATION: synthetic sequence

<400> SEQUENCE: 168

```
ctggagaacg ggaaggacaa gctggagcgc gctgaccccc caaagacaca cgtgacccac    60
caccccatct ctgaccatga ggccaccctg aggtgctggg ccctggg                 107
```

<210> SEQ ID NO 169
<211> LENGTH: 99
<212> TYPE: DNA
<213> ORGANISM: Artificial Sequence
<220> FEATURE:
<223> OTHER INFORMATION: synthetic sequence

<400> SEQUENCE: 169

```
acatcggaac tgcgactcag catgcagaag tcaatgcaaa atcatgctgc cgtgttccgt    60
gtgggaagcg tgttgcaaga aggttgtggg aaaatcagc                           99
```

<210> SEQ ID NO 170
<211> LENGTH: 105
<212> TYPE: DNA
<213> ORGANISM: Artificial Sequence
<220> FEATURE:
<223> OTHER INFORMATION: synthetic sequence

<400> SEQUENCE: 170

```
tcctaccgag agtggataca ggtagacttg ggccttctgc gctttgtcac ggctgtcggg    60
acacagggcg ccatttcaaa agaaaccaag aagaaatatt atgtc                   105
```

<210> SEQ ID NO 171
<211> LENGTH: 109
<212> TYPE: DNA
<213> ORGANISM: Artificial Sequence
<220> FEATURE:
<223> OTHER INFORMATION: synthetic sequence

<400> SEQUENCE: 171
gctgcgcgct tccaccgggt ggggcccatt gaagccacgt ccttcatcct cagggctgtg      60
cggccccgag ccaggtacta cgtccaagtg gcggctcagg acctcacag                 109

<210> SEQ ID NO 172
<211> LENGTH: 101
<212> TYPE: DNA
<213> ORGANISM: Artificial Sequence
<220> FEATURE:
<223> OTHER INFORMATION: synthetic sequence

<400> SEQUENCE: 172
ggagaggaag tctgagtcag cccatcctgt tgggagccct ggagagagtg gcacatcagg      60
gtggcgaggg ggggacactc ccagcccccct ctgtctcttg c                        101

<210> SEQ ID NO 173
<211> LENGTH: 107
<212> TYPE: DNA
<213> ORGANISM: Artificial Sequence
<220> FEATURE:
<223> OTHER INFORMATION: synthetic sequence

<400> SEQUENCE: 173
cctgcaaggt ggagcacgag agctttgaga agcctcagct gctgactgtg aacctcaccg      60
tgtactaccc cccagaggta tccatctctg gctatgataa caactgg                   107

<210> SEQ ID NO 174
<211> LENGTH: 102
<212> TYPE: DNA
<213> ORGANISM: Artificial Sequence
<220> FEATURE:
<223> OTHER INFORMATION: synthetic sequence

<400> SEQUENCE: 174
tatcttcagc ttgtgataaa gagtcaaata tggaacgaag agtgatcacg atttctaaat      60
cagaatattc tgtgcactca tctttggcat ccaaagttga tg                        102

<210> SEQ ID NO 175
<211> LENGTH: 103
<212> TYPE: DNA
<213> ORGANISM: Artificial Sequence
<220> FEATURE:
<223> OTHER INFORMATION: synthetic sequence

<400> SEQUENCE: 175
atgaataaca ctctaagaaa ggatggaaag aaagattgct gttttgaaat ctctgctcct      60
gataaacgta tatatcagtt tacagcagct tctcccaaag atg                       103

<210> SEQ ID NO 176
<211> LENGTH: 106
<212> TYPE: DNA
<213> ORGANISM: Artificial Sequence
<220> FEATURE:
<223> OTHER INFORMATION: synthetic sequence

<400> SEQUENCE: 176

```
agtttccatg tggtacacac tcccccgctg caccctgact tcaagagggc cctcggggac      60
ctgccccacc acttcaacgc ctccacccag cccgcctacc tcaggc                    106

<210> SEQ ID NO 177
<211> LENGTH: 106
<212> TYPE: DNA
<213> ORGANISM: Artificial Sequence
<220> FEATURE:
<223> OTHER INFORMATION: synthetic sequence

<400> SEQUENCE: 177
tccaaaacag acttgggtga aatatattgt gcgtctcctc agtaaaaaag tcaagaacat      60
gtaaaaactg tggctttttct ggaatggaat tggacatagc ccaaga                   106

<210> SEQ ID NO 178
<211> LENGTH: 108
<212> TYPE: DNA
<213> ORGANISM: Artificial Sequence
<220> FEATURE:
<223> OTHER INFORMATION: synthetic sequence

<400> SEQUENCE: 178
gactgcatgt gtgtccagcc tgaattccac tgcggagacc cttgctgcac gacctgccgg      60 caccacccctt gtcccccagg ccaggggta cagtcccagg ggaaattc                  108

<210> SEQ ID NO 179
<211> LENGTH: 104
<212> TYPE: DNA
<213> ORGANISM: Artificial Sequence
<220> FEATURE:
<223> OTHER INFORMATION: synthetic sequence

<400> SEQUENCE: 179
gaaaacctat ggcaaacaat acaaggaaaa gaatgaagaa gcagtacgac gtctcatctg      60
ggaaaagaat ctaaagtttg tgatgcttca caacctggag catt                      104

<210> SEQ ID NO 180
<211> LENGTH: 107
<212> TYPE: DNA
<213> ORGANISM: Artificial Sequence
<220> FEATURE:
<223> OTHER INFORMATION: synthetic sequence

<400> SEQUENCE: 180
ctcctggtcc ttctacctgg gctgggtctc agctatcctc ttgctctgta caggtgccct      60
gagcctgggt gctcactgtg gcggtccccg tcctggctat gaaacct                   107

<210> SEQ ID NO 181
<211> LENGTH: 107
<212> TYPE: DNA
<213> ORGANISM: Artificial Sequence
<220> FEATURE:
<223> OTHER INFORMATION: synthetic sequence

<400> SEQUENCE: 181
caggagcttg tgccgtggcc cacagcccac agcccacagc catgggctgg gacctgacgg      60
tgaagatgct ggcgggcaac gaattccagg tgtccctgag cagctcc                   107

<210> SEQ ID NO 182
<211> LENGTH: 101
<212> TYPE: DNA
<213> ORGANISM: Artificial Sequence
```

<220> FEATURE:
<223> OTHER INFORMATION: synthetic sequence

<400> SEQUENCE: 182

```
gactccccag acaggccctg gaaccccccc accttctccc cagccctgct cgtggtgacc    60
gaagggggaca acgccacctt cacctgcagc ttctccaaca c                      101
```

<210> SEQ ID NO 183
<211> LENGTH: 108
<212> TYPE: DNA
<213> ORGANISM: Artificial Sequence
<220> FEATURE:
<223> OTHER INFORMATION: synthetic sequence

<400> SEQUENCE: 183

```
tacagcgagc tgcaggactc taatccagag tttaccttcc agcagcccta cgaccaggcc    60
cacctgctgg cagccatccc acctccggag atcctcaacc ccaccgcc                108
```

<210> SEQ ID NO 184
<211> LENGTH: 100
<212> TYPE: DNA
<213> ORGANISM: Artificial Sequence
<220> FEATURE:
<223> OTHER INFORMATION: synthetic sequence

<400> SEQUENCE: 184

```
gttgttcaag gcttccccat gttcaaaaga ggacgctgtc tttgcatagg ccctggggta    60
aaagcagtga agtggcaga tattgagaaa gcctccataa                         100
```

<210> SEQ ID NO 185
<211> LENGTH: 103
<212> TYPE: DNA
<213> ORGANISM: Artificial Sequence
<220> FEATURE:
<223> OTHER INFORMATION: synthetic sequence

<400> SEQUENCE: 185

```
ggacctggct ggagaagaag agattgagct ctactcagaa cccgacacag acaccatcaa    60
ctgcgaccag ttcagcaggc tgttgtgtga catggaaggt gat                    103
```

<210> SEQ ID NO 186
<211> LENGTH: 107
<212> TYPE: DNA
<213> ORGANISM: Artificial Sequence
<220> FEATURE:
<223> OTHER INFORMATION: synthetic sequence

<400> SEQUENCE: 186

```
tagtttccaa tttgcggatc cactgccctc tgcttgcggg ctctgctctg atcacctttg    60
atgaccccaa agtggctgag caggtgctgc aacaaaagga gcacacg                107
```

<210> SEQ ID NO 187
<211> LENGTH: 87
<212> TYPE: DNA
<213> ORGANISM: Artificial Sequence
<220> FEATURE:
<223> OTHER INFORMATION: synthetic sequence

<400> SEQUENCE: 187

```
ggcccaaaat gttctgctga tcgatgggcc cctgagctgg tacagtgacc caggcctggc    60
aggcgtgtcc ctgacggggg gcctgag                                       87
```

<210> SEQ ID NO 188
<211> LENGTH: 106
<212> TYPE: DNA
<213> ORGANISM: Artificial Sequence
<220> FEATURE:
<223> OTHER INFORMATION: synthetic sequence

<400> SEQUENCE: 188
gcagatgcag gacaagtact ccaaaagtgg cattgcttgt ttcttaaaag aagatgacag    60
ttattgggac cccaatgacg aagagagtat gaacagcccc tgctgg                 106

<210> SEQ ID NO 189
<211> LENGTH: 108
<212> TYPE: DNA
<213> ORGANISM: Artificial Sequence
<220> FEATURE:
<223> OTHER INFORMATION: synthetic sequence

<400> SEQUENCE: 189
tgagaaggat ggcaagtacg gcttctgtcc ccatgaagcc ctgttcacca tgggcggcaa    60
cgctgaagga cagccctgca gtttccatt ccgcttccag ggcacatc                108

<210> SEQ ID NO 190
<211> LENGTH: 105
<212> TYPE: DNA
<213> ORGANISM: Artificial Sequence
<220> FEATURE:
<223> OTHER INFORMATION: synthetic sequence

<400> SEQUENCE: 190
ccaactgcct gacaatctgt accccgagga gatccccagc gcgctcaacc tcttctccgg    60
cagcagcgac tcggtagtcc attacaatca gatggctaca gagaa                  105

<210> SEQ ID NO 191
<211> LENGTH: 111
<212> TYPE: DNA
<213> ORGANISM: Artificial Sequence
<220> FEATURE:
<223> OTHER INFORMATION: synthetic sequence

<400> SEQUENCE: 191
ctgagggacg gcgtagagtt cggccgaagg aacctgaccc aggctctgtg aggaggcaag    60
gttttcaggg gacaggccaa cccagaggac aggattccct ggaggccaca g           111

<210> SEQ ID NO 192
<211> LENGTH: 103
<212> TYPE: DNA
<213> ORGANISM: Artificial Sequence
<220> FEATURE:
<223> OTHER INFORMATION: synthetic sequence

<400> SEQUENCE: 192
gtccttcaga gcaagtggcc tctgtaatct gctcaggaaa ccagtcccaa acactgtcct    60
cgtgcaattc atcgtctttg ggcccaacaa ggcctaccat tcc                    103

<210> SEQ ID NO 193
<211> LENGTH: 105
<212> TYPE: DNA
<213> ORGANISM: Artificial Sequence
<220> FEATURE:
<223> OTHER INFORMATION: synthetic sequence

<400> SEQUENCE: 193
agtgaggaac aagccagagc tgtgcagatg agtacaaaag tcctgatcca gttcctgcag    60
aaaaaggcaa agaatctaga tgcaataacc acccctgacc caacc    105

<210> SEQ ID NO 194
<211> LENGTH: 97
<212> TYPE: DNA
<213> ORGANISM: Artificial Sequence
<220> FEATURE:
<223> OTHER INFORMATION: synthetic sequence

<400> SEQUENCE: 194
gaatatctgg aaccgtgaat ggtattctca ctttgacttt gatctccttg atcctgttgg    60
tttctcaggg agtattgcta aaatgccaaa aggaag    97

<210> SEQ ID NO 195
<211> LENGTH: 110
<212> TYPE: DNA
<213> ORGANISM: Artificial Sequence
<220> FEATURE:
<223> OTHER INFORMATION: synthetic sequence

<400> SEQUENCE: 195
ccagttgggc cggactctcc aaacctgctt ccgcaatggg tgggttgtga gtgctggtaa    60
tgaggagccg tgggtgcagc cagccttgga gatgccgaag agacgggaca    110

<210> SEQ ID NO 196
<211> LENGTH: 104
<212> TYPE: DNA
<213> ORGANISM: Artificial Sequence
<220> FEATURE:
<223> OTHER INFORMATION: synthetic sequence

<400> SEQUENCE: 196
acaggaggca gaggcatcat ggagggtccc cggggatggc tggtgctctg tgtgctggcc    60
atatcgctgg cctctatggt gaccgaggac ttgtgccgag cacc    104

<210> SEQ ID NO 197
<211> LENGTH: 108
<212> TYPE: DNA
<213> ORGANISM: Artificial Sequence
<220> FEATURE:
<223> OTHER INFORMATION: synthetic sequence

<400> SEQUENCE: 197
aattgtaaga agaagcttgg gaagctgcca cctcagtatg ccctggagct cctgacggtc    60
tatgcttggg agcgagggag catgaaaaca catttcaaca cagcccag    108

<210> SEQ ID NO 198
<211> LENGTH: 102
<212> TYPE: DNA
<213> ORGANISM: Artificial Sequence
<220> FEATURE:
<223> OTHER INFORMATION: synthetic sequence

<400> SEQUENCE: 198
gcccaatgtg cttatggtac ataaaaggag tcacactggt gaacgcccct tccactgtaa    60
ccagtgtgga gcttctttta ctcagaaggg caaccttctg ag    102

<210> SEQ ID NO 199
<211> LENGTH: 108
<212> TYPE: DNA

<213> ORGANISM: Artificial Sequence
<220> FEATURE:
<223> OTHER INFORMATION: synthetic sequence

<400> SEQUENCE: 199

```
cccctgcccc ccagcatggg tttctgccgc agcgccctgc acccgctgtc tctcctggtg      60
caggccatca tgctggccat gaccctggcc ctgggtacct tgcctgcc                  108
```

<210> SEQ ID NO 200
<211> LENGTH: 106
<212> TYPE: DNA
<213> ORGANISM: Artificial Sequence
<220> FEATURE:
<223> OTHER INFORMATION: synthetic sequence

<400> SEQUENCE: 200

```
cgcgggctgc ggcaagacct acaccaagag ttcgcatctg aaggcgcatc tgcgcacgca      60
cacaggtgag aagccctacc actgcaactg gacggctgc ggctgg                    106
```

<210> SEQ ID NO 201
<211> LENGTH: 105
<212> TYPE: DNA
<213> ORGANISM: Artificial Sequence
<220> FEATURE:
<223> OTHER INFORMATION: synthetic sequence

<400> SEQUENCE: 201

```
ttgcagggtt tcaccaggat ccacctctga tgttcactga agagtaccag aaaagtctgc      60
tagagcagta ccatctgggt ctggatcaaa aacgcagaaa atacg                    105
```

<210> SEQ ID NO 202
<211> LENGTH: 106
<212> TYPE: DNA
<213> ORGANISM: Artificial Sequence
<220> FEATURE:
<223> OTHER INFORMATION: synthetic sequence

<400> SEQUENCE: 202

```
gtcaatgctc aggagccctg taatggccgg actgcccttc acctcgcagt ggacctgcaa      60
aatcctgacc tggtgtcact cctgttgaag tgtggggctg atgtca                   106
```

<210> SEQ ID NO 203
<211> LENGTH: 105
<212> TYPE: DNA
<213> ORGANISM: Artificial Sequence
<220> FEATURE:
<223> OTHER INFORMATION: synthetic sequence

<400> SEQUENCE: 203

```
gagatggctg tgaccccaa ggactcaggg acaacagtca gttctgcttg caaaggatcc       60
accagggtct gatttttat gagaagctgc taggatcgga tattt                     105
```

<210> SEQ ID NO 204
<211> LENGTH: 104
<212> TYPE: DNA
<213> ORGANISM: Artificial Sequence
<220> FEATURE:
<223> OTHER INFORMATION: synthetic sequence

<400> SEQUENCE: 204

```
ctgtgtgtga aatgagtaaa caatctttgc aagtcctaaa gaagtgttgg gcattttgc       60 aagaatcttc tctgaatccg ctgatccaga tgcttaaagc agcc                     104
```

<210> SEQ ID NO 205
<211> LENGTH: 109
<212> TYPE: DNA
<213> ORGANISM: Artificial Sequence
<220> FEATURE:
<223> OTHER INFORMATION: synthetic sequence

<400> SEQUENCE: 205
atgtgctgct ggtggtggtg cctgtctcgc tgctcctgat gctggttact ctcttctctg    60
cctggcactg gtgcccctgc tcagggaaaa agaaaaagga tgtccatgc                109

<210> SEQ ID NO 206
<211> LENGTH: 106
<212> TYPE: DNA
<213> ORGANISM: Artificial Sequence
<220> FEATURE:
<223> OTHER INFORMATION: synthetic sequence

<400> SEQUENCE: 206
cactgccttc gaagtccggc gccccccggg agggaactgg gtggccgcac cctcccggct    60
gcggtggctg tcgccccca ccctgcagcc aggactcgat ggagaa                    106

<210> SEQ ID NO 207
<211> LENGTH: 107
<212> TYPE: DNA
<213> ORGANISM: Artificial Sequence
<220> FEATURE:
<223> OTHER INFORMATION: synthetic sequence

<400> SEQUENCE: 207
caaccagacc tctacattcc attttggaag aagactaaaa atggtgtttc caatgtggac    60
actgaagaga caaattctta ccttttttaa cataatccta atttcca                  107

<210> SEQ ID NO 208
<211> LENGTH: 109
<212> TYPE: DNA
<213> ORGANISM: Artificial Sequence
<220> FEATURE:
<223> OTHER INFORMATION: synthetic sequence

<400> SEQUENCE: 208
aatgcactgg gtcagctgag ttctggctcc acacccagcc ccgaggttta tgcagggctc    60
attgatctgt ataaatcctc ggacctcccg ggaggagagt tttctacct               109

<210> SEQ ID NO 209
<211> LENGTH: 108
<212> TYPE: DNA
<213> ORGANISM: Artificial Sequence
<220> FEATURE:
<223> OTHER INFORMATION: synthetic sequence

<400> SEQUENCE: 209
caaagaagaa catgtgatca tccaggccga gttctatctg aatcctgacc aatcaggcga    60
gtttatgttt gactttgatg gtgatgagat tttccatgtg gatatggc                 108

<210> SEQ ID NO 210
<211> LENGTH: 105
<212> TYPE: DNA
<213> ORGANISM: Artificial Sequence
<220> FEATURE:
<223> OTHER INFORMATION: synthetic sequence

<400> SEQUENCE: 210
gtaagcacaa aggaagtgaa agtgattgtg ctggcaactc ctttcaagcc aatcctggaa    60
gcttcagtta tcagaaagca aaatggagaa gaacatgttg tactc                   105

<210> SEQ ID NO 211
<211> LENGTH: 109
<212> TYPE: DNA
<213> ORGANISM: Artificial Sequence
<220> FEATURE:
<223> OTHER INFORMATION: synthetic sequence

<400> SEQUENCE: 211
gcagaggagg cccaggcagt gccaggagtc aaggcctgtt ggatctcatc atccatatcc    60
ctgttgatac gtttacctgc tgctcctgaa gaagtcgtca tgcctcccg               109

<210> SEQ ID NO 212
<211> LENGTH: 106
<212> TYPE: DNA
<213> ORGANISM: Artificial Sequence
<220> FEATURE:
<223> OTHER INFORMATION: synthetic sequence

<400> SEQUENCE: 212
gccctgatgg gcagtcaaca gctaaaacct tcctcaccgt gtactggact ccagaacggg    60
tggaactggc acccctcccc tcttggcagc cagtgggcaa gaacct                  106

<210> SEQ ID NO 213
<211> LENGTH: 108
<212> TYPE: DNA
<213> ORGANISM: Artificial Sequence
<220> FEATURE:
<223> OTHER INFORMATION: synthetic sequence

<400> SEQUENCE: 213
cgcctgtttg agaagcagcg ggcaagaaag acgcaagccc agaggccctg ccatttctgt    60
gggctcaggt ccctactggc tcaggcccct gcctccctcg gcaaggcc                108

<210> SEQ ID NO 214
<211> LENGTH: 108
<212> TYPE: DNA
<213> ORGANISM: Artificial Sequence
<220> FEATURE:
<223> OTHER INFORMATION: synthetic sequence

<400> SEQUENCE: 214
ttgctcagta ccacgatcct gatgatgaac cagtggccga tccttatgat cagtcctttg    60
aaagcaggga cctccttata gatgagtgga aaagcctgac ctatgatg                108

<210> SEQ ID NO 215
<211> LENGTH: 88
<212> TYPE: DNA
<213> ORGANISM: Artificial Sequence
<220> FEATURE:
<223> OTHER INFORMATION: synthetic sequence

<400> SEQUENCE: 215
ccaggaggcg tctgacacag tatgatgatg aagatcccat ggggcagcat cccagtactg    60
atgttgctcc tgctcctggg cctaatcg                                       88

<210> SEQ ID NO 216
<211> LENGTH: 109

<212> TYPE: DNA
<213> ORGANISM: Artificial Sequence
<220> FEATURE:
<223> OTHER INFORMATION: synthetic sequence

<400> SEQUENCE: 216
ctgtgcctgt cttcctgggt ttgagggtca gaattgtgaa gtgaacgtgg acgactgtcc    60
aggacaccga tgtctcaatg gggggacatg cgtggatggc gtcaacacc              109

<210> SEQ ID NO 217
<211> LENGTH: 108
<212> TYPE: DNA
<213> ORGANISM: Artificial Sequence
<220> FEATURE:
<223> OTHER INFORMATION: synthetic sequence

<400> SEQUENCE: 217
tccccttcgc caactgggac atcttccgac atggcctgga tgctgttgct catcttgatc    60
atggtccatc caggatcctg tgctctctgg gtgtcccagc cccctgag               108

<210> SEQ ID NO 218
<211> LENGTH: 105
<212> TYPE: DNA
<213> ORGANISM: Artificial Sequence
<220> FEATURE:
<223> OTHER INFORMATION: synthetic sequence

<400> SEQUENCE: 218
ggccgaggtc ctgagctggc agttctcctc caccaccaag cgaggactga gcatcgagca    60
gctgactaca ctggcagaga aactcttggg acctggtgtg aatta                  105

<210> SEQ ID NO 219
<211> LENGTH: 101
<212> TYPE: DNA
<213> ORGANISM: Artificial Sequence
<220> FEATURE:
<223> OTHER INFORMATION: synthetic sequence

<400> SEQUENCE: 219
ccattctgcg ctgctgcaag ttacggaatg aaaaattaga caacagaaa catggaaaac     60 atgttccttc agtcgtcaat gctgacctgc attttcctgc t                      101

<210> SEQ ID NO 220
<211> LENGTH: 107
<212> TYPE: DNA
<213> ORGANISM: Artificial Sequence
<220> FEATURE:
<223> OTHER INFORMATION: synthetic sequence

<400> SEQUENCE: 220
tgcagatctg ctgcaactgc tggagagcca gatgcaggaa aggaacaatg ccggcttcct    60
cagctacaac atctacctca ctggctggga tgagtctcag gccaatc                107

<210> SEQ ID NO 221
<211> LENGTH: 106
<212> TYPE: DNA
<213> ORGANISM: Artificial Sequence
<220> FEATURE:
<223> OTHER INFORMATION: synthetic sequence

<400> SEQUENCE: 221
taatggaatc tttattttgt gaaagtagcg gggactcatc tctggagaag gagttcctcg    60

```
gggccccagt ggggccctcg gtgagcaccc ccaacagcca gcactc            106
```

<210> SEQ ID NO 222
<211> LENGTH: 106
<212> TYPE: DNA
<213> ORGANISM: Artificial Sequence
<220> FEATURE:
<223> OTHER INFORMATION: synthetic sequence

<400> SEQUENCE: 222

```
tgccattgca gatgcaacca gagaagatcc atttaaagag aaacttctag aaataatgac   60
aaggattcaa acttattgtc aaatgagtcc aatgtcagat tttgga               106
```

<210> SEQ ID NO 223
<211> LENGTH: 103
<212> TYPE: DNA
<213> ORGANISM: Artificial Sequence
<220> FEATURE:
<223> OTHER INFORMATION: synthetic sequence

<400> SEQUENCE: 223

```
ggggatccca ggatctcaca atctcaggga ccatgggctg tggctgcagc tcacacccgg   60
aagatgactg gatggaaaac atcgatgtgt gtgagaactg cca                  103
```

<210> SEQ ID NO 224
<211> LENGTH: 109
<212> TYPE: DNA
<213> ORGANISM: Artificial Sequence
<220> FEATURE:
<223> OTHER INFORMATION: synthetic sequence

<400> SEQUENCE: 224

```
caaatcaaca caaaccccaa gtcctccttg ccaggccttc aaccactatc tcagtgcaat   60
ggcttccatg aggcaggctg aacctgcaga tatgcgccca gagatatgg            109
```

<210> SEQ ID NO 225
<211> LENGTH: 106
<212> TYPE: DNA
<213> ORGANISM: Artificial Sequence
<220> FEATURE:
<223> OTHER INFORMATION: synthetic sequence

<400> SEQUENCE: 225

```
ggagcgcttg ccctctcact ccgactttct ggctgagctt cggaaggccc ccgtggtgaa   60
ctgctccatc gctgtctgcc agagaatcca gtgtgacatc ccgttc               106
```

<210> SEQ ID NO 226
<211> LENGTH: 110
<212> TYPE: DNA
<213> ORGANISM: Artificial Sequence
<220> FEATURE:
<223> OTHER INFORMATION: synthetic sequence

<400> SEQUENCE: 226

```
gagaaggagc agcaacaact caactggaag caggacagta atcctctcta caaaagtgcc   60
atcacgacca ccatcaatcc tcgctttcaa gaggcagaca gtcccactct            110
```

<210> SEQ ID NO 227
<211> LENGTH: 104
<212> TYPE: DNA
<213> ORGANISM: Artificial Sequence
<220> FEATURE:
<223> OTHER INFORMATION: synthetic sequence

<400> SEQUENCE: 227
agtcaagatg aagaaccatt tgcttttctg gggagtcctg gcggttttta ttaaggctgt    60
tcatgtgaaa gcccaagaag atgaaaggat tgttcttgtt gaca                   104

<210> SEQ ID NO 228
<211> LENGTH: 109
<212> TYPE: DNA
<213> ORGANISM: Artificial Sequence
<220> FEATURE:
<223> OTHER INFORMATION: synthetic sequence

<400> SEQUENCE: 228
gaagtaaccg cttcacctgg atgggacttt cagatctaaa tcaggaaggc acgtggcaat    60
gggtggacgg ctcacctctg ttgcccagct tcaagcagta ttggaacag              109

<210> SEQ ID NO 229
<211> LENGTH: 104
<212> TYPE: DNA
<213> ORGANISM: Artificial Sequence
<220> FEATURE:
<223> OTHER INFORMATION: synthetic sequence

<400> SEQUENCE: 229
atacggttta ctccactgtg gaaataccga aaaagatgga aaatccccac tcactgctca    60
cgatgccaga cacaccaagg ctatttgcct atgagaatgt tatc                   104

<210> SEQ ID NO 230
<211> LENGTH: 107
<212> TYPE: DNA
<213> ORGANISM: Artificial Sequence
<220> FEATURE:
<223> OTHER INFORMATION: synthetic sequence

<400> SEQUENCE: 230
gcctttaata agctccaaga gaaaggcatc tacaaagcca tgagtgagtt tgacatcttc    60
atcaactaca tagaagccta catgacaatg aagatacgaa actgaga                107

<210> SEQ ID NO 231
<211> LENGTH: 103
<212> TYPE: DNA
<213> ORGANISM: Artificial Sequence
<220> FEATURE:
<223> OTHER INFORMATION: synthetic sequence

<400> SEQUENCE: 231
gaagcagtga aatttgacat gggtgcttat aagtcatcaa aggatgatgc taaaattacc    60
gtgattctaa gaatctcaaa aactcaattg tatgtgactg ccc                    103

<210> SEQ ID NO 232
<211> LENGTH: 317
<212> TYPE: DNA
<213> ORGANISM: Artificial Sequence
<220> FEATURE:
<223> OTHER INFORMATION: synthetic sequence

<400> SEQUENCE: 232
ccctcagtga cccggtgcag ctagaagtcc atatcggctg gctgttgctc caggcccctc    60
ggtgggtgtt caaggaggaa gaccctattc acctgaggtg tcacagctgg aagaacactg   120
ctctgcataa ggtcacatat ttacagaatg gcaaaggcag gaagtatttt catcataatt   180

```
ctgacttcta cattccaaaa gccacactca aagacagcgg ctcctacttc tgcaggggc      240 tttttgggag taaaaatgtg tcttcagaga ctgtgaacat caccatcact caaggtttgg    300
cagtgtcaac catctca                                                    317
```

```
<210> SEQ ID NO 233
<211> LENGTH: 97
<212> TYPE: DNA
<213> ORGANISM: Artificial Sequence
<220> FEATURE:
<223> OTHER INFORMATION: synthetic sequence

<400> SEQUENCE: 233
caaagactca cttctataac caccacgagt tgaatcaaaa ttttcaaatg ttttcagcag     60
tgtaaagaag cgtcgtgtat acctgtgcag gcactag                              97
```

```
<210> SEQ ID NO 234
<211> LENGTH: 105
<212> TYPE: DNA
<213> ORGANISM: Artificial Sequence
<220> FEATURE:
<223> OTHER INFORMATION: synthetic sequence

<400> SEQUENCE: 234
cccaatgccg aactgggagg cccctttgac cagatgaacg gagtggccgg agatggcatg     60
atcaacattg acatgactgg agagaagagg tcgttggatc tccca                    105
```

```
<210> SEQ ID NO 235
<211> LENGTH: 103
<212> TYPE: DNA
<213> ORGANISM: Artificial Sequence
<220> FEATURE:
<223> OTHER INFORMATION: synthetic sequence

<400> SEQUENCE: 235
ccaactttga tgtgcgtgaa attgtaaata acatcaggcg tttgatggat ggagaagaac     60
ctttgccaat gcttccaagt tacaagaact tcaagggtac tat                      103
```

```
<210> SEQ ID NO 236
<211> LENGTH: 110
<212> TYPE: DNA
<213> ORGANISM: Artificial Sequence
<220> FEATURE:
<223> OTHER INFORMATION: synthetic sequence

<400> SEQUENCE: 236
gcggcctcta ctgctgcctg gtggtggaga tcaggcacca ccactcggag cacagggtcc     60
atggtgccat ggagctgcag gtgcagacag gcaaagatgc accatccaac                110
```

```
<210> SEQ ID NO 237
<211> LENGTH: 111
<212> TYPE: DNA
<213> ORGANISM: Artificial Sequence
<220> FEATURE:
<223> OTHER INFORMATION: synthetic sequence

<400> SEQUENCE: 237
ctttgaaaga catctatacg tggattgagg accactttcc ctactttaag cacattgcca     60
agccaggctg gaagaactcc atccgccaca acctttccct gcacgacatg t             111
```

```
<210> SEQ ID NO 238
<211> LENGTH: 109
```

```
<212> TYPE: DNA
<213> ORGANISM: Artificial Sequence
<220> FEATURE:
<223> OTHER INFORMATION: synthetic sequence

<400> SEQUENCE: 238
tcgcctgaag cagcctgcgg actgtctgga tggactgtat gccttgatgt cgcggtgctg       60
ggagctaaat ccccaggacc ggccaagttt tacagagctg cgggaagat                 109

<210> SEQ ID NO 239
<211> LENGTH: 105
<212> TYPE: DNA
<213> ORGANISM: Artificial Sequence
<220> FEATURE:
<223> OTHER INFORMATION: synthetic sequence

<400> SEQUENCE: 239
ggagactcag gagttttgag agcaaaatga caacacccag aaattcagta aatgggactt       60
tcccggcaga gccaatgaaa ggccctattg ctatgcaatc tggtc                     105

<210> SEQ ID NO 240
<211> LENGTH: 109
<212> TYPE: DNA
<213> ORGANISM: Artificial Sequence
<220> FEATURE:
<223> OTHER INFORMATION: synthetic sequence

<400> SEQUENCE: 240
cagcaggctc cgggctgaag attgcttctc ttctctcctc caaggtctag tgacggagcc       60
cgcgcgcggc gccaccatgc ggcagaaggc ggtatcgctt tcttgtgc                  109

<210> SEQ ID NO 241
<211> LENGTH: 103
<212> TYPE: DNA
<213> ORGANISM: Artificial Sequence
<220> FEATURE:
<223> OTHER INFORMATION: synthetic sequence

<400> SEQUENCE: 241
tcattatcga atgtgccaga gctgtgtgga gctggatcca gccaccgtgg ctggcatcat       60
tgtcactgat gtcattgcca ctctgctcct tgctttggga gtc                       103

<210> SEQ ID NO 242
<211> LENGTH: 102
<212> TYPE: DNA
<213> ORGANISM: Artificial Sequence
<220> FEATURE:
<223> OTHER INFORMATION: synthetic sequence

<400> SEQUENCE: 242
atgctcatct ctcacacaga cttttgatgg acaggagttt ctaagtatca tgcctaccaa       60
caagctgtaa aatgatcacc ctgaacaatc aagatcaacc tg                        102

<210> SEQ ID NO 243
<211> LENGTH: 101
<212> TYPE: DNA
<213> ORGANISM: Artificial Sequence
<220> FEATURE:
<223> OTHER INFORMATION: synthetic sequence

<400> SEQUENCE: 243
gaggaggaat tgaactcagg actcagagta gtccaggtgt tctcctccta ttcagttccc       60
```
agaatcaaag caatgcattt tggaaagctc ctagcagaga g               101

<210> SEQ ID NO 244
<211> LENGTH: 108
<212> TYPE: DNA
<213> ORGANISM: Artificial Sequence
<220> FEATURE:
<223> OTHER INFORMATION: synthetic sequence

<400> SEQUENCE: 244
cggcccacga gcggatgccc tggtaccaca gcagcctgac gcgtgaggag gccgagcgca     60
aactttactc tggggcgcag accgacggca agttcctgct gaggccgc                108

<210> SEQ ID NO 245
<211> LENGTH: 108
<212> TYPE: DNA
<213> ORGANISM: Artificial Sequence
<220> FEATURE:
<223> OTHER INFORMATION: synthetic sequence

<400> SEQUENCE: 245
gctgtgggcc aggggggcctt gggcgtggaa gtgcgagcca aggaccagga catcttggat    60
ctggtgggtg tgctgcacga tcccgagact ctgcttcgct gcatcgct                 108

<210> SEQ ID NO 246
<211> LENGTH: 107
<212> TYPE: DNA
<213> ORGANISM: Artificial Sequence
<220> FEATURE:
<223> OTHER INFORMATION: synthetic sequence

<400> SEQUENCE: 246
gagcttgctc ctgctccagt tgcggtcatc atgactacgc ccgcctcccg cagaccatgt     60
tccatgtttc ttttaggtat atctttggac ttcctcccct gatcctt                  107

<210> SEQ ID NO 247
<211> LENGTH: 102
<212> TYPE: DNA
<213> ORGANISM: Artificial Sequence
<220> FEATURE:
<223> OTHER INFORMATION: synthetic sequence

<400> SEQUENCE: 247
ggaatcagta agctaaaaac aaaatcaacc gggacccag cttttcagaa ctgcagggaa      60
acagccatca tgagtgaggt caccaagaat tccctggaga aa                       102

<210> SEQ ID NO 248
<211> LENGTH: 101
<212> TYPE: DNA
<213> ORGANISM: Artificial Sequence
<220> FEATURE:
<223> OTHER INFORMATION: synthetic sequence

<400> SEQUENCE: 248
aaacaaatat tttgcagtat gcttccacca ggccccctac cttgtcacca atacctcaca     60
ttcctcgaag cccttacaag tttcctagtt caccottacg g                        101

<210> SEQ ID NO 249
<211> LENGTH: 107
<212> TYPE: DNA
<213> ORGANISM: Artificial Sequence
<220> FEATURE:
<223> OTHER INFORMATION: synthetic sequence

<400> SEQUENCE: 249
agtcttttaa tgagtaccgc aaacgcttta tgctgaagcc ctatgaatca tttgaagaac    60
ttacaggaga aaaggaaatg tctgcagagt tggaagcact ctatggt    107

<210> SEQ ID NO 250
<211> LENGTH: 106
<212> TYPE: DNA
<213> ORGANISM: Artificial Sequence
<220> FEATURE:
<223> OTHER INFORMATION: synthetic sequence

<400> SEQUENCE: 250
aaagtggagc agcacgtgga gctgtaccag aaatacagca acaattcctg gcgatacctc    60
agcaaccggc tgctggcacc cagcgactcg ccagagtggt tatctt    106

<210> SEQ ID NO 251
<211> LENGTH: 108
<212> TYPE: DNA
<213> ORGANISM: Artificial Sequence
<220> FEATURE:
<223> OTHER INFORMATION: synthetic sequence

<400> SEQUENCE: 251
gtaccgcgac agacatcacc ggccccatca tcctgcagac gtaccgcgcc attgccaact    60
acgagaagac ctcgggctcc gagatggctc tgtccacggg ggacgtgg    108

<210> SEQ ID NO 252
<211> LENGTH: 104
<212> TYPE: DNA
<213> ORGANISM: Artificial Sequence
<220> FEATURE:
<223> OTHER INFORMATION: synthetic sequence

<400> SEQUENCE: 252
gggggcctgg tccatgtccg cgtcccacta gcaggcggag cccccacccc cctcagcagg    60
gccggagacc tagatgtcat tgtttccaga gaaggagaaa atgg    104

<210> SEQ ID NO 253
<211> LENGTH: 110
<212> TYPE: DNA
<213> ORGANISM: Artificial Sequence
<220> FEATURE:
<223> OTHER INFORMATION: synthetic sequence

<400> SEQUENCE: 253
ccaggccaaa cagttgcacc tgcactggtc cgacttgcca tataagggct cggagcacag    60
cctcgatggg gagcactttg ccatggagat gcacatagta catgagaaag    110

<210> SEQ ID NO 254
<211> LENGTH: 106
<212> TYPE: DNA
<213> ORGANISM: Artificial Sequence
<220> FEATURE:
<223> OTHER INFORMATION: synthetic sequence

<400> SEQUENCE: 254
acccttgtgc taagtcaaga ggctcaatgg gctgcagaag aactagagaa ggaccaagca    60
aagccatgat atttccatgg aaatgtcaga gcacccagag ggactt    106

<210> SEQ ID NO 255

<211> LENGTH: 98
<212> TYPE: DNA
<213> ORGANISM: Artificial Sequence
<220> FEATURE:
<223> OTHER INFORMATION: synthetic sequence

<400> SEQUENCE: 255

```
ggccgtcatc ctactgctcc tcctcctcct cctcctcttc ctcatcctcc gacatcgacg    60
tcagggcaaa cactggacat cgacccagag aaaggctg                            98
```

<210> SEQ ID NO 256
<211> LENGTH: 106
<212> TYPE: DNA
<213> ORGANISM: Artificial Sequence
<220> FEATURE:
<223> OTHER INFORMATION: synthetic sequence

<400> SEQUENCE: 256

```
gcacttccag agcctgtccg gagctcagag gttcggaaga cttatcgacc atggagcgcg    60
cgtcctgctt gttgctgctg ctgctgccgc tggtgcacgt ctctgc                  106
```

<210> SEQ ID NO 257
<211> LENGTH: 106
<212> TYPE: DNA
<213> ORGANISM: Artificial Sequence
<220> FEATURE:
<223> OTHER INFORMATION: synthetic sequence

<400> SEQUENCE: 257

```
caccctgcac atcaacacac tcgcccggga gctgcttatc gtgccagggc aggtggtgga    60
caggtccaca ggcatcggca ttgaaggctt ctctgagttg atacag                  106
```

<210> SEQ ID NO 258
<211> LENGTH: 110
<212> TYPE: DNA
<213> ORGANISM: Artificial Sequence
<220> FEATURE:
<223> OTHER INFORMATION: synthetic sequence

<400> SEQUENCE: 258

```
tccagccatg gctgccatta cctgaccagc gccacagccg gtctctctgc aggcgccggg    60
agaagtgacc agagcaattt ctgcttttca cagggcgggt ttctcaacgg              110
```

<210> SEQ ID NO 259
<211> LENGTH: 104
<212> TYPE: DNA
<213> ORGANISM: Artificial Sequence
<220> FEATURE:
<223> OTHER INFORMATION: synthetic sequence

<400> SEQUENCE: 259

```
gggactgggc agttctagac agtcccgaag ttctcaaggc acaggtctct tcctggtttg    60
actgtcctta ccccgggag gcagtgcagc cagctgcaag cccc                    104
```

<210> SEQ ID NO 260
<211> LENGTH: 104
<212> TYPE: DNA
<213> ORGANISM: Artificial Sequence
<220> FEATURE:
<223> OTHER INFORMATION: synthetic sequence

<400> SEQUENCE: 260

```
tttcatggtt ctggttgcct tggtaggatt gggcctgggg atgtttcagc tcttccacct    60
```
acagaaggag ctggcagaac tccgagagtc taccagccag atgc        104

<210> SEQ ID NO 261
<211> LENGTH: 108
<212> TYPE: DNA
<213> ORGANISM: Artificial Sequence
<220> FEATURE:
<223> OTHER INFORMATION: synthetic sequence

<400> SEQUENCE: 261
cttttacacc tttctactg tacaccccat cccagacgaa gacagtccct ggatcaccga        60
cagcacagac agaatccctg ctaccacttt gatgagcact agtgctac        108

<210> SEQ ID NO 262
<211> LENGTH: 107
<212> TYPE: DNA
<213> ORGANISM: Artificial Sequence
<220> FEATURE:
<223> OTHER INFORMATION: synthetic sequence

<400> SEQUENCE: 262
tggccaagag gaaggtgcct atggctggat tactatcaac tatctgctgg gcaaattcag        60
tcagaaaaca aggtggttca gcatagtccc atatgaaacc aataatc        107

<210> SEQ ID NO 263
<211> LENGTH: 107
<212> TYPE: DNA
<213> ORGANISM: Artificial Sequence
<220> FEATURE:
<223> OTHER INFORMATION: synthetic sequence

<400> SEQUENCE: 263
ggagacatgg aggaggaaga ggctgagggg aagatggaag aaggagggaa ggaaggagaa        60
atctttgctt ttgggtaatc aggtgtttct agctgtgtac agggact        107

<210> SEQ ID NO 264
<211> LENGTH: 105
<212> TYPE: DNA
<213> ORGANISM: Artificial Sequence
<220> FEATURE:
<223> OTHER INFORMATION: synthetic sequence

<400> SEQUENCE: 264
ggtcttgaag gacactggga tcctgtaaca cagccccgga tatctgtgtt accagccttg        60
tctcggccac ctcaaggata atcactaaat tctgccgaaa ggact        105

<210> SEQ ID NO 265
<211> LENGTH: 105
<212> TYPE: DNA
<213> ORGANISM: Artificial Sequence
<220> FEATURE:
<223> OTHER INFORMATION: synthetic sequence

<400> SEQUENCE: 265
tgtagcaaac cctcaagctg aggggcagct ccagtggctg aaccgccggg ccaatgccct        60
cctggccaat ggcgtggagc tgagagataa ccagctggtg gtgcc        105

<210> SEQ ID NO 266
<211> LENGTH: 105
<212> TYPE: DNA
<213> ORGANISM: Artificial Sequence
<220> FEATURE:

<223> OTHER INFORMATION: synthetic sequence

<400> SEQUENCE: 266
ttctgcagct ctgtgtgaag gtgcagtttt gccaaggagt gctaaagaac ttagatgtca    60
gtgcataaag acatactcca aacctttcca ccccaaattt atcaa    105

<210> SEQ ID NO 267
<211> LENGTH: 100
<212> TYPE: DNA
<213> ORGANISM: Artificial Sequence
<220> FEATURE:
<223> OTHER INFORMATION: synthetic sequence

<400> SEQUENCE: 267
tgtgttacag tgggctgaaa aaggatacta caccatgagc aacaacttgg taaccctgga    60
aaatgggaaa cagctgaccg ttaaaagaca aggactctat    100

<210> SEQ ID NO 268
<211> LENGTH: 103
<212> TYPE: DNA
<213> ORGANISM: Artificial Sequence
<220> FEATURE:
<223> OTHER INFORMATION: synthetic sequence

<400> SEQUENCE: 268
tcccagacgc ggaggttggg gtcatggcgc cccgaagcct cctcctgctg ctctcagggg    60
ccctggccct gaccgatact tgggcgggct cccactcctt gag    103

<210> SEQ ID NO 269
<211> LENGTH: 108
<212> TYPE: DNA
<213> ORGANISM: Artificial Sequence
<220> FEATURE:
<223> OTHER INFORMATION: synthetic sequence

<400> SEQUENCE: 269
ctgtgcaacg cctgcgggct ctatcacaaa atgaacggac agaaccggcc cctcattaag    60
cccaagcgaa ggctgtctgc agccaggaga gcagggacgt cctgtgcg    108

<210> SEQ ID NO 270
<211> LENGTH: 102
<212> TYPE: DNA
<213> ORGANISM: Artificial Sequence
<220> FEATURE:
<223> OTHER INFORMATION: synthetic sequence

<400> SEQUENCE: 270
aaggtgtgag ttggccagaa ctctgaaaag attgggaatg gatggctaca ggggaatcag    60
cctagcaaac tggatgtgtt tggccaaatg ggagagtggt ta    102

<210> SEQ ID NO 271
<211> LENGTH: 104
<212> TYPE: DNA
<213> ORGANISM: Artificial Sequence
<220> FEATURE:
<223> OTHER INFORMATION: synthetic sequence

<400> SEQUENCE: 271
aaaggctggt ctgcttgaga aacttaaaga acaagagtgt gatgtgaagg attatgggga    60
cctgcccttt gctgacatcc ctaatgacag tcccttttcaa attg    104

<210> SEQ ID NO 272
<211> LENGTH: 108
<212> TYPE: DNA
<213> ORGANISM: Artificial Sequence
<220> FEATURE:
<223> OTHER INFORMATION: synthetic sequence

<400> SEQUENCE: 272
cccagctgag ctcagagcat ggaggagacg tccagaagtg gctctcttcg cccttcccct      60
catcgtcctt cagccctggc ggcctggcac ctgagatctc gccactag                 108

<210> SEQ ID NO 273
<211> LENGTH: 108
<212> TYPE: DNA
<213> ORGANISM: Artificial Sequence
<220> FEATURE:
<223> OTHER INFORMATION: synthetic sequence

<400> SEQUENCE: 273
tgccgtgggc atgggccgcg ctgagcaggt catctttgtc cgagagaccc ccaacacagc      60
aggcgcaggg gccacaggcg gcatcatcgg gggcatcatc gccgccat                 108

<210> SEQ ID NO 274
<211> LENGTH: 108
<212> TYPE: DNA
<213> ORGANISM: Artificial Sequence
<220> FEATURE:
<223> OTHER INFORMATION: synthetic sequence

<400> SEQUENCE: 274
gcccggaaga tcgtgggggc catggtccag atcatcactt accgggacta cctgcccctg      60
gtgctggggc caacggccat gaggaagtac ctgcccacgt accgttcc                 108

<210> SEQ ID NO 275
<211> LENGTH: 98
<212> TYPE: DNA
<213> ORGANISM: Artificial Sequence
<220> FEATURE:
<223> OTHER INFORMATION: synthetic sequence

<400> SEQUENCE: 275
tgctgagaag cctgacatac caggactgcc tgagacaagc cacaagctga acagagaaag      60
tggattgaac aaggacgcat ttccccagta catccaca                             98

<210> SEQ ID NO 276
<211> LENGTH: 105
<212> TYPE: DNA
<213> ORGANISM: Artificial Sequence
<220> FEATURE:
<223> OTHER INFORMATION: synthetic sequence

<400> SEQUENCE: 276
ctgtacttca gggccgtaca ctgctcaaat cattcctggt acaggaaaca agcttctgat      60
gtcttctcct aattgtgaga tatattatca aagtccttta tcact                    105

<210> SEQ ID NO 277
<211> LENGTH: 102
<212> TYPE: DNA
<213> ORGANISM: Artificial Sequence
<220> FEATURE:
<223> OTHER INFORMATION: synthetic sequence

<400> SEQUENCE: 277

```
gccatccgca tcccgctccg gtacaatggc ttggtgaccg gcacgagggc taagggcatc    60
attgccatct gctgggtgct gtcgtttgcc atcggcctga ct                      102
```

<210> SEQ ID NO 278
<211> LENGTH: 110
<212> TYPE: DNA
<213> ORGANISM: Artificial Sequence
<220> FEATURE:
<223> OTHER INFORMATION: synthetic sequence

<400> SEQUENCE: 278

```
gacgtccgtg atgagaaggt caaggtgttg aaatgcatct cagaggtgca ggccaacaat    60
gtggtcctgg gccagtacgt ggggaacccc gatggagagg gcgaggccac              110
```

<210> SEQ ID NO 279
<211> LENGTH: 105
<212> TYPE: DNA
<213> ORGANISM: Artificial Sequence
<220> FEATURE:
<223> OTHER INFORMATION: synthetic sequence

<400> SEQUENCE: 279

```
ctggaccact agtatttcag gtatgctgct gaaagtggga atcctctaca ttggtgggca    60
gctggtgacc agtggggctg taagcagtgg gaaccttgtc acatt                   105
```

<210> SEQ ID NO 280
<211> LENGTH: 104
<212> TYPE: DNA
<213> ORGANISM: Artificial Sequence
<220> FEATURE:
<223> OTHER INFORMATION: synthetic sequence

<400> SEQUENCE: 280

```
cgaagtggac atcgcaaaag ctgatccagc tgctgcatcc cacctctat tactgaatgg     60 agatgctact gtggcccaga aaaatccagg ctcggtggct gaga                    104
```

<210> SEQ ID NO 281
<211> LENGTH: 101
<212> TYPE: DNA
<213> ORGANISM: Artificial Sequence
<220> FEATURE:
<223> OTHER INFORMATION: synthetic sequence

<400> SEQUENCE: 281

```
gctgagcacc ccagtggctg aggccagaga ctttcccaag gatttcttgg tccagtttaa    60
gggcatgtgc tacttcacca acgggacaga gcgcgtgcgc g                       101
```

<210> SEQ ID NO 282
<211> LENGTH: 108
<212> TYPE: DNA
<213> ORGANISM: Artificial Sequence
<220> FEATURE:
<223> OTHER INFORMATION: synthetic sequence

<400> SEQUENCE: 282

```
ccgggggtct ccttctctcc tgaccaccac acccggcccc actgtgagag ctgtcggcac    60
tgtaactctg gtcttctcgt tcgcaactgc accatcactg ccaatgct                108
```

<210> SEQ ID NO 283
<211> LENGTH: 109
<212> TYPE: DNA
<213> ORGANISM: Artificial Sequence
<220> FEATURE:
<223> OTHER INFORMATION: synthetic sequence

<400> SEQUENCE: 283

```
catccctgag gctgcagcgc gtgcgtgtgg cggacgaggg cagcttcacc tgcttcgtga    60
gcatccggga tttcggcagc gctgccgtca gcctgcaggt ggccgctcc              109
```

<210> SEQ ID NO 284
<211> LENGTH: 107
<212> TYPE: DNA
<213> ORGANISM: Artificial Sequence
<220> FEATURE:
<223> OTHER INFORMATION: synthetic sequence

<400> SEQUENCE: 284

```
gggactgtga ggggcgcttc tgactttgga cttgagcact gcctgggacc tgtgctgaga    60
gagcgctagc atgtctcagt ggaatcaagt ccaacagtta gaaatca                 107
```

<210> SEQ ID NO 285
<211> LENGTH: 110
<212> TYPE: DNA
<213> ORGANISM: Artificial Sequence
<220> FEATURE:
<223> OTHER INFORMATION: synthetic sequence

<400> SEQUENCE: 285

```
tctgcgcact gctggacacc cccttacccg ctgggccctt cagcgccagc cacccagccc    60
caagcaactg gaagaagaat tcttgaagat cccttcaaac tttgtcagcc              110
```

<210> SEQ ID NO 286
<211> LENGTH: 107
<212> TYPE: DNA
<213> ORGANISM: Artificial Sequence
<220> FEATURE:
<223> OTHER INFORMATION: synthetic sequence

<400> SEQUENCE: 286

```
gacaaccacc ctcagccttg cacaccacag ctctgctgcc ttacctgcac gcacctccaa    60
caccaccatc acagcgaaca cctcagatgc ctaccttaat gcctctg                 107
```

<210> SEQ ID NO 287
<211> LENGTH: 107
<212> TYPE: DNA
<213> ORGANISM: Artificial Sequence
<220> FEATURE:
<223> OTHER INFORMATION: synthetic sequence

<400> SEQUENCE: 287

```
atcagctata aatatcgaga ggacttgtct gcacatctca tggtagctgg ctgggaccaa    60
cgtgaaggag gtcaggtata tggaaccctg ggaggaatgc tgactcg                 107
```

<210> SEQ ID NO 288
<211> LENGTH: 105
<212> TYPE: DNA
<213> ORGANISM: Artificial Sequence
<220> FEATURE:
<223> OTHER INFORMATION: synthetic sequence

<400> SEQUENCE: 288

```
ctcaggactg tcagaatgcc catcaggaat tcagattttg gccgttttg gtgatcatcg     60
tgattctaag cgcactgttc cttggcaccc ttgcctgctt ctgtg                   105
```

<210> SEQ ID NO 289
<211> LENGTH: 108
<212> TYPE: DNA
<213> ORGANISM: Artificial Sequence
<220> FEATURE:
<223> OTHER INFORMATION: synthetic sequence

<400> SEQUENCE: 289 gggatcagt atatacactt cagataacta caccgaggaa atgggctcag gggactatga    60
ctccatgaag gaaccctgtt ccgtgaaga aaatgctaat ttcaataa                108

<210> SEQ ID NO 290
<211> LENGTH: 101
<212> TYPE: DNA
<213> ORGANISM: Artificial Sequence
<220> FEATURE:
<223> OTHER INFORMATION: synthetic sequence

<400> SEQUENCE: 290
tttgtcagga caagggctca gaggactgga cgtgctcaga catcggtgtt cttcttccca    60
gttcttgacc cctggtcctg tctccagccc gtcttggctt a                      101

<210> SEQ ID NO 291
<211> LENGTH: 103
<212> TYPE: DNA
<213> ORGANISM: Artificial Sequence
<220> FEATURE:
<223> OTHER INFORMATION: synthetic sequence

<400> SEQUENCE: 291
atccagcgtt tcgtagaaac cccagctcat ttctcttgga agaaagtta ttaccgatcc    60 accatgtccc agagcacaca gacaaatgaa ttcctcagtc cag                    103

<210> SEQ ID NO 292
<211> LENGTH: 109
<212> TYPE: DNA
<213> ORGANISM: Artificial Sequence
<220> FEATURE:
<223> OTHER INFORMATION: synthetic sequence

<400> SEQUENCE: 292
tatgcttgtg ccccacctga gtcccaggct cccggagtcc ccacagagcc aagcataagg    60
tctgccgaag ccttggcgtt ctcagactgc cggctgcaca tctgcctgt              109

<210> SEQ ID NO 293
<211> LENGTH: 105
<212> TYPE: DNA
<213> ORGANISM: Artificial Sequence
<220> FEATURE:
<223> OTHER INFORMATION: synthetic sequence

<400> SEQUENCE: 293
tcatagctga ctactttgag acgagcagcc agtgctccaa gcccggtgtc atcttcctaa    60
ccaagcgaag ccggcaggtc tgtgctgacc ccagtgagga gtggg                  105

<210> SEQ ID NO 294
<211> LENGTH: 98
<212> TYPE: DNA
<213> ORGANISM: Artificial Sequence
<220> FEATURE:
<223> OTHER INFORMATION: synthetic sequence

<400> SEQUENCE: 294

```
tattctgaaa ccagccccca gtgccccaag ccaggtgtca tcctcctaac caagagaggc    60
cggcagatct gtgctgaccc caataagaag tgggtcca                             98

<210> SEQ ID NO 295
<211> LENGTH: 107
<212> TYPE: DNA
<213> ORGANISM: Artificial Sequence
<220> FEATURE:
<223> OTHER INFORMATION: synthetic sequence

<400> SEQUENCE: 295
ttaatacatc acacttgcaa aagaagtatg taaaagtttt aatgcacgat gtagcttacc    60
gccaggaaaa ggatgaaaac aaatggacgc atgtgaattt atccagc                 107

<210> SEQ ID NO 296
<211> LENGTH: 105
<212> TYPE: DNA
<213> ORGANISM: Artificial Sequence
<220> FEATURE:
<223> OTHER INFORMATION: synthetic sequence

<400> SEQUENCE: 296
acaggattcc tgagctgaaa tgcagatgac cacattcaag gaagaacttt ctgccccggc    60
tttgcaggat gaaaagcttt cctgcttggc agttattctt ccaca                   105

<210> SEQ ID NO 297
<211> LENGTH: 102
<212> TYPE: DNA
<213> ORGANISM: Artificial Sequence
<220> FEATURE:
<223> OTHER INFORMATION: synthetic sequence

<400> SEQUENCE: 297
gtgaaataca gaacccagcg agtgcaaact tcagtgaccc agtcaccctg aatgtcctct    60
atggcccaga tgcccccacc atttcccctt cagacaccta tt                      102

<210> SEQ ID NO 298
<211> LENGTH: 105
<212> TYPE: DNA
<213> ORGANISM: Artificial Sequence
<220> FEATURE:
<223> OTHER INFORMATION: synthetic sequence

<400> SEQUENCE: 298
aatttactga aagcagttag caaggaaagg tctaaaagat ctccttaaaa ccagagggga    60
gcaaaatcga tgcagtgctt ccaaggatgg accacacaga ggctg                   105

<210> SEQ ID NO 299
<211> LENGTH: 104
<212> TYPE: DNA
<213> ORGANISM: Artificial Sequence
<220> FEATURE:
<223> OTHER INFORMATION: synthetic sequence

<400> SEQUENCE: 299
gcaagtgtcc caaagaagct gtgatcttca agaccattgt ggccaaggag atctgtgctg    60
accccaagca gaagtgggtt caggattcca tggaccacct ggac                    104

<210> SEQ ID NO 300
<211> LENGTH: 98
<212> TYPE: DNA
```

```
<213> ORGANISM: Artificial Sequence
<220> FEATURE:
<223> OTHER INFORMATION: synthetic sequence

<400> SEQUENCE: 300
tgccttgaag aaaaaggacc aatgttcgaa ctacttccag gtgaatccaa caagatcccc    60
cgtctgagga ctgaccttttt tccaaagacg agaatcca                           98

<210> SEQ ID NO 301
<211> LENGTH: 984
<212> TYPE: DNA
<213> ORGANISM: Artificial Sequence
<220> FEATURE:
<223> OTHER INFORMATION: synthetic sequence

<400> SEQUENCE: 301
tgggggcctt ctacctgtgc cagccggggc cccctctga gaaggcctgg cagcctggct     60
ggacagtcaa tgtggagggc agcggggagc tgttccggtg gaatgttttcg gacctaggtg  120 gcctgggctg tggcctgaag aacaggtcct cagagggccc cagctcccct tccgggaagc  180
tcatgagccc caagctgtat gtgtgggcca agaccgccc tgagatctgg gagggagagc   240
ctccgtgtct cccaccgagg gacagcctga accagagcc cagccaggac ctcaccatgg   300
cccctggctc cacactctgg ctgtcctgtg gggtacccc tgactctgtg tccaggggcc   360
ccctctcctg gacccatgtg caccccaagg ggcctaagtc attgctgagc ctagagctga   420
aggacgatcg cccggccaga gatatgtggg taatggagac gggtctgttg ttgccccggg   480
ccacagctca agacgctgga aagtattatt gtcaccgtgg caacctgacc atgtcattcc   540
acctggagat cactgctcgg ccagtactat ggcactggct gctgaggact ggtggctgga   600
aggtctcagc tgtgactttg gcttatctga tcttctgcct gtgttccctt gtgggcattc   660
ttcatcttca agagccctg gtcctgagga ggaaaagaaa gcgaatgact gaccccacca    720
ggagattctt caaagtgacg cctcccccag gaagcgggcc ccagaaccag tacgggaacg   780
tgctgtctct ccccacaccc acctcaggcc tcggacgcgc ccagcgttgg gccgcaggcc   840 tgggggcac tgccccgtct tatggaaacc cgagcagcga cgtccaggcg gatgagcct    900 tggggtcccg gagcccgccg ggagtgggcc cagaagaaga ggaaggggag ggctatgagg   960
aacctgacag tgaggaggac tccg                                          984

<210> SEQ ID NO 302
<211> LENGTH: 98
<212> TYPE: DNA
<213> ORGANISM: Artificial Sequence
<220> FEATURE:
<223> OTHER INFORMATION: synthetic sequence

<400> SEQUENCE: 302
ctcaatgaaa gacgatttgg agaatgtaaa aagtcttgga acagatctga tgaatgaaat    60
gaggaggatt acttcggact tcagaattgg atttggct                           98

<210> SEQ ID NO 303
<211> LENGTH: 100
<212> TYPE: DNA
<213> ORGANISM: Artificial Sequence
<220> FEATURE:
<223> OTHER INFORMATION: synthetic sequence

<400> SEQUENCE: 303
cgtgaagtct aggacagga agatggttgg cgacgtgacc ggggcccagg cctatgcctc    60
```
caccgccaag tgcctgaaca tctgggccct gattctgggc          100

<210> SEQ ID NO 304
<211> LENGTH: 107
<212> TYPE: DNA
<213> ORGANISM: Artificial Sequence
<220> FEATURE:
<223> OTHER INFORMATION: synthetic sequence

<400> SEQUENCE: 304
aagggctcca aaggctgcaa gaggactgag cggtcacaga ccccctaaagg gccatagccc          60 agtgagcagc ctggagccct ggagacccca ccagcctcac cagcgct          107

<210> SEQ ID NO 305
<211> LENGTH: 105
<212> TYPE: DNA
<213> ORGANISM: Artificial Sequence
<220> FEATURE:
<223> OTHER INFORMATION: synthetic sequence

<400> SEQUENCE: 305
ggaaccacag acaatctgtg ctccagaggt tatgaagcca tgtatacgct actaggcaat          60
gccaatggag caacctgtgc attcccgttc aagtttgaaa acaag          105

<210> SEQ ID NO 306
<211> LENGTH: 100
<212> TYPE: DNA
<213> ORGANISM: Artificial Sequence
<220> FEATURE:
<223> OTHER INFORMATION: synthetic sequence

<400> SEQUENCE: 306
gcccatcctg tgtctccctg ctgcgctgca ccggctgctg cggcgatgag aatctgcact          60
gtgtgccggt ggagacggcc aatgtcacca tgcagctcct          100

<210> SEQ ID NO 307
<211> LENGTH: 103
<212> TYPE: DNA
<213> ORGANISM: Artificial Sequence
<220> FEATURE:
<223> OTHER INFORMATION: synthetic sequence

<400> SEQUENCE: 307
ccagaacacc tatctgagtg gcctgtgtta cctcttccgc cagaatctgc agggtcccat          60
gctgcagggg cgccctggtt ttcaggaatg tatcaagggc aac          103

<210> SEQ ID NO 308
<211> LENGTH: 100
<212> TYPE: DNA
<213> ORGANISM: Artificial Sequence
<220> FEATURE:
<223> OTHER INFORMATION: synthetic sequence

<400> SEQUENCE: 308
tgtggctgaa taagcggtgt tcatgatttc ttttattctt tgcacaacaa caacaacaac          60
aaattcacgg aatcttttaa gtgctgaact tattttcaa          100

<210> SEQ ID NO 309
<211> LENGTH: 107
<212> TYPE: DNA
<213> ORGANISM: Artificial Sequence
<220> FEATURE:

<223> OTHER INFORMATION: synthetic sequence

<400> SEQUENCE: 309
cgtgggcccg ggaaggtcgg aagaagtgtt cctgcaagtg cagtatgccc cggaaccttc    60
cacggttcag atcctccact caccggctgt ggagggaagt caagtcg    107

<210> SEQ ID NO 310
<211> LENGTH: 106
<212> TYPE: DNA
<213> ORGANISM: Artificial Sequence
<220> FEATURE:
<223> OTHER INFORMATION: synthetic sequence

<400> SEQUENCE: 310
tctgaggact gctccaggga tgccatcgtt tttgtaactg tgcagggcag ggccatctgt    60
tcggacccca acaacaagag agtgaagaat gcagttaaat acctgc    106

<210> SEQ ID NO 311
<211> LENGTH: 106
<212> TYPE: DNA
<213> ORGANISM: Artificial Sequence
<220> FEATURE:
<223> OTHER INFORMATION: synthetic sequence

<400> SEQUENCE: 311
atatctttca acaaatctct atatgaggga ctgaatgcag agaaccacag aactaagatc    60
actgtcgtct tcctgaaaga tgagaagtac cattctttgc ctatca    106

<210> SEQ ID NO 312
<211> LENGTH: 100
<212> TYPE: DNA
<213> ORGANISM: Artificial Sequence
<220> FEATURE:
<223> OTHER INFORMATION: synthetic sequence

<400> SEQUENCE: 312
gacctgggac cttaacagaa atgtgaccga tatcgagtgt gttaaagacg ccgactattc    60
tatgccggca gtgaacaata gctattgcca gtttggagca    100

<210> SEQ ID NO 313
<211> LENGTH: 104
<212> TYPE: DNA
<213> ORGANISM: Artificial Sequence
<220> FEATURE:
<223> OTHER INFORMATION: synthetic sequence

<400> SEQUENCE: 313
aggtatgcct gtgtcaagat gaggtcacgg acgattacat cggagacaac accacagtgg    60
actacacttt gttcgagtct ttgtgctcca agaaggacgt gcgg    104

<210> SEQ ID NO 314
<211> LENGTH: 104
<212> TYPE: DNA
<213> ORGANISM: Artificial Sequence
<220> FEATURE:
<223> OTHER INFORMATION: synthetic sequence

<400> SEQUENCE: 314
tatggtttaa gaagcactgc tcatatcagg acatcctgtg agactcttcc ccctgactcc    60
cccattgtgt taagaaccca gcaacccagg agcctagtac aata    104

```
<210> SEQ ID NO 315
<211> LENGTH: 106
<212> TYPE: DNA
<213> ORGANISM: Artificial Sequence
<220> FEATURE:
<223> OTHER INFORMATION: synthetic sequence

<400> SEQUENCE: 315
tccctggcca tggcgctgca gctctcccgg gagcagggaa tcaccctgcg cgggagcgcc      60
gaaatcgtgg ccgagttctt ctcattcggc atcaacagca ttttat                   106

<210> SEQ ID NO 316
<211> LENGTH: 111
<212> TYPE: DNA
<213> ORGANISM: Artificial Sequence
<220> FEATURE:
<223> OTHER INFORMATION: synthetic sequence

<400> SEQUENCE: 316
gcagcctatg gatacggcat tcggtatgaa tatgggattt tcaatcagaa gatccgagat      60
ggatggcagg tagaagaagc agatgattgg ctcagatatg gaaacccttg g              111

<210> SEQ ID NO 317
<211> LENGTH: 107
<212> TYPE: DNA
<213> ORGANISM: Artificial Sequence
<220> FEATURE:
<223> OTHER INFORMATION: synthetic sequence

<400> SEQUENCE: 317
cacactgcca ccagcacaaa tactgcgacc ccaacctagg gcttcgggtc cagcagaagg      60
gcacctcaga aacagacacc atctgcacct gtgaagaagg ctggcac                  107

<210> SEQ ID NO 318
<211> LENGTH: 101
<212> TYPE: DNA
<213> ORGANISM: Artificial Sequence
<220> FEATURE:
<223> OTHER INFORMATION: synthetic sequence

<400> SEQUENCE: 318
atcaccccaa cctcacatgc acagccagca accctgtcag caggagttcc caccagtttc      60
tttctgagaa catctgttca ggacctgaga gaaacacaaa g                        101

<210> SEQ ID NO 319
<211> LENGTH: 325
<212> TYPE: DNA
<213> ORGANISM: Artificial Sequence
<220> FEATURE:
<223> OTHER INFORMATION: synthetic sequence

<400> SEQUENCE: 319
gcagaccctg cgcggctact acaaccagag cgaggccagt tctcacaccc tccagtggat      60
gattggctgc gacctggggt ccgacggacg cctcctccgc gggtatgaac agtatgccta    120
cgatggcaag gattacctcg ccctgaacga ggacctgcgc tcctggaccg cagcggacac    180
tgcggctcag atctccaagc gcaagtgtga ggcggccaat gtggctgaac aaaggagagc    240
ctacctggag ggcacgtgcg tggagtggct ccacagatac ctggagaacg gaaggagat    300 gctgcagcgc gcggacccc ccaag                                           325

<210> SEQ ID NO 320
```

```
<211> LENGTH: 102
<212> TYPE: DNA
<213> ORGANISM: Artificial Sequence
<220> FEATURE:
<223> OTHER INFORMATION: synthetic sequence

<400> SEQUENCE: 320
ttgaactaga agcaattgtt aacagcatca aaagaagcag aaaaattatt tttgttataa      60
cacaccatct attaaaagac ccattatgca aagattcaa gg                         102

<210> SEQ ID NO 321
<211> LENGTH: 103
<212> TYPE: DNA
<213> ORGANISM: Artificial Sequence
<220> FEATURE:
<223> OTHER INFORMATION: synthetic sequence

<400> SEQUENCE: 321
gcagcaagaa tggcacggtc tgcctcagtc caccctgtac cctggcccgg tcctttggag      60
tagaatggat tgcaagttgg ctagtggtca cggtgcccac cat                       103

<210> SEQ ID NO 322
<211> LENGTH: 104
<212> TYPE: DNA
<213> ORGANISM: Artificial Sequence
<220> FEATURE:
<223> OTHER INFORMATION: synthetic sequence

<400> SEQUENCE: 322
ggagtaccac caagccacgg gcaccctcag tgcccacttc aggaacatgt cactgaagag      60
gatcaagcgt gctgaccggc ggggtgcaga gtccgtgaca gagg                      104

<210> SEQ ID NO 323
<211> LENGTH: 105
<212> TYPE: DNA
<213> ORGANISM: Artificial Sequence
<220> FEATURE:
<223> OTHER INFORMATION: synthetic sequence

<400> SEQUENCE: 323
caaaaggcag acagcgggca ctaccactgc agtggcatct tccagagccc tggtcctggg      60
atcccagaaa cagcatctgt tgtggctatc acagtccaag aactg                     105

<210> SEQ ID NO 324
<211> LENGTH: 107
<212> TYPE: DNA
<213> ORGANISM: Artificial Sequence
<220> FEATURE:
<223> OTHER INFORMATION: synthetic sequence

<400> SEQUENCE: 324
cactctggag agaagcccta caaatgcgaa acctgcggag ccagatttgt acaggtggcc      60
cacctccgtg cccatgtgct tatccacact ggtgagaagc cctatcc                   107

<210> SEQ ID NO 325
<211> LENGTH: 101
<212> TYPE: DNA
<213> ORGANISM: Artificial Sequence
<220> FEATURE:
<223> OTHER INFORMATION: synthetic sequence

<400> SEQUENCE: 325
ccccaggtgt aagcgcagaa agcaggcgaa cccgcggcgc aataacgtta caaattataa      60
```
tactgtggta gaaacaaatt cagattcaga tgatgaagac a                101

<210> SEQ ID NO 326
<211> LENGTH: 109
<212> TYPE: DNA
<213> ORGANISM: Artificial Sequence
<220> FEATURE:
<223> OTHER INFORMATION: synthetic sequence

<400> SEQUENCE: 326
actgccctct gcgctcctgc atctgcctcc ccatattcct cggacaccac accctgctgc    60
tttgcctaca ttgcccgccc actgccccgt gcccacatca aggagtatt                109

<210> SEQ ID NO 327
<211> LENGTH: 101
<212> TYPE: DNA
<213> ORGANISM: Artificial Sequence
<220> FEATURE:
<223> OTHER INFORMATION: synthetic sequence

<400> SEQUENCE: 327
ctggccagct tcgagaaaga gttgagaagt taaacatgct cagcattgat catctcacag    60
accacaagtc acagcgcctt gcacgtctag ttctgggatg c                        101

<210> SEQ ID NO 328
<211> LENGTH: 106
<212> TYPE: DNA
<213> ORGANISM: Artificial Sequence
<220> FEATURE:
<223> OTHER INFORMATION: synthetic sequence

<400> SEQUENCE: 328
cagcttcggg aagaggaaag gaacctcaga ccttccagat cgcttcctct cgcaacaaac    60
tatttgtcgc aggaataaag atggctgctg aaccagtaga agacaa                  106

<210> SEQ ID NO 329
<211> LENGTH: 104
<212> TYPE: DNA
<213> ORGANISM: Artificial Sequence
<220> FEATURE:
<223> OTHER INFORMATION: synthetic sequence

<400> SEQUENCE: 329
gttgttaaac ggggcagaaa gaaactcctg tatatattca acaaccatt tatgagacca     60 gtacaaacta ctcaagagga agatggctgt agctgccgat ttcc                    104

<210> SEQ ID NO 330
<211> LENGTH: 102
<212> TYPE: DNA
<213> ORGANISM: Artificial Sequence
<220> FEATURE:
<223> OTHER INFORMATION: synthetic sequence

<400> SEQUENCE: 330
ggtggatatg tctgggttga aactcaagca actgtcatat ataacaccaa gaattctcaa    60
ccacagtgca ttgtatgtgt gaattacgtt gtgagtggta tt                      102

<210> SEQ ID NO 331
<211> LENGTH: 105
<212> TYPE: DNA
<213> ORGANISM: Artificial Sequence
<220> FEATURE:

<223> OTHER INFORMATION: synthetic sequence

<400> SEQUENCE: 331

```
ggtgctgctc acatctgtgg tccagggcag ggccactcca gagaattacc ttttccaggg      60
acggcaggaa tgctacgcgt ttaatgggac acagcgcttc ctgga                    105
```

<210> SEQ ID NO 332
<211> LENGTH: 105
<212> TYPE: DNA
<213> ORGANISM: Artificial Sequence
<220> FEATURE:
<223> OTHER INFORMATION: synthetic sequence

<400> SEQUENCE: 332

```
aaggataagg gtgacagcaa cagctcggcg ggctggaaga attcaattcg tcataatctg      60
tccctacaca gcaagttcat tcgtgtgcag aatgaaggaa ctgga                    105
```

<210> SEQ ID NO 333
<211> LENGTH: 106
<212> TYPE: DNA
<213> ORGANISM: Artificial Sequence
<220> FEATURE:
<223> OTHER INFORMATION: synthetic sequence

<400> SEQUENCE: 333

```
cttctttcgg atggagagag gaagtaccaa atacagttac aaatctcccc agctctctgt      60
gcatgtgaca gacttgaccc acaggcccaa aatcctcatc cctggc                   106
```

<210> SEQ ID NO 334
<211> LENGTH: 106
<212> TYPE: DNA
<213> ORGANISM: Artificial Sequence
<220> FEATURE:
<223> OTHER INFORMATION: synthetic sequence

<400> SEQUENCE: 334

```
tctgcaaaat tttctcaaga aggagaataa gaatgaaaag gtcatagaac acatcatgga      60
ggacctggac acaaatgcag acaagcagct gagcttcgag gagttc                   106
```

<210> SEQ ID NO 335
<211> LENGTH: 108
<212> TYPE: DNA
<213> ORGANISM: Artificial Sequence
<220> FEATURE:
<223> OTHER INFORMATION: synthetic sequence

<400> SEQUENCE: 335

```
ggggctcctg agcccatcct tcgggactgg acacctgggc tgtcccccat gcagaccctg      60
aaggtttctg tgtctgcagt gactctgggc ctgggcctca tcatcttc                 108
```

<210> SEQ ID NO 336
<211> LENGTH: 100
<212> TYPE: DNA
<213> ORGANISM: Artificial Sequence
<220> FEATURE:
<223> OTHER INFORMATION: synthetic sequence

<400> SEQUENCE: 336

```
acacggaatg tgaaggccca gtcacagact gaccgagtgg acctggggac cctgcgcggc      60
tactacaacc agagcgaggc cggttctcac accatccaga                          100
```

```
<210> SEQ ID NO 337
<211> LENGTH: 106
<212> TYPE: DNA
<213> ORGANISM: Artificial Sequence
<220> FEATURE:
<223> OTHER INFORMATION: synthetic sequence

<400> SEQUENCE: 337
taccttgtgt ttgcaagatc tgcggcaagg cgttttccag accctggttg cttcaaggac     60
acattagaac tcacacgggg gagaagcctt tttcttgccc tcactg                   106

<210> SEQ ID NO 338
<211> LENGTH: 105
<212> TYPE: DNA
<213> ORGANISM: Artificial Sequence
<220> FEATURE:
<223> OTHER INFORMATION: synthetic sequence

<400> SEQUENCE: 338
tattttgaca gtttgttgca tgcttgcata ccttgtcaac ttcgatgttc ttctaatact     60
cctcctctaa catgtcagcg ttattgtaat gcaagtgtga ccaat                    105

<210> SEQ ID NO 339
<211> LENGTH: 106
<212> TYPE: DNA
<213> ORGANISM: Artificial Sequence
<220> FEATURE:
<223> OTHER INFORMATION: synthetic sequence

<400> SEQUENCE: 339
ggcccaatgg gctaagcctg acatcccgg ctgggcgcct ctactgggtg gatgccttct      60
acgaccgcat cgagacgata ctgctcaatg cacagaccg gaagat                    106

<210> SEQ ID NO 340
<211> LENGTH: 168
<212> TYPE: DNA
<213> ORGANISM: Artificial Sequence
<220> FEATURE:
<223> OTHER INFORMATION: synthetic sequence

<400> SEQUENCE: 340
cgcagcttga gactggcgga gggaagcccg cccaggctct ataaggagac aaggttctga     60
gcagacaggc caaccggagg acaggattcc ctggaggcca cagaggagca ccaaggagaa    120
gatctgcctg tgggtcccca ttgcccagct tttgcctgca ctcttgcc                 168

<210> SEQ ID NO 341
<211> LENGTH: 345
<212> TYPE: DNA
<213> ORGANISM: Artificial Sequence
<220> FEATURE:
<223> OTHER INFORMATION: synthetic sequence

<400> SEQUENCE: 341 ttcctcccttt ctgctgatga gatttatgac tgcaaggtgg agcactgggg cctggaccag    60
cctcttctga aacactggga gcctgagatt ccagccccta tgtcagagct cacagagact   120
gtggtctgtg ccctggggtt gtctgtgggc ctcatgggca ttgtggtggg cactgtcttc   180
atcatccaag gcctgcgttc agttggtgct tccagacacc aagggccatt gtgaatccca   240
tcctggaagg gaaggtgcat cgccatctac aggagcagaa gaatggactt gctaaatgac   300
ctagcactat tctctggccc gatttatcat atcccttttc tcctc                   345
```

<210> SEQ ID NO 342
<211> LENGTH: 107
<212> TYPE: DNA
<213> ORGANISM: Artificial Sequence
<220> FEATURE:
<223> OTHER INFORMATION: synthetic sequence

<400> SEQUENCE: 342
ggcctccttg agtcagggaa gtcggaactg aagaagcaag tgaagcccaa ggcctggctg    60
tcccgtggcc ccagtcctgg ccctggccgt ctgctgctgg tgtgcca                 107

<210> SEQ ID NO 343
<211> LENGTH: 105
<212> TYPE: DNA
<213> ORGANISM: Artificial Sequence
<220> FEATURE:
<223> OTHER INFORMATION: synthetic sequence

<400> SEQUENCE: 343
atgagaagcg tatggccaca gaagttgctg ctgacgctct gggtgaagaa tggaagggtt    60
atgtggtccg aatcagtggt gggaacgaca acaaggtttc cccca                   105

<210> SEQ ID NO 344
<211> LENGTH: 105
<212> TYPE: DNA
<213> ORGANISM: Artificial Sequence
<220> FEATURE:
<223> OTHER INFORMATION: synthetic sequence

<400> SEQUENCE: 344
ctcttctgac cctgatgaga aagctcaaga ttccaaggcc tattcaaaaa tcactgaagg    60
aaaagtttca ggaaatcctc aggtacatat caagaatgtc aaaga                   105

<210> SEQ ID NO 345
<211> LENGTH: 108
<212> TYPE: DNA
<213> ORGANISM: Artificial Sequence
<220> FEATURE:
<223> OTHER INFORMATION: synthetic sequence

<400> SEQUENCE: 345
gtatggcgga catcacgttt gtggaggtgt tctgattgat ccacagtggg tgctgacagc    60
agcccactgc caatatcggt ttaccaaagg ccagtctccc actgtggt                108

<210> SEQ ID NO 346
<211> LENGTH: 106
<212> TYPE: DNA
<213> ORGANISM: Artificial Sequence
<220> FEATURE:
<223> OTHER INFORMATION: synthetic sequence

<400> SEQUENCE: 346
gatgcctggg ggtccaggag tcctccaagc tctgcctgcc accatcttcc tcctcttcct    60
gctgtctgct gtctacctgg gccctgggtg ccaggccctg tggatg                  106

<210> SEQ ID NO 347
<211> LENGTH: 109
<212> TYPE: DNA
<213> ORGANISM: Artificial Sequence
<220> FEATURE:
<223> OTHER INFORMATION: synthetic sequence

<400> SEQUENCE: 347

```
accatccaaa agtacggcac aaccccgag gagaccgcgg ccgaggagag ctgggactat    60
gtgcagttcc agctgcgctg ctgcggctgg cactacccgc aggactggt             109
```

<210> SEQ ID NO 348
<211> LENGTH: 108
<212> TYPE: DNA
<213> ORGANISM: Artificial Sequence
<220> FEATURE:
<223> OTHER INFORMATION: synthetic sequence

<400> SEQUENCE: 348

```
gcagtggtat agcatatcct cacatttcta gtgcccttga gactgtgcta tggaaccaat    60
cttgaacata catgcattga cttgacaagt tactgagtaa gcagcata              108
```

<210> SEQ ID NO 349
<211> LENGTH: 106
<212> TYPE: DNA
<213> ORGANISM: Artificial Sequence
<220> FEATURE:
<223> OTHER INFORMATION: synthetic sequence

<400> SEQUENCE: 349

```
tgactttctc aggatgatgc tgggcaagag atctgccatc ctaaaaatga tcctgatgta    60
tgaggaaaaa gcgagagaaa aggaaaagcc aacaggcccc ccagcc                106
```

<210> SEQ ID NO 350
<211> LENGTH: 95
<212> TYPE: DNA
<213> ORGANISM: Artificial Sequence
<220> FEATURE:
<223> OTHER INFORMATION: synthetic sequence

<400> SEQUENCE: 350

```
accagagaga agccgggatg gaaactccaa acaccacaga ggactatgac acgaccacag    60
agtttgacta tggggatgca actccgtgcc agaag                             95
```

<210> SEQ ID NO 351
<211> LENGTH: 104
<212> TYPE: DNA
<213> ORGANISM: Artificial Sequence
<220> FEATURE:
<223> OTHER INFORMATION: synthetic sequence

<400> SEQUENCE: 351

```
caaggaatct gcttttcaag tatgccacca acagtgaaga ggttattgga gtgatgagta    60
aagaatacat accaaagggc acacgttttg gacccctaat aggt                  104
```

<210> SEQ ID NO 352
<211> LENGTH: 105
<212> TYPE: DNA
<213> ORGANISM: Artificial Sequence
<220> FEATURE:
<223> OTHER INFORMATION: synthetic sequence

<400> SEQUENCE: 352

```
ctacagggat attaatatta cttcactact atgtgtttag tacagcgatt ggattaacct    60
ccttcgtcat tgccatattg gttattcagg tgatagccta tatcc                 105
```

<210> SEQ ID NO 353
<211> LENGTH: 109
<212> TYPE: DNA

```
<213> ORGANISM: Artificial Sequence
<220> FEATURE:
<223> OTHER INFORMATION: synthetic sequence

<400> SEQUENCE: 353
aagcccactg acgctccacc gaaagtactg accaagtgcc aggaagaggt cagccacatc    60
cctgctgtcc acccgggttc attcaggccc aagtgcgacg agaacggca               109

<210> SEQ ID NO 354
<211> LENGTH: 108
<212> TYPE: DNA
<213> ORGANISM: Artificial Sequence
<220> FEATURE:
<223> OTHER INFORMATION: synthetic sequence

<400> SEQUENCE: 354
ggatgtgagc caggcccagg ctgggaccta cacctgccat atccatctgc aggaacagca    60
gctcaatgcc actgtcacat tggcaatcat cacagtgact cccaaatc                108

<210> SEQ ID NO 355
<211> LENGTH: 85
<212> TYPE: DNA
<213> ORGANISM: Artificial Sequence
<220> FEATURE:
<223> OTHER INFORMATION: synthetic sequence

<400> SEQUENCE: 355
cctcagaagt gggagtgagc ggaagcagct gtgcacggcc acacaggaca cagtctgccg    60
ctgccgggcg ggcacccagc ccctg                                         85

<210> SEQ ID NO 356
<211> LENGTH: 102
<212> TYPE: DNA
<213> ORGANISM: Artificial Sequence
<220> FEATURE:
<223> OTHER INFORMATION: synthetic sequence

<400> SEQUENCE: 356
tcaatatatg atacaaaagg aaaaaatgtg ttggaaaaaa tatttgattt gaagattcaa    60
gagagggtct caaaaccaaa gatctcctgg acttgtatca ac                      102

<210> SEQ ID NO 357
<211> LENGTH: 99
<212> TYPE: DNA
<213> ORGANISM: Artificial Sequence
<220> FEATURE:
<223> OTHER INFORMATION: synthetic sequence

<400> SEQUENCE: 357
gctgccttct gctctccagc gctctcagca ccaatgggct cagaccctcc caccgcctgc    60
tgcttttctt acactgcgag gaagcttcct cgcaacttt                          99

<210> SEQ ID NO 358
<211> LENGTH: 117
<212> TYPE: DNA
<213> ORGANISM: Artificial Sequence
<220> FEATURE:
<223> OTHER INFORMATION: synthetic sequence

<400> SEQUENCE: 358
ggcctgagcg gtaggagtgg ggctggagca gtaagatggc ggccagagcg gttttctgg    60 cattgtctgc ccagctgctc caagccaggc tgatgaagga ggagtcccct gtggtga      117
```

<210> SEQ ID NO 359
<211> LENGTH: 101
<212> TYPE: DNA
<213> ORGANISM: Artificial Sequence
<220> FEATURE:
<223> OTHER INFORMATION: synthetic sequence

<400> SEQUENCE: 359
ctccaagggg tcaggtgcaa aggcctgcca gatgattatg ggaagctgga acccagtagg       60
tgtgggccgc tacctcaaca cctggctgat ggagacaaag g                         101

<210> SEQ ID NO 360
<211> LENGTH: 92
<212> TYPE: DNA
<213> ORGANISM: Artificial Sequence
<220> FEATURE:
<223> OTHER INFORMATION: synthetic sequence

<400> SEQUENCE: 360
tttctacaac cagcttgcat tttttctgcc cacaatgagc ggggaatcaa tgaatttcag       60
cgatgttttc gactccagtg aagattattt tg                                    92

<210> SEQ ID NO 361
<211> LENGTH: 104
<212> TYPE: DNA
<213> ORGANISM: Artificial Sequence
<220> FEATURE:
<223> OTHER INFORMATION: synthetic sequence

<400> SEQUENCE: 361
gcatccagcg cttcgcacag gctcagcagc agctgccgct cgagtcactt gggtgggacg       60
tagctgagct gcagctgaat cacacaggac ctcagcagga cccc                      104

<210> SEQ ID NO 362
<211> LENGTH: 111
<212> TYPE: DNA
<213> ORGANISM: Artificial Sequence
<220> FEATURE:
<223> OTHER INFORMATION: synthetic sequence

<400> SEQUENCE: 362
ggtgactgat gatctaagtt tcccgaggtt tctcagagcc tctctggttc tttcactggt       60
gaccagccag cccctcctct ttcttcctcc ggtgctggcg aagagccccc c              111

<210> SEQ ID NO 363
<211> LENGTH: 247
<212> TYPE: DNA
<213> ORGANISM: Artificial Sequence
<220> FEATURE:
<223> OTHER INFORMATION: synthetic sequence

<400> SEQUENCE: 363
gctgcagatg cggggccagg gggccggaga gccgcctgct tgagttctac ctcgccatgc       60
ctttcgcgac acccatggaa gcagagctgg cccgcaggag cctggcccag gatgccccac      120
cgcttcccgt gccaggggtg cttctgaagg agttcactgt gtccggcaac atactgacta      180
tccgactgac tgctgcagac caccgccaac tgcagctctc catcagctcc tgtctccagc      240
agctttc                                                               247

<210> SEQ ID NO 364

```
<211> LENGTH: 356
<212> TYPE: DNA
<213> ORGANISM: Artificial Sequence
<220> FEATURE:
<223> OTHER INFORMATION: synthetic sequence

<400> SEQUENCE: 364
ctctcccccg accaggggcg gttctgaagg acttcaccgt gtccggcaac ctactgttta    60
tgtcagttcg ggaccaggac agggaaggcg ctgggcggat gagggtggtg ggttgggggc   120
tgggatccgc ctccccggag gggcagaaag ctagagatct cagaacaccc aaacacaagg   180
tctcagaaca gagacctggt acaccaggcc cgccgccacc cgagggagcc cagggagatg   240
ggtgcagagg tgtcgccttt aatgtgatgt tctctgcccc tcacatttag ccgactgact   300
gctgcagacc accgccaact gcagctctcc atcagctcct gtctccagca gctttc       356

<210> SEQ ID NO 365
<211> LENGTH: 105
<212> TYPE: DNA
<213> ORGANISM: Artificial Sequence
<220> FEATURE:
<223> OTHER INFORMATION: synthetic sequence

<400> SEQUENCE: 365
gctgactgca gggcctgctc cctgcccccc acctccaggt tggggccttc accatggatc    60
agttccctga atcagtgaca gaaaactttg agtacgatga tttgg                   105

<210> SEQ ID NO 366
<211> LENGTH: 107
<212> TYPE: DNA
<213> ORGANISM: Artificial Sequence
<220> FEATURE:
<223> OTHER INFORMATION: synthetic sequence

<400> SEQUENCE: 366
gtggctgact ggcagatcca gaggttccct tggcagtcca cgccaggcct tcaccatgga    60
tcagttccct gaatcagtga cagaaaactt tgagtacgat gatttgg                  107

<210> SEQ ID NO 367
<211> LENGTH: 130
<212> TYPE: DNA
<213> ORGANISM: Artificial Sequence
<220> FEATURE:
<223> OTHER INFORMATION: synthetic sequence

<400> SEQUENCE: 367
gcgtttaagt tggcagactt ggatttcagg aagagctctc tggcttctgg gtggagaatg    60
gccagtgggg ccttcaccat ggatcagttc cctgaatcag tgacagaaaa ctttgagtac   120
gatgatttgg                                                          130

<210> SEQ ID NO 368
<211> LENGTH: 85
<212> TYPE: DNA
<213> ORGANISM: Artificial Sequence
<220> FEATURE:
<223> OTHER INFORMATION: synthetic sequence

<400> SEQUENCE: 368
ctcggaacac cacagcgact agaggccttc accatggatc agttccctga atcagtgaca    60
gaaaactttg agtacgatga tttgg                                         85
```

<210> SEQ ID NO 369
<211> LENGTH: 116
<212> TYPE: DNA
<213> ORGANISM: Artificial Sequence
<220> FEATURE:
<223> OTHER INFORMATION: synthetic sequence

<400> SEQUENCE: 369
acctattatc ggcctagacc aagacgctac gtagagcctc ctgaaatgat tgggcctatg    60
cggcccgagc agttcagtga tgaagtggaa ccagcaacac ctgaagaagg ggaacc      116

<210> SEQ ID NO 370
<211> LENGTH: 116
<212> TYPE: DNA
<213> ORGANISM: Artificial Sequence
<220> FEATURE:
<223> OTHER INFORMATION: synthetic sequence

<400> SEQUENCE: 370
acctattatc ggcctagacc aagacgctac gtagagcctc ctgaaatgat tgggcctatg    60
cggcccgagc agttcagtga tgaagtggaa ccagcaacac ctgaagaagg ggaacc      116

<210> SEQ ID NO 371
<211> LENGTH: 116
<212> TYPE: DNA
<213> ORGANISM: Artificial Sequence
<220> FEATURE:
<223> OTHER INFORMATION: synthetic sequence

<400> SEQUENCE: 371
acctattatc ggcctagacc aagacgctac gtagagcctc ctgaaatgat tgggcctatg    60
cggcccgagc agttcagtga tgaagtggaa ccagcaacac ctgaagaagg ggaacc      116

<210> SEQ ID NO 372
<211> LENGTH: 116
<212> TYPE: DNA
<213> ORGANISM: Artificial Sequence
<220> FEATURE:
<223> OTHER INFORMATION: synthetic sequence

<400> SEQUENCE: 372
acctattatc ggcctagacc aagacgctac gtagagcctc ctgaaatgat tgggcctatg    60
cggcccgagc agttcagtga tgaagtggaa ccagcaacac ctgaagaagg ggaacc      116

<210> SEQ ID NO 373
<211> LENGTH: 116
<212> TYPE: DNA
<213> ORGANISM: Artificial Sequence
<220> FEATURE:
<223> OTHER INFORMATION: synthetic sequence

<400> SEQUENCE: 373
acctattatc ggcctagacc aagacgctac gtagagcctc ctgaaatgat tgggcctatg    60
cggcccgagc agttcagtga tgaagtggaa ccagcaacac ctgaagaagg ggaacc      116

<210> SEQ ID NO 374
<211> LENGTH: 112
<212> TYPE: DNA
<213> ORGANISM: Artificial Sequence
<220> FEATURE:
<223> OTHER INFORMATION: synthetic sequence

<400> SEQUENCE: 374

```
gacatgtccc aagtttcagg gaaggaaagc cccctgtaa gcgatactcc agatgagggc      60
gatgagccca tgccgatccc cgaggacctc tccaccacct cgggaggaca gc            112
```

<210> SEQ ID NO 375
<211> LENGTH: 87
<212> TYPE: DNA
<213> ORGANISM: Artificial Sequence
<220> FEATURE:
<223> OTHER INFORMATION: synthetic sequence

<400> SEQUENCE: 375

```
ctcagattac tacaaccgat ccacctcacc ttggaatctc caccgcaatg aggaccctga    60
gagatatccc tctgtgatct gggaggc                                        87
```

<210> SEQ ID NO 376
<211> LENGTH: 85
<212> TYPE: DNA
<213> ORGANISM: Artificial Sequence
<220> FEATURE:
<223> OTHER INFORMATION: synthetic sequence

<400> SEQUENCE: 376

```
cttaatcagc aatatcaacg taatagttct ggaactaaag ggatctgaaa caacattcat    60
gtgtgaatat gctgatgaga cagca                                          85
```

<210> SEQ ID NO 377
<211> LENGTH: 82
<212> TYPE: DNA
<213> ORGANISM: Artificial Sequence
<220> FEATURE:
<223> OTHER INFORMATION: synthetic sequence

<400> SEQUENCE: 377

```
cttccacaaa tgcagggaga agacagaaac acagactaac atgcccttca tgtgattctt    60
atgagaaaaa accacccaaa ga                                             82
```

<210> SEQ ID NO 378
<211> LENGTH: 86
<212> TYPE: DNA
<213> ORGANISM: Artificial Sequence
<220> FEATURE:
<223> OTHER INFORMATION: synthetic sequence

<400> SEQUENCE: 378

```
gacgttcgtc tcattgggga gaaactgttc cacggagtca gtatgagtga gcgctgctat    60
ctgatgaagc aggtgctgaa cttcac                                         86
```

<210> SEQ ID NO 379
<211> LENGTH: 722
<212> TYPE: DNA
<213> ORGANISM: Artificial Sequence
<220> FEATURE:
<223> OTHER INFORMATION: synthetic sequence

<400> SEQUENCE: 379

```
ccatgtcgct catggtcgtc agcatggcgt gtgttgggtt cttcttgctg cagggggcct    60
ggccacatga gggagtccac agaaaacctt ccctcctggc ccacccaggt ccctggtga    120 aatcagaaga gacagtcatc ctgcaatgtt ggtcagatgt caggtttgag cacttccttc   180
tgcacagaga gggaagtat aaggacactt gcacctcat ggagagcac catgatgggg     240 tctccaaggc caacttctcc atcggtccca tgatgcaaga ccttgcaggg acctacagat   300
```

```
gctacggttc tgttactcac tccccctatc agttgtcagc tcccagtgac cctctggaca      360
tcgtcatcac aggtctatat gagaaacctt ctctctcagc ccagccgggc cccacggttt      420
tggcaggaga gagcgtgacc ttgtcctgca gctcccggag ctcctatgac atgtaccatc      480
tatccaggga gggggaggcc catgaacgta ggttctctgc agggcccaag gtcaacggaa      540
cattccaggc cgactttcct ctgggccctg ccacccacgg aggaacctac agatgcttcg      600
gctctttccg tgactctccc tatgagtggt caaactcgag tgacccactg cttgtttctg      660
tcacaggaaa cccttcaaat agttggcctt cacccactga accaagctcc aaaaccggta      720
ac                                                                    722
```

<210> SEQ ID NO 380
<211> LENGTH: 103
<212> TYPE: DNA
<213> ORGANISM: Artificial Sequence
<220> FEATURE:
<223> OTHER INFORMATION: synthetic sequence

<400> SEQUENCE: 380

```
ctatgagtgg tcaaactcga gtgacccact gcttgtttct gtcacaggaa acccttcaaa       60
tagttggcct tcacccactg aaccaagctc caaaaccggt aac                        103
```

<210> SEQ ID NO 381
<211> LENGTH: 79
<212> TYPE: DNA
<213> ORGANISM: Artificial Sequence
<220> FEATURE:
<223> OTHER INFORMATION: synthetic sequence

<400> SEQUENCE: 381

```
tgggacacca cagagcagca ctgaaggaga agacctgcct gtgggtcccc atcgcccaag       60
tcctgcccac actcccacc                                                   79
```

<210> SEQ ID NO 382
<211> LENGTH: 113
<212> TYPE: DNA
<213> ORGANISM: Artificial Sequence
<220> FEATURE:
<223> OTHER INFORMATION: synthetic sequence

<400> SEQUENCE: 382

```
tccgagctca cccagcagct ggcgcaggcc accggcaagc cccccagta catcgcggtg        60 cacgtggtcc cggaccagct catggccttc ggcggctcca gcgagccgtg cgc            113
```

<210> SEQ ID NO 383
<211> LENGTH: 133
<212> TYPE: DNA
<213> ORGANISM: Artificial Sequence
<220> FEATURE:
<223> OTHER INFORMATION: synthetic sequence

<400> SEQUENCE: 383

```
tcacttctcg ctcgacacag ccagagctgg aggtgggtgc ccggcacgga ggggcctgcg       60
gaccaatggc tctgccctgc accttagggc tcgggatgct gctggccctg ccaggggcct     120
tgggctcggg tgg                                                        133
```

<210> SEQ ID NO 384
<211> LENGTH: 116
<212> TYPE: DNA

```
<213> ORGANISM: Artificial Sequence
<220> FEATURE:
<223> OTHER INFORMATION: synthetic sequence

<400> SEQUENCE: 384
ctcggagaaa atcttctatg tgtatatgaa gagaaagtat gaggctatga ctaaactagg    60
tttcaaggcc accctcccac ctttcatgtg taataaacgg gccgaagact tccagg        116

<210> SEQ ID NO 385
<211> LENGTH: 122
<212> TYPE: DNA
<213> ORGANISM: Artificial Sequence
<220> FEATURE:
<223> OTHER INFORMATION: synthetic sequence

<400> SEQUENCE: 385
ctctctacga acatttcaac agcccacatc ccacccctgc acctgcggac atcagccaga    60
agcaagttca caggcctctg cagacccctg acctctctgg cttctactcc ctgacctcag   120
gc                                                                  122

<210> SEQ ID NO 386
<211> LENGTH: 78
<212> TYPE: DNA
<213> ORGANISM: Artificial Sequence
<220> FEATURE:
<223> OTHER INFORMATION: synthetic sequence

<400> SEQUENCE: 386
agataatacc taaagaggaa cactgtaaaa tgccagaagc aggtgaagag caaccacaag    60
tttaaatgaa gacaagct                                                 78

<210> SEQ ID NO 387
<211> LENGTH: 102
<212> TYPE: DNA
<213> ORGANISM: Artificial Sequence
<220> FEATURE:
<223> OTHER INFORMATION: synthetic sequence

<400> SEQUENCE: 387
gtgaaataca gaacccagcg agtgcaaact tcagtgaccc agtcaccctg aatgtcctct    60
atggcccaga tgcccccacc atttcccctt cagacaccta tt                      102

<210> SEQ ID NO 388
<211> LENGTH: 127
<212> TYPE: DNA
<213> ORGANISM: Artificial Sequence
<220> FEATURE:
<223> OTHER INFORMATION: synthetic sequence

<400> SEQUENCE: 388
caccaaagca gaggggcagg cagcacacca cccagcagcc agagcaccag cccagccatg    60
gtccttgagg tgagtgacca ccaagtgcta aatgacgccg aggttgccgc cctcctggag   120
aacttca                                                             127

<210> SEQ ID NO 389
<211> LENGTH: 105
<212> TYPE: DNA
<213> ORGANISM: Artificial Sequence
<220> FEATURE:
<223> OTHER INFORMATION: synthetic sequence

<400> SEQUENCE: 389
```
ccattgctca ggcatgggaa agcatcgcta cacatcagca ggaatatctg tcactgtgaa      60
agagctattt ccagctccag tgctgaatgc atctgtgaca tcccc                     105

<210> SEQ ID NO 390
<211> LENGTH: 102
<212> TYPE: DNA
<213> ORGANISM: Artificial Sequence
<220> FEATURE:
<223> OTHER INFORMATION: synthetic sequence

<400> SEQUENCE: 390
agcggctcct acttctgcag ggggcttgtt gggagtaaaa atgtgtcttc agagactgtg      60
aacatcacca tcactcaagg tttggcagtg tcaaccatct ca                        102

<210> SEQ ID NO 391
<211> LENGTH: 104
<212> TYPE: DNA
<213> ORGANISM: Artificial Sequence
<220> FEATURE:
<223> OTHER INFORMATION: synthetic sequence

<400> SEQUENCE: 391
ctggaaacag tactagcaaa ggccagacgt cttactcaac aacttccctg ccaccacctc      60
caccatccca tccggccagc caaccaccat tgccagcatc tcac                      104

<210> SEQ ID NO 392
<211> LENGTH: 104
<212> TYPE: DNA
<213> ORGANISM: Artificial Sequence
<220> FEATURE:
<223> OTHER INFORMATION: synthetic sequence

<400> SEQUENCE: 392
gcagcacgag gggctgcaag agcccctcac cctgagctgg gagccatctt cccagcccac      60
catccccatc atgggcatcg ttgctggcct ggctgtcctg gttg                      104

<210> SEQ ID NO 393
<211> LENGTH: 97
<212> TYPE: DNA
<213> ORGANISM: Artificial Sequence
<220> FEATURE:
<223> OTHER INFORMATION: synthetic sequence

<400> SEQUENCE: 393
aggaaggtgc atcaccatct acaggagaag aagaatggac ttgctaaatg acctagcact      60
attctctggc ctgatttatc atatcccttt tctcctc                              97

<210> SEQ ID NO 394
<211> LENGTH: 100
<212> TYPE: DNA
<213> ORGANISM: Artificial Sequence
<220> FEATURE:
<223> OTHER INFORMATION: synthetic sequence

<400> SEQUENCE: 394
gtgtggagac catcaaggaa gacatgaatg tcaagttttt caatagcaac aaaaagaaac      60
gagatgactt cgaaaagctg actaattatt cggtaactga                           100

<210> SEQ ID NO 395
<211> LENGTH: 133
<212> TYPE: DNA

```
<213> ORGANISM: Artificial Sequence
<220> FEATURE:
<223> OTHER INFORMATION: synthetic sequence

<400> SEQUENCE: 395
cgcggctgcc tgtctgctcc ggcagcacca tgtcgctctt ggtcgtcagc atggcgtgtg     60
ttgggttctt cttgctgcag ggggcctggc cacatgaggg agtccacaga aaaccttccc    120
tcctggccca ccc                                                       133

<210> SEQ ID NO 396
<211> LENGTH: 102
<212> TYPE: DNA
<213> ORGANISM: Artificial Sequence
<220> FEATURE:
<223> OTHER INFORMATION: synthetic sequence

<400> SEQUENCE: 396
aacttcatga agatgttctt tgatgcggag ctgtcccaga tgcagacgca tgtctctgac     60
acctcagtgg tcctctccat ggacaacaac cgcaacctgg ac                       102

<210> SEQ ID NO 397
<211> LENGTH: 108
<212> TYPE: DNA
<213> ORGANISM: Artificial Sequence
<220> FEATURE:
<223> OTHER INFORMATION: synthetic sequence

<400> SEQUENCE: 397
aaggagctga aagcgcgcaa taccaagaag gagggtgacc tgatagctgc tcaggctcgg     60
ctgaaggacc tggaggctct gctgaactcc aaggaggccg cactgagc                 108

<210> SEQ ID NO 398
<211> LENGTH: 107
<212> TYPE: DNA
<213> ORGANISM: Artificial Sequence
<220> FEATURE:
<223> OTHER INFORMATION: synthetic sequence

<400> SEQUENCE: 398
ctcccgagtg attgtcatga caacgaaaga agtggagaga ggaaagagta aatgtgtcaa     60
atactggcct gatgagtatg ctctaaaaga atatggcgtc atgcgtg                  107

<210> SEQ ID NO 399
<211> LENGTH: 22
<212> TYPE: DNA
<213> ORGANISM: Artificial Sequence
<220> FEATURE:
<223> OTHER INFORMATION: synthetic sequence

<400> SEQUENCE: 399
ttccatgucg aagaaccgag uc                                              22

<210> SEQ ID NO 400
<211> LENGTH: 20
<212> TYPE: DNA
<213> ORGANISM: Artificial Sequence
<220> FEATURE:
<223> OTHER INFORMATION: synthetic sequence

<400> SEQUENCE: 400
gcagcuacca ccagcacaut                                                 20
```

```
<210> SEQ ID NO 401
<211> LENGTH: 21
<212> TYPE: DNA
<213> ORGANISM: Artificial Sequence
<220> FEATURE:
<223> OTHER INFORMATION: synthetic sequence

<400> SEQUENCE: 401
cgtcaugaag ggtccucca a                                          21

<210> SEQ ID NO 402
<211> LENGTH: 21
<212> TYPE: DNA
<213> ORGANISM: Artificial Sequence
<220> FEATURE:
<223> OTHER INFORMATION: synthetic sequence

<400> SEQUENCE: 402
atggctgtcu gatggcatug a                                         21

<210> SEQ ID NO 403
<211> LENGTH: 21
<212> TYPE: DNA
<213> ORGANISM: Artificial Sequence
<220> FEATURE:
<223> OTHER INFORMATION: synthetic sequence

<400> SEQUENCE: 403
caatcctgca uccccauag t                                          21

<210> SEQ ID NO 404
<211> LENGTH: 26
<212> TYPE: DNA
<213> ORGANISM: Artificial Sequence
<220> FEATURE:
<223> OTHER INFORMATION: synthetic sequence

<400> SEQUENCE: 404
tgtctctctt tccucttctg ttccua                                    26

<210> SEQ ID NO 405
<211> LENGTH: 26
<212> TYPE: DNA
<213> ORGANISM: Artificial Sequence
<220> FEATURE:
<223> OTHER INFORMATION: synthetic sequence

<400> SEQUENCE: 405
gugaacagaa aactuggaac gaaagt                                    26

<210> SEQ ID NO 406
<211> LENGTH: 20
<212> TYPE: DNA
<213> ORGANISM: Artificial Sequence
<220> FEATURE:
<223> OTHER INFORMATION: synthetic sequence

<400> SEQUENCE: 406
cggtgtgcuc ctcactguaa                                           20

<210> SEQ ID NO 407
<211> LENGTH: 21
<212> TYPE: DNA
<213> ORGANISM: Artificial Sequence
<220> FEATURE:
<223> OTHER INFORMATION: synthetic sequence
```

<400> SEQUENCE: 407
ccaugacuca aggcacagac t                                      21

<210> SEQ ID NO 408
<211> LENGTH: 21
<212> TYPE: DNA
<213> ORGANISM: Artificial Sequence
<220> FEATURE:
<223> OTHER INFORMATION: synthetic sequence

<400> SEQUENCE: 408
tccccacauc actgucgaaa c                                      21

<210> SEQ ID NO 409
<211> LENGTH: 26
<212> TYPE: DNA
<213> ORGANISM: Artificial Sequence
<220> FEATURE:
<223> OTHER INFORMATION: synthetic sequence

<400> SEQUENCE: 409
tctcaacaua agacagtgac caguct                                 26

<210> SEQ ID NO 410
<211> LENGTH: 22
<212> TYPE: DNA
<213> ORGANISM: Artificial Sequence
<220> FEATURE:
<223> OTHER INFORMATION: synthetic sequence

<400> SEQUENCE: 410
accagggagg ugtcgttaua gt                                     22

<210> SEQ ID NO 411
<211> LENGTH: 19
<212> TYPE: DNA
<213> ORGANISM: Artificial Sequence
<220> FEATURE:
<223> OTHER INFORMATION: synthetic sequence

<400> SEQUENCE: 411
ctggccagua cacctguca                                         19

<210> SEQ ID NO 412
<211> LENGTH: 23
<212> TYPE: DNA
<213> ORGANISM: Artificial Sequence
<220> FEATURE:
<223> OTHER INFORMATION: synthetic sequence

<400> SEQUENCE: 412
tcttggccuc gcatctuaga aag                                    23

<210> SEQ ID NO 413
<211> LENGTH: 19
<212> TYPE: DNA
<213> ORGANISM: Artificial Sequence
<220> FEATURE:
<223> OTHER INFORMATION: synthetic sequence

<400> SEQUENCE: 413
gcaaacccgg cuactugga                                         19

<210> SEQ ID NO 414
<211> LENGTH: 22

```
<212> TYPE: DNA
<213> ORGANISM: Artificial Sequence
<220> FEATURE:
<223> OTHER INFORMATION: synthetic sequence

<400> SEQUENCE: 414
catcatacac cuccacgctg ut                                              22

<210> SEQ ID NO 415
<211> LENGTH: 26
<212> TYPE: DNA
<213> ORGANISM: Artificial Sequence
<220> FEATURE:
<223> OTHER INFORMATION: synthetic sequence

<400> SEQUENCE: 415
tgtggaatta ucacccatca tcaucc                                          26

<210> SEQ ID NO 416
<211> LENGTH: 24
<212> TYPE: DNA
<213> ORGANISM: Artificial Sequence
<220> FEATURE:
<223> OTHER INFORMATION: synthetic sequence

<400> SEQUENCE: 416
acaagatcuc ccaagtcctc caua                                            24

<210> SEQ ID NO 417
<211> LENGTH: 20
<212> TYPE: DNA
<213> ORGANISM: Artificial Sequence
<220> FEATURE:
<223> OTHER INFORMATION: synthetic sequence

<400> SEQUENCE: 417
tgutcctgca ucagcaccaa                                                 20

<210> SEQ ID NO 418
<211> LENGTH: 28
<212> TYPE: DNA
<213> ORGANISM: Artificial Sequence
<220> FEATURE:
<223> OTHER INFORMATION: synthetic sequence

<400> SEQUENCE: 418
gctgaatctg gguttagaca tgttugaa                                        28

<210> SEQ ID NO 419
<211> LENGTH: 19
<212> TYPE: DNA
<213> ORGANISM: Artificial Sequence
<220> FEATURE:
<223> OTHER INFORMATION: synthetic sequence

<400> SEQUENCE: 419
cagcccugga atcccugat                                                  19

<210> SEQ ID NO 420
<211> LENGTH: 20
<212> TYPE: DNA
<213> ORGANISM: Artificial Sequence
<220> FEATURE:
<223> OTHER INFORMATION: synthetic sequence

<400> SEQUENCE: 420
```
aaactgggcc accucgatut                                              20

<210> SEQ ID NO 421
<211> LENGTH: 28
<212> TYPE: DNA
<213> ORGANISM: Artificial Sequence
<220> FEATURE:
<223> OTHER INFORMATION: synthetic sequence

<400> SEQUENCE: 421
gaaatggaua aactcatcgc ucagaaag                                     28

<210> SEQ ID NO 422
<211> LENGTH: 20
<212> TYPE: DNA
<213> ORGANISM: Artificial Sequence
<220> FEATURE:
<223> OTHER INFORMATION: synthetic sequence

<400> SEQUENCE: 422
ccgcccauca tcagaaguga                                              20

<210> SEQ ID NO 423
<211> LENGTH: 26
<212> TYPE: DNA
<213> ORGANISM: Artificial Sequence
<220> FEATURE:
<223> OTHER INFORMATION: synthetic sequence

<400> SEQUENCE: 423
cagcttgagt uaaacgaacg tactug                                       26

<210> SEQ ID NO 424
<211> LENGTH: 19
<212> TYPE: DNA
<213> ORGANISM: Artificial Sequence
<220> FEATURE:
<223> OTHER INFORMATION: synthetic sequence

<400> SEQUENCE: 424
cggcagcgug gtttctgua                                               19

<210> SEQ ID NO 425
<211> LENGTH: 20
<212> TYPE: DNA
<213> ORGANISM: Artificial Sequence
<220> FEATURE:
<223> OTHER INFORMATION: synthetic sequence

<400> SEQUENCE: 425
ctgagcaucc cucccaacat                                              20

<210> SEQ ID NO 426
<211> LENGTH: 21
<212> TYPE: DNA
<213> ORGANISM: Artificial Sequence
<220> FEATURE:
<223> OTHER INFORMATION: synthetic sequence

<400> SEQUENCE: 426
ttgttccagc ugtcccugaa g                                            21

<210> SEQ ID NO 427
<211> LENGTH: 20
<212> TYPE: DNA
<213> ORGANISM: Artificial Sequence
<220> FEATURE:
<223> OTHER INFORMATION: synthetic sequence

<400> SEQUENCE: 427
ggcccaucag tucacacagg                    20

<210> SEQ ID NO 428
<211> LENGTH: 21
<212> TYPE: DNA
<213> ORGANISM: Artificial Sequence
<220> FEATURE:
<223> OTHER INFORMATION: synthetic sequence

<400> SEQUENCE: 428
ctgcagtccu ttctccaguc t                  21

<210> SEQ ID NO 429
<211> LENGTH: 19
<212> TYPE: DNA
<213> ORGANISM: Artificial Sequence
<220> FEATURE:
<223> OTHER INFORMATION: synthetic sequence

<400> SEQUENCE: 429
cuagagtgcu cgcagcagt                     19

<210> SEQ ID NO 430
<211> LENGTH: 21
<212> TYPE: DNA
<213> ORGANISM: Artificial Sequence
<220> FEATURE:
<223> OTHER INFORMATION: synthetic sequence

<400> SEQUENCE: 430
actggcagca ggaugagttu c                  21

<210> SEQ ID NO 431
<211> LENGTH: 27
<212> TYPE: DNA
<213> ORGANISM: Artificial Sequence
<220> FEATURE:
<223> OTHER INFORMATION: synthetic sequence

<400> SEQUENCE: 431
gtctaccaca aguactccct gauaaag             27

<210> SEQ ID NO 432
<211> LENGTH: 28
<212> TYPE: DNA
<213> ORGANISM: Artificial Sequence
<220> FEATURE:
<223> OTHER INFORMATION: synthetic sequence

<400> SEQUENCE: 432
accatcagtg tugatatcca actcttug             28

<210> SEQ ID NO 433
<211> LENGTH: 22
<212> TYPE: DNA
<213> ORGANISM: Artificial Sequence
<220> FEATURE:
<223> OTHER INFORMATION: synthetic sequence

<400> SEQUENCE: 433
gcttctcuga aaggctctcc ut                  22

<210> SEQ ID NO 434
<211> LENGTH: 19
<212> TYPE: DNA
<213> ORGANISM: Artificial Sequence
<220> FEATURE:
<223> OTHER INFORMATION: synthetic sequence

<400> SEQUENCE: 434
aaauacggcu gcaccgagt                                                  19

<210> SEQ ID NO 435
<211> LENGTH: 20
<212> TYPE: DNA
<213> ORGANISM: Artificial Sequence
<220> FEATURE:
<223> OTHER INFORMATION: synthetic sequence

<400> SEQUENCE: 435
ccaggctaca ugcaggacut                                                 20

<210> SEQ ID NO 436
<211> LENGTH: 21
<212> TYPE: DNA
<213> ORGANISM: Artificial Sequence
<220> FEATURE:
<223> OTHER INFORMATION: synthetic sequence

<400> SEQUENCE: 436
gggtgacacc uggaagttgu a                                               21

<210> SEQ ID NO 437
<211> LENGTH: 20
<212> TYPE: DNA
<213> ORGANISM: Artificial Sequence
<220> FEATURE:
<223> OTHER INFORMATION: synthetic sequence

<400> SEQUENCE: 437
tggttgtccu cgtcctccut                                                 20

<210> SEQ ID NO 438
<211> LENGTH: 24
<212> TYPE: DNA
<213> ORGANISM: Artificial Sequence
<220> FEATURE:
<223> OTHER INFORMATION: synthetic sequence

<400> SEQUENCE: 438
agtctgaggu ccagtagaag tgut                                            24

<210> SEQ ID NO 439
<211> LENGTH: 22
<212> TYPE: DNA
<213> ORGANISM: Artificial Sequence
<220> FEATURE:
<223> OTHER INFORMATION: synthetic sequence

<400> SEQUENCE: 439
tggaggtguc ctacagguga aa                                              22

<210> SEQ ID NO 440
<211> LENGTH: 21
<212> TYPE: DNA
<213> ORGANISM: Artificial Sequence
<220> FEATURE:
<223> OTHER INFORMATION: synthetic sequence -continued

<400> SEQUENCE: 440
ggcaggguag agctgtaacu g                                              21

<210> SEQ ID NO 441
<211> LENGTH: 21
<212> TYPE: DNA
<213> ORGANISM: Artificial Sequence
<220> FEATURE:
<223> OTHER INFORMATION: synthetic sequence

<400> SEQUENCE: 441
tgcagaacgg cugcctaatu t                                              21

<210> SEQ ID NO 442
<211> LENGTH: 28
<212> TYPE: DNA
<213> ORGANISM: Artificial Sequence
<220> FEATURE:
<223> OTHER INFORMATION: synthetic sequence

<400> SEQUENCE: 442
caagactctg ttutctaaat caggcaut                                       28

<210> SEQ ID NO 443
<211> LENGTH: 26
<212> TYPE: DNA
<213> ORGANISM: Artificial Sequence
<220> FEATURE:
<223> OTHER INFORMATION: synthetic sequence

<400> SEQUENCE: 443
gcagaagagg aagauttcug aagagt                                         26

<210> SEQ ID NO 444
<211> LENGTH: 24
<212> TYPE: DNA
<213> ORGANISM: Artificial Sequence
<220> FEATURE:
<223> OTHER INFORMATION: synthetic sequence

<400> SEQUENCE: 444
tcaagttcca ggugaaatgg caut                                           24

<210> SEQ ID NO 445
<211> LENGTH: 20
<212> TYPE: DNA
<213> ORGANISM: Artificial Sequence
<220> FEATURE:
<223> OTHER INFORMATION: synthetic sequence

<400> SEQUENCE: 445
cagacagccu agctggacut                                                20

<210> SEQ ID NO 446
<211> LENGTH: 22
<212> TYPE: DNA
<213> ORGANISM: Artificial Sequence
<220> FEATURE:
<223> OTHER INFORMATION: synthetic sequence

<400> SEQUENCE: 446
cgtgaaggau ggcagcaaag ua                                             22

<210> SEQ ID NO 447

```
<211> LENGTH: 21
<212> TYPE: DNA
<213> ORGANISM: Artificial Sequence
<220> FEATURE:
<223> OTHER INFORMATION: synthetic sequence

<400> SEQUENCE: 447
ctcccauccc cagaagggua t                                                 21

<210> SEQ ID NO 448
<211> LENGTH: 22
<212> TYPE: DNA
<213> ORGANISM: Artificial Sequence
<220> FEATURE:
<223> OTHER INFORMATION: synthetic sequence

<400> SEQUENCE: 448
tctgtcugcc aggattctcu ca                                                22

<210> SEQ ID NO 449
<211> LENGTH: 19
<212> TYPE: DNA
<213> ORGANISM: Artificial Sequence
<220> FEATURE:
<223> OTHER INFORMATION: synthetic sequence

<400> SEQUENCE: 449
accgaguguc ccagacaga                                                    19

<210> SEQ ID NO 450
<211> LENGTH: 27
<212> TYPE: DNA
<213> ORGANISM: Artificial Sequence
<220> FEATURE:
<223> OTHER INFORMATION: synthetic sequence

<400> SEQUENCE: 450
tcaactggat acugcagagg tatuaca                                           27

<210> SEQ ID NO 451
<211> LENGTH: 20
<212> TYPE: DNA
<213> ORGANISM: Artificial Sequence
<220> FEATURE:
<223> OTHER INFORMATION: synthetic sequence

<400> SEQUENCE: 451
gtccacugac aggctgtugt                                                   20

<210> SEQ ID NO 452
<211> LENGTH: 19
<212> TYPE: DNA
<213> ORGANISM: Artificial Sequence
<220> FEATURE:
<223> OTHER INFORMATION: synthetic sequence

<400> SEQUENCE: 452
atcgttgccc ucgcatcut                                                    19

<210> SEQ ID NO 453
<211> LENGTH: 23
<212> TYPE: DNA
<213> ORGANISM: Artificial Sequence
<220> FEATURE:
<223> OTHER INFORMATION: synthetic sequence

<400> SEQUENCE: 453
```
gactttgugt ggacacugag aga                                            23

<210> SEQ ID NO 454
<211> LENGTH: 25
<212> TYPE: DNA
<213> ORGANISM: Artificial Sequence
<220> FEATURE:
<223> OTHER INFORMATION: synthetic sequence

<400> SEQUENCE: 454
atacagagtc ugggcaggtu aaaag                                          25

<210> SEQ ID NO 455
<211> LENGTH: 20
<212> TYPE: DNA
<213> ORGANISM: Artificial Sequence
<220> FEATURE:
<223> OTHER INFORMATION: synthetic sequence

<400> SEQUENCE: 455
gcgcaagggu ttctggttug                                                20

<210> SEQ ID NO 456
<211> LENGTH: 22
<212> TYPE: DNA
<213> ORGANISM: Artificial Sequence
<220> FEATURE:
<223> OTHER INFORMATION: synthetic sequence

<400> SEQUENCE: 456
ccagtgccau aaggcatcat ug                                             22

<210> SEQ ID NO 457
<211> LENGTH: 23
<212> TYPE: DNA
<213> ORGANISM: Artificial Sequence
<220> FEATURE:
<223> OTHER INFORMATION: synthetic sequence

<400> SEQUENCE: 457
gctggacaga gcuacagacc uat                                            23

<210> SEQ ID NO 458
<211> LENGTH: 19
<212> TYPE: DNA
<213> ORGANISM: Artificial Sequence
<220> FEATURE:
<223> OTHER INFORMATION: synthetic sequence

<400> SEQUENCE: 458
gccgcugcac tttttcugg                                                 19

<210> SEQ ID NO 459
<211> LENGTH: 20
<212> TYPE: DNA
<213> ORGANISM: Artificial Sequence
<220> FEATURE:
<223> OTHER INFORMATION: synthetic sequence

<400> SEQUENCE: 459
ctcagctuag ccagguggaa                                                20

<210> SEQ ID NO 460
<211> LENGTH: 22
<212> TYPE: DNA

```
<213> ORGANISM: Artificial Sequence
<220> FEATURE:
<223> OTHER INFORMATION: synthetic sequence

<400> SEQUENCE: 460
gagatgacaa gutccggagu ga                                           22

<210> SEQ ID NO 461
<211> LENGTH: 21
<212> TYPE: DNA
<213> ORGANISM: Artificial Sequence
<220> FEATURE:
<223> OTHER INFORMATION: synthetic sequence

<400> SEQUENCE: 461
acgtgcagca agaugacauc a                                            21

<210> SEQ ID NO 462
<211> LENGTH: 21
<212> TYPE: DNA
<213> ORGANISM: Artificial Sequence
<220> FEATURE:
<223> OTHER INFORMATION: synthetic sequence

<400> SEQUENCE: 462
gtccttgacc cautgctccu t                                            21

<210> SEQ ID NO 463
<211> LENGTH: 21
<212> TYPE: DNA
<213> ORGANISM: Artificial Sequence
<220> FEATURE:
<223> OTHER INFORMATION: synthetic sequence

<400> SEQUENCE: 463
agggtucacc ttggcaucaa t                                            21

<210> SEQ ID NO 464
<211> LENGTH: 22
<212> TYPE: DNA
<213> ORGANISM: Artificial Sequence
<220> FEATURE:
<223> OTHER INFORMATION: synthetic sequence

<400> SEQUENCE: 464
tgctcugttg aatguccaca ct                                           22

<210> SEQ ID NO 465
<211> LENGTH: 29
<212> TYPE: DNA
<213> ORGANISM: Artificial Sequence
<220> FEATURE:
<223> OTHER INFORMATION: synthetic sequence

<400> SEQUENCE: 465
cggtatccuc gaattcaaag taucaaagt                                    29

<210> SEQ ID NO 466
<211> LENGTH: 28
<212> TYPE: DNA
<213> ORGANISM: Artificial Sequence
<220> FEATURE:
<223> OTHER INFORMATION: synthetic sequence

<400> SEQUENCE: 466
gagatgagau aaaacccatc acagtuga                                     28
```

<210> SEQ ID NO 467
<211> LENGTH: 25
<212> TYPE: DNA
<213> ORGANISM: Artificial Sequence
<220> FEATURE:
<223> OTHER INFORMATION: synthetic sequence

<400> SEQUENCE: 467
cctgagatca ccuaaaaagc tgcua                                              25

<210> SEQ ID NO 468
<211> LENGTH: 20
<212> TYPE: DNA
<213> ORGANISM: Artificial Sequence
<220> FEATURE:
<223> OTHER INFORMATION: synthetic sequence

<400> SEQUENCE: 468
tggtttggcu ggtgtcgtut                                                    20

<210> SEQ ID NO 469
<211> LENGTH: 26
<212> TYPE: DNA
<213> ORGANISM: Artificial Sequence
<220> FEATURE:
<223> OTHER INFORMATION: synthetic sequence

<400> SEQUENCE: 469
gtctgtgtgg uttgaagcag aattut                                             26

<210> SEQ ID NO 470
<211> LENGTH: 20
<212> TYPE: DNA
<213> ORGANISM: Artificial Sequence
<220> FEATURE:
<223> OTHER INFORMATION: synthetic sequence

<400> SEQUENCE: 470
gacagggtcu ggctacagut                                                    20

<210> SEQ ID NO 471
<211> LENGTH: 22
<212> TYPE: DNA
<213> ORGANISM: Artificial Sequence
<220> FEATURE:
<223> OTHER INFORMATION: synthetic sequence

<400> SEQUENCE: 471
accacacgga cugagactga ut                                                 22

<210> SEQ ID NO 472
<211> LENGTH: 19
<212> TYPE: DNA
<213> ORGANISM: Artificial Sequence
<220> FEATURE:
<223> OTHER INFORMATION: synthetic sequence

<400> SEQUENCE: 472
gtccguagga gcccatgug                                                     19

<210> SEQ ID NO 473
<211> LENGTH: 21
<212> TYPE: DNA
<213> ORGANISM: Artificial Sequence
<220> FEATURE:

```
<223> OTHER INFORMATION: synthetic sequence

<400> SEQUENCE: 473
tgtgccugga ccatagucag a                                              21

<210> SEQ ID NO 474
<211> LENGTH: 22
<212> TYPE: DNA
<213> ORGANISM: Artificial Sequence
<220> FEATURE:
<223> OTHER INFORMATION: synthetic sequence

<400> SEQUENCE: 474
aacagcauct gctggtugaa ga                                             22

<210> SEQ ID NO 475
<211> LENGTH: 21
<212> TYPE: DNA
<213> ORGANISM: Artificial Sequence
<220> FEATURE:
<223> OTHER INFORMATION: synthetic sequence

<400> SEQUENCE: 475
ggccagaaga gcugagacau c                                              21

<210> SEQ ID NO 476
<211> LENGTH: 19
<212> TYPE: DNA
<213> ORGANISM: Artificial Sequence
<220> FEATURE:
<223> OTHER INFORMATION: synthetic sequence

<400> SEQUENCE: 476
ggctgcgaut tgctucaca                                                 19

<210> SEQ ID NO 477
<211> LENGTH: 23
<212> TYPE: DNA
<213> ORGANISM: Artificial Sequence
<220> FEATURE:
<223> OTHER INFORMATION: synthetic sequence

<400> SEQUENCE: 477
agtggaaaga ugaactgcga ugt                                            23

<210> SEQ ID NO 478
<211> LENGTH: 23
<212> TYPE: DNA
<213> ORGANISM: Artificial Sequence
<220> FEATURE:
<223> OTHER INFORMATION: synthetic sequence

<400> SEQUENCE: 478
agtggaaaga ugaactgcga ugt                                            23

<210> SEQ ID NO 479
<211> LENGTH: 19
<212> TYPE: DNA
<213> ORGANISM: Artificial Sequence
<220> FEATURE:
<223> OTHER INFORMATION: synthetic sequence

<400> SEQUENCE: 479
tggcggagga ggutaccut                                                 19
```

```
<210> SEQ ID NO 480
<211> LENGTH: 20
<212> TYPE: DNA
<213> ORGANISM: Artificial Sequence
<220> FEATURE:
<223> OTHER INFORMATION: synthetic sequence

<400> SEQUENCE: 480
cgatgggcuc agcttucaga                                               20

<210> SEQ ID NO 481
<211> LENGTH: 21
<212> TYPE: DNA
<213> ORGANISM: Artificial Sequence
<220> FEATURE:
<223> OTHER INFORMATION: synthetic sequence

<400> SEQUENCE: 481
acaaaaccuc guccacggaa t                                             21

<210> SEQ ID NO 482
<211> LENGTH: 21
<212> TYPE: DNA
<213> ORGANISM: Artificial Sequence
<220> FEATURE:
<223> OTHER INFORMATION: synthetic sequence

<400> SEQUENCE: 482
cagaugagga gguccagcaa a                                             21

<210> SEQ ID NO 483
<211> LENGTH: 20
<212> TYPE: DNA
<213> ORGANISM: Artificial Sequence
<220> FEATURE:
<223> OTHER INFORMATION: synthetic sequence

<400> SEQUENCE: 483
tgctccucgg gtgatacuga                                               20

<210> SEQ ID NO 484
<211> LENGTH: 20
<212> TYPE: DNA
<213> ORGANISM: Artificial Sequence
<220> FEATURE:
<223> OTHER INFORMATION: synthetic sequence

<400> SEQUENCE: 484
cugaaagcca gggagtuggt                                               20

<210> SEQ ID NO 485
<211> LENGTH: 24
<212> TYPE: DNA
<213> ORGANISM: Artificial Sequence
<220> FEATURE:
<223> OTHER INFORMATION: synthetic sequence

<400> SEQUENCE: 485 cutgttttcac tcucacaccc agat                                         24

<210> SEQ ID NO 486
<211> LENGTH: 23
<212> TYPE: DNA
<213> ORGANISM: Artificial Sequence
<220> FEATURE:
<223> OTHER INFORMATION: synthetic sequence
```

<400> SEQUENCE: 486
tgtgctguca accctaagtt ugt    23

<210> SEQ ID NO 487
<211> LENGTH: 20
<212> TYPE: DNA
<213> ORGANISM: Artificial Sequence
<220> FEATURE:
<223> OTHER INFORMATION: synthetic sequence

<400> SEQUENCE: 487
caggcgaugt cuagcacagg    20

<210> SEQ ID NO 488
<211> LENGTH: 20
<212> TYPE: DNA
<213> ORGANISM: Artificial Sequence
<220> FEATURE:
<223> OTHER INFORMATION: synthetic sequence

<400> SEQUENCE: 488
ggaugcgcca ggaagttuca    20

<210> SEQ ID NO 489
<211> LENGTH: 18
<212> TYPE: DNA
<213> ORGANISM: Artificial Sequence
<220> FEATURE:
<223> OTHER INFORMATION: synthetic sequence

<400> SEQUENCE: 489
ctctggcuct ccgtcgut    18

<210> SEQ ID NO 490
<211> LENGTH: 21
<212> TYPE: DNA
<213> ORGANISM: Artificial Sequence
<220> FEATURE:
<223> OTHER INFORMATION: synthetic sequence

<400> SEQUENCE: 490
gtgggaagau ggctccatuc t    21

<210> SEQ ID NO 491
<211> LENGTH: 22
<212> TYPE: DNA
<213> ORGANISM: Artificial Sequence
<220> FEATURE:
<223> OTHER INFORMATION: synthetic sequence

<400> SEQUENCE: 491
acacagucct ttgcaugcag at    22

<210> SEQ ID NO 492
<211> LENGTH: 24
<212> TYPE: DNA
<213> ORGANISM: Artificial Sequence
<220> FEATURE:
<223> OTHER INFORMATION: synthetic sequence

<400> SEQUENCE: 492
tcatctcugg aacaaacugg caaa    24

<210> SEQ ID NO 493
<211> LENGTH: 21

```
<212> TYPE: DNA
<213> ORGANISM: Artificial Sequence
<220> FEATURE:
<223> OTHER INFORMATION: synthetic sequence

<400> SEQUENCE: 493
cttgctgaac ugcaggaagu c                                              21

<210> SEQ ID NO 494
<211> LENGTH: 23
<212> TYPE: DNA
<213> ORGANISM: Artificial Sequence
<220> FEATURE:
<223> OTHER INFORMATION: synthetic sequence

<400> SEQUENCE: 494
agcgugcaga taaugacaag gaa                                            23

<210> SEQ ID NO 495
<211> LENGTH: 22
<212> TYPE: DNA
<213> ORGANISM: Artificial Sequence
<220> FEATURE:
<223> OTHER INFORMATION: synthetic sequence

<400> SEQUENCE: 495
gatttgacgg cucctctacu gt                                             22

<210> SEQ ID NO 496
<211> LENGTH: 20
<212> TYPE: DNA
<213> ORGANISM: Artificial Sequence
<220> FEATURE:
<223> OTHER INFORMATION: synthetic sequence

<400> SEQUENCE: 496
ccuggaacag gcagctguat                                                20

<210> SEQ ID NO 497
<211> LENGTH: 24
<212> TYPE: DNA
<213> ORGANISM: Artificial Sequence
<220> FEATURE:
<223> OTHER INFORMATION: synthetic sequence

<400> SEQUENCE: 497
ttccagggaa gutcaaggca auag                                           24

<210> SEQ ID NO 498
<211> LENGTH: 23
<212> TYPE: DNA
<213> ORGANISM: Artificial Sequence
<220> FEATURE:
<223> OTHER INFORMATION: synthetic sequence

<400> SEQUENCE: 498
actactccag uccctccaau gac                                            23

<210> SEQ ID NO 499
<211> LENGTH: 21
<212> TYPE: DNA
<213> ORGANISM: Artificial Sequence
<220> FEATURE:
<223> OTHER INFORMATION: synthetic sequence

<400> SEQUENCE: 499
```
gccgacacuc gtagtaucca t                                             21

<210> SEQ ID NO 500
<211> LENGTH: 23
<212> TYPE: DNA
<213> ORGANISM: Artificial Sequence
<220> FEATURE:
<223> OTHER INFORMATION: synthetic sequence

<400> SEQUENCE: 500
aagtggatga tugcagtgag gut                                           23

<210> SEQ ID NO 501
<211> LENGTH: 27
<212> TYPE: DNA
<213> ORGANISM: Artificial Sequence
<220> FEATURE:
<223> OTHER INFORMATION: synthetic sequence

<400> SEQUENCE: 501
caaatcugaa gcatagttuc caaccat                                       27

<210> SEQ ID NO 502
<211> LENGTH: 19
<212> TYPE: DNA
<213> ORGANISM: Artificial Sequence
<220> FEATURE:
<223> OTHER INFORMATION: synthetic sequence

<400> SEQUENCE: 502
tgaccctcug cagctccua                                                19

<210> SEQ ID NO 503
<211> LENGTH: 21
<212> TYPE: DNA
<213> ORGANISM: Artificial Sequence
<220> FEATURE:
<223> OTHER INFORMATION: synthetic sequence

<400> SEQUENCE: 503
gacagtgaug aaggcgaugg a                                             21

<210> SEQ ID NO 504
<211> LENGTH: 19
<212> TYPE: DNA
<213> ORGANISM: Artificial Sequence
<220> FEATURE:
<223> OTHER INFORMATION: synthetic sequence

<400> SEQUENCE: 504
cgucatcgtc auccccgat                                                19

<210> SEQ ID NO 505
<211> LENGTH: 26
<212> TYPE: DNA
<213> ORGANISM: Artificial Sequence
<220> FEATURE:
<223> OTHER INFORMATION: synthetic sequence

<400> SEQUENCE: 505
cagccacaaa gaggguatat tggtua                                        26

<210> SEQ ID NO 506
<211> LENGTH: 26
<212> TYPE: DNA
<213> ORGANISM: Artificial Sequence

```
<220> FEATURE:
<223> OTHER INFORMATION: synthetic sequence

<400> SEQUENCE: 506
gatcttacac atutgttcca tggcut                                              26

<210> SEQ ID NO 507
<211> LENGTH: 19
<212> TYPE: DNA
<213> ORGANISM: Artificial Sequence
<220> FEATURE:
<223> OTHER INFORMATION: synthetic sequence

<400> SEQUENCE: 507
gatgtcccau ggcguaggt                                                      19

<210> SEQ ID NO 508
<211> LENGTH: 22
<212> TYPE: DNA
<213> ORGANISM: Artificial Sequence
<220> FEATURE:
<223> OTHER INFORMATION: synthetic sequence

<400> SEQUENCE: 508
cttggaccau tctcaugcca ac                                                  22

<210> SEQ ID NO 509
<211> LENGTH: 23
<212> TYPE: DNA
<213> ORGANISM: Artificial Sequence
<220> FEATURE:
<223> OTHER INFORMATION: synthetic sequence

<400> SEQUENCE: 509
gcacauccta tggguaacca gaa                                                 23

<210> SEQ ID NO 510
<211> LENGTH: 24
<212> TYPE: DNA
<213> ORGANISM: Artificial Sequence
<220> FEATURE:
<223> OTHER INFORMATION: synthetic sequence

<400> SEQUENCE: 510
agagccaaca uttgcttcaa gtuc                                                24

<210> SEQ ID NO 511
<211> LENGTH: 20
<212> TYPE: DNA
<213> ORGANISM: Artificial Sequence
<220> FEATURE:
<223> OTHER INFORMATION: synthetic sequence

<400> SEQUENCE: 511
ggaagcugag ctggtgaugt                                                     20

<210> SEQ ID NO 512
<211> LENGTH: 20
<212> TYPE: DNA
<213> ORGANISM: Artificial Sequence
<220> FEATURE:
<223> OTHER INFORMATION: synthetic sequence

<400> SEQUENCE: 512
tgcaugtucc aggagcacaa                                                     20
```

<210> SEQ ID NO 513
<211> LENGTH: 22
<212> TYPE: DNA
<213> ORGANISM: Artificial Sequence
<220> FEATURE:
<223> OTHER INFORMATION: synthetic sequence

<400> SEQUENCE: 513
cttctccttc ugccacttcu ca                                            22

<210> SEQ ID NO 514
<211> LENGTH: 22
<212> TYPE: DNA
<213> ORGANISM: Artificial Sequence
<220> FEATURE:
<223> OTHER INFORMATION: synthetic sequence

<400> SEQUENCE: 514
atgaggaacu tgaggcaagu ca                                            22

<210> SEQ ID NO 515
<211> LENGTH: 23
<212> TYPE: DNA
<213> ORGANISM: Artificial Sequence
<220> FEATURE:
<223> OTHER INFORMATION: synthetic sequence

<400> SEQUENCE: 515
ccaggccccc guagatacat aua                                           23

<210> SEQ ID NO 516
<211> LENGTH: 21
<212> TYPE: DNA
<213> ORGANISM: Artificial Sequence
<220> FEATURE:
<223> OTHER INFORMATION: synthetic sequence

<400> SEQUENCE: 516
cggcgcucat gaguaagaac a                                             21

<210> SEQ ID NO 517
<211> LENGTH: 24
<212> TYPE: DNA
<213> ORGANISM: Artificial Sequence
<220> FEATURE:
<223> OTHER INFORMATION: synthetic sequence

<400> SEQUENCE: 517
cggacactug aacttcttcc ugat                                          24

<210> SEQ ID NO 518
<211> LENGTH: 22
<212> TYPE: DNA
<213> ORGANISM: Artificial Sequence
<220> FEATURE:
<223> OTHER INFORMATION: synthetic sequence

<400> SEQUENCE: 518
cuggttgtga gucaccaagg aa                                            22

<210> SEQ ID NO 519
<211> LENGTH: 20
<212> TYPE: DNA
<213> ORGANISM: Artificial Sequence
<220> FEATURE:
<223> OTHER INFORMATION: synthetic sequence

<400> SEQUENCE: 519
tgcaautgcu ccagccagaa                                        20

<210> SEQ ID NO 520
<211> LENGTH: 21
<212> TYPE: DNA
<213> ORGANISM: Artificial Sequence
<220> FEATURE:
<223> OTHER INFORMATION: synthetic sequence

<400> SEQUENCE: 520
acagucacag ccattguagc a                                      21

<210> SEQ ID NO 521
<211> LENGTH: 26
<212> TYPE: DNA
<213> ORGANISM: Artificial Sequence
<220> FEATURE:
<223> OTHER INFORMATION: synthetic sequence

<400> SEQUENCE: 521
ggaaattgaa guggaaggct tguaaa                                 26

<210> SEQ ID NO 522
<211> LENGTH: 20
<212> TYPE: DNA
<213> ORGANISM: Artificial Sequence
<220> FEATURE:
<223> OTHER INFORMATION: synthetic sequence

<400> SEQUENCE: 522
tgagccugga attgcagcut                                        20

<210> SEQ ID NO 523
<211> LENGTH: 22
<212> TYPE: DNA
<213> ORGANISM: Artificial Sequence
<220> FEATURE:
<223> OTHER INFORMATION: synthetic sequence

<400> SEQUENCE: 523
tggctgttat ugctccaagg ut                                     22

<210> SEQ ID NO 524
<211> LENGTH: 21
<212> TYPE: DNA
<213> ORGANISM: Artificial Sequence
<220> FEATURE:
<223> OTHER INFORMATION: synthetic sequence

<400> SEQUENCE: 524
ctctgttcgc ucaggtcctu t                                      21

<210> SEQ ID NO 525
<211> LENGTH: 19
<212> TYPE: DNA
<213> ORGANISM: Artificial Sequence
<220> FEATURE:
<223> OTHER INFORMATION: synthetic sequence

<400> SEQUENCE: 525
gcctccutcc guaccacat                                         19

<210> SEQ ID NO 526

<211> LENGTH: 20
<212> TYPE: DNA
<213> ORGANISM: Artificial Sequence
<220> FEATURE:
<223> OTHER INFORMATION: synthetic sequence

<400> SEQUENCE: 526
tcccaagugc aacctctguc                                                    20

<210> SEQ ID NO 527
<211> LENGTH: 23
<212> TYPE: DNA
<213> ORGANISM: Artificial Sequence
<220> FEATURE:
<223> OTHER INFORMATION: synthetic sequence

<400> SEQUENCE: 527
ggtgcagaag cucttgtauc act                                                23

<210> SEQ ID NO 528
<211> LENGTH: 27
<212> TYPE: DNA
<213> ORGANISM: Artificial Sequence
<220> FEATURE:
<223> OTHER INFORMATION: synthetic sequence

<400> SEQUENCE: 528
cactatggga cugagtaaca ttctcut                                            27

<210> SEQ ID NO 529
<211> LENGTH: 21
<212> TYPE: DNA
<213> ORGANISM: Artificial Sequence
<220> FEATURE:
<223> OTHER INFORMATION: synthetic sequence

<400> SEQUENCE: 529
ctagctcacu caggcttugg t                                                  21

<210> SEQ ID NO 530
<211> LENGTH: 20
<212> TYPE: DNA
<213> ORGANISM: Artificial Sequence
<220> FEATURE:
<223> OTHER INFORMATION: synthetic sequence

<400> SEQUENCE: 530
ctactgcugc cggauccaaa                                                    20

<210> SEQ ID NO 531
<211> LENGTH: 19
<212> TYPE: DNA
<213> ORGANISM: Artificial Sequence
<220> FEATURE:
<223> OTHER INFORMATION: synthetic sequence

<400> SEQUENCE: 531
tgtccccugg tgguaagca                                                     19

<210> SEQ ID NO 532
<211> LENGTH: 22
<212> TYPE: DNA
<213> ORGANISM: Artificial Sequence
<220> FEATURE:
<223> OTHER INFORMATION: synthetic sequence

<400> SEQUENCE: 532
ggcctttgut cagtttcugc aa                                         22

<210> SEQ ID NO 533
<211> LENGTH: 22
<212> TYPE: DNA
<213> ORGANISM: Artificial Sequence
<220> FEATURE:
<223> OTHER INFORMATION: synthetic sequence

<400> SEQUENCE: 533
gtccgctccu gttccttgau at                                         22

<210> SEQ ID NO 534
<211> LENGTH: 22
<212> TYPE: DNA
<213> ORGANISM: Artificial Sequence
<220> FEATURE:
<223> OTHER INFORMATION: synthetic sequence

<400> SEQUENCE: 534
cccctatucc tgtaacgguc aa                                         22

<210> SEQ ID NO 535
<211> LENGTH: 21
<212> TYPE: DNA
<213> ORGANISM: Artificial Sequence
<220> FEATURE:
<223> OTHER INFORMATION: synthetic sequence

<400> SEQUENCE: 535
gcataccccu gctgaacuga g                                          21

<210> SEQ ID NO 536
<211> LENGTH: 22
<212> TYPE: DNA
<213> ORGANISM: Artificial Sequence
<220> FEATURE:
<223> OTHER INFORMATION: synthetic sequence

<400> SEQUENCE: 536
cggaagacag uggcatctac ut                                         22

<210> SEQ ID NO 537
<211> LENGTH: 21
<212> TYPE: DNA
<213> ORGANISM: Artificial Sequence
<220> FEATURE:
<223> OTHER INFORMATION: synthetic sequence

<400> SEQUENCE: 537
gtaaccggca cacuctctuc t                                          21

<210> SEQ ID NO 538
<211> LENGTH: 23
<212> TYPE: DNA
<213> ORGANISM: Artificial Sequence
<220> FEATURE:
<223> OTHER INFORMATION: synthetic sequence

<400> SEQUENCE: 538
gtggatgacu gagtaccuga acc                                        23

<210> SEQ ID NO 539
<211> LENGTH: 21
<212> TYPE: DNA

```
<213> ORGANISM: Artificial Sequence
<220> FEATURE:
<223> OTHER INFORMATION: synthetic sequence

<400> SEQUENCE: 539
ggccaaacug agcagagtcu t                                              21

<210> SEQ ID NO 540
<211> LENGTH: 18
<212> TYPE: DNA
<213> ORGANISM: Artificial Sequence
<220> FEATURE:
<223> OTHER INFORMATION: synthetic sequence

<400> SEQUENCE: 540
cgaaugguac ccgagcct                                                  18

<210> SEQ ID NO 541
<211> LENGTH: 22
<212> TYPE: DNA
<213> ORGANISM: Artificial Sequence
<220> FEATURE:
<223> OTHER INFORMATION: synthetic sequence

<400> SEQUENCE: 541
gctgccagut cacaatcatc ug                                             22

<210> SEQ ID NO 542
<211> LENGTH: 19
<212> TYPE: DNA
<213> ORGANISM: Artificial Sequence
<220> FEATURE:
<223> OTHER INFORMATION: synthetic sequence

<400> SEQUENCE: 542
gcgtgtcuct ggacagcua                                                 19

<210> SEQ ID NO 543
<211> LENGTH: 20
<212> TYPE: DNA
<213> ORGANISM: Artificial Sequence
<220> FEATURE:
<223> OTHER INFORMATION: synthetic sequence

<400> SEQUENCE: 543
gggtccaacu gcatccugaa                                                20

<210> SEQ ID NO 544
<211> LENGTH: 25
<212> TYPE: DNA
<213> ORGANISM: Artificial Sequence
<220> FEATURE:
<223> OTHER INFORMATION: synthetic sequence

<400> SEQUENCE: 544
ccagactaug acagctcttg gaaua                                          25

<210> SEQ ID NO 545
<211> LENGTH: 24
<212> TYPE: DNA
<213> ORGANISM: Artificial Sequence
<220> FEATURE:
<223> OTHER INFORMATION: synthetic sequence

<400> SEQUENCE: 545
cttggatgac cutcttcagu cgat                                           24
```

<210> SEQ ID NO 546
<211> LENGTH: 23
<212> TYPE: DNA
<213> ORGANISM: Artificial Sequence
<220> FEATURE:
<223> OTHER INFORMATION: synthetic sequence

<400> SEQUENCE: 546
gaaccgaaga cgugttugca aat                                          23

<210> SEQ ID NO 547
<211> LENGTH: 21
<212> TYPE: DNA
<213> ORGANISM: Artificial Sequence
<220> FEATURE:
<223> OTHER INFORMATION: synthetic sequence

<400> SEQUENCE: 547
ggaaggacut gctcccucaa a                                            21

<210> SEQ ID NO 548
<211> LENGTH: 26
<212> TYPE: DNA
<213> ORGANISM: Artificial Sequence
<220> FEATURE:
<223> OTHER INFORMATION: synthetic sequence

<400> SEQUENCE: 548
ggaagatgga tucatacctg ctgaug                                       26

<210> SEQ ID NO 549
<211> LENGTH: 26
<212> TYPE: DNA
<213> ORGANISM: Artificial Sequence
<220> FEATURE:
<223> OTHER INFORMATION: synthetic sequence

<400> SEQUENCE: 549
agttcaacat ggutccttcc ttguag                                       26

<210> SEQ ID NO 550
<211> LENGTH: 22
<212> TYPE: DNA
<213> ORGANISM: Artificial Sequence
<220> FEATURE:
<223> OTHER INFORMATION: synthetic sequence

<400> SEQUENCE: 550
tggcgguctt cagaaucaac at                                           22

<210> SEQ ID NO 551
<211> LENGTH: 27
<212> TYPE: DNA
<213> ORGANISM: Artificial Sequence
<220> FEATURE:
<223> OTHER INFORMATION: synthetic sequence

<400> SEQUENCE: 551
gcttctgacg guatgtatta agtucct                                      27

<210> SEQ ID NO 552
<211> LENGTH: 20
<212> TYPE: DNA
<213> ORGANISM: Artificial Sequence
<220> FEATURE:

<223> OTHER INFORMATION: synthetic sequence

<400> SEQUENCE: 552
cacgcaggga gaagugaucc                                                20

<210> SEQ ID NO 553
<211> LENGTH: 21
<212> TYPE: DNA
<213> ORGANISM: Artificial Sequence
<220> FEATURE:
<223> OTHER INFORMATION: synthetic sequence

<400> SEQUENCE: 553
gcagcgttuc cagaggtgau a                                              21

<210> SEQ ID NO 554
<211> LENGTH: 21
<212> TYPE: DNA
<213> ORGANISM: Artificial Sequence
<220> FEATURE:
<223> OTHER INFORMATION: synthetic sequence

<400> SEQUENCE: 554
gtcggaguac gggaacauca c                                              21

<210> SEQ ID NO 555
<211> LENGTH: 19
<212> TYPE: DNA
<213> ORGANISM: Artificial Sequence
<220> FEATURE:
<223> OTHER INFORMATION: synthetic sequence

<400> SEQUENCE: 555
gctgaccgcu gcttctuca                                                 19

<210> SEQ ID NO 556
<211> LENGTH: 22
<212> TYPE: DNA
<213> ORGANISM: Artificial Sequence
<220> FEATURE:
<223> OTHER INFORMATION: synthetic sequence

<400> SEQUENCE: 556
agagctacca ugtcctctug ga                                             22

<210> SEQ ID NO 557
<211> LENGTH: 20
<212> TYPE: DNA
<213> ORGANISM: Artificial Sequence
<220> FEATURE:
<223> OTHER INFORMATION: synthetic sequence

<400> SEQUENCE: 557
cggaacaccu ggcagtctut                                                20

<210> SEQ ID NO 558
<211> LENGTH: 20
<212> TYPE: DNA
<213> ORGANISM: Artificial Sequence
<220> FEATURE:
<223> OTHER INFORMATION: synthetic sequence

<400> SEQUENCE: 558
ctgggtctut ggcctgtuca                                                20

```
<210> SEQ ID NO 559
<211> LENGTH: 19
<212> TYPE: DNA
<213> ORGANISM: Artificial Sequence
<220> FEATURE:
<223> OTHER INFORMATION: synthetic sequence

<400> SEQUENCE: 559
ggcccacutc cggtatuct                                               19

<210> SEQ ID NO 560
<211> LENGTH: 21
<212> TYPE: DNA
<213> ORGANISM: Artificial Sequence
<220> FEATURE:
<223> OTHER INFORMATION: synthetic sequence

<400> SEQUENCE: 560
accaagcaag acugugagac c                                            21

<210> SEQ ID NO 561
<211> LENGTH: 27
<212> TYPE: DNA
<213> ORGANISM: Artificial Sequence
<220> FEATURE:
<223> OTHER INFORMATION: synthetic sequence

<400> SEQUENCE: 561
gtgtttctct cugaagattc ggtaugt                                      27

<210> SEQ ID NO 562
<211> LENGTH: 20
<212> TYPE: DNA
<213> ORGANISM: Artificial Sequence
<220> FEATURE:
<223> OTHER INFORMATION: synthetic sequence

<400> SEQUENCE: 562
gctgggcutc acggacauag                                              20

<210> SEQ ID NO 563
<211> LENGTH: 23
<212> TYPE: DNA
<213> ORGANISM: Artificial Sequence
<220> FEATURE:
<223> OTHER INFORMATION: synthetic sequence

<400> SEQUENCE: 563
ttttcccaat guagccagtg uca                                          23

<210> SEQ ID NO 564
<211> LENGTH: 20
<212> TYPE: DNA
<213> ORGANISM: Artificial Sequence
<220> FEATURE:
<223> OTHER INFORMATION: synthetic sequence

<400> SEQUENCE: 564
gcgcccugaa gacagaaugt                                              20

<210> SEQ ID NO 565
<211> LENGTH: 22
<212> TYPE: DNA
<213> ORGANISM: Artificial Sequence
<220> FEATURE:
<223> OTHER INFORMATION: synthetic sequence
```

<400> SEQUENCE: 565
cctgttggtc uatgcgtctg ua					22

<210> SEQ ID NO 566
<211> LENGTH: 22
<212> TYPE: DNA
<213> ORGANISM: Artificial Sequence
<220> FEATURE:
<223> OTHER INFORMATION: synthetic sequence

<400> SEQUENCE: 566
cttctctguc acctggcuca at					22

<210> SEQ ID NO 567
<211> LENGTH: 19
<212> TYPE: DNA
<213> ORGANISM: Artificial Sequence
<220> FEATURE:
<223> OTHER INFORMATION: synthetic sequence

<400> SEQUENCE: 567
gcgaugagcc agcaaucag					19

<210> SEQ ID NO 568
<211> LENGTH: 22
<212> TYPE: DNA
<213> ORGANISM: Artificial Sequence
<220> FEATURE:
<223> OTHER INFORMATION: synthetic sequence

<400> SEQUENCE: 568
ctacgtgaag auccgccatu ct					22

<210> SEQ ID NO 569
<211> LENGTH: 19
<212> TYPE: DNA
<213> ORGANISM: Artificial Sequence
<220> FEATURE:
<223> OTHER INFORMATION: synthetic sequence

<400> SEQUENCE: 569
tggtcccagu cccacagut					19

<210> SEQ ID NO 570
<211> LENGTH: 21
<212> TYPE: DNA
<213> ORGANISM: Artificial Sequence
<220> FEATURE:
<223> OTHER INFORMATION: synthetic sequence

<400> SEQUENCE: 570
ccauctgcat uggacccaac a					21

<210> SEQ ID NO 571
<211> LENGTH: 22
<212> TYPE: DNA
<213> ORGANISM: Artificial Sequence
<220> FEATURE:
<223> OTHER INFORMATION: synthetic sequence

<400> SEQUENCE: 571
gcacuggaat gttcucccca aa					22

<210> SEQ ID NO 572
<211> LENGTH: 24

```
<212> TYPE: DNA
<213> ORGANISM: Artificial Sequence
<220> FEATURE:
<223> OTHER INFORMATION: synthetic sequence

<400> SEQUENCE: 572
tgaactctcc cuatgtgtgg tcut                                      24

<210> SEQ ID NO 573
<211> LENGTH: 21
<212> TYPE: DNA
<213> ORGANISM: Artificial Sequence
<220> FEATURE:
<223> OTHER INFORMATION: synthetic sequence

<400> SEQUENCE: 573
ccgacaucag agacacacug g                                         21

<210> SEQ ID NO 574
<211> LENGTH: 22
<212> TYPE: DNA
<213> ORGANISM: Artificial Sequence
<220> FEATURE:
<223> OTHER INFORMATION: synthetic sequence

<400> SEQUENCE: 574
tgtggacauc acctgctact uc                                        22

<210> SEQ ID NO 575
<211> LENGTH: 20
<212> TYPE: DNA
<213> ORGANISM: Artificial Sequence
<220> FEATURE:
<223> OTHER INFORMATION: synthetic sequence

<400> SEQUENCE: 575
atgggctccu tggactcauc                                           20

<210> SEQ ID NO 576
<211> LENGTH: 20
<212> TYPE: DNA
<213> ORGANISM: Artificial Sequence
<220> FEATURE:
<223> OTHER INFORMATION: synthetic sequence

<400> SEQUENCE: 576
gtcgcugacc gtgaacgaua                                           20

<210> SEQ ID NO 577
<211> LENGTH: 22
<212> TYPE: DNA
<213> ORGANISM: Artificial Sequence
<220> FEATURE:
<223> OTHER INFORMATION: synthetic sequence

<400> SEQUENCE: 577
atggcuccaa gcaatggaau ct                                        22

<210> SEQ ID NO 578
<211> LENGTH: 19
<212> TYPE: DNA
<213> ORGANISM: Artificial Sequence
<220> FEATURE:
<223> OTHER INFORMATION: synthetic sequence

<400> SEQUENCE: 578
```
tgccgccuca cucagaaag                                              19

<210> SEQ ID NO 579
<211> LENGTH: 20
<212> TYPE: DNA
<213> ORGANISM: Artificial Sequence
<220> FEATURE:
<223> OTHER INFORMATION: synthetic sequence

<400> SEQUENCE: 579
acugaagcga caaggtgugt                                             20

<210> SEQ ID NO 580
<211> LENGTH: 22
<212> TYPE: DNA
<213> ORGANISM: Artificial Sequence
<220> FEATURE:
<223> OTHER INFORMATION: synthetic sequence

<400> SEQUENCE: 580
catctggttc uccctggttc ut                                          22

<210> SEQ ID NO 581
<211> LENGTH: 24
<212> TYPE: DNA
<213> ORGANISM: Artificial Sequence
<220> FEATURE:
<223> OTHER INFORMATION: synthetic sequence

<400> SEQUENCE: 581
cugagggaaa ggacaagaug aagt                                        24

<210> SEQ ID NO 582
<211> LENGTH: 26
<212> TYPE: DNA
<213> ORGANISM: Artificial Sequence
<220> FEATURE:
<223> OTHER INFORMATION: synthetic sequence

<400> SEQUENCE: 582
tgacaccata gaugaagagg atucca                                      26

<210> SEQ ID NO 583
<211> LENGTH: 21
<212> TYPE: DNA
<213> ORGANISM: Artificial Sequence
<220> FEATURE:
<223> OTHER INFORMATION: synthetic sequence

<400> SEQUENCE: 583
caacaacacc ucggaggtcu a                                           21

<210> SEQ ID NO 584
<211> LENGTH: 23
<212> TYPE: DNA
<213> ORGANISM: Artificial Sequence
<220> FEATURE:
<223> OTHER INFORMATION: synthetic sequence

<400> SEQUENCE: 584
ggcacgauga tgaagaggau gat                                         23

<210> SEQ ID NO 585
<211> LENGTH: 24
<212> TYPE: DNA
<213> ORGANISM: Artificial Sequence

```
<220> FEATURE:
<223> OTHER INFORMATION: synthetic sequence

<400> SEQUENCE: 585
caattgattg augcucacca gcut                                                  24

<210> SEQ ID NO 586
<211> LENGTH: 20
<212> TYPE: DNA
<213> ORGANISM: Artificial Sequence
<220> FEATURE:
<223> OTHER INFORMATION: synthetic sequence

<400> SEQUENCE: 586
ccucuccuuc cugccagaca                                                       20

<210> SEQ ID NO 587
<211> LENGTH: 19
<212> TYPE: DNA
<213> ORGANISM: Artificial Sequence
<220> FEATURE:
<223> OTHER INFORMATION: synthetic sequence

<400> SEQUENCE: 587
gcacaagcag cugauccga                                                        19

<210> SEQ ID NO 588
<211> LENGTH: 26
<212> TYPE: DNA
<213> ORGANISM: Artificial Sequence
<220> FEATURE:
<223> OTHER INFORMATION: synthetic sequence

<400> SEQUENCE: 588
ctctctcatg aucgtcttta gcctut                                                26

<210> SEQ ID NO 589
<211> LENGTH: 20
<212> TYPE: DNA
<213> ORGANISM: Artificial Sequence
<220> FEATURE:
<223> OTHER INFORMATION: synthetic sequence

<400> SEQUENCE: 589
actgagaccg agucgccuua                                                       20

<210> SEQ ID NO 590
<211> LENGTH: 20
<212> TYPE: DNA
<213> ORGANISM: Artificial Sequence
<220> FEATURE:
<223> OTHER INFORMATION: synthetic sequence

<400> SEQUENCE: 590 ggcucagga atggcuggat                                                        20

<210> SEQ ID NO 591
<211> LENGTH: 19
<212> TYPE: DNA
<213> ORGANISM: Artificial Sequence
<220> FEATURE:
<223> OTHER INFORMATION: synthetic sequence

<400> SEQUENCE: 591
gacattgccu gccatgcut                                                        19
```

<210> SEQ ID NO 592
<211> LENGTH: 24
<212> TYPE: DNA
<213> ORGANISM: Artificial Sequence
<220> FEATURE:
<223> OTHER INFORMATION: synthetic sequence

<400> SEQUENCE: 592
tctcctgcua agatggagtg tuca                                              24

<210> SEQ ID NO 593
<211> LENGTH: 20
<212> TYPE: DNA
<213> ORGANISM: Artificial Sequence
<220> FEATURE:
<223> OTHER INFORMATION: synthetic sequence

<400> SEQUENCE: 593
ccatgagcga cguggctaut                                                   20

<210> SEQ ID NO 594
<211> LENGTH: 20
<212> TYPE: DNA
<213> ORGANISM: Artificial Sequence
<220> FEATURE:
<223> OTHER INFORMATION: synthetic sequence

<400> SEQUENCE: 594
ctcacgtugg tccacaucct                                                   20

<210> SEQ ID NO 595
<211> LENGTH: 19
<212> TYPE: DNA
<213> ORGANISM: Artificial Sequence
<220> FEATURE:
<223> OTHER INFORMATION: synthetic sequence

<400> SEQUENCE: 595
tgcatuggaa gccgtggut                                                    19

<210> SEQ ID NO 596
<211> LENGTH: 26
<212> TYPE: DNA
<213> ORGANISM: Artificial Sequence
<220> FEATURE:
<223> OTHER INFORMATION: synthetic sequence

<400> SEQUENCE: 596
aaaagttccc guggtattca guaaca                                            26

<210> SEQ ID NO 597
<211> LENGTH: 24
<212> TYPE: DNA
<213> ORGANISM: Artificial Sequence
<220> FEATURE:
<223> OTHER INFORMATION: synthetic sequence

<400> SEQUENCE: 597
tggtggacaa gauggatgat gaug                                              24

<210> SEQ ID NO 598
<211> LENGTH: 25
<212> TYPE: DNA
<213> ORGANISM: Artificial Sequence
<220> FEATURE:
<223> OTHER INFORMATION: synthetic sequence

<400> SEQUENCE: 598
cctccgtgau gatgatcttc ttcut                                    25

<210> SEQ ID NO 599
<211> LENGTH: 27
<212> TYPE: DNA
<213> ORGANISM: Artificial Sequence
<220> FEATURE:
<223> OTHER INFORMATION: synthetic sequence

<400> SEQUENCE: 599
ccaacatcug cctttacatu gacaaac                                  27

<210> SEQ ID NO 600
<211> LENGTH: 20
<212> TYPE: DNA
<213> ORGANISM: Artificial Sequence
<220> FEATURE:
<223> OTHER INFORMATION: synthetic sequence

<400> SEQUENCE: 600
ggctcagacu ccggttctut                                          20

<210> SEQ ID NO 601
<211> LENGTH: 21
<212> TYPE: DNA
<213> ORGANISM: Artificial Sequence
<220> FEATURE:
<223> OTHER INFORMATION: synthetic sequence

<400> SEQUENCE: 601
cctgtccugc gtgtugaaag a                                        21

<210> SEQ ID NO 602
<211> LENGTH: 22
<212> TYPE: DNA
<213> ORGANISM: Artificial Sequence
<220> FEATURE:
<223> OTHER INFORMATION: synthetic sequence

<400> SEQUENCE: 602
gggaacuggg cagactcaaa ut                                       22

<210> SEQ ID NO 603
<211> LENGTH: 21
<212> TYPE: DNA
<213> ORGANISM: Artificial Sequence
<220> FEATURE:
<223> OTHER INFORMATION: synthetic sequence

<400> SEQUENCE: 603
cguctctgtu cagccaagga g                                        21

<210> SEQ ID NO 604
<211> LENGTH: 25
<212> TYPE: DNA
<213> ORGANISM: Artificial Sequence
<220> FEATURE:
<223> OTHER INFORMATION: synthetic sequence

<400> SEQUENCE: 604
tggtctatgt gutcgtatcg catut                                    25

<210> SEQ ID NO 605

```
<211> LENGTH: 26
<212> TYPE: DNA
<213> ORGANISM: Artificial Sequence
<220> FEATURE:
<223> OTHER INFORMATION: synthetic sequence

<400> SEQUENCE: 605
cccaaccgau atcatttctg atcugt                                          26

<210> SEQ ID NO 606
<211> LENGTH: 21
<212> TYPE: DNA
<213> ORGANISM: Artificial Sequence
<220> FEATURE:
<223> OTHER INFORMATION: synthetic sequence

<400> SEQUENCE: 606
ttgggccagu tttccttguc t                                               21

<210> SEQ ID NO 607
<211> LENGTH: 20
<212> TYPE: DNA
<213> ORGANISM: Artificial Sequence
<220> FEATURE:
<223> OTHER INFORMATION: synthetic sequence

<400> SEQUENCE: 607
cccaacuccc aaguggcaaa                                                 20

<210> SEQ ID NO 608
<211> LENGTH: 22
<212> TYPE: DNA
<213> ORGANISM: Artificial Sequence
<220> FEATURE:
<223> OTHER INFORMATION: synthetic sequence

<400> SEQUENCE: 608
tgugatcagg tugcaaagga ca                                              22

<210> SEQ ID NO 609
<211> LENGTH: 21
<212> TYPE: DNA
<213> ORGANISM: Artificial Sequence
<220> FEATURE:
<223> OTHER INFORMATION: synthetic sequence

<400> SEQUENCE: 609
gtaccgcugc atgatcagcu a                                               21

<210> SEQ ID NO 610
<211> LENGTH: 19
<212> TYPE: DNA
<213> ORGANISM: Artificial Sequence
<220> FEATURE:
<223> OTHER INFORMATION: synthetic sequence

<400> SEQUENCE: 610
gtagcccuca gccugacat                                                  19

<210> SEQ ID NO 611
<211> LENGTH: 19
<212> TYPE: DNA
<213> ORGANISM: Artificial Sequence
<220> FEATURE:
<223> OTHER INFORMATION: synthetic sequence

<400> SEQUENCE: 611
```
gcagucgggc attccuuca                                                19

<210> SEQ ID NO 612
<211> LENGTH: 22
<212> TYPE: DNA
<213> ORGANISM: Artificial Sequence
<220> FEATURE:
<223> OTHER INFORMATION: synthetic sequence

<400> SEQUENCE: 612
gtguagucag acgagcacuc at                                            22

<210> SEQ ID NO 613
<211> LENGTH: 21
<212> TYPE: DNA
<213> ORGANISM: Artificial Sequence
<220> FEATURE:
<223> OTHER INFORMATION: synthetic sequence

<400> SEQUENCE: 613
ctgcagcugg ttatccugac a                                             21

<210> SEQ ID NO 614
<211> LENGTH: 20
<212> TYPE: DNA
<213> ORGANISM: Artificial Sequence
<220> FEATURE:
<223> OTHER INFORMATION: synthetic sequence

<400> SEQUENCE: 614
aaggtggugg cgatggatut                                               20

<210> SEQ ID NO 615
<211> LENGTH: 20
<212> TYPE: DNA
<213> ORGANISM: Artificial Sequence
<220> FEATURE:
<223> OTHER INFORMATION: synthetic sequence

<400> SEQUENCE: 615
gcggaccauc ttctggauga                                               20

<210> SEQ ID NO 616
<211> LENGTH: 20
<212> TYPE: DNA
<213> ORGANISM: Artificial Sequence
<220> FEATURE:
<223> OTHER INFORMATION: synthetic sequence

<400> SEQUENCE: 616
agccttgguc agtgccatut                                               20

<210> SEQ ID NO 617
<211> LENGTH: 24
<212> TYPE: DNA
<213> ORGANISM: Artificial Sequence
<220> FEATURE:
<223> OTHER INFORMATION: synthetic sequence

<400> SEQUENCE: 617
gaagatguac caggtggagt ucaa                                          24

<210> SEQ ID NO 618
<211> LENGTH: 23
<212> TYPE: DNA

```
<213> ORGANISM: Artificial Sequence
<220> FEATURE:
<223> OTHER INFORMATION: synthetic sequence

<400> SEQUENCE: 618
gatttttgug gcacagtcuc act                                          23

<210> SEQ ID NO 619
<211> LENGTH: 22
<212> TYPE: DNA
<213> ORGANISM: Artificial Sequence
<220> FEATURE:
<223> OTHER INFORMATION: synthetic sequence

<400> SEQUENCE: 619
agaguttgta ugccgcaaga ca                                           22

<210> SEQ ID NO 620
<211> LENGTH: 22
<212> TYPE: DNA
<213> ORGANISM: Artificial Sequence
<220> FEATURE:
<223> OTHER INFORMATION: synthetic sequence

<400> SEQUENCE: 620
ggcgagtugg attttggacu ga                                           22

<210> SEQ ID NO 621
<211> LENGTH: 21
<212> TYPE: DNA
<213> ORGANISM: Artificial Sequence
<220> FEATURE:
<223> OTHER INFORMATION: synthetic sequence

<400> SEQUENCE: 621
gtgtgctugt ggactcucac a                                            21

<210> SEQ ID NO 622
<211> LENGTH: 22
<212> TYPE: DNA
<213> ORGANISM: Artificial Sequence
<220> FEATURE:
<223> OTHER INFORMATION: synthetic sequence

<400> SEQUENCE: 622
gccagcgaga ugagaaauag ca                                           22

<210> SEQ ID NO 623
<211> LENGTH: 26
<212> TYPE: DNA
<213> ORGANISM: Artificial Sequence
<220> FEATURE:
<223> OTHER INFORMATION: synthetic sequence

<400> SEQUENCE: 623
aattgtcata guggacatct gcauca                                       26

<210> SEQ ID NO 624
<211> LENGTH: 20
<212> TYPE: DNA
<213> ORGANISM: Artificial Sequence
<220> FEATURE:
<223> OTHER INFORMATION: synthetic sequence

<400> SEQUENCE: 624
gtggtggccu ctccttgtut                                              20
```

<210> SEQ ID NO 625
<211> LENGTH: 21
<212> TYPE: DNA
<213> ORGANISM: Artificial Sequence
<220> FEATURE:
<223> OTHER INFORMATION: synthetic sequence

<400> SEQUENCE: 625
agtttcacug cctggtgtug a                                                   21

<210> SEQ ID NO 626
<211> LENGTH: 22
<212> TYPE: DNA
<213> ORGANISM: Artificial Sequence
<220> FEATURE:
<223> OTHER INFORMATION: synthetic sequence

<400> SEQUENCE: 626
gtacacguga aggtgagcuc at                                                  22

<210> SEQ ID NO 627
<211> LENGTH: 26
<212> TYPE: DNA
<213> ORGANISM: Artificial Sequence
<220> FEATURE:
<223> OTHER INFORMATION: synthetic sequence

<400> SEQUENCE: 627
ggactaacau gttcaatgug ggacaa                                              26

<210> SEQ ID NO 628
<211> LENGTH: 21
<212> TYPE: DNA
<213> ORGANISM: Artificial Sequence
<220> FEATURE:
<223> OTHER INFORMATION: synthetic sequence

<400> SEQUENCE: 628
gagtggatut cccgtguagc a                                                   21

<210> SEQ ID NO 629
<211> LENGTH: 29
<212> TYPE: DNA
<213> ORGANISM: Artificial Sequence
<220> FEATURE:
<223> OTHER INFORMATION: synthetic sequence

<400> SEQUENCE: 629
catatcctta cuggagagat ggtagcuat                                           29

<210> SEQ ID NO 630
<211> LENGTH: 20
<212> TYPE: DNA
<213> ORGANISM: Artificial Sequence
<220> FEATURE:
<223> OTHER INFORMATION: synthetic sequence

<400> SEQUENCE: 630
ggctgtcuct agcacauggt                                                     20

<210> SEQ ID NO 631
<211> LENGTH: 25
<212> TYPE: DNA
<213> ORGANISM: Artificial Sequence
<220> FEATURE:

<223> OTHER INFORMATION: synthetic sequence

<400> SEQUENCE: 631
agagtgactu caaatgacag ugcaa                                          25

<210> SEQ ID NO 632
<211> LENGTH: 19
<212> TYPE: DNA
<213> ORGANISM: Artificial Sequence
<220> FEATURE:
<223> OTHER INFORMATION: synthetic sequence

<400> SEQUENCE: 632
tcaggaagcu ccgcagtuc                                                 19

<210> SEQ ID NO 633
<211> LENGTH: 21
<212> TYPE: DNA
<213> ORGANISM: Artificial Sequence
<220> FEATURE:
<223> OTHER INFORMATION: synthetic sequence

<400> SEQUENCE: 633
caccugcgtg augaggagaa a                                              21

<210> SEQ ID NO 634
<211> LENGTH: 22
<212> TYPE: DNA
<213> ORGANISM: Artificial Sequence
<220> FEATURE:
<223> OTHER INFORMATION: synthetic sequence

<400> SEQUENCE: 634
gtgggcttau ccaccatctu ct                                             22

<210> SEQ ID NO 635
<211> LENGTH: 20
<212> TYPE: DNA
<213> ORGANISM: Artificial Sequence
<220> FEATURE:
<223> OTHER INFORMATION: synthetic sequence

<400> SEQUENCE: 635
ctccgugctt cucagacagt                                                20

<210> SEQ ID NO 636
<211> LENGTH: 22
<212> TYPE: DNA
<213> ORGANISM: Artificial Sequence
<220> FEATURE:
<223> OTHER INFORMATION: synthetic sequence

<400> SEQUENCE: 636
gacctccttu gctggctcta ut                                             22

<210> SEQ ID NO 637
<211> LENGTH: 23
<212> TYPE: DNA
<213> ORGANISM: Artificial Sequence
<220> FEATURE:
<223> OTHER INFORMATION: synthetic sequence

<400> SEQUENCE: 637
cctcaacaac aaguttgccu cct                                            23

```
<210> SEQ ID NO 638
<211> LENGTH: 22
<212> TYPE: DNA
<213> ORGANISM: Artificial Sequence
<220> FEATURE:
<223> OTHER INFORMATION: synthetic sequence

<400> SEQUENCE: 638
agcaatcugg gcctcaaaga ug                                              22

<210> SEQ ID NO 639
<211> LENGTH: 23
<212> TYPE: DNA
<213> ORGANISM: Artificial Sequence
<220> FEATURE:
<223> OTHER INFORMATION: synthetic sequence

<400> SEQUENCE: 639
ccgagcaaaa gucaaatgau gcc                                             23

<210> SEQ ID NO 640
<211> LENGTH: 19
<212> TYPE: DNA
<213> ORGANISM: Artificial Sequence
<220> FEATURE:
<223> OTHER INFORMATION: synthetic sequence

<400> SEQUENCE: 640
ggtggtgagu cacgtgugt                                                  19

<210> SEQ ID NO 641
<211> LENGTH: 19
<212> TYPE: DNA
<213> ORGANISM: Artificial Sequence
<220> FEATURE:
<223> OTHER INFORMATION: synthetic sequence

<400> SEQUENCE: 641
gaacgcacug cccucagat                                                  19

<210> SEQ ID NO 642
<211> LENGTH: 26
<212> TYPE: DNA
<213> ORGANISM: Artificial Sequence
<220> FEATURE:
<223> OTHER INFORMATION: synthetic sequence

<400> SEQUENCE: 642
catcaaactc uggtctggaa gaauca                                          26

<210> SEQ ID NO 643
<211> LENGTH: 20
<212> TYPE: DNA
<213> ORGANISM: Artificial Sequence
<220> FEATURE:
<223> OTHER INFORMATION: synthetic sequence

<400> SEQUENCE: 643
gtgcgucagc agcaatgtut                                                 20

<210> SEQ ID NO 644
<211> LENGTH: 19
<212> TYPE: DNA
<213> ORGANISM: Artificial Sequence
<220> FEATURE:
<223> OTHER INFORMATION: synthetic sequence
```

<400> SEQUENCE: 644
gcaccacugt ggcatcuga                                              19

<210> SEQ ID NO 645
<211> LENGTH: 20
<212> TYPE: DNA
<213> ORGANISM: Artificial Sequence
<220> FEATURE:
<223> OTHER INFORMATION: synthetic sequence

<400> SEQUENCE: 645
cgggagggcu tctaucgaga                                             20

<210> SEQ ID NO 646
<211> LENGTH: 19
<212> TYPE: DNA
<213> ORGANISM: Artificial Sequence
<220> FEATURE:
<223> OTHER INFORMATION: synthetic sequence

<400> SEQUENCE: 646 ccauccugc agggacact                                               19

<210> SEQ ID NO 647
<211> LENGTH: 25
<212> TYPE: DNA
<213> ORGANISM: Artificial Sequence
<220> FEATURE:
<223> OTHER INFORMATION: synthetic sequence

<400> SEQUENCE: 647
cctcctccut acctagacaa ugaga                                       25

<210> SEQ ID NO 648
<211> LENGTH: 22
<212> TYPE: DNA
<213> ORGANISM: Artificial Sequence
<220> FEATURE:
<223> OTHER INFORMATION: synthetic sequence

<400> SEQUENCE: 648
caagcuauag caagccagga ct                                          22

<210> SEQ ID NO 649
<211> LENGTH: 25
<212> TYPE: DNA
<213> ORGANISM: Artificial Sequence
<220> FEATURE:
<223> OTHER INFORMATION: synthetic sequence

<400> SEQUENCE: 649
atgtcaucac aatggauccc aaaga                                       25

<210> SEQ ID NO 650
<211> LENGTH: 20
<212> TYPE: DNA
<213> ORGANISM: Artificial Sequence
<220> FEATURE:
<223> OTHER INFORMATION: synthetic sequence

<400> SEQUENCE: 650
acagcaggug atgauggcaa                                             20

<210> SEQ ID NO 651
<211> LENGTH: 28

```
<212> TYPE: DNA
<213> ORGANISM: Artificial Sequence
<220> FEATURE:
<223> OTHER INFORMATION: synthetic sequence

<400> SEQUENCE: 651
gtgagttgau catcgaattc uccaaaat                                          28

<210> SEQ ID NO 652
<211> LENGTH: 19
<212> TYPE: DNA
<213> ORGANISM: Artificial Sequence
<220> FEATURE:
<223> OTHER INFORMATION: synthetic sequence

<400> SEQUENCE: 652
ccaccacguc gtccatguc                                                    19

<210> SEQ ID NO 653
<211> LENGTH: 19
<212> TYPE: DNA
<213> ORGANISM: Artificial Sequence
<220> FEATURE:
<223> OTHER INFORMATION: synthetic sequence

<400> SEQUENCE: 653
cctgagcaag ccuggcaut                                                    19

<210> SEQ ID NO 654
<211> LENGTH: 22
<212> TYPE: DNA
<213> ORGANISM: Artificial Sequence
<220> FEATURE:
<223> OTHER INFORMATION: synthetic sequence

<400> SEQUENCE: 654
atcgagggug gtgtctgcta ua                                                22

<210> SEQ ID NO 655
<211> LENGTH: 20
<212> TYPE: DNA
<213> ORGANISM: Artificial Sequence
<220> FEATURE:
<223> OTHER INFORMATION: synthetic sequence

<400> SEQUENCE: 655
gagattcucg cccugagcaa                                                   20

<210> SEQ ID NO 656
<211> LENGTH: 23
<212> TYPE: DNA
<213> ORGANISM: Artificial Sequence
<220> FEATURE:
<223> OTHER INFORMATION: synthetic sequence

<400> SEQUENCE: 656
agatcttcuc cttcagtgcu cct                                               23

<210> SEQ ID NO 657
<211> LENGTH: 21
<212> TYPE: DNA
<213> ORGANISM: Artificial Sequence
<220> FEATURE:
<223> OTHER INFORMATION: synthetic sequence

<400> SEQUENCE: 657
```

```
gtgugagagc ccggaagatu t                                              21

<210> SEQ ID NO 658
<211> LENGTH: 21
<212> TYPE: DNA
<213> ORGANISM: Artificial Sequence
<220> FEATURE:
<223> OTHER INFORMATION: synthetic sequence

<400> SEQUENCE: 658
tctgggcggc aauacgattu t                                              21

<210> SEQ ID NO 659
<211> LENGTH: 21
<212> TYPE: DNA
<213> ORGANISM: Artificial Sequence
<220> FEATURE:
<223> OTHER INFORMATION: synthetic sequence

<400> SEQUENCE: 659
agtgaggccu tttgctggau t                                              21

<210> SEQ ID NO 660
<211> LENGTH: 21
<212> TYPE: DNA
<213> ORGANISM: Artificial Sequence
<220> FEATURE:
<223> OTHER INFORMATION: synthetic sequence

<400> SEQUENCE: 660
acagcutgag gctugaagac c                                              21

<210> SEQ ID NO 661
<211> LENGTH: 19
<212> TYPE: DNA
<213> ORGANISM: Artificial Sequence
<220> FEATURE:
<223> OTHER INFORMATION: synthetic sequence

<400> SEQUENCE: 661
cgccgcucaa gtgaggaut                                                 19

<210> SEQ ID NO 662
<211> LENGTH: 25
<212> TYPE: DNA
<213> ORGANISM: Artificial Sequence
<220> FEATURE:
<223> OTHER INFORMATION: synthetic sequence

<400> SEQUENCE: 662
ggguacccat gagtuagaag aggat                                          25

<210> SEQ ID NO 663
<211> LENGTH: 24
<212> TYPE: DNA
<213> ORGANISM: Artificial Sequence
<220> FEATURE:
<223> OTHER INFORMATION: synthetic sequence

<400> SEQUENCE: 663
gctggaagau catcgagagc taug                                           24

<210> SEQ ID NO 664
<211> LENGTH: 20
<212> TYPE: DNA
<213> ORGANISM: Artificial Sequence
```

```
<220> FEATURE:
<223> OTHER INFORMATION: synthetic sequence

<400> SEQUENCE: 664
ccuccaccac ctucccaaag                                                    20

<210> SEQ ID NO 665
<211> LENGTH: 20
<212> TYPE: DNA
<213> ORGANISM: Artificial Sequence
<220> FEATURE:
<223> OTHER INFORMATION: synthetic sequence

<400> SEQUENCE: 665
cgccatacua cctgggcaua                                                    20

<210> SEQ ID NO 666
<211> LENGTH: 25
<212> TYPE: DNA
<213> ORGANISM: Artificial Sequence
<220> FEATURE:
<223> OTHER INFORMATION: synthetic sequence

<400> SEQUENCE: 666
tcaaagaaac agcugugagg agaaa                                              25

<210> SEQ ID NO 667
<211> LENGTH: 25
<212> TYPE: DNA
<213> ORGANISM: Artificial Sequence
<220> FEATURE:
<223> OTHER INFORMATION: synthetic sequence

<400> SEQUENCE: 667
cattcaagaa cucaaggagc ucaga                                              25

<210> SEQ ID NO 668
<211> LENGTH: 23
<212> TYPE: DNA
<213> ORGANISM: Artificial Sequence
<220> FEATURE:
<223> OTHER INFORMATION: synthetic sequence

<400> SEQUENCE: 668
acttagccau acagggctcc tua                                                23

<210> SEQ ID NO 669
<211> LENGTH: 22
<212> TYPE: DNA
<213> ORGANISM: Artificial Sequence
<220> FEATURE:
<223> OTHER INFORMATION: synthetic sequence

<400> SEQUENCE: 669
ccaaacugtc ggctucaaag ag                                                 22

<210> SEQ ID NO 670
<211> LENGTH: 21
<212> TYPE: DNA
<213> ORGANISM: Artificial Sequence
<220> FEATURE:
<223> OTHER INFORMATION: synthetic sequence

<400> SEQUENCE: 670
tcctccucag cagttcctuc a                                                  21
```

<210> SEQ ID NO 671
<211> LENGTH: 27
<212> TYPE: DNA
<213> ORGANISM: Artificial Sequence
<220> FEATURE:
<223> OTHER INFORMATION: synthetic sequence

<400> SEQUENCE: 671
agtaactcct cautcaagac ccuacat                                27

<210> SEQ ID NO 672
<211> LENGTH: 20
<212> TYPE: DNA
<213> ORGANISM: Artificial Sequence
<220> FEATURE:
<223> OTHER INFORMATION: synthetic sequence

<400> SEQUENCE: 672
tgagccccaa gaaugaccug                                        20

<210> SEQ ID NO 673
<211> LENGTH: 26
<212> TYPE: DNA
<213> ORGANISM: Artificial Sequence
<220> FEATURE:
<223> OTHER INFORMATION: synthetic sequence

<400> SEQUENCE: 673
cccttatgug acaatgtgaa cacuca                                 26

<210> SEQ ID NO 674
<211> LENGTH: 18
<212> TYPE: DNA
<213> ORGANISM: Artificial Sequence
<220> FEATURE:
<223> OTHER INFORMATION: synthetic sequence

<400> SEQUENCE: 674
agcacccutt cggcctut                                          18

<210> SEQ ID NO 675
<211> LENGTH: 24
<212> TYPE: DNA
<213> ORGANISM: Artificial Sequence
<220> FEATURE:
<223> OTHER INFORMATION: synthetic sequence

<400> SEQUENCE: 675
caaagaagcc ucttcctcct acuc                                   24

<210> SEQ ID NO 676
<211> LENGTH: 20
<212> TYPE: DNA
<213> ORGANISM: Artificial Sequence
<220> FEATURE:
<223> OTHER INFORMATION: synthetic sequence

<400> SEQUENCE: 676
tguccagcag gcagtacuct                                        20

<210> SEQ ID NO 677
<211> LENGTH: 22
<212> TYPE: DNA
<213> ORGANISM: Artificial Sequence
<220> FEATURE:
<223> OTHER INFORMATION: synthetic sequence

<400> SEQUENCE: 677
cttaagacgg ugaggtcagc ut                                            22

<210> SEQ ID NO 678
<211> LENGTH: 21
<212> TYPE: DNA
<213> ORGANISM: Artificial Sequence
<220> FEATURE:
<223> OTHER INFORMATION: synthetic sequence

<400> SEQUENCE: 678
acactgguca ctgctgauga g                                             21

<210> SEQ ID NO 679
<211> LENGTH: 21
<212> TYPE: DNA
<213> ORGANISM: Artificial Sequence
<220> FEATURE:
<223> OTHER INFORMATION: synthetic sequence

<400> SEQUENCE: 679
ctcaatccca cugcccacua c                                             21

<210> SEQ ID NO 680
<211> LENGTH: 24
<212> TYPE: DNA
<213> ORGANISM: Artificial Sequence
<220> FEATURE:
<223> OTHER INFORMATION: synthetic sequence

<400> SEQUENCE: 680
aggagactcu gggtgaacau acat                                          24

<210> SEQ ID NO 681
<211> LENGTH: 20
<212> TYPE: DNA
<213> ORGANISM: Artificial Sequence
<220> FEATURE:
<223> OTHER INFORMATION: synthetic sequence

<400> SEQUENCE: 681
caggacucca ccucagacct                                               20

<210> SEQ ID NO 682
<211> LENGTH: 23
<212> TYPE: DNA
<213> ORGANISM: Artificial Sequence
<220> FEATURE:
<223> OTHER INFORMATION: synthetic sequence

<400> SEQUENCE: 682
ttttgcgggu ctttgtcttc uct                                           23

<210> SEQ ID NO 683
<211> LENGTH: 28
<212> TYPE: DNA
<213> ORGANISM: Artificial Sequence
<220> FEATURE:
<223> OTHER INFORMATION: synthetic sequence

<400> SEQUENCE: 683
ccaagtgtcc auacctcaat ttcttuca                                      28

<210> SEQ ID NO 684

<210> SEQ ID NO 684
<211> LENGTH: 21
<212> TYPE: DNA
<213> ORGANISM: Artificial Sequence
<220> FEATURE:
<223> OTHER INFORMATION: synthetic sequence

<400> SEQUENCE: 684
ttgugccagc tctucaacag a                                           21

<210> SEQ ID NO 685
<211> LENGTH: 21
<212> TYPE: DNA
<213> ORGANISM: Artificial Sequence
<220> FEATURE:
<223> OTHER INFORMATION: synthetic sequence

<400> SEQUENCE: 685
ccgaaacacu accagcugca a                                           21

<210> SEQ ID NO 686
<211> LENGTH: 29
<212> TYPE: DNA
<213> ORGANISM: Artificial Sequence
<220> FEATURE:
<223> OTHER INFORMATION: synthetic sequence

<400> SEQUENCE: 686
tccgctctgt atutcttaaa agtctctuc                                   29

<210> SEQ ID NO 687
<211> LENGTH: 22
<212> TYPE: DNA
<213> ORGANISM: Artificial Sequence
<220> FEATURE:
<223> OTHER INFORMATION: synthetic sequence

<400> SEQUENCE: 687
tgtguccaag agagctcagu ct                                          22

<210> SEQ ID NO 688
<211> LENGTH: 20
<212> TYPE: DNA
<213> ORGANISM: Artificial Sequence
<220> FEATURE:
<223> OTHER INFORMATION: synthetic sequence

<400> SEQUENCE: 688
ccattcagcu tgagggucca                                             20

<210> SEQ ID NO 689
<211> LENGTH: 23
<212> TYPE: DNA
<213> ORGANISM: Artificial Sequence
<220> FEATURE:
<223> OTHER INFORMATION: synthetic sequence

<400> SEQUENCE: 689
ggaagaggca uctcgtttgu act                                         23

<210> SEQ ID NO 690
<211> LENGTH: 25
<212> TYPE: DNA
<213> ORGANISM: Artificial Sequence
<220> FEATURE:
<223> OTHER INFORMATION: synthetic sequence

<400> SEQUENCE: 690

```
gcctccatua aatctcgacc auagg                                    25
```

<210> SEQ ID NO 691
<211> LENGTH: 22
<212> TYPE: DNA
<213> ORGANISM: Artificial Sequence
<220> FEATURE:
<223> OTHER INFORMATION: synthetic sequence

<400> SEQUENCE: 691

```
cgatcuccag cccaagatga ut                                       22
```

<210> SEQ ID NO 692
<211> LENGTH: 21
<212> TYPE: DNA
<213> ORGANISM: Artificial Sequence
<220> FEATURE:
<223> OTHER INFORMATION: synthetic sequence

<400> SEQUENCE: 692

```
cgacaguaga ggagggugag g                                        21
```

<210> SEQ ID NO 693
<211> LENGTH: 21
<212> TYPE: DNA
<213> ORGANISM: Artificial Sequence
<220> FEATURE:
<223> OTHER INFORMATION: synthetic sequence

<400> SEQUENCE: 693

```
cacacctgga utcccttccu t                                        21
```

<210> SEQ ID NO 694
<211> LENGTH: 22
<212> TYPE: DNA
<213> ORGANISM: Artificial Sequence
<220> FEATURE:
<223> OTHER INFORMATION: synthetic sequence

<400> SEQUENCE: 694

```
gutttccagu cagagggaca gt                                       22
```

<210> SEQ ID NO 695
<211> LENGTH: 20
<212> TYPE: DNA
<213> ORGANISM: Artificial Sequence
<220> FEATURE:
<223> OTHER INFORMATION: synthetic sequence

<400> SEQUENCE: 695

```
ggaagtggug ctggtuagga                                          20
```

<210> SEQ ID NO 696
<211> LENGTH: 24
<212> TYPE: DNA
<213> ORGANISM: Artificial Sequence
<220> FEATURE:
<223> OTHER INFORMATION: synthetic sequence

<400> SEQUENCE: 696

```
cttagggagu gggagaaguc aaag                                     24
```

<210> SEQ ID NO 697
<211> LENGTH: 22
<212> TYPE: DNA

```
<213> ORGANISM: Artificial Sequence
<220> FEATURE:
<223> OTHER INFORMATION: synthetic sequence

<400> SEQUENCE: 697
cttugacagc gacaagaagu gg                                          22

<210> SEQ ID NO 698
<211> LENGTH: 19
<212> TYPE: DNA
<213> ORGANISM: Artificial Sequence
<220> FEATURE:
<223> OTHER INFORMATION: synthetic sequence

<400> SEQUENCE: 698
ccctcaguga agcgguaca                                              19

<210> SEQ ID NO 699
<211> LENGTH: 20
<212> TYPE: DNA
<213> ORGANISM: Artificial Sequence
<220> FEATURE:
<223> OTHER INFORMATION: synthetic sequence

<400> SEQUENCE: 699
cgcaatguca cccatcucct                                             20

<210> SEQ ID NO 700
<211> LENGTH: 23
<212> TYPE: DNA
<213> ORGANISM: Artificial Sequence
<220> FEATURE:
<223> OTHER INFORMATION: synthetic sequence

<400> SEQUENCE: 700
tttcttttgt ccutgggcct uct                                         23

<210> SEQ ID NO 701
<211> LENGTH: 19
<212> TYPE: DNA
<213> ORGANISM: Artificial Sequence
<220> FEATURE:
<223> OTHER INFORMATION: synthetic sequence

<400> SEQUENCE: 701
cttccccgau tgccacgua                                              19

<210> SEQ ID NO 702
<211> LENGTH: 20
<212> TYPE: DNA
<213> ORGANISM: Artificial Sequence
<220> FEATURE:
<223> OTHER INFORMATION: synthetic sequence

<400> SEQUENCE: 702
cgguccagca ggaattuggt                                             20

<210> SEQ ID NO 703
<211> LENGTH: 19
<212> TYPE: DNA
<213> ORGANISM: Artificial Sequence
<220> FEATURE:
<223> OTHER INFORMATION: synthetic sequence

<400> SEQUENCE: 703
ctcccagcuc tucaccgat                                              19
```

<210> SEQ ID NO 704
<211> LENGTH: 20
<212> TYPE: DNA
<213> ORGANISM: Artificial Sequence
<220> FEATURE:
<223> OTHER INFORMATION: synthetic sequence

<400> SEQUENCE: 704
ctcccattuc cctgcacuca                                                 20

<210> SEQ ID NO 705
<211> LENGTH: 20
<212> TYPE: DNA
<213> ORGANISM: Artificial Sequence
<220> FEATURE:
<223> OTHER INFORMATION: synthetic sequence

<400> SEQUENCE: 705
ggaggaaugu cagcaccaga                                                 20

<210> SEQ ID NO 706
<211> LENGTH: 25
<212> TYPE: DNA
<213> ORGANISM: Artificial Sequence
<220> FEATURE:
<223> OTHER INFORMATION: synthetic sequence

<400> SEQUENCE: 706
tcacacatat gautaggcca acugt                                           25

<210> SEQ ID NO 707
<211> LENGTH: 21
<212> TYPE: DNA
<213> ORGANISM: Artificial Sequence
<220> FEATURE:
<223> OTHER INFORMATION: synthetic sequence

<400> SEQUENCE: 707
tgcggaggaa cuttgugaac a                                               21

<210> SEQ ID NO 708
<211> LENGTH: 20
<212> TYPE: DNA
<213> ORGANISM: Artificial Sequence
<220> FEATURE:
<223> OTHER INFORMATION: synthetic sequence

<400> SEQUENCE: 708
aggcgaagau ggucagcaat                                                 20

<210> SEQ ID NO 709
<211> LENGTH: 21
<212> TYPE: DNA
<213> ORGANISM: Artificial Sequence
<220> FEATURE:
<223> OTHER INFORMATION: synthetic sequence

<400> SEQUENCE: 709
catggaagcu gttgccaagu t                                               21

<210> SEQ ID NO 710
<211> LENGTH: 25
<212> TYPE: DNA
<213> ORGANISM: Artificial Sequence
<220> FEATURE:

<223> OTHER INFORMATION: synthetic sequence

<400> SEQUENCE: 710
aaattctugg gcacatatcc tucct                                              25

<210> SEQ ID NO 711
<211> LENGTH: 19
<212> TYPE: DNA
<213> ORGANISM: Artificial Sequence
<220> FEATURE:
<223> OTHER INFORMATION: synthetic sequence

<400> SEQUENCE: 711
ggtcgacccu tgccacuac                                                     19

<210> SEQ ID NO 712
<211> LENGTH: 22
<212> TYPE: DNA
<213> ORGANISM: Artificial Sequence
<220> FEATURE:
<223> OTHER INFORMATION: synthetic sequence

<400> SEQUENCE: 712
agctgcugct acctuagaag ga                                                 22

<210> SEQ ID NO 713
<211> LENGTH: 20
<212> TYPE: DNA
<213> ORGANISM: Artificial Sequence
<220> FEATURE:
<223> OTHER INFORMATION: synthetic sequence

<400> SEQUENCE: 713
gatcggcauc ctgacaguga                                                    20

<210> SEQ ID NO 714
<211> LENGTH: 22
<212> TYPE: DNA
<213> ORGANISM: Artificial Sequence
<220> FEATURE:
<223> OTHER INFORMATION: synthetic sequence

<400> SEQUENCE: 714
cccttcttgu gggcatcttc ut                                                 22

<210> SEQ ID NO 715
<211> LENGTH: 20
<212> TYPE: DNA
<213> ORGANISM: Artificial Sequence
<220> FEATURE:
<223> OTHER INFORMATION: synthetic sequence

<400> SEQUENCE: 715
gagattcucg cccugagcaa                                                    20

<210> SEQ ID NO 716
<211> LENGTH: 18
<212> TYPE: DNA
<213> ORGANISM: Artificial Sequence
<220> FEATURE:
<223> OTHER INFORMATION: synthetic sequence

<400> SEQUENCE: 716
tggucagggc agcaggua                                                      18

```
<210> SEQ ID NO 717
<211> LENGTH: 26
<212> TYPE: DNA
<213> ORGANISM: Artificial Sequence
<220> FEATURE:
<223> OTHER INFORMATION: synthetic sequence

<400> SEQUENCE: 717
tgccgagcua aattacacat tgauga                                         26

<210> SEQ ID NO 718
<211> LENGTH: 20
<212> TYPE: DNA
<213> ORGANISM: Artificial Sequence
<220> FEATURE:
<223> OTHER INFORMATION: synthetic sequence

<400> SEQUENCE: 718
catggucaca gagccaccut                                                20

<210> SEQ ID NO 719
<211> LENGTH: 19
<212> TYPE: DNA
<213> ORGANISM: Artificial Sequence
<220> FEATURE:
<223> OTHER INFORMATION: synthetic sequence

<400> SEQUENCE: 719
gtggcccugt aggacctuc                                                 19

<210> SEQ ID NO 720
<211> LENGTH: 19
<212> TYPE: DNA
<213> ORGANISM: Artificial Sequence
<220> FEATURE:
<223> OTHER INFORMATION: synthetic sequence

<400> SEQUENCE: 720
cgatgucgca cggtaccug                                                 19

<210> SEQ ID NO 721
<211> LENGTH: 23
<212> TYPE: DNA
<213> ORGANISM: Artificial Sequence
<220> FEATURE:
<223> OTHER INFORMATION: synthetic sequence

<400> SEQUENCE: 721
ggcaccuacc tttuaaccac aga                                            23

<210> SEQ ID NO 722
<211> LENGTH: 20
<212> TYPE: DNA
<213> ORGANISM: Artificial Sequence
<220> FEATURE:
<223> OTHER INFORMATION: synthetic sequence

<400> SEQUENCE: 722
cttcctgcug agccagtcut                                                20

<210> SEQ ID NO 723
<211> LENGTH: 28
<212> TYPE: DNA
<213> ORGANISM: Artificial Sequence
<220> FEATURE:
<223> OTHER INFORMATION: synthetic sequence
```

```
<400> SEQUENCE: 723
ggattggaat ugaggaagac tgttacua                                28

<210> SEQ ID NO 724
<211> LENGTH: 19
<212> TYPE: DNA
<213> ORGANISM: Artificial Sequence
<220> FEATURE:
<223> OTHER INFORMATION: synthetic sequence

<400> SEQUENCE: 724
acgcaguctg gttcauccc                                          19

<210> SEQ ID NO 725
<211> LENGTH: 23
<212> TYPE: DNA
<213> ORGANISM: Artificial Sequence
<220> FEATURE:
<223> OTHER INFORMATION: synthetic sequence

<400> SEQUENCE: 725
atgacagugc aggaagaucg aaa                                     23

<210> SEQ ID NO 726
<211> LENGTH: 20
<212> TYPE: DNA
<213> ORGANISM: Artificial Sequence
<220> FEATURE:
<223> OTHER INFORMATION: synthetic sequence

<400> SEQUENCE: 726
ctgggccacc utgtuacaca                                         20

<210> SEQ ID NO 727
<211> LENGTH: 22
<212> TYPE: DNA
<213> ORGANISM: Artificial Sequence
<220> FEATURE:
<223> OTHER INFORMATION: synthetic sequence

<400> SEQUENCE: 727
ctccagccau acuccacaga at                                      22

<210> SEQ ID NO 728
<211> LENGTH: 24
<212> TYPE: DNA
<213> ORGANISM: Artificial Sequence
<220> FEATURE:
<223> OTHER INFORMATION: synthetic sequence

<400> SEQUENCE: 728
aacaaagagg ugaggtggaa gaug                                    24

<210> SEQ ID NO 729
<211> LENGTH: 20
<212> TYPE: DNA
<213> ORGANISM: Artificial Sequence
<220> FEATURE:
<223> OTHER INFORMATION: synthetic sequence

<400> SEQUENCE: 729
tgcctgggcu tcatagcaut                                         20

<210> SEQ ID NO 730
<211> LENGTH: 22
```

```
<212> TYPE: DNA
<213> ORGANISM: Artificial Sequence
<220> FEATURE:
<223> OTHER INFORMATION: synthetic sequence

<400> SEQUENCE: 730
gcagaatggu catgaagaug cc                                          22

<210> SEQ ID NO 731
<211> LENGTH: 21
<212> TYPE: DNA
<213> ORGANISM: Artificial Sequence
<220> FEATURE:
<223> OTHER INFORMATION: synthetic sequence

<400> SEQUENCE: 731
ccaagcgaau gaagcaucca a                                           21

<210> SEQ ID NO 732
<211> LENGTH: 19
<212> TYPE: DNA
<213> ORGANISM: Artificial Sequence
<220> FEATURE:
<223> OTHER INFORMATION: synthetic sequence

<400> SEQUENCE: 732
gcctgggucc ttcaaccuc                                              19

<210> SEQ ID NO 733
<211> LENGTH: 19
<212> TYPE: DNA
<213> ORGANISM: Artificial Sequence
<220> FEATURE:
<223> OTHER INFORMATION: synthetic sequence

<400> SEQUENCE: 733
ggagtggcuc cgcagauac                                              19

<210> SEQ ID NO 734
<211> LENGTH: 21
<212> TYPE: DNA
<213> ORGANISM: Artificial Sequence
<220> FEATURE:
<223> OTHER INFORMATION: synthetic sequence

<400> SEQUENCE: 734
gtgatcuccg caggguagaa a                                           21

<210> SEQ ID NO 735
<211> LENGTH: 27
<212> TYPE: DNA
<213> ORGANISM: Artificial Sequence
<220> FEATURE:
<223> OTHER INFORMATION: synthetic sequence

<400> SEQUENCE: 735
ttgagatttg cugatggaag cauaaga                                     27

<210> SEQ ID NO 736
<211> LENGTH: 24
<212> TYPE: DNA
<213> ORGANISM: Artificial Sequence
<220> FEATURE:
<223> OTHER INFORMATION: synthetic sequence

<400> SEQUENCE: 736
```
gtgctttagg uctccataga gcut					24

<210> SEQ ID NO 737
<211> LENGTH: 19
<212> TYPE: DNA
<213> ORGANISM: Artificial Sequence
<220> FEATURE:
<223> OTHER INFORMATION: synthetic sequence

<400> SEQUENCE: 737
guggacuccc ggagaggat					19

<210> SEQ ID NO 738
<211> LENGTH: 26
<212> TYPE: DNA
<213> ORGANISM: Artificial Sequence
<220> FEATURE:
<223> OTHER INFORMATION: synthetic sequence

<400> SEQUENCE: 738
gagcuaacgu cgaucuugua agucut					26

<210> SEQ ID NO 739
<211> LENGTH: 19
<212> TYPE: DNA
<213> ORGANISM: Artificial Sequence
<220> FEATURE:
<223> OTHER INFORMATION: synthetic sequence

<400> SEQUENCE: 739
ccguuacaag cgucaggga					19

<210> SEQ ID NO 740
<211> LENGTH: 21
<212> TYPE: DNA
<213> ORGANISM: Artificial Sequence
<220> FEATURE:
<223> OTHER INFORMATION: synthetic sequence

<400> SEQUENCE: 740
agucacucag ucccccguag u					21

<210> SEQ ID NO 741
<211> LENGTH: 20
<212> TYPE: DNA
<213> ORGANISM: Artificial Sequence
<220> FEATURE:
<223> OTHER INFORMATION: synthetic sequence

<400> SEQUENCE: 741
caggugucug ucugcugcaa					20

<210> SEQ ID NO 742
<211> LENGTH: 27
<212> TYPE: DNA
<213> ORGANISM: Artificial Sequence
<220> FEATURE:
<223> OTHER INFORMATION: synthetic sequence

<400> SEQUENCE: 742
gacgaagaau cagaagcagc aguaaua					27

<210> SEQ ID NO 743
<211> LENGTH: 20
<212> TYPE: DNA
<213> ORGANISM: Artificial Sequence

```
<220> FEATURE:
<223> OTHER INFORMATION: synthetic sequence

<400> SEQUENCE: 743
gguggacggc aagaatguga                                          20

<210> SEQ ID NO 744
<211> LENGTH: 20
<212> TYPE: DNA
<213> ORGANISM: Artificial Sequence
<220> FEATURE:
<223> OTHER INFORMATION: synthetic sequence

<400> SEQUENCE: 744
gcctcattcu ggccaaggua                                          20

<210> SEQ ID NO 745
<211> LENGTH: 22
<212> TYPE: DNA
<213> ORGANISM: Artificial Sequence
<220> FEATURE:
<223> OTHER INFORMATION: synthetic sequence

<400> SEQUENCE: 745
ggttcagagc uttctggagu ga                                       22

<210> SEQ ID NO 746
<211> LENGTH: 26
<212> TYPE: DNA
<213> ORGANISM: Artificial Sequence
<220> FEATURE:
<223> OTHER INFORMATION: synthetic sequence

<400> SEQUENCE: 746
cttgcaatac auaacaacct gcucaa                                   26

<210> SEQ ID NO 747
<211> LENGTH: 24
<212> TYPE: DNA
<213> ORGANISM: Artificial Sequence
<220> FEATURE:
<223> OTHER INFORMATION: synthetic sequence

<400> SEQUENCE: 747
gcaatagaug gctacagtgu caga                                     24

<210> SEQ ID NO 748
<211> LENGTH: 22
<212> TYPE: DNA
<213> ORGANISM: Artificial Sequence
<220> FEATURE:
<223> OTHER INFORMATION: synthetic sequence

<400> SEQUENCE: 748
agctgctgua cccattctuc ag                                       22

<210> SEQ ID NO 749
<211> LENGTH: 19
<212> TYPE: DNA
<213> ORGANISM: Artificial Sequence
<220> FEATURE:
<223> OTHER INFORMATION: synthetic sequence

<400> SEQUENCE: 749
ggtggagugc cgcttcuac                                           19
```

<210> SEQ ID NO 750
<211> LENGTH: 21
<212> TYPE: DNA
<213> ORGANISM: Artificial Sequence
<220> FEATURE:
<223> OTHER INFORMATION: synthetic sequence

<400> SEQUENCE: 750
gggtgccgua gttggagaua a                                              21

<210> SEQ ID NO 751
<211> LENGTH: 22
<212> TYPE: DNA
<213> ORGANISM: Artificial Sequence
<220> FEATURE:
<223> OTHER INFORMATION: synthetic sequence

<400> SEQUENCE: 751
aaaagtugtc tgtgugcgca aa                                             22

<210> SEQ ID NO 752
<211> LENGTH: 21
<212> TYPE: DNA
<213> ORGANISM: Artificial Sequence
<220> FEATURE:
<223> OTHER INFORMATION: synthetic sequence

<400> SEQUENCE: 752
ccccagcaag gutctttcug t                                              21

<210> SEQ ID NO 753
<211> LENGTH: 19
<212> TYPE: DNA
<213> ORGANISM: Artificial Sequence
<220> FEATURE:
<223> OTHER INFORMATION: synthetic sequence

<400> SEQUENCE: 753
ggagtgcugt tccgagugg                                                 19

<210> SEQ ID NO 754
<211> LENGTH: 23
<212> TYPE: DNA
<213> ORGANISM: Artificial Sequence
<220> FEATURE:
<223> OTHER INFORMATION: synthetic sequence

<400> SEQUENCE: 754
tcgauacacu ggaagccaaa act                                            23

<210> SEQ ID NO 755
<211> LENGTH: 20
<212> TYPE: DNA
<213> ORGANISM: Artificial Sequence
<220> FEATURE:
<223> OTHER INFORMATION: synthetic sequence

<400> SEQUENCE: 755
caccacuggc atctcuggaa                                                20

<210> SEQ ID NO 756
<211> LENGTH: 25
<212> TYPE: DNA
<213> ORGANISM: Artificial Sequence
<220> FEATURE:
<223> OTHER INFORMATION: synthetic sequence

<400> SEQUENCE: 756
agatcgtatg agugcattcc catug                                    25

<210> SEQ ID NO 757
<211> LENGTH: 21
<212> TYPE: DNA
<213> ORGANISM: Artificial Sequence
<220> FEATURE:
<223> OTHER INFORMATION: synthetic sequence

<400> SEQUENCE: 757
cccccagauc cagaccttcu t                                        21

<210> SEQ ID NO 758
<211> LENGTH: 20
<212> TYPE: DNA
<213> ORGANISM: Artificial Sequence
<220> FEATURE:
<223> OTHER INFORMATION: synthetic sequence

<400> SEQUENCE: 758
gctctugcct tctgcucaca                                          20

<210> SEQ ID NO 759
<211> LENGTH: 22
<212> TYPE: DNA
<213> ORGANISM: Artificial Sequence
<220> FEATURE:
<223> OTHER INFORMATION: synthetic sequence

<400> SEQUENCE: 759
agcgaactca uctttgccag ua                                       22

<210> SEQ ID NO 760
<211> LENGTH: 21
<212> TYPE: DNA
<213> ORGANISM: Artificial Sequence
<220> FEATURE:
<223> OTHER INFORMATION: synthetic sequence

<400> SEQUENCE: 760
cutcagctcu gacaccgaca t                                        21

<210> SEQ ID NO 761
<211> LENGTH: 19
<212> TYPE: DNA
<213> ORGANISM: Artificial Sequence
<220> FEATURE:
<223> OTHER INFORMATION: synthetic sequence

<400> SEQUENCE: 761
gcggccagga uggttctua                                           19

<210> SEQ ID NO 762
<211> LENGTH: 22
<212> TYPE: DNA
<213> ORGANISM: Artificial Sequence
<220> FEATURE:
<223> OTHER INFORMATION: synthetic sequence

<400> SEQUENCE: 762
gttuagcacg aagctcuccg at                                       22

<210> SEQ ID NO 763

```
<211> LENGTH: 20
<212> TYPE: DNA
<213> ORGANISM: Artificial Sequence
<220> FEATURE:
<223> OTHER INFORMATION: synthetic sequence

<400> SEQUENCE: 763
accccaaucg gaagccuaac                                                   20

<210> SEQ ID NO 764
<211> LENGTH: 19
<212> TYPE: DNA
<213> ORGANISM: Artificial Sequence
<220> FEATURE:
<223> OTHER INFORMATION: synthetic sequence

<400> SEQUENCE: 764
agaugagcat uggcagcga                                                    19

<210> SEQ ID NO 765
<211> LENGTH: 24
<212> TYPE: DNA
<213> ORGANISM: Artificial Sequence
<220> FEATURE:
<223> OTHER INFORMATION: synthetic sequence

<400> SEQUENCE: 765
ttggctgtga uattgtgtgc uaca                                              24

<210> SEQ ID NO 766
<211> LENGTH: 26
<212> TYPE: DNA
<213> ORGANISM: Artificial Sequence
<220> FEATURE:
<223> OTHER INFORMATION: synthetic sequence

<400> SEQUENCE: 766
tttgtcacag tugttacttg gguaca                                            26

<210> SEQ ID NO 767
<211> LENGTH: 25
<212> TYPE: DNA
<213> ORGANISM: Artificial Sequence
<220> FEATURE:
<223> OTHER INFORMATION: synthetic sequence

<400> SEQUENCE: 767
gcctcuacca cttctaugac cagat                                             25

<210> SEQ ID NO 768
<211> LENGTH: 22
<212> TYPE: DNA
<213> ORGANISM: Artificial Sequence
<220> FEATURE:
<223> OTHER INFORMATION: synthetic sequence

<400> SEQUENCE: 768
cataagccuc cctggtctct uc                                                22

<210> SEQ ID NO 769
<211> LENGTH: 20
<212> TYPE: DNA
<213> ORGANISM: Artificial Sequence
<220> FEATURE:
<223> OTHER INFORMATION: synthetic sequence

<400> SEQUENCE: 769
```
cccggaagug cctaagtcut                                           20

<210> SEQ ID NO 770
<211> LENGTH: 20
<212> TYPE: DNA
<213> ORGANISM: Artificial Sequence
<220> FEATURE:
<223> OTHER INFORMATION: synthetic sequence

<400> SEQUENCE: 770
cggcacucct ccatgtugat                                           20

<210> SEQ ID NO 771
<211> LENGTH: 18
<212> TYPE: DNA
<213> ORGANISM: Artificial Sequence
<220> FEATURE:
<223> OTHER INFORMATION: synthetic sequence

<400> SEQUENCE: 771
catgttugcg cagcuggt                                             18

<210> SEQ ID NO 772
<211> LENGTH: 23
<212> TYPE: DNA
<213> ORGANISM: Artificial Sequence
<220> FEATURE:
<223> OTHER INFORMATION: synthetic sequence

<400> SEQUENCE: 772
gctccttcgu gtcctctttg uag                                       23

<210> SEQ ID NO 773
<211> LENGTH: 24
<212> TYPE: DNA
<213> ORGANISM: Artificial Sequence
<220> FEATURE:
<223> OTHER INFORMATION: synthetic sequence

<400> SEQUENCE: 773
cgtgtacttu accaacgagc ugaa                                      24

<210> SEQ ID NO 774
<211> LENGTH: 20
<212> TYPE: DNA
<213> ORGANISM: Artificial Sequence
<220> FEATURE:
<223> OTHER INFORMATION: synthetic sequence

<400> SEQUENCE: 774
cggagtugcc acttgactug                                           20

<210> SEQ ID NO 775
<211> LENGTH: 21
<212> TYPE: DNA
<213> ORGANISM: Artificial Sequence
<220> FEATURE:
<223> OTHER INFORMATION: synthetic sequence

<400> SEQUENCE: 775
gtgcuccacc acctacaacu t                                         21

<210> SEQ ID NO 776
<211> LENGTH: 21
<212> TYPE: DNA

```
<213> ORGANISM: Artificial Sequence
<220> FEATURE:
<223> OTHER INFORMATION: synthetic sequence

<400> SEQUENCE: 776
tcagtggugc agctgtcaua g                                          21

<210> SEQ ID NO 777
<211> LENGTH: 23
<212> TYPE: DNA
<213> ORGANISM: Artificial Sequence
<220> FEATURE:
<223> OTHER INFORMATION: synthetic sequence

<400> SEQUENCE: 777
gtgaccauga gcagtttgcu aaa                                        23

<210> SEQ ID NO 778
<211> LENGTH: 22
<212> TYPE: DNA
<213> ORGANISM: Artificial Sequence
<220> FEATURE:
<223> OTHER INFORMATION: synthetic sequence

<400> SEQUENCE: 778
ggtcagaccg augtccatua ca                                         22

<210> SEQ ID NO 779
<211> LENGTH: 22
<212> TYPE: DNA
<213> ORGANISM: Artificial Sequence
<220> FEATURE:
<223> OTHER INFORMATION: synthetic sequence

<400> SEQUENCE: 779
agagagaagc gagguttcca ut                                         22

<210> SEQ ID NO 780
<211> LENGTH: 20
<212> TYPE: DNA
<213> ORGANISM: Artificial Sequence
<220> FEATURE:
<223> OTHER INFORMATION: synthetic sequence

<400> SEQUENCE: 780
tctccttggu gctcctcugt                                            20

<210> SEQ ID NO 781
<211> LENGTH: 27
<212> TYPE: DNA
<213> ORGANISM: Artificial Sequence
<220> FEATURE:
<223> OTHER INFORMATION: synthetic sequence

<400> SEQUENCE: 781
ctgtaactgc tcuaggtgct tcatuat                                    27

<210> SEQ ID NO 782
<211> LENGTH: 20
<212> TYPE: DNA
<213> ORGANISM: Artificial Sequence
<220> FEATURE:
<223> OTHER INFORMATION: synthetic sequence

<400> SEQUENCE: 782
aggccacagc acuttctuct                                            20
```

<210> SEQ ID NO 783
<211> LENGTH: 26
<212> TYPE: DNA
<213> ORGANISM: Artificial Sequence
<220> FEATURE:
<223> OTHER INFORMATION: synthetic sequence

<400> SEQUENCE: 783
agtaccucca gaacagattu gagagt        26

<210> SEQ ID NO 784
<211> LENGTH: 19
<212> TYPE: DNA
<213> ORGANISM: Artificial Sequence
<220> FEATURE:
<223> OTHER INFORMATION: synthetic sequence

<400> SEQUENCE: 784
tcagcaggcu ggcattugt        19

<210> SEQ ID NO 785
<211> LENGTH: 27
<212> TYPE: DNA
<213> ORGANISM: Artificial Sequence
<220> FEATURE:
<223> OTHER INFORMATION: synthetic sequence

<400> SEQUENCE: 785
cgttgcactg guataaaatc ttacugg        27

<210> SEQ ID NO 786
<211> LENGTH: 26
<212> TYPE: DNA
<213> ORGANISM: Artificial Sequence
<220> FEATURE:
<223> OTHER INFORMATION: synthetic sequence

<400> SEQUENCE: 786
cctcatacug agtggcattu gaacaa        26

<210> SEQ ID NO 787
<211> LENGTH: 19
<212> TYPE: DNA
<213> ORGANISM: Artificial Sequence
<220> FEATURE:
<223> OTHER INFORMATION: synthetic sequence

<400> SEQUENCE: 787
agcgaccccu tcucagact        19

<210> SEQ ID NO 788
<211> LENGTH: 21
<212> TYPE: DNA
<213> ORGANISM: Artificial Sequence
<220> FEATURE:
<223> OTHER INFORMATION: synthetic sequence

<400> SEQUENCE: 788
cgatgaggac gaucgcuagg a        21

<210> SEQ ID NO 789
<211> LENGTH: 22
<212> TYPE: DNA
<213> ORGANISM: Artificial Sequence
<220> FEATURE:

-continued

```
<223> OTHER INFORMATION: synthetic sequence

<400> SEQUENCE: 789
gagcatccag utggagtuga ca                                              22

<210> SEQ ID NO 790
<211> LENGTH: 20
<212> TYPE: DNA
<213> ORGANISM: Artificial Sequence
<220> FEATURE:
<223> OTHER INFORMATION: synthetic sequence

<400> SEQUENCE: 790
cctccccutt cttcccguct                                                 20

<210> SEQ ID NO 791
<211> LENGTH: 22
<212> TYPE: DNA
<213> ORGANISM: Artificial Sequence
<220> FEATURE:
<223> OTHER INFORMATION: synthetic sequence

<400> SEQUENCE: 791
cctagucaag cactgguacc aa                                              22

<210> SEQ ID NO 792
<211> LENGTH: 20
<212> TYPE: DNA
<213> ORGANISM: Artificial Sequence
<220> FEATURE:
<223> OTHER INFORMATION: synthetic sequence

<400> SEQUENCE: 792
tccaagaccg uccgaaaucc                                                 20

<210> SEQ ID NO 793
<211> LENGTH: 20
<212> TYPE: DNA
<213> ORGANISM: Artificial Sequence
<220> FEATURE:
<223> OTHER INFORMATION: synthetic sequence

<400> SEQUENCE: 793
tgtggcaugg tttgcatugg                                                 20

<210> SEQ ID NO 794
<211> LENGTH: 28
<212> TYPE: DNA
<213> ORGANISM: Artificial Sequence
<220> FEATURE:
<223> OTHER INFORMATION: synthetic sequence

<400> SEQUENCE: 794
cttctctcca gagugtaact ttatgugt                                        28

<210> SEQ ID NO 795
<211> LENGTH: 19
<212> TYPE: DNA
<213> ORGANISM: Artificial Sequence
<220> FEATURE:
<223> OTHER INFORMATION: synthetic sequence

<400> SEQUENCE: 795
gccagacccu cuggagaag                                                  19
```

```
<210> SEQ ID NO 796
<211> LENGTH: 20
<212> TYPE: DNA
<213> ORGANISM: Artificial Sequence
<220> FEATURE:
<223> OTHER INFORMATION: synthetic sequence

<400> SEQUENCE: 796
tggagcucac aggguaggaa                                                   20

<210> SEQ ID NO 797
<211> LENGTH: 19
<212> TYPE: DNA
<213> ORGANISM: Artificial Sequence
<220> FEATURE:
<223> OTHER INFORMATION: synthetic sequence

<400> SEQUENCE: 797
ccactcacac cugcagcua                                                    19

<210> SEQ ID NO 798
<211> LENGTH: 18
<212> TYPE: DNA
<213> ORGANISM: Artificial Sequence
<220> FEATURE:
<223> OTHER INFORMATION: synthetic sequence

<400> SEQUENCE: 798
gtcugagcgc gcaaacut                                                     18

<210> SEQ ID NO 799
<211> LENGTH: 21
<212> TYPE: DNA
<213> ORGANISM: Artificial Sequence
<220> FEATURE:
<223> OTHER INFORMATION: synthetic sequence

<400> SEQUENCE: 799
gcgaguaugg agcagaaacg a                                                 21

<210> SEQ ID NO 800
<211> LENGTH: 24
<212> TYPE: DNA
<213> ORGANISM: Artificial Sequence
<220> FEATURE:
<223> OTHER INFORMATION: synthetic sequence

<400> SEQUENCE: 800
aattccaaau gagctcucca acca                                              24

<210> SEQ ID NO 801
<211> LENGTH: 19
<212> TYPE: DNA
<213> ORGANISM: Artificial Sequence
<220> FEATURE:
<223> OTHER INFORMATION: synthetic sequence

<400> SEQUENCE: 801
ggtgtccutg ggtgcugat                                                    19

<210> SEQ ID NO 802
<211> LENGTH: 24
<212> TYPE: DNA
<213> ORGANISM: Artificial Sequence
<220> FEATURE:
<223> OTHER INFORMATION: synthetic sequence
```

```
<400> SEQUENCE: 802
aatagccctg guaggtaact cugt                                    24

<210> SEQ ID NO 803
<211> LENGTH: 25
<212> TYPE: DNA
<213> ORGANISM: Artificial Sequence
<220> FEATURE:
<223> OTHER INFORMATION: synthetic sequence

<400> SEQUENCE: 803
aatgatgttc cccauatcca gtgug                                   25

<210> SEQ ID NO 804
<211> LENGTH: 19
<212> TYPE: DNA
<213> ORGANISM: Artificial Sequence
<220> FEATURE:
<223> OTHER INFORMATION: synthetic sequence

<400> SEQUENCE: 804
agagaaggcu cccctguga                                          19

<210> SEQ ID NO 805
<211> LENGTH: 22
<212> TYPE: DNA
<213> ORGANISM: Artificial Sequence
<220> FEATURE:
<223> OTHER INFORMATION: synthetic sequence

<400> SEQUENCE: 805
ctggtggutc cattugcaaa gg                                      22

<210> SEQ ID NO 806
<211> LENGTH: 24
<212> TYPE: DNA
<213> ORGANISM: Artificial Sequence
<220> FEATURE:
<223> OTHER INFORMATION: synthetic sequence

<400> SEQUENCE: 806
ctgatgaagc agcugagaga ugat                                    24

<210> SEQ ID NO 807
<211> LENGTH: 21
<212> TYPE: DNA
<213> ORGANISM: Artificial Sequence
<220> FEATURE:
<223> OTHER INFORMATION: synthetic sequence

<400> SEQUENCE: 807
cagggaaggc cuccuacaaa g                                       21

<210> SEQ ID NO 808
<211> LENGTH: 20
<212> TYPE: DNA
<213> ORGANISM: Artificial Sequence
<220> FEATURE:
<223> OTHER INFORMATION: synthetic sequence

<400> SEQUENCE: 808
tctcuggacc cactctguca                                         20

<210> SEQ ID NO 809
<211> LENGTH: 19
```

```
<212> TYPE: DNA
<213> ORGANISM: Artificial Sequence
<220> FEATURE:
<223> OTHER INFORMATION: synthetic sequence

<400> SEQUENCE: 809
gaatcccagc ugacucgct                                              19

<210> SEQ ID NO 810
<211> LENGTH: 25
<212> TYPE: DNA
<213> ORGANISM: Artificial Sequence
<220> FEATURE:
<223> OTHER INFORMATION: synthetic sequence

<400> SEQUENCE: 810
ccacatggcc auatattgga augga                                       25

<210> SEQ ID NO 811
<211> LENGTH: 22
<212> TYPE: DNA
<213> ORGANISM: Artificial Sequence
<220> FEATURE:
<223> OTHER INFORMATION: synthetic sequence

<400> SEQUENCE: 811
acctctcatg cuctgctctc ut                                          22

<210> SEQ ID NO 812
<211> LENGTH: 21
<212> TYPE: DNA
<213> ORGANISM: Artificial Sequence
<220> FEATURE:
<223> OTHER INFORMATION: synthetic sequence

<400> SEQUENCE: 812
accatcuagc cccaaggagu t                                           21

<210> SEQ ID NO 813
<211> LENGTH: 22
<212> TYPE: DNA
<213> ORGANISM: Artificial Sequence
<220> FEATURE:
<223> OTHER INFORMATION: synthetic sequence

<400> SEQUENCE: 813
ctttgatgtg cutcctgcct ut                                          22

<210> SEQ ID NO 814
<211> LENGTH: 19
<212> TYPE: DNA
<213> ORGANISM: Artificial Sequence
<220> FEATURE:
<223> OTHER INFORMATION: synthetic sequence

<400> SEQUENCE: 814
cgcugcagga ctgugaaac                                              19

<210> SEQ ID NO 815
<211> LENGTH: 21
<212> TYPE: DNA
<213> ORGANISM: Artificial Sequence
<220> FEATURE:
<223> OTHER INFORMATION: synthetic sequence

<400> SEQUENCE: 815
```

```
cgctcaggaa ucatgggcua t                                              21

<210> SEQ ID NO 816
<211> LENGTH: 20
<212> TYPE: DNA
<213> ORGANISM: Artificial Sequence
<220> FEATURE:
<223> OTHER INFORMATION: synthetic sequence

<400> SEQUENCE: 816
gccagaccgu ctccttctut                                                20

<210> SEQ ID NO 817
<211> LENGTH: 24
<212> TYPE: DNA
<213> ORGANISM: Artificial Sequence
<220> FEATURE:
<223> OTHER INFORMATION: synthetic sequence

<400> SEQUENCE: 817
aagtgcttac autacagcga cuct                                           24

<210> SEQ ID NO 818
<211> LENGTH: 21
<212> TYPE: DNA
<213> ORGANISM: Artificial Sequence
<220> FEATURE:
<223> OTHER INFORMATION: synthetic sequence

<400> SEQUENCE: 818
gcutctcatg guggagcaca t                                              21

<210> SEQ ID NO 819
<211> LENGTH: 21
<212> TYPE: DNA
<213> ORGANISM: Artificial Sequence
<220> FEATURE:
<223> OTHER INFORMATION: synthetic sequence

<400> SEQUENCE: 819
acacagccua aagucagcac a                                              21

<210> SEQ ID NO 820
<211> LENGTH: 19
<212> TYPE: DNA
<213> ORGANISM: Artificial Sequence
<220> FEATURE:
<223> OTHER INFORMATION: synthetic sequence

<400> SEQUENCE: 820
cggaauggaa cgccuggaa                                                 19

<210> SEQ ID NO 821
<211> LENGTH: 24
<212> TYPE: DNA
<213> ORGANISM: Artificial Sequence
<220> FEATURE:
<223> OTHER INFORMATION: synthetic sequence

<400> SEQUENCE: 821
gccaaccaau gtgctatuca aact                                           24

<210> SEQ ID NO 822
<211> LENGTH: 18
<212> TYPE: DNA
<213> ORGANISM: Artificial Sequence
```

```
<220> FEATURE:
<223> OTHER INFORMATION: synthetic sequence

<400> SEQUENCE: 822
acctggcagc guagggua                                                 18

<210> SEQ ID NO 823
<211> LENGTH: 23
<212> TYPE: DNA
<213> ORGANISM: Artificial Sequence
<220> FEATURE:
<223> OTHER INFORMATION: synthetic sequence

<400> SEQUENCE: 823
agctccaagu cctcacacag aua                                           23

<210> SEQ ID NO 824
<211> LENGTH: 19
<212> TYPE: DNA
<213> ORGANISM: Artificial Sequence
<220> FEATURE:
<223> OTHER INFORMATION: synthetic sequence

<400> SEQUENCE: 824
ggacuccccg gttcatugt                                                19

<210> SEQ ID NO 825
<211> LENGTH: 19
<212> TYPE: DNA
<213> ORGANISM: Artificial Sequence
<220> FEATURE:
<223> OTHER INFORMATION: synthetic sequence

<400> SEQUENCE: 825
gccctugcac atgccuact                                                19

<210> SEQ ID NO 826
<211> LENGTH: 21
<212> TYPE: DNA
<213> ORGANISM: Artificial Sequence
<220> FEATURE:
<223> OTHER INFORMATION: synthetic sequence

<400> SEQUENCE: 826
gtggcacaaa gcugatgacu t                                             21

<210> SEQ ID NO 827
<211> LENGTH: 20
<212> TYPE: DNA
<213> ORGANISM: Artificial Sequence
<220> FEATURE:
<223> OTHER INFORMATION: synthetic sequence

<400> SEQUENCE: 827
ccucacagga caccagctuc                                               20

<210> SEQ ID NO 828
<211> LENGTH: 19
<212> TYPE: DNA
<213> ORGANISM: Artificial Sequence
<220> FEATURE:
<223> OTHER INFORMATION: synthetic sequence

<400> SEQUENCE: 828
agctgggccu gggagauat                                                19
```

<210> SEQ ID NO 829
<211> LENGTH: 19
<212> TYPE: DNA
<213> ORGANISM: Artificial Sequence
<220> FEATURE:
<223> OTHER INFORMATION: synthetic sequence

<400> SEQUENCE: 829
gtggcgaccu cactuacga                                                   19

<210> SEQ ID NO 830
<211> LENGTH: 21
<212> TYPE: DNA
<213> ORGANISM: Artificial Sequence
<220> FEATURE:
<223> OTHER INFORMATION: synthetic sequence

<400> SEQUENCE: 830
aggagggcac uggcagttau a                                                21

<210> SEQ ID NO 831
<211> LENGTH: 20
<212> TYPE: DNA
<213> ORGANISM: Artificial Sequence
<220> FEATURE:
<223> OTHER INFORMATION: synthetic sequence

<400> SEQUENCE: 831
cccagaccuc actgcucaga                                                  20

<210> SEQ ID NO 832
<211> LENGTH: 22
<212> TYPE: DNA
<213> ORGANISM: Artificial Sequence
<220> FEATURE:
<223> OTHER INFORMATION: synthetic sequence

<400> SEQUENCE: 832
aggatccutc caggguacga at                                               22

<210> SEQ ID NO 833
<211> LENGTH: 23
<212> TYPE: DNA
<213> ORGANISM: Artificial Sequence
<220> FEATURE:
<223> OTHER INFORMATION: synthetic sequence

<400> SEQUENCE: 833
ccaatuggaa cctgggauca agt                                              23

<210> SEQ ID NO 834
<211> LENGTH: 22
<212> TYPE: DNA
<213> ORGANISM: Artificial Sequence
<220> FEATURE:
<223> OTHER INFORMATION: synthetic sequence

<400> SEQUENCE: 834
ccatgtgauc tgacacccug aa                                               22

<210> SEQ ID NO 835
<211> LENGTH: 21
<212> TYPE: DNA
<213> ORGANISM: Artificial Sequence
<220> FEATURE:
<223> OTHER INFORMATION: synthetic sequence

```
<400> SEQUENCE: 835
ccacctccug catagagggu a                                              21

<210> SEQ ID NO 836
<211> LENGTH: 26
<212> TYPE: DNA
<213> ORGANISM: Artificial Sequence
<220> FEATURE:
<223> OTHER INFORMATION: synthetic sequence

<400> SEQUENCE: 836
cgcataacuc acaggaacca gataut                                         26

<210> SEQ ID NO 837
<211> LENGTH: 22
<212> TYPE: DNA
<213> ORGANISM: Artificial Sequence
<220> FEATURE:
<223> OTHER INFORMATION: synthetic sequence

<400> SEQUENCE: 837
acacacatgc cuttgagtgg ut                                             22

<210> SEQ ID NO 838
<211> LENGTH: 21
<212> TYPE: DNA
<213> ORGANISM: Artificial Sequence
<220> FEATURE:
<223> OTHER INFORMATION: synthetic sequence

<400> SEQUENCE: 838
caucatggug cacagcaaag t                                              21

<210> SEQ ID NO 839
<211> LENGTH: 23
<212> TYPE: DNA
<213> ORGANISM: Artificial Sequence
<220> FEATURE:
<223> OTHER INFORMATION: synthetic sequence

<400> SEQUENCE: 839
ggcccaagac uccaaccatt tua                                            23

<210> SEQ ID NO 840
<211> LENGTH: 20
<212> TYPE: DNA
<213> ORGANISM: Artificial Sequence
<220> FEATURE:
<223> OTHER INFORMATION: synthetic sequence

<400> SEQUENCE: 840
tgagugagcg gcuaggagaa                                                20

<210> SEQ ID NO 841
<211> LENGTH: 21
<212> TYPE: DNA
<213> ORGANISM: Artificial Sequence
<220> FEATURE:
<223> OTHER INFORMATION: synthetic sequence

<400> SEQUENCE: 841
acaggagcca ugcaagaagu t                                              21

<210> SEQ ID NO 842
```

```
<211> LENGTH: 23
<212> TYPE: DNA
<213> ORGANISM: Artificial Sequence
<220> FEATURE:
<223> OTHER INFORMATION: synthetic sequence

<400> SEQUENCE: 842
gcccattgut catagggtug agt                                          23

<210> SEQ ID NO 843
<211> LENGTH: 22
<212> TYPE: DNA
<213> ORGANISM: Artificial Sequence
<220> FEATURE:
<223> OTHER INFORMATION: synthetic sequence

<400> SEQUENCE: 843
agcttttcug tggctgguga at                                           22

<210> SEQ ID NO 844
<211> LENGTH: 24
<212> TYPE: DNA
<213> ORGANISM: Artificial Sequence
<220> FEATURE:
<223> OTHER INFORMATION: synthetic sequence

<400> SEQUENCE: 844
ccatccagug ggactatggg auaa                                         24

<210> SEQ ID NO 845
<211> LENGTH: 20
<212> TYPE: DNA
<213> ORGANISM: Artificial Sequence
<220> FEATURE:
<223> OTHER INFORMATION: synthetic sequence

<400> SEQUENCE: 845
ccagcaccca ugagttguga                                              20

<210> SEQ ID NO 846
<211> LENGTH: 18
<212> TYPE: DNA
<213> ORGANISM: Artificial Sequence
<220> FEATURE:
<223> OTHER INFORMATION: synthetic sequence

<400> SEQUENCE: 846
ccgcaacuct ugggcgat                                                18

<210> SEQ ID NO 847
<211> LENGTH: 19
<212> TYPE: DNA
<213> ORGANISM: Artificial Sequence
<220> FEATURE:
<223> OTHER INFORMATION: synthetic sequence

<400> SEQUENCE: 847
cgaguacgug ccacaccaa                                               19

<210> SEQ ID NO 848
<211> LENGTH: 25
<212> TYPE: DNA
<213> ORGANISM: Artificial Sequence
<220> FEATURE:
<223> OTHER INFORMATION: synthetic sequence

<400> SEQUENCE: 848
```

```
cattgaattc utcctggaug ccaaa                                          25

<210> SEQ ID NO 849
<211> LENGTH: 20
<212> TYPE: DNA
<213> ORGANISM: Artificial Sequence
<220> FEATURE:
<223> OTHER INFORMATION: synthetic sequence

<400> SEQUENCE: 849
gccgggaaua cagtcgctut                                                20

<210> SEQ ID NO 850
<211> LENGTH: 20
<212> TYPE: DNA
<213> ORGANISM: Artificial Sequence
<220> FEATURE:
<223> OTHER INFORMATION: synthetic sequence

<400> SEQUENCE: 850
agtgtcccuc cctcctucag                                                20

<210> SEQ ID NO 851
<211> LENGTH: 25
<212> TYPE: DNA
<213> ORGANISM: Artificial Sequence
<220> FEATURE:
<223> OTHER INFORMATION: synthetic sequence

<400> SEQUENCE: 851
tgctccagtt uttcagaaga aguga                                          25

<210> SEQ ID NO 852
<211> LENGTH: 21
<212> TYPE: DNA
<213> ORGANISM: Artificial Sequence
<220> FEATURE:
<223> OTHER INFORMATION: synthetic sequence

<400> SEQUENCE: 852
tccgggcaca cutacattug t                                              21

<210> SEQ ID NO 853
<211> LENGTH: 20
<212> TYPE: DNA
<213> ORGANISM: Artificial Sequence
<220> FEATURE:
<223> OTHER INFORMATION: synthetic sequence

<400> SEQUENCE: 853
cctacagcug cagtctucca                                                20

<210> SEQ ID NO 854
<211> LENGTH: 19
<212> TYPE: DNA
<213> ORGANISM: Artificial Sequence
<220> FEATURE:
<223> OTHER INFORMATION: synthetic sequence

<400> SEQUENCE: 854
aacgttgtug ggctcucct                                                 19

<210> SEQ ID NO 855
<211> LENGTH: 26
<212> TYPE: DNA
```

```
<213> ORGANISM: Artificial Sequence
<220> FEATURE:
<223> OTHER INFORMATION: synthetic sequence

<400> SEQUENCE: 855
aacaatccua aaggaagauc cagcaa                                          26

<210> SEQ ID NO 856
<211> LENGTH: 19
<212> TYPE: DNA
<213> ORGANISM: Artificial Sequence
<220> FEATURE:
<223> OTHER INFORMATION: synthetic sequence

<400> SEQUENCE: 856
gggagtgcac ugctgtcua                                                  19

<210> SEQ ID NO 857
<211> LENGTH: 20
<212> TYPE: DNA
<213> ORGANISM: Artificial Sequence
<220> FEATURE:
<223> OTHER INFORMATION: synthetic sequence

<400> SEQUENCE: 857
ccguggagca ggugaagaat                                                 20

<210> SEQ ID NO 858
<211> LENGTH: 23
<212> TYPE: DNA
<213> ORGANISM: Artificial Sequence
<220> FEATURE:
<223> OTHER INFORMATION: synthetic sequence

<400> SEQUENCE: 858
tctatagagu cgccaccctg aug                                             23

<210> SEQ ID NO 859
<211> LENGTH: 25
<212> TYPE: DNA
<213> ORGANISM: Artificial Sequence
<220> FEATURE:
<223> OTHER INFORMATION: synthetic sequence

<400> SEQUENCE: 859
ggctgcugca ttacataatc uggat                                           25

<210> SEQ ID NO 860
<211> LENGTH: 22
<212> TYPE: DNA
<213> ORGANISM: Artificial Sequence
<220> FEATURE:
<223> OTHER INFORMATION: synthetic sequence

<400> SEQUENCE: 860
agcactggtu ggtcttcatc ut                                              22

<210> SEQ ID NO 861
<211> LENGTH: 20
<212> TYPE: DNA
<213> ORGANISM: Artificial Sequence
<220> FEATURE:
<223> OTHER INFORMATION: synthetic sequence

<400> SEQUENCE: 861
gugccagaca aacctcucca                                                 20
```

<210> SEQ ID NO 862
<211> LENGTH: 23
<212> TYPE: DNA
<213> ORGANISM: Artificial Sequence
<220> FEATURE:
<223> OTHER INFORMATION: synthetic sequence

<400> SEQUENCE: 862
ttatgcagag cagugttctu cca                                          23

<210> SEQ ID NO 863
<211> LENGTH: 26
<212> TYPE: DNA
<213> ORGANISM: Artificial Sequence
<220> FEATURE:
<223> OTHER INFORMATION: synthetic sequence

<400> SEQUENCE: 863
tcacactttc augagttcct ccatut                                       26

<210> SEQ ID NO 864
<211> LENGTH: 27
<212> TYPE: DNA
<213> ORGANISM: Artificial Sequence
<220> FEATURE:
<223> OTHER INFORMATION: synthetic sequence

<400> SEQUENCE: 864
gacatcagca uggtcatctg taaagua                                      27

<210> SEQ ID NO 865
<211> LENGTH: 20
<212> TYPE: DNA
<213> ORGANISM: Artificial Sequence
<220> FEATURE:
<223> OTHER INFORMATION: synthetic sequence

<400> SEQUENCE: 865
ccacgtcggu gaccatctut                                              20

<210> SEQ ID NO 866
<211> LENGTH: 20
<212> TYPE: DNA
<213> ORGANISM: Artificial Sequence
<220> FEATURE:
<223> OTHER INFORMATION: synthetic sequence

<400> SEQUENCE: 866
ggagcaaagc ugctgggaua                                              20

<210> SEQ ID NO 867
<211> LENGTH: 20
<212> TYPE: DNA
<213> ORGANISM: Artificial Sequence
<220> FEATURE:
<223> OTHER INFORMATION: synthetic sequence

<400> SEQUENCE: 867
tgggtggucc tgcaaaaucc                                              20

<210> SEQ ID NO 868
<211> LENGTH: 27
<212> TYPE: DNA
<213> ORGANISM: Artificial Sequence
<220> FEATURE:

<223> OTHER INFORMATION: synthetic sequence

<400> SEQUENCE: 868
acatattgat tuggagccag ttctuca                                      27

<210> SEQ ID NO 869
<211> LENGTH: 20
<212> TYPE: DNA
<213> ORGANISM: Artificial Sequence
<220> FEATURE:
<223> OTHER INFORMATION: synthetic sequence

<400> SEQUENCE: 869
caacctgacc cugctggaua                                              20

<210> SEQ ID NO 870
<211> LENGTH: 20
<212> TYPE: DNA
<213> ORGANISM: Artificial Sequence
<220> FEATURE:
<223> OTHER INFORMATION: synthetic sequence

<400> SEQUENCE: 870
gaggaugggu acaccacaca                                              20

<210> SEQ ID NO 871
<211> LENGTH: 20
<212> TYPE: DNA
<213> ORGANISM: Artificial Sequence
<220> FEATURE:
<223> OTHER INFORMATION: synthetic sequence

<400> SEQUENCE: 871
cacugagagg aagcgcauga                                              20

<210> SEQ ID NO 872
<211> LENGTH: 18
<212> TYPE: DNA
<213> ORGANISM: Artificial Sequence
<220> FEATURE:
<223> OTHER INFORMATION: synthetic sequence

<400> SEQUENCE: 872
cagacgucuc ccggacaa                                                18

<210> SEQ ID NO 873
<211> LENGTH: 20
<212> TYPE: DNA
<213> ORGANISM: Artificial Sequence
<220> FEATURE:
<223> OTHER INFORMATION: synthetic sequence

<400> SEQUENCE: 873
gacuatcugc gccagggaaa                                              20

<210> SEQ ID NO 874
<211> LENGTH: 21
<212> TYPE: DNA
<213> ORGANISM: Artificial Sequence
<220> FEATURE:
<223> OTHER INFORMATION: synthetic sequence

<400> SEQUENCE: 874
ggcctucagt gtgttcucca a                                            21

<210> SEQ ID NO 875
<211> LENGTH: 21
<212> TYPE: DNA
<213> ORGANISM: Artificial Sequence
<220> FEATURE:
<223> OTHER INFORMATION: synthetic sequence

<400> SEQUENCE: 875
gcccttgaga uttgaggccu t                                    21

<210> SEQ ID NO 876
<211> LENGTH: 24
<212> TYPE: DNA
<213> ORGANISM: Artificial Sequence
<220> FEATURE:
<223> OTHER INFORMATION: synthetic sequence

<400> SEQUENCE: 876
acatcctccu gaagagtggt ttug                                 24

<210> SEQ ID NO 877
<211> LENGTH: 19
<212> TYPE: DNA
<213> ORGANISM: Artificial Sequence
<220> FEATURE:
<223> OTHER INFORMATION: synthetic sequence

<400> SEQUENCE: 877
cgctgctgug cccatcuat                                       19

<210> SEQ ID NO 878
<211> LENGTH: 21
<212> TYPE: DNA
<213> ORGANISM: Artificial Sequence
<220> FEATURE:
<223> OTHER INFORMATION: synthetic sequence

<400> SEQUENCE: 878
gcaagugaag agcagcaggu a                                    21

<210> SEQ ID NO 879
<211> LENGTH: 24
<212> TYPE: DNA
<213> ORGANISM: Artificial Sequence
<220> FEATURE:
<223> OTHER INFORMATION: synthetic sequence

<400> SEQUENCE: 879
ggacaaagaa uctaccgugc aagt                                 24

<210> SEQ ID NO 880
<211> LENGTH: 22
<212> TYPE: DNA
<213> ORGANISM: Artificial Sequence
<220> FEATURE:
<223> OTHER INFORMATION: synthetic sequence

<400> SEQUENCE: 880
tcucatgucc agcaaagcag aa                                   22

<210> SEQ ID NO 881
<211> LENGTH: 24
<212> TYPE: DNA
<213> ORGANISM: Artificial Sequence
<220> FEATURE:
<223> OTHER INFORMATION: synthetic sequence

<400> SEQUENCE: 881
cgacagaagu ggaagtgcug aaaa                                          24

<210> SEQ ID NO 882
<211> LENGTH: 24
<212> TYPE: DNA
<213> ORGANISM: Artificial Sequence
<220> FEATURE:
<223> OTHER INFORMATION: synthetic sequence

<400> SEQUENCE: 882
ctggatguga gctgtuaaaa ggga                                          24

<210> SEQ ID NO 883
<211> LENGTH: 22
<212> TYPE: DNA
<213> ORGANISM: Artificial Sequence
<220> FEATURE:
<223> OTHER INFORMATION: synthetic sequence

<400> SEQUENCE: 883
gccacctuca aggaaaccag ut                                            22

<210> SEQ ID NO 884
<211> LENGTH: 27
<212> TYPE: DNA
<213> ORGANISM: Artificial Sequence
<220> FEATURE:
<223> OTHER INFORMATION: synthetic sequence

<400> SEQUENCE: 884
cttgagtcua gatttagggc ugaaagt                                       27

<210> SEQ ID NO 885
<211> LENGTH: 22
<212> TYPE: DNA
<213> ORGANISM: Artificial Sequence
<220> FEATURE:
<223> OTHER INFORMATION: synthetic sequence

<400> SEQUENCE: 885
gtggagaagc ucattgcuac ga                                            22

<210> SEQ ID NO 886
<211> LENGTH: 20
<212> TYPE: DNA
<213> ORGANISM: Artificial Sequence
<220> FEATURE:
<223> OTHER INFORMATION: synthetic sequence

<400> SEQUENCE: 886
gtatgtgccc ugctcctucc                                               20

<210> SEQ ID NO 887
<211> LENGTH: 22
<212> TYPE: DNA
<213> ORGANISM: Artificial Sequence
<220> FEATURE:
<223> OTHER INFORMATION: synthetic sequence

<400> SEQUENCE: 887
gcacccugag gaatgcatgu at                                            22

<210> SEQ ID NO 888
<211> LENGTH: 19

```
<212> TYPE: DNA
<213> ORGANISM: Artificial Sequence
<220> FEATURE:
<223> OTHER INFORMATION: synthetic sequence

<400> SEQUENCE: 888
gccucaggaa ggcccuuc                                                      19

<210> SEQ ID NO 889
<211> LENGTH: 19
<212> TYPE: DNA
<213> ORGANISM: Artificial Sequence
<220> FEATURE:
<223> OTHER INFORMATION: synthetic sequence

<400> SEQUENCE: 889
gagtgactau gggcgguga                                                     19

<210> SEQ ID NO 890
<211> LENGTH: 24
<212> TYPE: DNA
<213> ORGANISM: Artificial Sequence
<220> FEATURE:
<223> OTHER INFORMATION: synthetic sequence

<400> SEQUENCE: 890
agaugatgct acuggcaaca gaac                                               24

<210> SEQ ID NO 891
<211> LENGTH: 23
<212> TYPE: DNA
<213> ORGANISM: Artificial Sequence
<220> FEATURE:
<223> OTHER INFORMATION: synthetic sequence

<400> SEQUENCE: 891
ggaaacctct ucagcatttg cut                                                23

<210> SEQ ID NO 892
<211> LENGTH: 22
<212> TYPE: DNA
<213> ORGANISM: Artificial Sequence
<220> FEATURE:
<223> OTHER INFORMATION: synthetic sequence

<400> SEQUENCE: 892
ggcauttcag ctguggaagg at                                                 22

<210> SEQ ID NO 893
<211> LENGTH: 21
<212> TYPE: DNA
<213> ORGANISM: Artificial Sequence
<220> FEATURE:
<223> OTHER INFORMATION: synthetic sequence

<400> SEQUENCE: 893
cggtcttcau gcagagacug a                                                  21

<210> SEQ ID NO 894
<211> LENGTH: 28
<212> TYPE: DNA
<213> ORGANISM: Artificial Sequence
<220> FEATURE:
<223> OTHER INFORMATION: synthetic sequence

<400> SEQUENCE: 894
```

```
gtgaaataua gatgttcccu ccaggaat                                      28

<210> SEQ ID NO 895
<211> LENGTH: 23
<212> TYPE: DNA
<213> ORGANISM: Artificial Sequence
<220> FEATURE:
<223> OTHER INFORMATION: synthetic sequence

<400> SEQUENCE: 895
ccagagcagg cagaugaaau acc                                           23

<210> SEQ ID NO 896
<211> LENGTH: 20
<212> TYPE: DNA
<213> ORGANISM: Artificial Sequence
<220> FEATURE:
<223> OTHER INFORMATION: synthetic sequence

<400> SEQUENCE: 896
agctccacag caucgatguc                                               20

<210> SEQ ID NO 897
<211> LENGTH: 21
<212> TYPE: DNA
<213> ORGANISM: Artificial Sequence
<220> FEATURE:
<223> OTHER INFORMATION: synthetic sequence

<400> SEQUENCE: 897
cgtctgcuga ggctcaagtu a                                             21

<210> SEQ ID NO 898
<211> LENGTH: 21
<212> TYPE: DNA
<213> ORGANISM: Artificial Sequence
<220> FEATURE:
<223> OTHER INFORMATION: synthetic sequence

<400> SEQUENCE: 898
gcacaacucc ggtgacauca a                                             21

<210> SEQ ID NO 899
<211> LENGTH: 21
<212> TYPE: DNA
<213> ORGANISM: Artificial Sequence
<220> FEATURE:
<223> OTHER INFORMATION: synthetic sequence

<400> SEQUENCE: 899
tgaugcccaa agauggcaag a                                             21

<210> SEQ ID NO 900
<211> LENGTH: 21
<212> TYPE: DNA
<213> ORGANISM: Artificial Sequence
<220> FEATURE:
<223> OTHER INFORMATION: synthetic sequence

<400> SEQUENCE: 900
cgctcttcuc tacgaccucc a                                             21

<210> SEQ ID NO 901
<211> LENGTH: 20
<212> TYPE: DNA
<213> ORGANISM: Artificial Sequence
```

```
<220> FEATURE:
<223> OTHER INFORMATION: synthetic sequence

<400> SEQUENCE: 901
ttctcgguct ggaggaugga                                           20

<210> SEQ ID NO 902
<211> LENGTH: 23
<212> TYPE: DNA
<213> ORGANISM: Artificial Sequence
<220> FEATURE:
<223> OTHER INFORMATION: synthetic sequence

<400> SEQUENCE: 902
cagctccaga guctctagac ugt                                       23

<210> SEQ ID NO 903
<211> LENGTH: 18
<212> TYPE: DNA
<213> ORGANISM: Artificial Sequence
<220> FEATURE:
<223> OTHER INFORMATION: synthetic sequence

<400> SEQUENCE: 903
aggactgccu gccccaua                                             18

<210> SEQ ID NO 904
<211> LENGTH: 22
<212> TYPE: DNA
<213> ORGANISM: Artificial Sequence
<220> FEATURE:
<223> OTHER INFORMATION: synthetic sequence

<400> SEQUENCE: 904
acattcctcg augtcccctu ct                                        22

<210> SEQ ID NO 905
<211> LENGTH: 20
<212> TYPE: DNA
<213> ORGANISM: Artificial Sequence
<220> FEATURE:
<223> OTHER INFORMATION: synthetic sequence

<400> SEQUENCE: 905 ccttgggca aggaccugag                                            20

<210> SEQ ID NO 906
<211> LENGTH: 24
<212> TYPE: DNA
<213> ORGANISM: Artificial Sequence
<220> FEATURE:
<223> OTHER INFORMATION: synthetic sequence

<400> SEQUENCE: 906
ccccacaacu tgaagatgtu ccat                                      24

<210> SEQ ID NO 907
<211> LENGTH: 21
<212> TYPE: DNA
<213> ORGANISM: Artificial Sequence
<220> FEATURE:
<223> OTHER INFORMATION: synthetic sequence

<400> SEQUENCE: 907
ggttgtgauc ggcatctugg t                                         21
```

<210> SEQ ID NO 908
<211> LENGTH: 21
<212> TYPE: DNA
<213> ORGANISM: Artificial Sequence
<220> FEATURE:
<223> OTHER INFORMATION: synthetic sequence

<400> SEQUENCE: 908
ccccugcagg atgtuggaaa t                                                 21

<210> SEQ ID NO 909
<211> LENGTH: 24
<212> TYPE: DNA
<213> ORGANISM: Artificial Sequence
<220> FEATURE:
<223> OTHER INFORMATION: synthetic sequence

<400> SEQUENCE: 909
ccgctgtgua ggaaagaagc uaaa                                              24

<210> SEQ ID NO 910
<211> LENGTH: 19
<212> TYPE: DNA
<213> ORGANISM: Artificial Sequence
<220> FEATURE:
<223> OTHER INFORMATION: synthetic sequence

<400> SEQUENCE: 910
acaaggttcu ggcgtgguc                                                    19

<210> SEQ ID NO 911
<211> LENGTH: 18
<212> TYPE: DNA
<213> ORGANISM: Artificial Sequence
<220> FEATURE:
<223> OTHER INFORMATION: synthetic sequence

<400> SEQUENCE: 911
gaucccgcac acccgaua                                                     18

<210> SEQ ID NO 912
<211> LENGTH: 25
<212> TYPE: DNA
<213> ORGANISM: Artificial Sequence
<220> FEATURE:
<223> OTHER INFORMATION: synthetic sequence

<400> SEQUENCE: 912
aatagttcag cugcttcatg tucct                                             25

<210> SEQ ID NO 913
<211> LENGTH: 18
<212> TYPE: DNA
<213> ORGANISM: Artificial Sequence
<220> FEATURE:
<223> OTHER INFORMATION: synthetic sequence

<400> SEQUENCE: 913
gccccatugt tcccggut                                                     18

<210> SEQ ID NO 914
<211> LENGTH: 18
<212> TYPE: DNA
<213> ORGANISM: Artificial Sequence
<220> FEATURE:
<223> OTHER INFORMATION: synthetic sequence

<400> SEQUENCE: 914
ggcacugccc acaaguca                                                      18

<210> SEQ ID NO 915
<211> LENGTH: 20
<212> TYPE: DNA
<213> ORGANISM: Artificial Sequence
<220> FEATURE:
<223> OTHER INFORMATION: synthetic sequence

<400> SEQUENCE: 915
tctcggccac cuttgaugag                                                    20

<210> SEQ ID NO 916
<211> LENGTH: 26
<212> TYPE: DNA
<213> ORGANISM: Artificial Sequence
<220> FEATURE:
<223> OTHER INFORMATION: synthetic sequence

<400> SEQUENCE: 916
atttgagctc agaugttctt cacugt                                             26

<210> SEQ ID NO 917
<211> LENGTH: 22
<212> TYPE: DNA
<213> ORGANISM: Artificial Sequence
<220> FEATURE:
<223> OTHER INFORMATION: synthetic sequence

<400> SEQUENCE: 917
gcctgtgtcu ccttgtgatg ut                                                 22

<210> SEQ ID NO 918
<211> LENGTH: 22
<212> TYPE: DNA
<213> ORGANISM: Artificial Sequence
<220> FEATURE:
<223> OTHER INFORMATION: synthetic sequence

<400> SEQUENCE: 918
gcctgtgtcu ccttgtgatg ut                                                 22

<210> SEQ ID NO 919
<211> LENGTH: 22
<212> TYPE: DNA
<213> ORGANISM: Artificial Sequence
<220> FEATURE:
<223> OTHER INFORMATION: synthetic sequence

<400> SEQUENCE: 919
gcagcactuc aggaggtuac at                                                 22

<210> SEQ ID NO 920
<211> LENGTH: 20
<212> TYPE: DNA
<213> ORGANISM: Artificial Sequence
<220> FEATURE:
<223> OTHER INFORMATION: synthetic sequence

<400> SEQUENCE: 920
tggttgcugt ctcagtugct                                                    20

<210> SEQ ID NO 921

```
<211> LENGTH: 21
<212> TYPE: DNA
<213> ORGANISM: Artificial Sequence
<220> FEATURE:
<223> OTHER INFORMATION: synthetic sequence

<400> SEQUENCE: 921
ccagggugcc aggatcatua c                                             21

<210> SEQ ID NO 922
<211> LENGTH: 22
<212> TYPE: DNA
<213> ORGANISM: Artificial Sequence
<220> FEATURE:
<223> OTHER INFORMATION: synthetic sequence

<400> SEQUENCE: 922
tccaaagcuc caaaggttuc ct                                            22

<210> SEQ ID NO 923
<211> LENGTH: 20
<212> TYPE: DNA
<213> ORGANISM: Artificial Sequence
<220> FEATURE:
<223> OTHER INFORMATION: synthetic sequence

<400> SEQUENCE: 923
cugtgattcu gcccacggaa                                               20

<210> SEQ ID NO 924
<211> LENGTH: 23
<212> TYPE: DNA
<213> ORGANISM: Artificial Sequence
<220> FEATURE:
<223> OTHER INFORMATION: synthetic sequence

<400> SEQUENCE: 924
ccaatgtgag uccctcagcca auc                                          23

<210> SEQ ID NO 925
<211> LENGTH: 25
<212> TYPE: DNA
<213> ORGANISM: Artificial Sequence
<220> FEATURE:
<223> OTHER INFORMATION: synthetic sequence

<400> SEQUENCE: 925
gacagacuga agaaacaucc aaggt                                         25

<210> SEQ ID NO 926
<211> LENGTH: 19
<212> TYPE: DNA
<213> ORGANISM: Artificial Sequence
<220> FEATURE:
<223> OTHER INFORMATION: synthetic sequence

<400> SEQUENCE: 926
tttccaggca ccgutccuc                                                19

<210> SEQ ID NO 927
<211> LENGTH: 20
<212> TYPE: DNA
<213> ORGANISM: Artificial Sequence
<220> FEATURE:
<223> OTHER INFORMATION: synthetic sequence

<400> SEQUENCE: 927
```
gacaagccug tagcccaugt                                              20

<210> SEQ ID NO 928
<211> LENGTH: 21
<212> TYPE: DNA
<213> ORGANISM: Artificial Sequence
<220> FEATURE:
<223> OTHER INFORMATION: synthetic sequence

<400> SEQUENCE: 928
atgagguaca ggcccucuga t                                            21

<210> SEQ ID NO 929
<211> LENGTH: 20
<212> TYPE: DNA
<213> ORGANISM: Artificial Sequence
<220> FEATURE:
<223> OTHER INFORMATION: synthetic sequence

<400> SEQUENCE: 929
ctctuggcag ccttccugat                                              20

<210> SEQ ID NO 930
<211> LENGTH: 25
<212> TYPE: DNA
<213> ORGANISM: Artificial Sequence
<220> FEATURE:
<223> OTHER INFORMATION: synthetic sequence

<400> SEQUENCE: 930
tccactctca aucactctca gtuct                                        25

<210> SEQ ID NO 931
<211> LENGTH: 23
<212> TYPE: DNA
<213> ORGANISM: Artificial Sequence
<220> FEATURE:
<223> OTHER INFORMATION: synthetic sequence

<400> SEQUENCE: 931
gaggccagca guaaaacaac auc                                          23

<210> SEQ ID NO 932
<211> LENGTH: 27
<212> TYPE: DNA
<213> ORGANISM: Artificial Sequence
<220> FEATURE:
<223> OTHER INFORMATION: synthetic sequence

<400> SEQUENCE: 932
acagaaggtg acutgggcat agataua                                      27

<210> SEQ ID NO 933
<211> LENGTH: 20
<212> TYPE: DNA
<213> ORGANISM: Artificial Sequence
<220> FEATURE:
<223> OTHER INFORMATION: synthetic sequence

<400> SEQUENCE: 933
ccccgcggga cucatattut                                              20

<210> SEQ ID NO 934
<211> LENGTH: 21
<212> TYPE: DNA

```
<213> ORGANISM: Artificial Sequence
<220> FEATURE:
<223> OTHER INFORMATION: synthetic sequence

<400> SEQUENCE: 934
gacacagcgg ugctgaaaua c                                     21

<210> SEQ ID NO 935
<211> LENGTH: 20
<212> TYPE: DNA
<213> ORGANISM: Artificial Sequence
<220> FEATURE:
<223> OTHER INFORMATION: synthetic sequence

<400> SEQUENCE: 935
gagauggcac gggacacuac                                       20

<210> SEQ ID NO 936
<211> LENGTH: 21
<212> TYPE: DNA
<213> ORGANISM: Artificial Sequence
<220> FEATURE:
<223> OTHER INFORMATION: synthetic sequence

<400> SEQUENCE: 936
ggttgtggug gtctgacagu t                                     21

<210> SEQ ID NO 937
<211> LENGTH: 20
<212> TYPE: DNA
<213> ORGANISM: Artificial Sequence
<220> FEATURE:
<223> OTHER INFORMATION: synthetic sequence

<400> SEQUENCE: 937
gtccagggca aggucttuga                                       20

<210> SEQ ID NO 938
<211> LENGTH: 26
<212> TYPE: DNA
<213> ORGANISM: Artificial Sequence
<220> FEATURE:
<223> OTHER INFORMATION: synthetic sequence

<400> SEQUENCE: 938
cattgtagtt tguagctcgt gtgtug                                26

<210> SEQ ID NO 939
<211> LENGTH: 24
<212> TYPE: DNA
<213> ORGANISM: Artificial Sequence
<220> FEATURE:
<223> OTHER INFORMATION: synthetic sequence

<400> SEQUENCE: 939
ggaagaaggc ccuacagtat ugag                                  24

<210> SEQ ID NO 940
<211> LENGTH: 22
<212> TYPE: DNA
<213> ORGANISM: Artificial Sequence
<220> FEATURE:
<223> OTHER INFORMATION: synthetic sequence

<400> SEQUENCE: 940
cccacagacc utggattctu ca                                    22
```

<210> SEQ ID NO 941
<211> LENGTH: 22
<212> TYPE: DNA
<213> ORGANISM: Artificial Sequence
<220> FEATURE:
<223> OTHER INFORMATION: synthetic sequence

<400> SEQUENCE: 941
ccagaccccu cgaagttctt ut                                                22

<210> SEQ ID NO 942
<211> LENGTH: 20
<212> TYPE: DNA
<213> ORGANISM: Artificial Sequence
<220> FEATURE:
<223> OTHER INFORMATION: synthetic sequence

<400> SEQUENCE: 942
cttgtcccuc tccagcacut                                                   20

<210> SEQ ID NO 943
<211> LENGTH: 20
<212> TYPE: DNA
<213> ORGANISM: Artificial Sequence
<220> FEATURE:
<223> OTHER INFORMATION: synthetic sequence

<400> SEQUENCE: 943
ttcgtcugca cagucaccaa                                                   20

<210> SEQ ID NO 944
<211> LENGTH: 20
<212> TYPE: DNA
<213> ORGANISM: Artificial Sequence
<220> FEATURE:
<223> OTHER INFORMATION: synthetic sequence

<400> SEQUENCE: 944
cagccacagc aguagcaaug                                                   20

<210> SEQ ID NO 945
<211> LENGTH: 20
<212> TYPE: DNA
<213> ORGANISM: Artificial Sequence
<220> FEATURE:
<223> OTHER INFORMATION: synthetic sequence

<400> SEQUENCE: 945
gggagaggcu cuaccaggaa                                                   20

<210> SEQ ID NO 946
<211> LENGTH: 22
<212> TYPE: DNA
<213> ORGANISM: Artificial Sequence
<220> FEATURE:
<223> OTHER INFORMATION: synthetic sequence

<400> SEQUENCE: 946
gtgggtccac ugagtcattg ua                                                22

<210> SEQ ID NO 947
<211> LENGTH: 28
<212> TYPE: DNA
<213> ORGANISM: Artificial Sequence
<220> FEATURE:

<223> OTHER INFORMATION: synthetic sequence

<400> SEQUENCE: 947
ttctacctcu agatctgttt ggtucagt                                    28

<210> SEQ ID NO 948
<211> LENGTH: 21
<212> TYPE: DNA
<213> ORGANISM: Artificial Sequence
<220> FEATURE:
<223> OTHER INFORMATION: synthetic sequence

<400> SEQUENCE: 948
aacgagatgu ggacagcaug t                                           21

<210> SEQ ID NO 949
<211> LENGTH: 21
<212> TYPE: DNA
<213> ORGANISM: Artificial Sequence
<220> FEATURE:
<223> OTHER INFORMATION: synthetic sequence

<400> SEQUENCE: 949
gtgguccacc ccaacuaaag a                                           21

<210> SEQ ID NO 950
<211> LENGTH: 24
<212> TYPE: DNA
<213> ORGANISM: Artificial Sequence
<220> FEATURE:
<223> OTHER INFORMATION: synthetic sequence

<400> SEQUENCE: 950
acagacttcc utttggccau acaa                                        24

<210> SEQ ID NO 951
<211> LENGTH: 20
<212> TYPE: DNA
<213> ORGANISM: Artificial Sequence
<220> FEATURE:
<223> OTHER INFORMATION: synthetic sequence

<400> SEQUENCE: 951
tcgccatuga ccgctacaut                                             20

<210> SEQ ID NO 952
<211> LENGTH: 22
<212> TYPE: DNA
<213> ORGANISM: Artificial Sequence
<220> FEATURE:
<223> OTHER INFORMATION: synthetic sequence

<400> SEQUENCE: 952
agttgtucca acctagcaug gg                                          22

<210> SEQ ID NO 953
<211> LENGTH: 19
<212> TYPE: DNA
<213> ORGANISM: Artificial Sequence
<220> FEATURE:
<223> OTHER INFORMATION: synthetic sequence

<400> SEQUENCE: 953
cgccuccacc aacucagat                                              19

```
<210> SEQ ID NO 954
<211> LENGTH: 20
<212> TYPE: DNA
<213> ORGANISM: Artificial Sequence
<220> FEATURE:
<223> OTHER INFORMATION: synthetic sequence

<400> SEQUENCE: 954
ggtcguccag gtaccctugg                                              20

<210> SEQ ID NO 955
<211> LENGTH: 21
<212> TYPE: DNA
<213> ORGANISM: Artificial Sequence
<220> FEATURE:
<223> OTHER INFORMATION: synthetic sequence

<400> SEQUENCE: 955
tgtggcctau gcagtcaacu c                                            21

<210> SEQ ID NO 956
<211> LENGTH: 24
<212> TYPE: DNA
<213> ORGANISM: Artificial Sequence
<220> FEATURE:
<223> OTHER INFORMATION: synthetic sequence

<400> SEQUENCE: 956
gtgaacugca tctgguagag aaca                                         24

<210> SEQ ID NO 957
<211> LENGTH: 26
<212> TYPE: DNA
<213> ORGANISM: Artificial Sequence
<220> FEATURE:
<223> OTHER INFORMATION: synthetic sequence

<400> SEQUENCE: 957
ttgcaaagaa ggaagauggt tgttuc                                       26

<210> SEQ ID NO 958
<211> LENGTH: 20
<212> TYPE: DNA
<213> ORGANISM: Artificial Sequence
<220> FEATURE:
<223> OTHER INFORMATION: synthetic sequence

<400> SEQUENCE: 958
atactggcug cacaggtugt                                              20

<210> SEQ ID NO 959
<211> LENGTH: 20
<212> TYPE: DNA
<213> ORGANISM: Artificial Sequence
<220> FEATURE:
<223> OTHER INFORMATION: synthetic sequence

<400> SEQUENCE: 959
gtgaccguga tgctggugat                                              20

<210> SEQ ID NO 960
<211> LENGTH: 25
<212> TYPE: DNA
<213> ORGANISM: Artificial Sequence
<220> FEATURE:
<223> OTHER INFORMATION: synthetic sequence
```

```
<400> SEQUENCE: 960
cggtuataga tgtatcuggc cacac                                          25

<210> SEQ ID NO 961
<211> LENGTH: 23
<212> TYPE: DNA
<213> ORGANISM: Artificial Sequence
<220> FEATURE:
<223> OTHER INFORMATION: synthetic sequence

<400> SEQUENCE: 961
ctgctcagtg ugatccttgc aua                                            23

<210> SEQ ID NO 962
<211> LENGTH: 19
<212> TYPE: DNA
<213> ORGANISM: Artificial Sequence
<220> FEATURE:
<223> OTHER INFORMATION: synthetic sequence

<400> SEQUENCE: 962
catugcgaca ggcacacuc                                                 19

<210> SEQ ID NO 963
<211> LENGTH: 19
<212> TYPE: DNA
<213> ORGANISM: Artificial Sequence
<220> FEATURE:
<223> OTHER INFORMATION: synthetic sequence

<400> SEQUENCE: 963
ctgcuggcac aaggcaaug                                                 19

<210> SEQ ID NO 964
<211> LENGTH: 20
<212> TYPE: DNA
<213> ORGANISM: Artificial Sequence
<220> FEATURE:
<223> OTHER INFORMATION: synthetic sequence

<400> SEQUENCE: 964
tcatgcuggg cttcgaguag                                                20

<210> SEQ ID NO 965
<211> LENGTH: 19
<212> TYPE: DNA
<213> ORGANISM: Artificial Sequence
<220> FEATURE:
<223> OTHER INFORMATION: synthetic sequence

<400> SEQUENCE: 965
cgtcagcggc uttctccua                                                 19

<210> SEQ ID NO 966
<211> LENGTH: 23
<212> TYPE: DNA
<213> ORGANISM: Artificial Sequence
<220> FEATURE:
<223> OTHER INFORMATION: synthetic sequence

<400> SEQUENCE: 966
ttgauccacc tgcuccaaaa act                                            23

<210> SEQ ID NO 967
<211> LENGTH: 20
```

<212> TYPE: DNA
<213> ORGANISM: Artificial Sequence
<220> FEATURE:
<223> OTHER INFORMATION: synthetic sequence

<400> SEQUENCE: 967
cgggagguca ccctacacut                                              20

<210> SEQ ID NO 968
<211> LENGTH: 19
<212> TYPE: DNA
<213> ORGANISM: Artificial Sequence
<220> FEATURE:
<223> OTHER INFORMATION: synthetic sequence

<400> SEQUENCE: 968
gggatgucca ggtctucgg                                               19

<210> SEQ ID NO 969
<211> LENGTH: 22
<212> TYPE: DNA
<213> ORGANISM: Artificial Sequence
<220> FEATURE:
<223> OTHER INFORMATION: synthetic sequence

<400> SEQUENCE: 969
ctacagaccc aguttcccca ut                                           22

<210> SEQ ID NO 970
<211> LENGTH: 21
<212> TYPE: DNA
<213> ORGANISM: Artificial Sequence
<220> FEATURE:
<223> OTHER INFORMATION: synthetic sequence

<400> SEQUENCE: 970
aagggcucag agtggttgtu t                                            21

<210> SEQ ID NO 971
<211> LENGTH: 23
<212> TYPE: DNA
<213> ORGANISM: Artificial Sequence
<220> FEATURE:
<223> OTHER INFORMATION: synthetic sequence

<400> SEQUENCE: 971
ctgcugcaaa tgtggugaga aat                                          23

<210> SEQ ID NO 972
<211> LENGTH: 20
<212> TYPE: DNA
<213> ORGANISM: Artificial Sequence
<220> FEATURE:
<223> OTHER INFORMATION: synthetic sequence

<400> SEQUENCE: 972
caccaauggc aaaaggcugt                                              20

<210> SEQ ID NO 973
<211> LENGTH: 22
<212> TYPE: DNA
<213> ORGANISM: Artificial Sequence
<220> FEATURE:
<223> OTHER INFORMATION: synthetic sequence

<400> SEQUENCE: 973
gaaagccaca cccugaaucu ca                                    22

<210> SEQ ID NO 974
<211> LENGTH: 22
<212> TYPE: DNA
<213> ORGANISM: Artificial Sequence
<220> FEATURE:
<223> OTHER INFORMATION: synthetic sequence

<400> SEQUENCE: 974
uccuuccucu uucuccucca ca                                    22

<210> SEQ ID NO 975
<211> LENGTH: 20
<212> TYPE: DNA
<213> ORGANISM: Artificial Sequence
<220> FEATURE:
<223> OTHER INFORMATION: synthetic sequence

<400> SEQUENCE: 975
gaaccagcgg utaccaugga                                       20

<210> SEQ ID NO 976
<211> LENGTH: 22
<212> TYPE: DNA
<213> ORGANISM: Artificial Sequence
<220> FEATURE:
<223> OTHER INFORMATION: synthetic sequence

<400> SEQUENCE: 976
gtagatggug ggcaggaaga ut                                    22

<210> SEQ ID NO 977
<211> LENGTH: 27
<212> TYPE: DNA
<213> ORGANISM: Artificial Sequence
<220> FEATURE:
<223> OTHER INFORMATION: synthetic sequence

<400> SEQUENCE: 977
gattccagcc aggauacaga tctuaaa                               27

<210> SEQ ID NO 978
<211> LENGTH: 22
<212> TYPE: DNA
<213> ORGANISM: Artificial Sequence
<220> FEATURE:
<223> OTHER INFORMATION: synthetic sequence

<400> SEQUENCE: 978
ggcucaaagg agucaaagug ga                                    22

<210> SEQ ID NO 979
<211> LENGTH: 21
<212> TYPE: DNA
<213> ORGANISM: Artificial Sequence
<220> FEATURE:
<223> OTHER INFORMATION: synthetic sequence

<400> SEQUENCE: 979
cagtactgcc cugaccctua c                                     21

<210> SEQ ID NO 980
<211> LENGTH: 26
<212> TYPE: DNA
<213> ORGANISM: Artificial Sequence -continued

```
<220> FEATURE:
<223> OTHER INFORMATION: synthetic sequence

<400> SEQUENCE: 980
aaaatcccag auatgcugga aaacct                                          26

<210> SEQ ID NO 981
<211> LENGTH: 20
<212> TYPE: DNA
<213> ORGANISM: Artificial Sequence
<220> FEATURE:
<223> OTHER INFORMATION: synthetic sequence

<400> SEQUENCE: 981
gccaggugac aggaacctut                                                 20

<210> SEQ ID NO 982
<211> LENGTH: 21
<212> TYPE: DNA
<213> ORGANISM: Artificial Sequence
<220> FEATURE:
<223> OTHER INFORMATION: synthetic sequence

<400> SEQUENCE: 982
tcacgaggau ttcccgguag t                                               21

<210> SEQ ID NO 983
<211> LENGTH: 21
<212> TYPE: DNA
<213> ORGANISM: Artificial Sequence
<220> FEATURE:
<223> OTHER INFORMATION: synthetic sequence

<400> SEQUENCE: 983
cccggcagau tccacagaau t                                               21

<210> SEQ ID NO 984
<211> LENGTH: 23
<212> TYPE: DNA
<213> ORGANISM: Artificial Sequence
<220> FEATURE:
<223> OTHER INFORMATION: synthetic sequence

<400> SEQUENCE: 984
caggtcgcug acatatttcu gga                                             23

<210> SEQ ID NO 985
<211> LENGTH: 28
<212> TYPE: DNA
<213> ORGANISM: Artificial Sequence
<220> FEATURE:
<223> OTHER INFORMATION: synthetic sequence

<400> SEQUENCE: 985
gcagatucca caaaagttca tagtugac                                        28

<210> SEQ ID NO 986
<211> LENGTH: 24
<212> TYPE: DNA
<213> ORGANISM: Artificial Sequence
<220> FEATURE:
<223> OTHER INFORMATION: synthetic sequence

<400> SEQUENCE: 986
agcttcaggu cgctgatgta ttuc                                            24
```

```
<210> SEQ ID NO 987
<211> LENGTH: 23
<212> TYPE: DNA
<213> ORGANISM: Artificial Sequence
<220> FEATURE:
<223> OTHER INFORMATION: synthetic sequence

<400> SEQUENCE: 987
agccaaugac tttgtggguga cat                                              23

<210> SEQ ID NO 988
<211> LENGTH: 20
<212> TYPE: DNA
<213> ORGANISM: Artificial Sequence
<220> FEATURE:
<223> OTHER INFORMATION: synthetic sequence

<400> SEQUENCE: 988
tgcaggagug tcagcttugt                                                   20

<210> SEQ ID NO 989
<211> LENGTH: 20
<212> TYPE: DNA
<213> ORGANISM: Artificial Sequence
<220> FEATURE:
<223> OTHER INFORMATION: synthetic sequence

<400> SEQUENCE: 989
gacacuctgg actucagcca                                                   20

<210> SEQ ID NO 990
<211> LENGTH: 21
<212> TYPE: DNA
<213> ORGANISM: Artificial Sequence
<220> FEATURE:
<223> OTHER INFORMATION: synthetic sequence

<400> SEQUENCE: 990
ggtccugaga aagccctcuc t                                                 21

<210> SEQ ID NO 991
<211> LENGTH: 20
<212> TYPE: DNA
<213> ORGANISM: Artificial Sequence
<220> FEATURE:
<223> OTHER INFORMATION: synthetic sequence

<400> SEQUENCE: 991
ccugccacgc caataacuca                                                   20

<210> SEQ ID NO 992
<211> LENGTH: 22
<212> TYPE: DNA
<213> ORGANISM: Artificial Sequence
<220> FEATURE:
<223> OTHER INFORMATION: synthetic sequence

<400> SEQUENCE: 992
aggtcaggtu cacagagtcc ut                                                22

<210> SEQ ID NO 993
<211> LENGTH: 22
<212> TYPE: DNA
<213> ORGANISM: Artificial Sequence
<220> FEATURE:
<223> OTHER INFORMATION: synthetic sequence
```

```
<400> SEQUENCE: 993
tccagaaucg aaggccauca ag                                    22

<210> SEQ ID NO 994
<211> LENGTH: 22
<212> TYPE: DNA
<213> ORGANISM: Artificial Sequence
<220> FEATURE:
<223> OTHER INFORMATION: synthetic sequence

<400> SEQUENCE: 994
tguagggaag tgaugggaga gg                                    22

<210> SEQ ID NO 995
<211> LENGTH: 24
<212> TYPE: DNA
<213> ORGANISM: Artificial Sequence
<220> FEATURE:
<223> OTHER INFORMATION: synthetic sequence

<400> SEQUENCE: 995
cgagcuatag aagaaucacc agca                                  24

<210> SEQ ID NO 996
<211> LENGTH: 22
<212> TYPE: DNA
<213> ORGANISM: Artificial Sequence
<220> FEATURE:
<223> OTHER INFORMATION: synthetic sequence

<400> SEQUENCE: 996
tcttcggagu ttgggtttgc ut                                    22

<210> SEQ ID NO 997
<211> LENGTH: 26
<212> TYPE: DNA
<213> ORGANISM: Artificial Sequence
<220> FEATURE:
<223> OTHER INFORMATION: synthetic sequence

<400> SEQUENCE: 997
gcaauccaga cagtaattcu gcaaac                                26

<210> SEQ ID NO 998
<211> LENGTH: 26
<212> TYPE: DNA
<213> ORGANISM: Artificial Sequence
<220> FEATURE:
<223> OTHER INFORMATION: synthetic sequence

<400> SEQUENCE: 998
aaagtgggaa gauacgattc aagucc                                26

<210> SEQ ID NO 999
<211> LENGTH: 21
<212> TYPE: DNA
<213> ORGANISM: Artificial Sequence
<220> FEATURE:
<223> OTHER INFORMATION: synthetic sequence

<400> SEQUENCE: 999
cacugccccg tcttauggaa a                                     21

<210> SEQ ID NO 1000
```

```
<211> LENGTH: 25
<212> TYPE: DNA
<213> ORGANISM: Artificial Sequence
<220> FEATURE:
<223> OTHER INFORMATION: synthetic sequence

<400> SEQUENCE: 1000
aggttggagu cgttctcaua gaact                                              25

<210> SEQ ID NO 1001
<211> LENGTH: 27
<212> TYPE: DNA
<213> ORGANISM: Artificial Sequence
<220> FEATURE:
<223> OTHER INFORMATION: synthetic sequence

<400> SEQUENCE: 1001
cctctactac ctuatggacc tgtctua                                            27

<210> SEQ ID NO 1002
<211> LENGTH: 25
<212> TYPE: DNA
<213> ORGANISM: Artificial Sequence
<220> FEATURE:
<223> OTHER INFORMATION: synthetic sequence

<400> SEQUENCE: 1002
ggcatcacag ucttttccac aaaug                                              25

<210> SEQ ID NO 1003
<211> LENGTH: 23
<212> TYPE: DNA
<213> ORGANISM: Artificial Sequence
<220> FEATURE:
<223> OTHER INFORMATION: synthetic sequence

<400> SEQUENCE: 1003
ggcttcatag cautcgccta cuc                                                23

<210> SEQ ID NO 1004
<211> LENGTH: 25
<212> TYPE: DNA
<213> ORGANISM: Artificial Sequence
<220> FEATURE:
<223> OTHER INFORMATION: synthetic sequence

<400> SEQUENCE: 1004
ggatgaaucc aatggtcaug aggat                                              25

<210> SEQ ID NO 1005
<211> LENGTH: 22
<212> TYPE: DNA
<213> ORGANISM: Artificial Sequence
<220> FEATURE:
<223> OTHER INFORMATION: synthetic sequence

<400> SEQUENCE: 1005
cuccaagacu ggcaagaaag ga                                                 22

<210> SEQ ID NO 1006
<211> LENGTH: 21
<212> TYPE: DNA
<213> ORGANISM: Artificial Sequence
<220> FEATURE:
<223> OTHER INFORMATION: synthetic sequence

<400> SEQUENCE: 1006
```
gcatcttggg utcaggctuc a                                          21

<210> SEQ ID NO 1007
<211> LENGTH: 26
<212> TYPE: DNA
<213> ORGANISM: Artificial Sequence
<220> FEATURE:
<223> OTHER INFORMATION: synthetic sequence

<400> SEQUENCE: 1007
gtttatggag cagguggaag atcuat                                     26

<210> SEQ ID NO 1008
<211> LENGTH: 19
<212> TYPE: DNA
<213> ORGANISM: Artificial Sequence
<220> FEATURE:
<223> OTHER INFORMATION: synthetic sequence

<400> SEQUENCE: 1008
tcgtgcaauc tgcguacca                                             19

<210> SEQ ID NO 1009
<211> LENGTH: 20
<212> TYPE: DNA
<213> ORGANISM: Artificial Sequence
<220> FEATURE:
<223> OTHER INFORMATION: synthetic sequence

<400> SEQUENCE: 1009
cgagguggag cacatgtuca                                            20

<210> SEQ ID NO 1010
<211> LENGTH: 20
<212> TYPE: DNA
<213> ORGANISM: Artificial Sequence
<220> FEATURE:
<223> OTHER INFORMATION: synthetic sequence

<400> SEQUENCE: 1010 ggucccaga acggatctut                                             20

<210> SEQ ID NO 1011
<211> LENGTH: 19
<212> TYPE: DNA
<213> ORGANISM: Artificial Sequence
<220> FEATURE:
<223> OTHER INFORMATION: synthetic sequence

<400> SEQUENCE: 1011
ggctgtcucg aacgtguga                                             19

<210> SEQ ID NO 1012
<211> LENGTH: 28
<212> TYPE: DNA
<213> ORGANISM: Artificial Sequence
<220> FEATURE:
<223> OTHER INFORMATION: synthetic sequence

<400> SEQUENCE: 1012
aaccatcaaa cagaaauacc aggtcuac                                   28

<210> SEQ ID NO 1013
<211> LENGTH: 24
<212> TYPE: DNA

```
<213> ORGANISM: Artificial Sequence
<220> FEATURE:
<223> OTHER INFORMATION: synthetic sequence

<400> SEQUENCE: 1013
atgtcaaaug acagcaaagc acug                                             24

<210> SEQ ID NO 1014
<211> LENGTH: 24
<212> TYPE: DNA
<213> ORGANISM: Artificial Sequence
<220> FEATURE:
<223> OTHER INFORMATION: synthetic sequence

<400> SEQUENCE: 1014
caacttgtcc uccttgtgaa augg                                             24

<210> SEQ ID NO 1015
<211> LENGTH: 21
<212> TYPE: DNA
<213> ORGANISM: Artificial Sequence
<220> FEATURE:
<223> OTHER INFORMATION: synthetic sequence

<400> SEQUENCE: 1015
ctgctgucag gtctccaaug a                                                21

<210> SEQ ID NO 1016
<211> LENGTH: 22
<212> TYPE: DNA
<213> ORGANISM: Artificial Sequence
<220> FEATURE:
<223> OTHER INFORMATION: synthetic sequence

<400> SEQUENCE: 1016
gccagugaca ugcaaagaaa ct                                               22

<210> SEQ ID NO 1017
<211> LENGTH: 21
<212> TYPE: DNA
<213> ORGANISM: Artificial Sequence
<220> FEATURE:
<223> OTHER INFORMATION: synthetic sequence

<400> SEQUENCE: 1017
ctgaagacgu gguaccagac a                                                21

<210> SEQ ID NO 1018
<211> LENGTH: 23
<212> TYPE: DNA
<213> ORGANISM: Artificial Sequence
<220> FEATURE:
<223> OTHER INFORMATION: synthetic sequence

<400> SEQUENCE: 1018
gcttcaagac cuctcaaggc tut                                              23

<210> SEQ ID NO 1019
<211> LENGTH: 23
<212> TYPE: DNA
<213> ORGANISM: Artificial Sequence
<220> FEATURE:
<223> OTHER INFORMATION: synthetic sequence

<400> SEQUENCE: 1019
ctgaactgca gauccttggu gaa                                              23
```

<210> SEQ ID NO 1020
<211> LENGTH: 21
<212> TYPE: DNA
<213> ORGANISM: Artificial Sequence
<220> FEATURE:
<223> OTHER INFORMATION: synthetic sequence

<400> SEQUENCE: 1020
caccaacgcu gcctttaaug a         21

<210> SEQ ID NO 1021
<211> LENGTH: 21
<212> TYPE: DNA
<213> ORGANISM: Artificial Sequence
<220> FEATURE:
<223> OTHER INFORMATION: synthetic sequence

<400> SEQUENCE: 1021
gaaagcaaag gcucagcagu t         21

<210> SEQ ID NO 1022
<211> LENGTH: 28
<212> TYPE: DNA
<213> ORGANISM: Artificial Sequence
<220> FEATURE:
<223> OTHER INFORMATION: synthetic sequence

<400> SEQUENCE: 1022
tgtagttggu cacttcacau aaggaaat         28

<210> SEQ ID NO 1023
<211> LENGTH: 22
<212> TYPE: DNA
<213> ORGANISM: Artificial Sequence
<220> FEATURE:
<223> OTHER INFORMATION: synthetic sequence

<400> SEQUENCE: 1023
gtggctcucc ttgtcatttu cc         22

<210> SEQ ID NO 1024
<211> LENGTH: 23
<212> TYPE: DNA
<213> ORGANISM: Artificial Sequence
<220> FEATURE:
<223> OTHER INFORMATION: synthetic sequence

<400> SEQUENCE: 1024
gggaggaacc aggcuttaaa gut         23

<210> SEQ ID NO 1025
<211> LENGTH: 27
<212> TYPE: DNA
<213> ORGANISM: Artificial Sequence
<220> FEATURE:
<223> OTHER INFORMATION: synthetic sequence

<400> SEQUENCE: 1025
ccttggtgat uctaatagtc cttgugt         27

<210> SEQ ID NO 1026
<211> LENGTH: 19
<212> TYPE: DNA
<213> ORGANISM: Artificial Sequence
<220> FEATURE:

```
<223> OTHER INFORMATION: synthetic sequence

<400> SEQUENCE: 1026
cgacgggaug gcatcacua                                                    19

<210> SEQ ID NO 1027
<211> LENGTH: 19
<212> TYPE: DNA
<213> ORGANISM: Artificial Sequence
<220> FEATURE:
<223> OTHER INFORMATION: synthetic sequence

<400> SEQUENCE: 1027
gcgcgugctt ttgtttgug                                                    19

<210> SEQ ID NO 1028
<211> LENGTH: 24
<212> TYPE: DNA
<213> ORGANISM: Artificial Sequence
<220> FEATURE:
<223> OTHER INFORMATION: synthetic sequence

<400> SEQUENCE: 1028
cagatggata uatgccacgc ugat                                              24

<210> SEQ ID NO 1029
<211> LENGTH: 19
<212> TYPE: DNA
<213> ORGANISM: Artificial Sequence
<220> FEATURE:
<223> OTHER INFORMATION: synthetic sequence

<400> SEQUENCE: 1029
catggcaacc cugggacut                                                    19

<210> SEQ ID NO 1030
<211> LENGTH: 20
<212> TYPE: DNA
<213> ORGANISM: Artificial Sequence
<220> FEATURE:
<223> OTHER INFORMATION: synthetic sequence

<400> SEQUENCE: 1030
aattcugggc gggacttcuc                                                   20

<210> SEQ ID NO 1031
<211> LENGTH: 23
<212> TYPE: DNA
<213> ORGANISM: Artificial Sequence
<220> FEATURE:
<223> OTHER INFORMATION: synthetic sequence

<400> SEQUENCE: 1031
ccuagacacc uggaacagag aga                                               23

<210> SEQ ID NO 1032
<211> LENGTH: 20
<212> TYPE: DNA
<213> ORGANISM: Artificial Sequence
<220> FEATURE:
<223> OTHER INFORMATION: synthetic sequence

<400> SEQUENCE: 1032
tcacaggccu cactcguaca                                                   20
```

<210> SEQ ID NO 1033
<211> LENGTH: 25
<212> TYPE: DNA
<213> ORGANISM: Artificial Sequence
<220> FEATURE:
<223> OTHER INFORMATION: synthetic sequence

<400> SEQUENCE: 1033
aatgtctcau ggagaagcag ugaaa                                        25

<210> SEQ ID NO 1034
<211> LENGTH: 24
<212> TYPE: DNA
<213> ORGANISM: Artificial Sequence
<220> FEATURE:
<223> OTHER INFORMATION: synthetic sequence

<400> SEQUENCE: 1034
caucaggaac aacccaaucc aaag                                         24

<210> SEQ ID NO 1035
<211> LENGTH: 23
<212> TYPE: DNA
<213> ORGANISM: Artificial Sequence
<220> FEATURE:
<223> OTHER INFORMATION: synthetic sequence

<400> SEQUENCE: 1035
gcacagacug acagaaugaa cct                                          23

<210> SEQ ID NO 1036
<211> LENGTH: 25
<212> TYPE: DNA
<213> ORGANISM: Artificial Sequence
<220> FEATURE:
<223> OTHER INFORMATION: synthetic sequence

<400> SEQUENCE: 1036
gccatcguag gcatactgtt cauac                                        25

<210> SEQ ID NO 1037
<211> LENGTH: 20
<212> TYPE: DNA
<213> ORGANISM: Artificial Sequence
<220> FEATURE:
<223> OTHER INFORMATION: synthetic sequence

<400> SEQUENCE: 1037
ggacttugag gcgggtgtut                                              20

<210> SEQ ID NO 1038
<211> LENGTH: 28
<212> TYPE: DNA
<213> ORGANISM: Artificial Sequence
<220> FEATURE:
<223> OTHER INFORMATION: synthetic sequence

<400> SEQUENCE: 1038
tcaatagctt gtugaactgc atgatgua                                     28

<210> SEQ ID NO 1039
<211> LENGTH: 22
<212> TYPE: DNA
<213> ORGANISM: Artificial Sequence
<220> FEATURE:
<223> OTHER INFORMATION: synthetic sequence

<400> SEQUENCE: 1039
tgccaaguca gcaattctgu ga                                                22

<210> SEQ ID NO 1040
<211> LENGTH: 24
<212> TYPE: DNA
<213> ORGANISM: Artificial Sequence
<220> FEATURE:
<223> OTHER INFORMATION: synthetic sequence

<400> SEQUENCE: 1040
tcucaggtaa guaacaggcc aaga                                              24

<210> SEQ ID NO 1041
<211> LENGTH: 20
<212> TYPE: DNA
<213> ORGANISM: Artificial Sequence
<220> FEATURE:
<223> OTHER INFORMATION: synthetic sequence

<400> SEQUENCE: 1041
ctgaacaacu gctgcgugat                                                   20

<210> SEQ ID NO 1042
<211> LENGTH: 25
<212> TYPE: DNA
<213> ORGANISM: Artificial Sequence
<220> FEATURE:
<223> OTHER INFORMATION: synthetic sequence

<400> SEQUENCE: 1042
gactcaaaca ggacugtgaa ctuct                                             25

<210> SEQ ID NO 1043
<211> LENGTH: 22
<212> TYPE: DNA
<213> ORGANISM: Artificial Sequence
<220> FEATURE:
<223> OTHER INFORMATION: synthetic sequence

<400> SEQUENCE: 1043
ggaattctcc aucaccgtgg ua                                                22

<210> SEQ ID NO 1044
<211> LENGTH: 21
<212> TYPE: DNA
<213> ORGANISM: Artificial Sequence
<220> FEATURE:
<223> OTHER INFORMATION: synthetic sequence

<400> SEQUENCE: 1044
tctgagaaut ggcgcuggaa a                                                 21

<210> SEQ ID NO 1045
<211> LENGTH: 23
<212> TYPE: DNA
<213> ORGANISM: Artificial Sequence
<220> FEATURE:
<223> OTHER INFORMATION: synthetic sequence

<400> SEQUENCE: 1045
acctgaaaac ccacacucga aut                                               23

<210> SEQ ID NO 1046
<211> LENGTH: 20

```
<212> TYPE: DNA
<213> ORGANISM: Artificial Sequence
<220> FEATURE:
<223> OTHER INFORMATION: synthetic sequence

<400> SEQUENCE: 1046
gggugccaca gauucacag                                                    20

<210> SEQ ID NO 1047
<211> LENGTH: 20
<212> TYPE: DNA
<213> ORGANISM: Artificial Sequence
<220> FEATURE:
<223> OTHER INFORMATION: synthetic sequence

<400> SEQUENCE: 1047
gagaggauca tggcggaugg                                                   20

<210> SEQ ID NO 1048
<211> LENGTH: 28
<212> TYPE: DNA
<213> ORGANISM: Artificial Sequence
<220> FEATURE:
<223> OTHER INFORMATION: synthetic sequence

<400> SEQUENCE: 1048
acactttctt ctuccacaat atgcagut                                          28

<210> SEQ ID NO 1049
<211> LENGTH: 21
<212> TYPE: DNA
<213> ORGANISM: Artificial Sequence
<220> FEATURE:
<223> OTHER INFORMATION: synthetic sequence

<400> SEQUENCE: 1049
ctcgctguca tcctcatugc t                                                 21

<210> SEQ ID NO 1050
<211> LENGTH: 20
<212> TYPE: DNA
<213> ORGANISM: Artificial Sequence
<220> FEATURE:
<223> OTHER INFORMATION: synthetic sequence

<400> SEQUENCE: 1050
gcactugcca ctggtguaga                                                   20

<210> SEQ ID NO 1051
<211> LENGTH: 27
<212> TYPE: DNA
<213> ORGANISM: Artificial Sequence
<220> FEATURE:
<223> OTHER INFORMATION: synthetic sequence

<400> SEQUENCE: 1051
ctaaacatcu gcctgatctc auagagt                                           27

<210> SEQ ID NO 1052
<211> LENGTH: 22
<212> TYPE: DNA
<213> ORGANISM: Artificial Sequence
<220> FEATURE:
<223> OTHER INFORMATION: synthetic sequence

<400> SEQUENCE: 1052
```
cccacacaua tgccatggug at                                             22

<210> SEQ ID NO 1053
<211> LENGTH: 19
<212> TYPE: DNA
<213> ORGANISM: Artificial Sequence
<220> FEATURE:
<223> OTHER INFORMATION: synthetic sequence

<400> SEQUENCE: 1053
ccacctgcug cagtcuaca                                                 19

<210> SEQ ID NO 1054
<211> LENGTH: 24
<212> TYPE: DNA
<213> ORGANISM: Artificial Sequence
<220> FEATURE:
<223> OTHER INFORMATION: synthetic sequence

<400> SEQUENCE: 1054
ttcatugcca caaagttgau gcaa                                           24

<210> SEQ ID NO 1055
<211> LENGTH: 19
<212> TYPE: DNA
<213> ORGANISM: Artificial Sequence
<220> FEATURE:
<223> OTHER INFORMATION: synthetic sequence

<400> SEQUENCE: 1055
cctcacgcuc cgtttcuct                                                 19

<210> SEQ ID NO 1056
<211> LENGTH: 27
<212> TYPE: DNA
<213> ORGANISM: Artificial Sequence
<220> FEATURE:
<223> OTHER INFORMATION: synthetic sequence

<400> SEQUENCE: 1056
agttcacatc cuccttcttc ttctuct                                        27

<210> SEQ ID NO 1057
<211> LENGTH: 23
<212> TYPE: DNA
<213> ORGANISM: Artificial Sequence
<220> FEATURE:
<223> OTHER INFORMATION: synthetic sequence

<400> SEQUENCE: 1057
agtacaggau gctugccaaa aga                                            23

<210> SEQ ID NO 1058
<211> LENGTH: 24
<212> TYPE: DNA
<213> ORGANISM: Artificial Sequence
<220> FEATURE:
<223> OTHER INFORMATION: synthetic sequence

<400> SEQUENCE: 1058
ggagaaaauc aagtcgtgcu gaat                                           24

<210> SEQ ID NO 1059
<211> LENGTH: 20
<212> TYPE: DNA
<213> ORGANISM: Artificial Sequence
<220> FEATURE:
<223> OTHER INFORMATION: synthetic sequence

<400> SEQUENCE: 1059
gctcugacgg cgttacugat                                          20

<210> SEQ ID NO 1060
<211> LENGTH: 24
<212> TYPE: DNA
<213> ORGANISM: Artificial Sequence
<220> FEATURE:
<223> OTHER INFORMATION: synthetic sequence

<400> SEQUENCE: 1060
tcctcccggu tgtagatgta tcuc                                     24

<210> SEQ ID NO 1061
<211> LENGTH: 20
<212> TYPE: DNA
<213> ORGANISM: Artificial Sequence
<220> FEATURE:
<223> OTHER INFORMATION: synthetic sequence

<400> SEQUENCE: 1061
tcaagagcgu gccctactuc                                          20

<210> SEQ ID NO 1062
<211> LENGTH: 25
<212> TYPE: DNA
<213> ORGANISM: Artificial Sequence
<220> FEATURE:
<223> OTHER INFORMATION: synthetic sequence

<400> SEQUENCE: 1062
gattgagcau ccaccaagaa cttut                                    25

<210> SEQ ID NO 1063
<211> LENGTH: 25
<212> TYPE: DNA
<213> ORGANISM: Artificial Sequence
<220> FEATURE:
<223> OTHER INFORMATION: synthetic sequence

<400> SEQUENCE: 1063
ccaggaggag ggauaatggt tcaua                                    25

<210> SEQ ID NO 1064
<211> LENGTH: 19
<212> TYPE: DNA
<213> ORGANISM: Artificial Sequence
<220> FEATURE:
<223> OTHER INFORMATION: synthetic sequence

<400> SEQUENCE: 1064
aguggccggg ttcuagagt                                           19

<210> SEQ ID NO 1065
<211> LENGTH: 22
<212> TYPE: DNA
<213> ORGANISM: Artificial Sequence
<220> FEATURE:
<223> OTHER INFORMATION: synthetic sequence

<400> SEQUENCE: 1065
tcaaagagcu ggugcgaaaa ga                                       22

<210> SEQ ID NO 1066
<211> LENGTH: 19
<212> TYPE: DNA
<213> ORGANISM: Artificial Sequence
<220> FEATURE:
<223> OTHER INFORMATION: synthetic sequence

<400> SEQUENCE: 1066
gcctcgccau cagcaugat                                                    19

<210> SEQ ID NO 1067
<211> LENGTH: 20
<212> TYPE: DNA
<213> ORGANISM: Artificial Sequence
<220> FEATURE:
<223> OTHER INFORMATION: synthetic sequence

<400> SEQUENCE: 1067
ccugtgtggu agagcacact                                                   20

<210> SEQ ID NO 1068
<211> LENGTH: 21
<212> TYPE: DNA
<213> ORGANISM: Artificial Sequence
<220> FEATURE:
<223> OTHER INFORMATION: synthetic sequence

<400> SEQUENCE: 1068
ccagcugauc acaccaagag a                                                 21

<210> SEQ ID NO 1069
<211> LENGTH: 20
<212> TYPE: DNA
<213> ORGANISM: Artificial Sequence
<220> FEATURE:
<223> OTHER INFORMATION: synthetic sequence

<400> SEQUENCE: 1069 cggaguaug ggaccaggag                                                    20

<210> SEQ ID NO 1070
<211> LENGTH: 21
<212> TYPE: DNA
<213> ORGANISM: Artificial Sequence
<220> FEATURE:
<223> OTHER INFORMATION: synthetic sequence

<400> SEQUENCE: 1070
ccacgucgca gccatacatu a                                                 21

<210> SEQ ID NO 1071
<211> LENGTH: 22
<212> TYPE: DNA
<213> ORGANISM: Artificial Sequence
<220> FEATURE:
<223> OTHER INFORMATION: synthetic sequence

<400> SEQUENCE: 1071
augcatatuc ggacccacac at                                                22

<210> SEQ ID NO 1072
<211> LENGTH: 22
<212> TYPE: DNA
<213> ORGANISM: Artificial Sequence
<220> FEATURE:
<223> OTHER INFORMATION: synthetic sequence

```
<400> SEQUENCE: 1072
cctgtctgca aaugctctgt ug                                          22

<210> SEQ ID NO 1073
<211> LENGTH: 20
<212> TYPE: DNA
<213> ORGANISM: Artificial Sequence
<220> FEATURE:
<223> OTHER INFORMATION: synthetic sequence

<400> SEQUENCE: 1073
ggcagtgcuc ccaaaaugaa                                             20

<210> SEQ ID NO 1074
<211> LENGTH: 22
<212> TYPE: DNA
<213> ORGANISM: Artificial Sequence
<220> FEATURE:
<223> OTHER INFORMATION: synthetic sequence

<400> SEQUENCE: 1074
tcgcattcgu tcctttcacu ga                                          22

<210> SEQ ID NO 1075
<211> LENGTH: 21
<212> TYPE: DNA
<213> ORGANISM: Artificial Sequence
<220> FEATURE:
<223> OTHER INFORMATION: synthetic sequence

<400> SEQUENCE: 1075
tcaccuccaa gacagtgctu t                                           21

<210> SEQ ID NO 1076
<211> LENGTH: 23
<212> TYPE: DNA
<213> ORGANISM: Artificial Sequence
<220> FEATURE:
<223> OTHER INFORMATION: synthetic sequence

<400> SEQUENCE: 1076
tcagcucagg accttcauac aca                                         23

<210> SEQ ID NO 1077
<211> LENGTH: 19
<212> TYPE: DNA
<213> ORGANISM: Artificial Sequence
<220> FEATURE:
<223> OTHER INFORMATION: synthetic sequence

<400> SEQUENCE: 1077
cgagctuctg cgtcugact                                              19

<210> SEQ ID NO 1078
<211> LENGTH: 22
<212> TYPE: DNA
<213> ORGANISM: Artificial Sequence
<220> FEATURE:
<223> OTHER INFORMATION: synthetic sequence

<400> SEQUENCE: 1078
agatcttcuc cttggtgcuc ct                                          22

<210> SEQ ID NO 1079
```

```
<211> LENGTH: 26
<212> TYPE: DNA
<213> ORGANISM: Artificial Sequence
<220> FEATURE:
<223> OTHER INFORMATION: synthetic sequence

<400> SEQUENCE: 1079
ccttcttcaa gaucagttac cucacc                                          26

<210> SEQ ID NO 1080
<211> LENGTH: 23
<212> TYPE: DNA
<213> ORGANISM: Artificial Sequence
<220> FEATURE:
<223> OTHER INFORMATION: synthetic sequence

<400> SEQUENCE: 1080
acagtctctg tgagctcuga cat                                             23

<210> SEQ ID NO 1081
<211> LENGTH: 20
<212> TYPE: DNA
<213> ORGANISM: Artificial Sequence
<220> FEATURE:
<223> OTHER INFORMATION: synthetic sequence

<400> SEQUENCE: 1081
ccugccccca atttgucagt                                                 20

<210> SEQ ID NO 1082
<211> LENGTH: 23
<212> TYPE: DNA
<213> ORGANISM: Artificial Sequence
<220> FEATURE:
<223> OTHER INFORMATION: synthetic sequence

<400> SEQUENCE: 1082
gctttgggua gaatccugag aca                                             23

<210> SEQ ID NO 1083
<211> LENGTH: 25
<212> TYPE: DNA
<213> ORGANISM: Artificial Sequence
<220> FEATURE:
<223> OTHER INFORMATION: synthetic sequence

<400> SEQUENCE: 1083
gatgaacgca aacutcgtac ttuct                                           25

<210> SEQ ID NO 1084
<211> LENGTH: 20
<212> TYPE: DNA
<213> ORGANISM: Artificial Sequence
<220> FEATURE:
<223> OTHER INFORMATION: synthetic sequence

<400> SEQUENCE: 1084
ggtcaagaca cccugctuca                                                 20

<210> SEQ ID NO 1085
<211> LENGTH: 23
<212> TYPE: DNA
<213> ORGANISM: Artificial Sequence
<220> FEATURE:
<223> OTHER INFORMATION: synthetic sequence

<400> SEQUENCE: 1085
```
cgtcgtgtcu caagatctag cut                                    23

<210> SEQ ID NO 1086
<211> LENGTH: 22
<212> TYPE: DNA
<213> ORGANISM: Artificial Sequence
<220> FEATURE:
<223> OTHER INFORMATION: synthetic sequence

<400> SEQUENCE: 1086
tgagtcatcu gcggtactgu ct                                     22

<210> SEQ ID NO 1087
<211> LENGTH: 21
<212> TYPE: DNA
<213> ORGANISM: Artificial Sequence
<220> FEATURE:
<223> OTHER INFORMATION: synthetic sequence

<400> SEQUENCE: 1087
gccatttaug gcctccaucc a                                      21

<210> SEQ ID NO 1088
<211> LENGTH: 21
<212> TYPE: DNA
<213> ORGANISM: Artificial Sequence
<220> FEATURE:
<223> OTHER INFORMATION: synthetic sequence

<400> SEQUENCE: 1088
gagagagagu gtgcgccuaa a                                      21

<210> SEQ ID NO 1089
<211> LENGTH: 22
<212> TYPE: DNA
<213> ORGANISM: Artificial Sequence
<220> FEATURE:
<223> OTHER INFORMATION: synthetic sequence

<400> SEQUENCE: 1089
acuaaccaac ccacugggag aa                                     22

<210> SEQ ID NO 1090
<211> LENGTH: 22
<212> TYPE: DNA
<213> ORGANISM: Artificial Sequence
<220> FEATURE:
<223> OTHER INFORMATION: synthetic sequence

<400> SEQUENCE: 1090
tcaatgatgc ugggaccttg ug                                     22

<210> SEQ ID NO 1091
<211> LENGTH: 19
<212> TYPE: DNA
<213> ORGANISM: Artificial Sequence
<220> FEATURE:
<223> OTHER INFORMATION: synthetic sequence

<400> SEQUENCE: 1091
gcgggacguc guagagaaa                                         19

<210> SEQ ID NO 1092
<211> LENGTH: 22
<212> TYPE: DNA

```
<213> ORGANISM: Artificial Sequence
<220> FEATURE:
<223> OTHER INFORMATION: synthetic sequence

<400> SEQUENCE: 1092
cctctcagga ugaggactug ga                                        22

<210> SEQ ID NO 1093
<211> LENGTH: 21
<212> TYPE: DNA
<213> ORGANISM: Artificial Sequence
<220> FEATURE:
<223> OTHER INFORMATION: synthetic sequence

<400> SEQUENCE: 1093
caggtucccc tcacagucaa t                                         21

<210> SEQ ID NO 1094
<211> LENGTH: 21
<212> TYPE: DNA
<213> ORGANISM: Artificial Sequence
<220> FEATURE:
<223> OTHER INFORMATION: synthetic sequence

<400> SEQUENCE: 1094
catgtagugg cacctgcuga a                                         21

<210> SEQ ID NO 1095
<211> LENGTH: 19
<212> TYPE: DNA
<213> ORGANISM: Artificial Sequence
<220> FEATURE:
<223> OTHER INFORMATION: synthetic sequence

<400> SEQUENCE: 1095
gggagacgut cagcuaccc                                            19

<210> SEQ ID NO 1096
<211> LENGTH: 24
<212> TYPE: DNA
<213> ORGANISM: Artificial Sequence
<220> FEATURE:
<223> OTHER INFORMATION: synthetic sequence

<400> SEQUENCE: 1096
gggcaacuca gagatagctt tcut                                      24

<210> SEQ ID NO 1097
<211> LENGTH: 20
<212> TYPE: DNA
<213> ORGANISM: Artificial Sequence
<220> FEATURE:
<223> OTHER INFORMATION: synthetic sequence

<400> SEQUENCE: 1097
cacggacaaa guccctugga                                           20

<210> SEQ ID NO 1098
<211> LENGTH: 20
<212> TYPE: DNA
<213> ORGANISM: Artificial Sequence
<220> FEATURE:
<223> OTHER INFORMATION: synthetic sequence

<400> SEQUENCE: 1098
ccaaaggccc uctcgtucac                                           20
```

<210> SEQ ID NO 1099
<211> LENGTH: 19
<212> TYPE: DNA
<213> ORGANISM: Artificial Sequence
<220> FEATURE:
<223> OTHER INFORMATION: synthetic sequence

<400> SEQUENCE: 1099
caggcggagg caucctuac                                              19

<210> SEQ ID NO 1100
<211> LENGTH: 27
<212> TYPE: DNA
<213> ORGANISM: Artificial Sequence
<220> FEATURE:
<223> OTHER INFORMATION: synthetic sequence

<400> SEQUENCE: 1100
aggaactgtg ucattggtgt agattuc                                     27

<210> SEQ ID NO 1101
<211> LENGTH: 25
<212> TYPE: DNA
<213> ORGANISM: Artificial Sequence
<220> FEATURE:
<223> OTHER INFORMATION: synthetic sequence

<400> SEQUENCE: 1101
actggccttg guttaattgt gacut                                       25

<210> SEQ ID NO 1102
<211> LENGTH: 19
<212> TYPE: DNA
<213> ORGANISM: Artificial Sequence
<220> FEATURE:
<223> OTHER INFORMATION: synthetic sequence

<400> SEQUENCE: 1102
cucaguccaa ccacagcga                                              19

<210> SEQ ID NO 1103
<211> LENGTH: 19
<212> TYPE: DNA
<213> ORGANISM: Artificial Sequence
<220> FEATURE:
<223> OTHER INFORMATION: synthetic sequence

<400> SEQUENCE: 1103
caggcacucc tuggagcaa                                              19

<210> SEQ ID NO 1104
<211> LENGTH: 20
<212> TYPE: DNA
<213> ORGANISM: Artificial Sequence
<220> FEATURE:
<223> OTHER INFORMATION: synthetic sequence

<400> SEQUENCE: 1104
gcactggagu ggcagauagt                                             20

<210> SEQ ID NO 1105
<211> LENGTH: 22
<212> TYPE: DNA
<213> ORGANISM: Artificial Sequence
<220> FEATURE:

```
<223> OTHER INFORMATION: synthetic sequence

<400> SEQUENCE: 1105
gcgacttuac ccttcgacua ga                                              22

<210> SEQ ID NO 1106
<211> LENGTH: 20
<212> TYPE: DNA
<213> ORGANISM: Artificial Sequence
<220> FEATURE:
<223> OTHER INFORMATION: synthetic sequence

<400> SEQUENCE: 1106
gggauccagg ugacccaaag                                                 20

<210> SEQ ID NO 1107
<211> LENGTH: 18
<212> TYPE: DNA
<213> ORGANISM: Artificial Sequence
<220> FEATURE:
<223> OTHER INFORMATION: synthetic sequence

<400> SEQUENCE: 1107
gcccugcacg tggtguaa                                                   18

<210> SEQ ID NO 1108
<211> LENGTH: 22
<212> TYPE: DNA
<213> ORGANISM: Artificial Sequence
<220> FEATURE:
<223> OTHER INFORMATION: synthetic sequence

<400> SEQUENCE: 1108
caactccagg cutgtagctg uc                                              22

<210> SEQ ID NO 1109
<211> LENGTH: 28
<212> TYPE: DNA
<213> ORGANISM: Artificial Sequence
<220> FEATURE:
<223> OTHER INFORMATION: synthetic sequence

<400> SEQUENCE: 1109
gaccgatgau caggatatct acaaggua                                        28

<210> SEQ ID NO 1110
<211> LENGTH: 20
<212> TYPE: DNA
<213> ORGANISM: Artificial Sequence
<220> FEATURE:
<223> OTHER INFORMATION: synthetic sequence

<400> SEQUENCE: 1110
acctcacagg ucagggtugt                                                 20

<210> SEQ ID NO 1111
<211> LENGTH: 24
<212> TYPE: DNA
<213> ORGANISM: Artificial Sequence
<220> FEATURE:
<223> OTHER INFORMATION: synthetic sequence

<400> SEQUENCE: 1111
gtcctgtctc ucctcatgct agua                                            24
```

```
<210> SEQ ID NO 1112
<211> LENGTH: 26
<212> TYPE: DNA
<213> ORGANISM: Artificial Sequence
<220> FEATURE:
<223> OTHER INFORMATION: synthetic sequence

<400> SEQUENCE: 1112
ctgctggtcu catagtaatc uaccac                                           26

<210> SEQ ID NO 1113
<211> LENGTH: 18
<212> TYPE: DNA
<213> ORGANISM: Artificial Sequence
<220> FEATURE:
<223> OTHER INFORMATION: synthetic sequence

<400> SEQUENCE: 1113
caggcuccaa ccuccagc                                                    18

<210> SEQ ID NO 1114
<211> LENGTH: 20
<212> TYPE: DNA
<213> ORGANISM: Artificial Sequence
<220> FEATURE:
<223> OTHER INFORMATION: synthetic sequence

<400> SEQUENCE: 1114
agcuggagtg tuaggagggc                                                  20

<210> SEQ ID NO 1115
<211> LENGTH: 19
<212> TYPE: DNA
<213> ORGANISM: Artificial Sequence
<220> FEATURE:
<223> OTHER INFORMATION: synthetic sequence

<400> SEQUENCE: 1115
agcccccaut cctgtugac                                                   19

<210> SEQ ID NO 1116
<211> LENGTH: 18
<212> TYPE: DNA
<213> ORGANISM: Artificial Sequence
<220> FEATURE:
<223> OTHER INFORMATION: synthetic sequence

<400> SEQUENCE: 1116
gatatcgcug ccgccugt                                                    18

<210> SEQ ID NO 1117
<211> LENGTH: 21
<212> TYPE: DNA
<213> ORGANISM: Artificial Sequence
<220> FEATURE:
<223> OTHER INFORMATION: synthetic sequence

<400> SEQUENCE: 1117
gggctgaacc auacactccu t                                                21

<210> SEQ ID NO 1118
<211> LENGTH: 33
<212> TYPE: DNA
<213> ORGANISM: Artificial Sequence
<220> FEATURE:
<223> OTHER INFORMATION: synthetic sequence
```

```
<400> SEQUENCE: 1118
aatcaactga gtaauatgaa gtattgacug aca                              33

<210> SEQ ID NO 1119
<211> LENGTH: 19
<212> TYPE: DNA
<213> ORGANISM: Artificial Sequence
<220> FEATURE:
<223> OTHER INFORMATION: synthetic sequence

<400> SEQUENCE: 1119
cccccugcca gtauagcct                                              19

<210> SEQ ID NO 1120
<211> LENGTH: 19
<212> TYPE: DNA
<213> ORGANISM: Artificial Sequence
<220> FEATURE:
<223> OTHER INFORMATION: synthetic sequence

<400> SEQUENCE: 1120
gtgatcugcc tcgtggugt                                              19

<210> SEQ ID NO 1121
<211> LENGTH: 20
<212> TYPE: DNA
<213> ORGANISM: Artificial Sequence
<220> FEATURE:
<223> OTHER INFORMATION: synthetic sequence

<400> SEQUENCE: 1121
gaagtguggc cagaagugga                                             20

<210> SEQ ID NO 1122
<211> LENGTH: 28
<212> TYPE: DNA
<213> ORGANISM: Artificial Sequence
<220> FEATURE:
<223> OTHER INFORMATION: synthetic sequence

<400> SEQUENCE: 1122
tcgtttggct ggaucataga ttaacaut                                    28

<210> SEQ ID NO 1123
<211> LENGTH: 17
<212> TYPE: DNA
<213> ORGANISM: Artificial Sequence
<220> FEATURE:
<223> OTHER INFORMATION: synthetic sequence

<400> SEQUENCE: 1123
catccugggc caggcuc                                                17

<210> SEQ ID NO 1124
<211> LENGTH: 20
<212> TYPE: DNA
<213> ORGANISM: Artificial Sequence
<220> FEATURE:
<223> OTHER INFORMATION: synthetic sequence

<400> SEQUENCE: 1124
ggctucaggg ctgaauggat                                             20

<210> SEQ ID NO 1125
<211> LENGTH: 21
```

```
<212> TYPE: DNA
<213> ORGANISM: Artificial Sequence
<220> FEATURE:
<223> OTHER INFORMATION: synthetic sequence

<400> SEQUENCE: 1125
tgcgtgaucc acaucaacag g                                              21

<210> SEQ ID NO 1126
<211> LENGTH: 17
<212> TYPE: DNA
<213> ORGANISM: Artificial Sequence
<220> FEATURE:
<223> OTHER INFORMATION: synthetic sequence

<400> SEQUENCE: 1126
gucccgggau gccgcac                                                   17

<210> SEQ ID NO 1127
<211> LENGTH: 23
<212> TYPE: DNA
<213> ORGANISM: Artificial Sequence
<220> FEATURE:
<223> OTHER INFORMATION: synthetic sequence

<400> SEQUENCE: 1127
ataacaggcc ucagccaaau cat                                            23

<210> SEQ ID NO 1128
<211> LENGTH: 22
<212> TYPE: DNA
<213> ORGANISM: Artificial Sequence
<220> FEATURE:
<223> OTHER INFORMATION: synthetic sequence

<400> SEQUENCE: 1128
gguaaagtcu gagcaggaca gg                                             22

<210> SEQ ID NO 1129
<211> LENGTH: 26
<212> TYPE: DNA
<213> ORGANISM: Artificial Sequence
<220> FEATURE:
<223> OTHER INFORMATION: synthetic sequence

<400> SEQUENCE: 1129
aatataacag gccucagcca aaucat                                         26

<210> SEQ ID NO 1130
<211> LENGTH: 20
<212> TYPE: DNA
<213> ORGANISM: Artificial Sequence
<220> FEATURE:
<223> OTHER INFORMATION: synthetic sequence

<400> SEQUENCE: 1130
agctgactgu gctgtgctut                                                20

<210> SEQ ID NO 1131
<211> LENGTH: 23
<212> TYPE: DNA
<213> ORGANISM: Artificial Sequence
<220> FEATURE:
<223> OTHER INFORMATION: synthetic sequence

<400> SEQUENCE: 1131
```

```
gtccccaaua taacaggccu cag                                              23

<210> SEQ ID NO 1132
<211> LENGTH: 17
<212> TYPE: DNA
<213> ORGANISM: Artificial Sequence
<220> FEATURE:
<223> OTHER INFORMATION: synthetic sequence

<400> SEQUENCE: 1132
acagagcacc cgcuguc                                                     17

<210> SEQ ID NO 1133
<211> LENGTH: 22
<212> TYPE: DNA
<213> ORGANISM: Artificial Sequence
<220> FEATURE:
<223> OTHER INFORMATION: synthetic sequence

<400> SEQUENCE: 1133
ccccaataua acaggccuca gc                                               22

<210> SEQ ID NO 1134
<211> LENGTH: 21
<212> TYPE: DNA
<213> ORGANISM: Artificial Sequence
<220> FEATURE:
<223> OTHER INFORMATION: synthetic sequence

<400> SEQUENCE: 1134
aggaugagag aaccccugga g                                                21

<210> SEQ ID NO 1135
<211> LENGTH: 22
<212> TYPE: DNA
<213> ORGANISM: Artificial Sequence
<220> FEATURE:
<223> OTHER INFORMATION: synthetic sequence

<400> SEQUENCE: 1135
tatgagtugg cgaggaagau cg                                               22

<210> SEQ ID NO 1136
<211> LENGTH: 21
<212> TYPE: DNA
<213> ORGANISM: Artificial Sequence
<220> FEATURE:
<223> OTHER INFORMATION: synthetic sequence

<400> SEQUENCE: 1136
ggatccugac gttgagtugc t                                                21

<210> SEQ ID NO 1137
<211> LENGTH: 22
<212> TYPE: DNA
<213> ORGANISM: Artificial Sequence
<220> FEATURE:
<223> OTHER INFORMATION: synthetic sequence

<400> SEQUENCE: 1137
tatgagtugg cgaggaagau cg                                               22

<210> SEQ ID NO 1138
<211> LENGTH: 21
<212> TYPE: DNA
<213> ORGANISM: Artificial Sequence
```

```
<220> FEATURE:
<223> OTHER INFORMATION: synthetic sequence

<400> SEQUENCE: 1138
ggatccugac gttgagtugc t                                              21

<210> SEQ ID NO 1139
<211> LENGTH: 22
<212> TYPE: DNA
<213> ORGANISM: Artificial Sequence
<220> FEATURE:
<223> OTHER INFORMATION: synthetic sequence

<400> SEQUENCE: 1139
tatgagtugg cgaggaagau cg                                             22

<210> SEQ ID NO 1140
<211> LENGTH: 21
<212> TYPE: DNA
<213> ORGANISM: Artificial Sequence
<220> FEATURE:
<223> OTHER INFORMATION: synthetic sequence

<400> SEQUENCE: 1140
ggatccugac gttgagtugc t                                              21

<210> SEQ ID NO 1141
<211> LENGTH: 22
<212> TYPE: DNA
<213> ORGANISM: Artificial Sequence
<220> FEATURE:
<223> OTHER INFORMATION: synthetic sequence

<400> SEQUENCE: 1141
tatgagtugg cgaggaagau cg                                             22

<210> SEQ ID NO 1142
<211> LENGTH: 21
<212> TYPE: DNA
<213> ORGANISM: Artificial Sequence
<220> FEATURE:
<223> OTHER INFORMATION: synthetic sequence

<400> SEQUENCE: 1142
ggatccugac gttgagtugc t                                              21

<210> SEQ ID NO 1143
<211> LENGTH: 22
<212> TYPE: DNA
<213> ORGANISM: Artificial Sequence
<220> FEATURE:
<223> OTHER INFORMATION: synthetic sequence

<400> SEQUENCE: 1143
tatgagtugg cgaggaagau cg                                             22

<210> SEQ ID NO 1144
<211> LENGTH: 21
<212> TYPE: DNA
<213> ORGANISM: Artificial Sequence
<220> FEATURE:
<223> OTHER INFORMATION: synthetic sequence

<400> SEQUENCE: 1144
ggatccugac gttgagtugc t                                              21
```

<210> SEQ ID NO 1145
<211> LENGTH: 22
<212> TYPE: DNA
<213> ORGANISM: Artificial Sequence
<220> FEATURE:
<223> OTHER INFORMATION: synthetic sequence

<400> SEQUENCE: 1145
catggatgcu gatgagdguc aa                                       22

<210> SEQ ID NO 1146
<211> LENGTH: 23
<212> TYPE: DNA
<213> ORGANISM: Artificial Sequence
<220> FEATURE:
<223> OTHER INFORMATION: synthetic sequence

<400> SEQUENCE: 1146
gactctgtca cucttggagc tut                                      23

<210> SEQ ID NO 1147
<211> LENGTH: 27
<212> TYPE: DNA
<213> ORGANISM: Artificial Sequence
<220> FEATURE:
<223> OTHER INFORMATION: synthetic sequence

<400> SEQUENCE: 1147
gaataccaat accaauccca aaagguc                                  27

<210> SEQ ID NO 1148
<211> LENGTH: 17
<212> TYPE: DNA
<213> ORGANISM: Artificial Sequence
<220> FEATURE:
<223> OTHER INFORMATION: synthetic sequence

<400> SEQUENCE: 1148
ccaaguggcg gcactut                                             17

<210> SEQ ID NO 1149
<211> LENGTH: 30
<212> TYPE: DNA
<213> ORGANISM: Artificial Sequence
<220> FEATURE:
<223> OTHER INFORMATION: synthetic sequence

<400> SEQUENCE: 1149
aatccatctg tucagaaatt ctacaauggt                               30

<210> SEQ ID NO 1150
<211> LENGTH: 26
<212> TYPE: DNA
<213> ORGANISM: Artificial Sequence
<220> FEATURE:
<223> OTHER INFORMATION: synthetic sequence

<400> SEQUENCE: 1150
aaaaacuttc actuaagacc caggga                                   26

<210> SEQ ID NO 1151
<211> LENGTH: 32
<212> TYPE: DNA
<213> ORGANISM: Artificial Sequence
<220> FEATURE:
<223> OTHER INFORMATION: synthetic sequence

```
<400> SEQUENCE: 1151
tttggagaag ugatttgaat ctttcuagga at                              32

<210> SEQ ID NO 1152
<211> LENGTH: 28
<212> TYPE: DNA
<213> ORGANISM: Artificial Sequence
<220> FEATURE:
<223> OTHER INFORMATION: synthetic sequence

<400> SEQUENCE: 1152
tcaautaaaa agcugaagag gaaaccac                                   28

<210> SEQ ID NO 1153
<211> LENGTH: 22
<212> TYPE: DNA
<213> ORGANISM: Artificial Sequence
<220> FEATURE:
<223> OTHER INFORMATION: synthetic sequence

<400> SEQUENCE: 1153
agggaacagc acutctucaa gg                                         22

<210> SEQ ID NO 1154
<211> LENGTH: 24
<212> TYPE: DNA
<213> ORGANISM: Artificial Sequence
<220> FEATURE:
<223> OTHER INFORMATION: synthetic sequence

<400> SEQUENCE: 1154
gctagcutgg ctgauaacaa caca                                       24

<210> SEQ ID NO 1155
<211> LENGTH: 19
<212> TYPE: DNA
<213> ORGANISM: Artificial Sequence
<220> FEATURE:
<223> OTHER INFORMATION: synthetic sequence

<400> SEQUENCE: 1155
ccugtcugca cagacagca                                             19

<210> SEQ ID NO 1156
<211> LENGTH: 17
<212> TYPE: DNA
<213> ORGANISM: Artificial Sequence
<220> FEATURE:
<223> OTHER INFORMATION: synthetic sequence

<400> SEQUENCE: 1156
caggcgaccu ggguggg                                               17

<210> SEQ ID NO 1157
<211> LENGTH: 20
<212> TYPE: DNA
<213> ORGANISM: Artificial Sequence
<220> FEATURE:
<223> OTHER INFORMATION: synthetic sequence

<400> SEQUENCE: 1157
ggctcttucc gtgactcucc                                            20

<210> SEQ ID NO 1158
```

```
<211> LENGTH: 19
<212> TYPE: DNA
<213> ORGANISM: Artificial Sequence
<220> FEATURE:
<223> OTHER INFORMATION: synthetic sequence

<400> SEQUENCE: 1158
gaacaugcag gtgtcuggg                                                      19

<210> SEQ ID NO 1159
<211> LENGTH: 24
<212> TYPE: DNA
<213> ORGANISM: Artificial Sequence
<220> FEATURE:
<223> OTHER INFORMATION: synthetic sequence

<400> SEQUENCE: 1159
atgatgactc ugatcagggu agca                                                24

<210> SEQ ID NO 1160
<211> LENGTH: 22
<212> TYPE: DNA
<213> ORGANISM: Artificial Sequence
<220> FEATURE:
<223> OTHER INFORMATION: synthetic sequence

<400> SEQUENCE: 1160
gagagcaaga ggucaagagc ug                                                  22

<210> SEQ ID NO 1161
<211> LENGTH: 17
<212> TYPE: DNA
<213> ORGANISM: Artificial Sequence
<220> FEATURE:
<223> OTHER INFORMATION: synthetic sequence

<400> SEQUENCE: 1161
tgccggacgg gutccuc                                                        17

<210> SEQ ID NO 1162
<211> LENGTH: 17
<212> TYPE: DNA
<213> ORGANISM: Artificial Sequence
<220> FEATURE:
<223> OTHER INFORMATION: synthetic sequence

<400> SEQUENCE: 1162
tgugcaggcu gcagagc                                                        17

<210> SEQ ID NO 1163
<211> LENGTH: 17
<212> TYPE: DNA
<213> ORGANISM: Artificial Sequence
<220> FEATURE:
<223> OTHER INFORMATION: synthetic sequence

<400> SEQUENCE: 1163
cgctgtccuc cgcgcug                                                        17

<210> SEQ ID NO 1164
<211> LENGTH: 19
<212> TYPE: DNA
<213> ORGANISM: Artificial Sequence
<220> FEATURE:
<223> OTHER INFORMATION: synthetic sequence

<400> SEQUENCE: 1164
```
cugcagacga gcacugagc                                              19

<210> SEQ ID NO 1165
<211> LENGTH: 28
<212> TYPE: DNA
<213> ORGANISM: Artificial Sequence
<220> FEATURE:
<223> OTHER INFORMATION: synthetic sequence

<400> SEQUENCE: 1165
cgguuagggu cauuauccaa aucaucc                                     28

<210> SEQ ID NO 1166
<211> LENGTH: 25
<212> TYPE: DNA
<213> ORGANISM: Artificial Sequence
<220> FEATURE:
<223> OTHER INFORMATION: synthetic sequence

<400> SEQUENCE: 1166
aggaagagug ggaaaagaug aaagc                                       25

<210> SEQ ID NO 1167
<211> LENGTH: 18
<212> TYPE: DNA
<213> ORGANISM: Artificial Sequence
<220> FEATURE:
<223> OTHER INFORMATION: synthetic sequence

<400> SEQUENCE: 1167
acggtguccc ccaacuct                                               18

<210> SEQ ID NO 1168
<211> LENGTH: 17
<212> TYPE: DNA
<213> ORGANISM: Artificial Sequence
<220> FEATURE:
<223> OTHER INFORMATION: synthetic sequence

<400> SEQUENCE: 1168
gggagcugcc ccaugct                                                17

<210> SEQ ID NO 1169
<211> LENGTH: 18
<212> TYPE: DNA
<213> ORGANISM: Artificial Sequence
<220> FEATURE:
<223> OTHER INFORMATION: synthetic sequence

<400> SEQUENCE: 1169
gttccggcgu caagguga                                               18

<210> SEQ ID NO 1170
<211> LENGTH: 30
<212> TYPE: DNA
<213> ORGANISM: Artificial Sequence
<220> FEATURE:
<223> OTHER INFORMATION: synthetic sequence

<400> SEQUENCE: 1170
atctaatata aaaccagcut gcgttgttuc                                  30

<210> SEQ ID NO 1171
<211> LENGTH: 25
<212> TYPE: DNA

```
<213> ORGANISM: Artificial Sequence
<220> FEATURE:
<223> OTHER INFORMATION: synthetic sequence

<400> SEQUENCE: 1171
aggaatgacg uaggacccta ugaat                                    25

<210> SEQ ID NO 1172
<211> LENGTH: 23
<212> TYPE: DNA
<213> ORGANISM: Artificial Sequence
<220> FEATURE:
<223> OTHER INFORMATION: synthetic sequence

<400> SEQUENCE: 1172
gttgagattu acccctgcau ggt                                      23

<210> SEQ ID NO 1173
<211> LENGTH: 27
<212> TYPE: DNA
<213> ORGANISM: Artificial Sequence
<220> FEATURE:
<223> OTHER INFORMATION: synthetic sequence

<400> SEQUENCE: 1173
cgttttcucc atagtcauag gaagagc                                  27

<210> SEQ ID NO 1174
<211> LENGTH: 21
<212> TYPE: DNA
<213> ORGANISM: Artificial Sequence
<220> FEATURE:
<223> OTHER INFORMATION: synthetic sequence

<400> SEQUENCE: 1174
cugcaggttu ccaaccacaa g                                        21

<210> SEQ ID NO 1175
<211> LENGTH: 25
<212> TYPE: DNA
<213> ORGANISM: Artificial Sequence
<220> FEATURE:
<223> OTHER INFORMATION: synthetic sequence

<400> SEQUENCE: 1175
ccaacataag ucacaatggc accua                                    25

<210> SEQ ID NO 1176
<211> LENGTH: 20
<212> TYPE: DNA
<213> ORGANISM: Artificial Sequence
<220> FEATURE:
<223> OTHER INFORMATION: synthetic sequence

<400> SEQUENCE: 1176
ccagautccc cuccaggagt                                          20

<210> SEQ ID NO 1177
<211> LENGTH: 25
<212> TYPE: DNA
<213> ORGANISM: Artificial Sequence
<220> FEATURE:
<223> OTHER INFORMATION: synthetic sequence

<400> SEQUENCE: 1177
catuccaaaa gccacacuca aagat                                    25
```

-continued

<210> SEQ ID NO 1178
<211> LENGTH: 22
<212> TYPE: DNA
<213> ORGANISM: Artificial Sequence
<220> FEATURE:
<223> OTHER INFORMATION: synthetic sequence

<400> SEQUENCE: 1178
ggtacccagg uggagagaau ga                                      22

<210> SEQ ID NO 1179
<211> LENGTH: 25
<212> TYPE: DNA
<213> ORGANISM: Artificial Sequence
<220> FEATURE:
<223> OTHER INFORMATION: synthetic sequence

<400> SEQUENCE: 1179
ctgacgaaat uccacaaaac ctcut                                   25

<210> SEQ ID NO 1180
<211> LENGTH: 20
<212> TYPE: DNA
<213> ORGANISM: Artificial Sequence
<220> FEATURE:
<223> OTHER INFORMATION: synthetic sequence

<400> SEQUENCE: 1180
gggactggug gttgtgaugg                                         20

<210> SEQ ID NO 1181
<211> LENGTH: 23
<212> TYPE: DNA
<213> ORGANISM: Artificial Sequence
<220> FEATURE:
<223> OTHER INFORMATION: synthetic sequence

<400> SEQUENCE: 1181
gagcagagau acacgtgcca uat                                     23

<210> SEQ ID NO 1182
<211> LENGTH: 20
<212> TYPE: DNA
<213> ORGANISM: Artificial Sequence
<220> FEATURE:
<223> OTHER INFORMATION: synthetic sequence

<400> SEQUENCE: 1182
agcuccaagg acagcuagga                                         20

<210> SEQ ID NO 1183
<211> LENGTH: 25
<212> TYPE: DNA
<213> ORGANISM: Artificial Sequence
<220> FEATURE:
<223> OTHER INFORMATION: synthetic sequence

<400> SEQUENCE: 1183
ggctcttaug aatcccatcc ugaaa                                   25

<210> SEQ ID NO 1184
<211> LENGTH: 28
<212> TYPE: DNA
<213> ORGANISM: Artificial Sequence
<220> FEATURE:

<223> OTHER INFORMATION: synthetic sequence

<400> SEQUENCE: 1184
agagaagagg ugagagaaga aacattug                              28

<210> SEQ ID NO 1185
<211> LENGTH: 28
<212> TYPE: DNA
<213> ORGANISM: Artificial Sequence
<220> FEATURE:
<223> OTHER INFORMATION: synthetic sequence

<400> SEQUENCE: 1185
tttaaagaug accagagcau ccaaaaga                              28

<210> SEQ ID NO 1186
<211> LENGTH: 22
<212> TYPE: DNA
<213> ORGANISM: Artificial Sequence
<220> FEATURE:
<223> OTHER INFORMATION: synthetic sequence

<400> SEQUENCE: 1186
tgctttgcgu tggacatuca ag                                    22

<210> SEQ ID NO 1187
<211> LENGTH: 17
<212> TYPE: DNA
<213> ORGANISM: Artificial Sequence
<220> FEATURE:
<223> OTHER INFORMATION: synthetic sequence

<400> SEQUENCE: 1187
gctgagcuga gcucggt                                          17

<210> SEQ ID NO 1188
<211> LENGTH: 20
<212> TYPE: DNA
<213> ORGANISM: Artificial Sequence
<220> FEATURE:
<223> OTHER INFORMATION: synthetic sequence

<400> SEQUENCE: 1188
cugattucac caggcgacct                                       20

<210> SEQ ID NO 1189
<211> LENGTH: 25
<212> TYPE: DNA
<213> ORGANISM: Artificial Sequence
<220> FEATURE:
<223> OTHER INFORMATION: synthetic sequence

<400> SEQUENCE: 1189
ggttgatgca cugatggatg agaut                                 25

<210> SEQ ID NO 1190
<211> LENGTH: 22
<212> TYPE: DNA
<213> ORGANISM: Artificial Sequence
<220> FEATURE:
<223> OTHER INFORMATION: synthetic sequence

<400> SEQUENCE: 1190
cctcagcgau gatgctaucc ag                                    22

```
<210> SEQ ID NO 1191
<211> LENGTH: 21
<212> TYPE: DNA
<213> ORGANISM: Artificial Sequence
<220> FEATURE:
<223> OTHER INFORMATION: synthetic sequence

<400> SEQUENCE: 1191
agcaaagtgc gugaggagtu t                                             21

<210> SEQ ID NO 1192
<211> LENGTH: 20
<212> TYPE: DNA
<213> ORGANISM: Artificial Sequence
<220> FEATURE:
<223> OTHER INFORMATION: synthetic sequence

<400> SEQUENCE: 1192
cgcutctcac ugagagcagt                                               20

<210> SEQ ID NO 1193
<211> LENGTH: 21
<212> TYPE: DNA
<213> ORGANISM: Artificial Sequence
<220> FEATURE:
<223> OTHER INFORMATION: synthetic sequence

<400> SEQUENCE: 1193
gcggauggtg tuccaagaaa a                                             21

<210> SEQ ID NO 1194
<211> LENGTH: 22
<212> TYPE: DNA
<213> ORGANISM: Artificial Sequence
<220> FEATURE:
<223> OTHER INFORMATION: synthetic sequence

<400> SEQUENCE: 1194
gcgctttctu tgacgttccu aa                                            22
```

COMPOSITIONS AND METHODS FOR ASSESSING IMMUNE RESPONSE

RELATED APPLICATIONS

This application is a U.S. National Application filed under 35 U.S.C. § 371 of International Application No. PCT/US2017/053077, filed on Sep. 22, 2017, which claims priority to and the benefit of U.S. Provisional Application No. 62/398,756 filed Sep. 23, 2016 and U.S. Provisional Application No. 62/419,091 filed Nov. 8, 2016. The entire contents of each of the aforementioned applications are incorporated herein by reference.

SEQUENCE LISTING

This application hereby incorporates by reference the material of the electronic Sequence Listing filed concurrently herewith. The material in the electronic Sequence Listing is submitted as a text (.txt) file entitled "LT01193_ST25.txt" created on Sep. 22, 2017, and is herein incorporated by reference in its entirety.

BACKGROUND

Advances in cancer immunotherapies have started to provide promising results across oncology. Immune checkpoint inhibitors, cancer vaccines and T-cell therapies have shown sustainable results in responsive populations over conventional or targeted therapies. However, effective identification of responsive candidates and/or monitoring response has proven challenging. The need of a better understanding of the tumor microenvironment, tumor-lymphocyte interactions and drug response biomarkers is immediate. In particular, for example, while the presence of PD-L1 has been reported to be a promising marker to predict positive response to anti-PD-L1 therapy, current methods using immunohistochemistry to measure PD-L1 protein levels are inefficient and highly variable. Higher-throughput, systematic and standardized solutions are a more desirable alternative.

BRIEF SUMMARY OF THE INVENTION

In one aspect of the invention compositions are provided for a single stream multiplex determination of an immune response in a sample. In some embodiments the composition consists of a plurality of primer pair reagents directed to a plurality of target sequences to measure the expression levels of the targets in the sample. Provided compositions target immune response genes and housekeeping gene sequences wherein the plurality of immune response target gene sequences are selected from targets among the following function: checkpoint pathways, T cell related signaling pathways, markers of tumor infiltrating lymphocytes (TILs), tumor markers, and housekeeping genes. In some embodiments the plurality of immune response target genes are selected from targets among immune checkpoint pathways and targets; T and B cell signaling genes, markers of lymphocyte subsets, interferon signaling genes, cytokine signaling genes; tumor markers, tumor antigens, and proliferation markers. In particular embodiments, provided compositions include a plurality of primer pair reagents selected from Table 2. In some embodiments a multiplex assay comprising compositions of the invention is provided. In some embodiments a test kit comprising compositions of the invention is provided.

In another aspect of the invention, methods are provided for determining immune response activity in a biological sample. Such methods comprise performing multiplex amplification of a plurality of target expression sequences from a biological sample containing target sequences. Amplification comprises contacting at least a portion of the sample comprising multiple target sequences of interest using a plurality of target-specific primer pairs in the presence of a polymerase under amplification conditions to produce a plurality of amplified target expression sequences. The methods further comprise detecting the level of expression of each of the plurality of target immune response sequences, wherein a change in the level of expression of one or more target immune response markers as compared with a control sample determines a change in immune response activity in the sample. The methods described herein utilize compositions of the invention provided herein.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 1 depicts exemplary repeatibility results of immune response research assay. Immune responses assay produced correlation greater than 0.98 between replicates of FFPE research samples of NSCLC, melanoma, and normal liver tissue.

FIG. 2A-2C depicts exemplary result of immune response assay to determine limits of detection and dymamic range: FIG. 2A depicts ratios of samples of HL-60 and human lung total RNA measured individually and mixed at 4 different ratios to evaluate dynamic range; FIG. 2B depicts exemplary results of correlation of fold changes between pure and mixed samples; and FIG. 2C depicts exemplary results of correlations among rank order of fold change between pure and mixed samples.

FIG. 3 depicts exemplary results of correlations between quantitative RT-PCR detection and the immune response NGS assay of the invention. Twenty two genes were selected and tested by quantitative RT-PCR in NSCLC and melanoma FFPE samples. Results demonstrated correlations between quantitative RT-PCR and NGS are 0.85 to 0.95.

FIG. 4 depicts exemplary results of correlation among fresh frozen and FFPE samples. NSCLC fresh frozen and FFPE samples showed greater than 0.96 correlation.

FIG. 5A-5D depicts exemplary results of the immune response assay. FIG. 5A is gene expression distribution plot; FIG. 5B is a bar graph depicting housekeeping gene expression; FIG. 5C is a sample correlation heatmap; and FIG. 5D depicts results of two principle component analysis for samples tested.

FIG. 6 depicts exemplary results of sample correlation of the immune response assay.

FIG. 7 depicts exemplary heatmap results of all targets of the immune response assay.

FIG. 8 depicts results of a simulated CPM normalization applied to measure the expression of genes and calculate fold change. Using endogenous controls accurately estimates fold change, because while most genes do not change between samples, fold change estimate is negligible error; however, when many genes do change, fold change estimate is wildly inaccurate.

FIG. 9A-B depicts results suggesting housekeeping gene control allow for better expression estimates. FIG. 9A depicts results of correlation of estimated and true expression among various genes, including an assay made of only the 5 genes associated with the leukocyte inhibition category. Assuming only interest in a leukocyte inhibition assay, and using just those genes, we do not get a high correlation with true expression; adding leukocyte migration only helps mildly (21 genes); adding stemness and tumor makers (uncorrelated categories; 27 genes) increases the correlation. However, using only targets and 11 housekeeping (HK) genes works just as well as including non-informative genes and true expression. FIG. 9B depicts results comparing performance of HK normalization, CPM and CPM without housekeeping, demonstrating housekeeping normalization increases correlation with true expression as expression decreases.

DESCRIPTION OF THE INVENTION

The following description of various exemplary embodiments is exemplary and explanatory only and is not to be construed as limiting or restrictive in any way. Other embodiments, features, objects, and advantages of the present teachings will be apparent from the description and accompanying drawings, and from the claims. Unless defined otherwise, all technical and scientific terms used herein have the same meaning as is commonly understood by one of ordinary skill in the art to which these inventions belong.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or.

As used herein, "amplify", "amplifying" or "amplification reaction" and their derivatives, refer to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

As used herein, "amplification conditions" and its derivatives, refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and themocycling conditions. In some embodiments, the conditions suitable for amplifying one or more nucleic acid sequences includes polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc) and can also include various modifiers of ionic strength.

As used herein, "target sequence" or "target sequence of interest" and its derivatives, refers to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises cDNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a expressed RNA, fresh-frozen or formalin-fixed paraffin-embedded nucleic acid specimen.

As used herein, "contacting" and its derivatives, when used in reference to two or more components, refers to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. Where one or more of the referenced components to be contacted includes a plurality (e.g, "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some embodiments, the primer includes one or more cleavable groups at one or more locations within the primer.

As used herein, "target-specific primer" and its derivatives, refers to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer can be at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer can be substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3'end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, "polymerase" and its derivatives, refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

As used herein, the term "nucleotide" and its variants comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. .alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3'OH end of the nucleic acid molecule by the polymerase.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure, the amplified target sequences are typically less than 50% complementary to any portion of another amplified target sequence in the reaction.

As used herein, the terms "ligating", "ligation" and their derivatives refer to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the litgation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase can be used. For the purposes of this disclosure, an amplified target sequence can be ligated to an adapter to generate an adapter-ligated amplified target sequence.

As used herein, "ligase" and its derivatives, refers to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

As used herein, "blunt-end ligation" and its derivatives, refers to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in Mitra and Varley, US2010/0129874, published May 27, 2010. In some embodiments, blunt-ended ligation includes a nick translation reaction to seal a nick created during the ligation process.

As used herein, the terms "adapter" or "adapter and its complements" and their derivatives, refers to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "reamplifying" or "reamplification" and their derivatives refer to any process whereby at least a portion of an amplified nucleic acid molecule is further amplified via any suitable amplification process (referred to in some embodiments as a "secondary" amplification or "reamplification", thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As defined herein, a "cleavable group" refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, "cleavage step" and its derivatives, refers to any process by which a cleavable group is cleaved or otherwise removed from a target-specific primer, an amplified sequence, an adapter or a nucleic acid molecule of the sample. In some embodiments, the cleavage steps involves a chemical, thermal, photo-oxidative or digestive process.

As used herein, the term "hybridization" is consistent with its use in the art, and refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase "hybridizing under stringent conditions" and its variants refers to conditions under which hybridization of a target-specific primer to a target sequence occurs in the presence of high hybridization temperature and low ionic strength. In one exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof. As used herein, the phrase "standard hybridization conditions" and its variants refers to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, "GC content" and its derivatives, refers to the cytosine and guanine content of a nucleic acid molecule. The GC content of a target-specific primer (or adapter) of the disclosure is 85% or lower. More typically, the GC content of a target-specific primer or adapter of the disclosure is between 15-85%.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. One or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3'end. In some embodiments, the term "3' end" when referring to a target-specific primer can include nucleotides located at nucleotide positions 10 or fewer from the 3' terminus.

As used herein, "5' end", and its derivatives, refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. One or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a a 3' hydroxyl group, or to the 3'end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5'end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, "DNA barcode" or "DNA tagging sequence" and its derivatives, refers to a unique short (6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

As used herein, the phrases "two rounds of target-specific hybridization" or "two rounds of target-specific selection" and their derivatives refers to any process whereby the same target sequence is subjected to two consecutive rounds of hybridization-based target-specific selection, wherein a target sequence is hybridized to a target-specific sequence. Each round of hybridization based target-specific selection can include multiple target-specific hybridizations to at least some portion of a target-specific sequence. In one exemplary embodiment, a round of target-specific selection includes a first target-specific hybridization involving a first region of the target sequence and a second target-specific hybridization involving a second region of the target sequence. The first and second regions can be the same or different. In some embodiments, each round of hybridization-based target-specific selection can include use of two target specific oligonucleotides (e.g., a forward target-specific primer and a reverse target-specific primer), such that each round of selection includes two target-specific hybridizations.

As used herein, "comparable maximal minimum melting temperatures" and its derivatives, refers to the melting temperature (Tm) of each nucleic acid fragment for a single adapter or target-specific primer after cleavage of the cleavable groups. The hybridization temperature of each nucleic acid fragment generated by a single adapter or target-specific primer is compared to determine the maximal minimum temperature required preventing hybridization of any nucleic acid fragment from the target-specific primer or adapter to the target sequence. Once the maximal hybridization temperature is known, it is possible to manipulate the adapter or target-specific primer, for example by moving the location of the cleavable group along the length of the primer, to achieve a comparable maximal minimum melting temperature with respect to each nucleic acid fragment.

As used herein, "addition only" and its derivatives, refers to a series of steps in which reagents and components are added to a first or single reaction mixture. Typically, the series of steps excludes the removal of the reaction mixture from a first vessel to a second vessel in order to complete the series of steps. An addition only process excludes the manipulation of the reaction mixture outside the vessel containing the reaction mixture. Typically, an addition-only process is amenable to automation and high-throughput.

As used herein, "synthesizing" and its derivatives, refers to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP) or dideoxynucleoside triphosphate (ddNTP) to the 3' hydroxyl of an extending oligonucleotide chain. For the purposes of this disclosure, synthesizing includes to the serial extension of a hybridized adapter or a target-specific primer via transfer of a nucleoside monophosphate from a deoxynucleoside triphosphate.

As used herein, "polymerizing conditions" and its derivatives, refers to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions can be practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As defined herein, the term "nick translation" and its variants comprise the translocation of one or more nicks or gaps within a nucleic acid strand to a new position along the nucleic acid strand. In some embodiments, a nick can be formed when a double stranded adapter is ligated to a double stranded amplified target sequence. In one example, the primer can include at its 5' end, a phosphate group that can ligate to the double stranded amplified target sequence, leaving a nick between the adapter and the amplified target sequence in the complementary strand. In some embodiments, nick translation results in the movement of the nick to the 3' end of the nucleic acid strand. In some embodiments, moving the nick can include performing a nick translation reaction on the adapter-ligated amplified target sequence. In some embodiments, the nick translation reaction can be a coupled 5' to 3' DNA polymerization/degradation reaction, or coupled to a 5' to 3' DNA polymerization/strand displacement reaction. In some embodiments, moving the nick can include performing a DNA strand extension reaction at the nick site. In some embodiments, moving the nick can include performing a single strand exonuclease reaction on the nick to form a single stranded portion of the adapter-ligated amplified target sequence and performing a DNA strand extension reaction on the single stranded portion of the adapter-ligated amplified target sequence to a new position. In some embodiments, a nick is formed in the nucleic acid strand opposite the site of ligation.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of expressed RNA or cDNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}P$-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from RNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers to the number of different target-specific sequences that are amplified during that single multiplex amplification. In some embodiments, the plexy can be about 12-plex, 24-plex, 48-plex, 74-plex, 96-plex, 120-plex, 144-plex, 168-plex, 192-plex, 216-plex, 240-plex, 264-plex, 288-plex, 312-plex, 336-plex, 360-plex, 384-plex, or 398-plex.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, preparation of nucleic acid libraries, nucleic acid sequencing and analysis, and the like. Specific illustrations of suitable techniques can be used by reference to the examples provided herein. Other equivalent conventional procedures can also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

We have developed a multiplex next generation sequencing workflow to measure expression of genes involved in immune response, e.g., checkpoint pathways, T cell related signaling pathways, markers of different tumor infiltrating lymphocyte (TIL) subsets, and tumor markers, in order to determine immune response in a sample. The immune response assay compositions and methods of the invention offer a specific and robust solution for biomarker screening and for understanding mechanisms involved with tumor immune response. Thus, provided are multiplex gene expression compositions for multiplex library preparation and use in conjunction with next generation sequencing technologies and workflow solutions (e.g., Ion Torrent™ NGS workflow), manual or automated, to evaluate pathways that shield tumors from the immune response.

Thus, provided are compositions for a single stream multiplex determination of an immune response in a sample. In some embodiments, the composition consists of a plurality of sets of primer pair reagents directed to a plurality of target sequences to measure the expression levels of the targets in the sample, wherein the target genes are selected from immune response genes consisting of the following function: checkpoint pathways, T cell related signaling pathways, markers of tumor infiltrating lymphocytes (TILs), tumor markers, and housekeeping genes. In some embodiments, the target genes are selected from immune response genes consisting of one or more function of Table A. In some embodiments, the target genes are selected from immune response genes consisting of the following function: immune checkpoint pathways and targets; T and B cell signaling genes, markers of lymphocyte subsets, interferon signaling genes, cytokine signaling genes; tumor markers, tumor antigens, proliferation markers; and housekeeping genes. In some embodiments, the target genes are selected from immune response genes that elucidate T and B lymphocyte functions, from activation to antigen processing, including, e.g., genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation and TCR coexpression. In some embodiments, the target genes are selected from immune response genes that elucidate the level of inflammation and activation and co-op by helper cells, including, e.g., genes consisting of the following function: chemokine signaling, cytokine signaling, interferon signaling, Type I interferon signaling, and Type II interferon signaling. In some embodiments, the target genes identify the presence of various relevant cell types, including, e.g., genes selected from immune response genes consisting of the following function: B cell marker, dendritic cell, dendritic cell/macrophage, helper T cell, macrophage, myeloid, neutrophil, NK activation, NK cell, and T cell differentiation. In some embodiments, the target genes elucidate the mechanism of action, including, e.g., genes selected from immune response genes consisting of the following function: checkpoint pathway, PD-signaling, and drug target. In some embodiments, the target genes demonstrate the proliferative activity and/or sternness characteristics of tumor cells, including, e.g., genes selected from immune response genes consisting of the following function: adhesion/migration, apoptosis, proliferation, tumor antigen, and tumor marker. In total, the various functions of genes comprising the provided multiplex panel of the invention provide a comprehensive picture of complex activities of the tumor microenvironment.

In some embodiments, immune response target sequences are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker.

TABLE A

Immune Response Genes

| NCBI Accession No | Gene ID | Gene Function |
|---|---|---|
| NM_001025091 | ABCF1 | Housekeeping |
| NM_078481 | ADGRE5 | Adhesion, migration |
| NM_000675 | ADORA2A | Checkpoint pathway |
| NM_001623 | AIF1 | Macrophage |
| NM_001014431 | AKT1 | Tumor marker |
| NM_001141 | ALOX15B | Macrophage |
| NM_000045 | ARG1 | Myeloid marker |
| NM_021913 | AXL | Innate immune response |
| NM_018644 | B3GAT1 | NK activation |
| NM_182482 | BAGE | Tumor antigen |
| NM_006399 | BATF | Helper T cells |
| NM_000633 | BCL2 | Apoptosis |
| NM_138621 | BCL2L11 | Apoptosis |
| NM_001706 | BCL6 | Type II interferon signaling |
| NM_007300 | BRCA1 | Tumor marker |
| NM_000059 | BRCA2 | Tumor marker |
| NM_004335 | BST2 | Type I interferon signaling |
| NM_181780 | BTLA | Checkpoint pathway |
| NM_004336 | BUB1 | Proliferation |
| NM_022153 | C10orf54 | Checkpoint pathway |
| NM_015991 | C1QA | Innate immune response |
| NM_000491 | C1QB | Innate immune response |
| NM_000717 | CA4 | Neutrophil |
| NM_170662 | CBLB | T cell receptor signaling |
| NM_002987 | CCL17 | Chemokine signaling |
| NM_002988 | CCL18 | Lymphocyte infiltrate |
| NM_002982 | CCL2 | Lymphocyte infiltrate |
| NM_004591 | CCL20 | Chemokine signaling |
| NM_002989 | CCL21 | Lymphocyte infiltrate |
| NM_002990 | CCL22 | Chemokine signaling |
| NM_002983 | CCL3 | Lymphocyte infiltrate |
| NM_002984 | CCL4 | Lymphocyte infiltrate |
| NM_002985 | CCL5 | Lymphocyte infiltrate |
| NM_004701 | CCNB2 | Proliferation |
| NM_001295 | CCR1 | Cytokine signaling |
| NM_001123396 | CCR2 | Helper T cells |
| NM_005508 | CCR4 | Chemokine signaling |

TABLE A-continued

Immune Response Genes

| NCBI Accession No | Gene ID | Gene Function |
|---|---|---|
| NM_001100168 | CCR5 | Lymphocyte infiltrate |
| NM_004367 | CCR6 | Chemokine signaling |
| NM_001838 | CCR7 | TCR coexpression |
| NM_000591 | CD14 | Dendridic cell, macrophage |
| NM_007053 | CD160 | Checkpoint pathway |
| NM_004244 | CD163 | Macrophage |
| NM_001178098 | CD19 | B cell marker |
| NM_001765 | CD1C | Antigen presentation |
| NM_001766 | CD1D | Antigen presentation |
| NM_001767 | CD2 | Lymphocyte infiltrate |
| NM_021155 | CD209 | Dendridic cell, macrophage |
| NM_001771 | CD22 | B cell marker |
| NM_006566 | CD226 | Adhesion, migration |
| NM_001166663 | CD244 | Checkpoint pathway |
| NM_198053 | CD247 | TCR coexpression |
| NM_001242 | CD27 | Drug target |
| NM_014143 | CD274 | Checkpoint pathway |
| NM_001024736 | CD276 | Checkpoint pathway |
| NM_006139 | CD28 | Checkpoint pathway |
| NM_001772 | CD33 | Myeloid marker |
| NM_001774 | CD37 | Lymphocyte infiltrate |
| NM_001775 | CD38 | Adhesion, migration |
| NM_000732 | CD3D | TCR coexpression |
| NM_000733 | CD3E | TCR coexpression |
| NM_000073 | CD3G | TCR coexpression |
| NM_000616 | CD4 | Helper T cells |
| NM_001250 | CD40 | Drug target |
| NM_000074 | CD40LG | T cell receptor signaling |
| NM_000610 | CD44 | Adhesion, migration |
| NM_001777 | CD47 | Adhesion, migration |
| NM_001778 | CD48 | Checkpoint pathway |
| NM_001803 | CD52 | Lymphocyte infiltrate |
| NM_001040033 | CD53 | Adhesion, migration |
| NM_006725 | CD6 | TCR coexpression |
| NM_001780 | CD63 | Lymphocyte infiltrate |
| NM_001251 | CD68 | Macrophage |
| NM_001781 | CD69 | Checkpoint pathway |
| NM_001252 | CD70 | Drug target |
| NM_001025159 | CD74 | Antigen processing |
| NM_001783 | CD79A | B cell receptor signaling |
| NM_001039933 | CD79B | B cell receptor signaling |
| NM_005191 | CD80 | Checkpoint pathway |
| NM_004233 | CD83 | Antigen presentation |
| NM_175862 | CD86 | Checkpoint pathway |
| NM_171827 | CD8A | TCR coexpression |
| NM_172213 | CD8B | TCR coexpression |
| NM_001786 | CDK1 | Proliferation |
| NM_000077 | CDKN2A | Tumor marker |
| NM_005192 | CDKN3 | Proliferation |
| NM_001712 | CEACAM1 | Checkpoint pathway |
| NM_001816 | CEACAM8 | Myeloid marker |
| NM_000246 | CIITA | Type II interferon signaling |
| NM_130441 | CLEC4C | Dendridic cell |
| NM_001142345 | CMKLR1 | Dendridic cell, macrophage |
| NM_007074 | CORO1A | Lymphocyte infiltrate |
| NM_019604 | CRTAM | TCR coexpression |
| NM_005211 | CSF1R | Cytokine signaling |
| NM_000395 | CSF2RB | Cytokine signaling |
| NM_001327 | CTAG1B | Tumor antigen |
| ENST00000369585 | CTAG2 | Tumor antigen |
| NM_005214 | CTLA4 | Drug target |
| NM_004079 | CTSS | Lymphocyte infiltrate |
| NM_002996 | CX3CL1 | Type II interferon signaling |
| ENST00000399220 | CX3CR1 | Lymphocyte infiltrate |
| ENST00000435290 | CX3CR1 | Lymphocyte infiltrate |
| ENST00000541347 | CX3CR1 | Lymphocyte infiltrate |
| NM_001171174 | CX3CR1 | Lymphocyte infiltrate |
| NM_001511 | CXCL1 | Chemokine signaling |
| NM_001565 | CXCL10 | Type II interferon signaling |
| NM_005409 | CXCL11 | Type II interferon signaling |
| NM_006419 | CXCL13 | Type II interferon signaling |
| NM_000584 | CXCL8 | Cytokine signaling |
| NM_002416 | CXCL9 | Type II interferon signaling |
| NM_001557 | CXCR2 | Chemokine signaling |
| NM_001504 | CXCR3 | Chemokine signaling |
| NM_003467 | CXCR4 | Lymphocyte infiltrate |
| NM_001716 | CXCR5 | Type II interferon signaling |
| NM_006564 | CXCR6 | Lymphocyte infiltrate |
| NM_000397 | CYBB | Type II interferon signaling |
| NM_014314 | DDX58 | Interferon signaling |
| NM_032564 | DGAT2 | Neutrophil |
| NM_007329 | DMBT1 | Innate immune response |
| NM_005755 | EBI3 | T cell regulation |
| NM_005227 | EFNA4 | Tumor marker |
| NM_005228 | EGFR | Tumor marker |
| NM_000399 | EGR2 | T cell differentiation |
| NM_004430 | EGR3 | Tumor marker |
| NM_001135651 | EIF2AK2 | Type II interferon signaling |
| NM_001098175 | ENTPD1 | Checkpoint pathway |
| NM_005442 | EOMES | Checkpoint pathway |
| NM_000043 | FAS | B cell receptor signaling |
| NM_000639 | FASLG | Type II interferon signaling |
| NM_004106 | FCER1G | Lymphocyte infiltrate |
| NM_000566 | FCGR1A | B cell marker |
| NM_004001 | FCGR2B | B cell marker |
| NM_000569 | FCGR3A | Macrophage |
| NM_000570 | FCGR3B | NK activation |
| NM_001184866 | FCRLA | B cell marker |
| NM_021953 | FOXM1 | Proliferation |
| NM_002015 | FOXO1 | PD-1 signaling, tumor marker |
| NM_014009 | FOXP3 | T cell regulation |
| NM_002033 | FUT4 | Myeloid marker, stem cell |
| NM_001465 | FYB | Lymphocyte infiltrate |
| NM_000402 | G6PD | Housekeeping |
| NM_052850 | GADD45GIP1 | Apoptosis |
| NM_001040663 | GAGE1, GAGE12I, GAGE12F | Tumor antigen |
| NM_001098413 | GAGE10 | Tumor antigen |
| NM_001098406 | GAGE12J | Tumor antigen |
| NM_001098412 | GAGE13 | Tumor antigen |
| NM_001472 | GAGE2C, GAGE2A, GAGE2E | Tumor antigen |
| NM_001002295 | GATA3 | Helper T cells |
| NM_002053 | GBP1 | Type II interferon signaling |
| NM_006433 | GNLY | NK activation |
| NM_001098200 | GPR18 | TCR coexpression |
| NM_004810 | GRAP2 | TCR coexpression |
| NM_000181 | GUSB | Housekeeping |
| NM_006144 | GZMA | Lymphocyte infiltrate |
| NM_004131 | GZMB | Lymphocyte infiltrate |
| NM_033423 | GZMH | Lymphocyte infiltrate |
| NM_002104 | GZMK | Lymphocyte infiltrate |
| NM_032782 | HAVCR2 | Checkpoint pathway |
| NM_017912 | HERC6 | Dendridic cell |
| NM_000601 | HGF | Cytokine signaling |
| NM_001530 | HIF1A | PD-1 signaling, tumor marker |
| NM_002116 | HLA-A | Antigen processing |
| NM_005514 | HLA-B | Antigen processing |
| NM_002117 | HLA-C | Antigen processing |
| NM_006120 | HLA-DMA | Antigen processing |
| NM_002118 | HLA-DMB | Antigen processing |
| NM_002119 | HLA-DOA | Antigen processing |
| NM_002120 | HLA-DOB | Antigen processing |
| NM_033554 | HLA-DPA1 | Antigen processing |
| NM_002121 | HLA-DPB1 | Antigen processing |
| NM_002122 | HLA-DQA1 | Antigen processing |
| NM_020056 | HLA-DQA2 | Antigen processing |
| NM_001198858 | HLA-DQB2 | Antigen processing |
| NM_019111 | HLA-DRA | Antigen processing |
| NM_002124 | HLA-DRB1 | Antigen processing |
| NM_005516 | HLA-E | Antigen processing |
| NM_001098479 | HLA-F | Antigen processing |
| NR_026972 | HLA-F-AS1 | Antigen processing |
| NM_002127 | HLA-G | Antigen processing |
| NM_000190 | HMBS | Housekeeping |
| NM_000201 | ICAM1 | Type II interferon signaling |
| NM_012092 | ICOS | Checkpoint pathway |
| NM_015259 | ICOSLG | Checkpoint pathway |
| NM_002166 | ID2 | T cell regulation |
| NM_002167 | ID3 | T cell regulation |

TABLE A-continued

Immune Response Genes

| NCBI Accession No | Gene ID | Gene Function |
|---|---|---|
| NM_002164 | IDO1 | Drug target |
| NM_194294 | IDO2 | Checkpoint pathway |
| NM_005532 | IFI27 | Type I interferon signaling |
| NM_005533 | IFI35 | Interferon signaling |
| NM_006820 | IFI44L | Interferon signaling |
| NM_022873 | IFI6 | Interferon signaling |
| NM_022168 | IFIH1 | Innate immune response |
| NM_001548 | IFIT1 | Type I interferon signaling |
| NM_001547 | IFIT2 | Cytokine signaling |
| NM_001031683 | IFIT3 | Type I interferon signaling |
| NM_003641 | IFITM1 | Type I interferon signaling |
| NM_006435 | IFITM2 | Type I interferon signaling |
| NM_021268 | IFNA17 | T cell receptor signaling |
| NM_002176 | IFNB1 | Type II interferon signaling |
| NM_000619 | IFNG | Type II interferon signaling |
| NM_000875 | IGF1R | Adhesion, migration |
| NM_005849 | IGSF6 | Lymphocyte infiltrate |
| NM_006060 | IKZF1 | Lymphocyte development |
| NM_016260 | IKZF2 | Lymphocyte development |
| NM_012481 | IKZF3 | TCR coexpression |
| NM_022465 | IKZF4 | Lymphocyte development |
| NM_000572 | IL10 | Drug target |
| NM_001558 | IL10RA | Lymphocyte infiltrate |
| NM_000882 | IL12A | Drug target |
| NM_002187 | IL12B | Drug target |
| NM_002188 | IL13 | Cytokine signaling |
| NM_000585 | IL15 | T cell regulation |
| NM_002190 | IL17A | Helper T cells |
| NM_052872 | IL17F | Dendridic cell, macrophage |
| NM_001562 | IL18 | T cell regulation |
| NM_000575 | IL1A | Cytokine signaling |
| NM_000576 | IL1B | Type II interferon signaling |
| NM_000586 | IL2 | Drug target |
| NM_021803 | IL21 | Cytokine signaling |
| NM_020525 | IL22 | T cell regulation |
| NM_016584 | IL23A | Dendridic cell, macrophage |
| NM_000417 | IL2RA | Cytokine signaling |
| NM_000878 | IL2RB | TCR coexpression |
| NM_000206 | IL2RG | Lymphocyte infiltrate |
| NM_002183 | IL3RA | Dendridic cell |
| NM_000589 | IL4 | Cytokine signaling |
| NM_000600 | IL6 | Cytokine signaling |
| NM_000880 | IL7 | Cytokine signaling |
| NM_002185 | IL7R | TCR coexpression |
| NM_002198 | IRF1 | Type II interferon signaling |
| NM_002460 | IRF4 | Interferon signaling |
| NM_006084 | IRF9 | Type II interferon signaling |
| NM_005544 | IRS1 | Tumor marker |
| NM_005101 | ISG15 | Type I interferon signaling |
| NM_002201 | ISG20 | Type I interferon signaling |
| NM_181501 | ITGA1 | Adhesion, migration |
| NM_002208 | ITGAE | Adhesion, migration |
| NM_002209 | ITGAL | Leukocyte migration |
| NM_001145808 | ITGAM | Leukocyte migration |
| NM_000887 | ITGAX | Dendridic cell |
| NM_002211 | ITGB1 | Adhesion, migration |
| NM_000211 | ITGB2 | Lymphocyte infiltrate |
| NM_000889 | ITGB7 | Leukocyte migration |
| NM_005546 | ITK | TCR coexpression |
| NM_001098526 | JAML | Lymphocyte infiltrate |
| NM_144646 | JCHAIN | B cell marker |
| NM_014736 | KIAA0101 | Proliferation |
| NM_014218 | KIR2DL1 | Drug target |
| ENST00000344867 | KIR2DL2 | NK cell marker |
| NM_015868 | KIR2DL3 | NK cell marker |
| NM_016270 | KLF2 | T cell regulation, trafficking |
| NM_002258 | KLRB1 | NK activation |
| NM_002262 | KLRD1 | Drug target |
| NM_016523 | KLRF1 | NK activation |
| NM_005810 | KLRG1 | NK activation |
| NM_007360 | KLRK1 | NK activation |
| NM_032045 | KREMEN1 | Neutrophil |
| NM_000424 | KRT5 | Tumor marker |
| NM_005556 | KRT7 | Tumor marker |
| NM_002286 | LAG3 | Drug target |
| NM_005561 | LAMP1 | Lymphocyte infiltrate |
| NM_014398 | LAMP3 | TCR coexpression |
| NM_006762 | LAPTM5 | Lymphocyte infiltrate |
| NM_001042771 | LCK | TCR coexpression |
| NM_005564 | LCN2 | Innate immune response |
| NM_001110533 | LEXM | T cell differentiation |
| NM_001081637 | LILRB1 | Leukocyte inhibition |
| NM_001080978 | LILRB2 | Lymphocyte infiltrate |
| NM_170707 | LMNA | Housekeeping |
| NM_052972 | LRG1 | Neutrophil |
| NM_002332 | LRP1 | Housekeeping |
| NM_007161 | LST1 | Leukocyte inhibition |
| NM_002348 | LY9 | Lymphocyte infiltrate |
| NM_000239 | LYZ | Innate immune response |
| NM_002355 | M6PR | T cell regulation |
| NM_002358 | MAD2L1 | Proliferation |
| NM_130760 | MADCAM1 | Adhesion, migration |
| NM_004988 | MAGEA1 | Tumor antigen |
| NM_021048 | MAGEA10 | Tumor antigen |
| NM_005367 | MAGEA12 | Tumor antigen |
| NM_005362 | MAGEA3 | Tumor antigen |
| NM_001011548 | MAGEA4 | Tumor antigen |
| NM_016249 | MAGEC2 | Tumor antigen |
| NM_002745 | MAPK1 | Tumor marker |
| NM_139012 | MAPK14 | Innate immune response |
| NM_014791 | MELK | Proliferation |
| NM_002415 | MIF | Innate immune response |
| NM_002417 | MKI67 | Proliferation |
| NM_005511 | MLANA | Tumor antigen |
| NM_004530 | MMP2 | Tumor marker |
| NM_004994 | MMP9 | Tumor marker |
| NM_000250 | MPO | Myeloid marker |
| NM_002438 | MRC1 | Dendridic cell, macrophage |
| NM_021950 | MS4A1 | Drug target |
| NM_004958 | MTOR | PD-1 signaling, tumor marker |
| NM_001178046 | MX1 | Interferon signaling |
| NM_002467 | MYC | Tumor marker |
| NM_181351 | NCAM1 | Adhesion, migration |
| NM_000265 | NCF1 | Chemokine signaling |
| NM_004829 | NCR1 | NK cell marker |
| NM_147130 | NCR3 | NK cell marker |
| NM_001042724 | NECTIN2 | Adhesion, migration |
| NM_172387 | NFATC1 | PD-1 signaling |
| NM_020529 | NFKBIA | T cell receptor signaling |
| NM_005601 | NKG7 | Lymphocyte infiltrate |
| NM_000625 | NOS2 | Innate immune response |
| NM_000435 | NOTCH3 | Tumor marker |
| NM_003873 | NRP1 | Dendridic cell |
| NM_002526 | NT5E | Checkpoint pathway |
| NM_006181 | NTN3 | B cell marker |
| NM_016816 | OAS1 | Type II interferon signaling |
| NM_016817 | OAS2 | Interferon signaling |
| NM_006187 | OAS3 | Interferon signaling |
| NM_005018 | PDCD1 | Drug target |
| NM_002239 | PDCD1LG2 | Checkpoint pathway |
| NM_000442 | PECAM1 | Adhesion, migration |
| NM_002632 | PGF | Tumor marker |
| NM_006218 | PIK3CA | PD-1 signaling, tumor marker |
| NM_005026 | PIK3CD | PD-1 signaling, tumor marker |
| NM_006928 | PMEL | Drug target |
| NM_000937 | POLR2A | Housekeeping |
| NM_006235 | POU2AF1 | B cell marker |
| NM_001198 | PRDM1 | PD-1 signaling |
| NM_005041 | PRF1 | NK activation |
| NM_002800 | PSMB9 | Type II interferon signaling |
| NM_000314 | PTEN | PD-1 signaling, tumor marker |
| NM_000963 | PTGS2 | Tumor marker |
| NM_002821 | PTK7 | Tumor marker |
| NM_002834 | PTPN11 | PD-1 signaling, tumor marker |
| NM_080548 | PTPN6 | T cell receptor signaling |
| NM_001199797 | PTPN7 | Lymphocyte infiltrate |
| NM_002838 | PTPRC | Lymphocyte infiltrate |
| ENST00000326294 | PTPRCAP | TCR coexpression |
| NM_006505 | PVR | Checkpoint pathway |
| NM_002863 | PYGL | Neutrophil |
| NM_000321 | RB1 | Tumor marker |
| NM_005060 | RORC | Helper T cells |

TABLE A-continued

Immune Response Genes

| NCBI Accession No | Gene ID | Gene Function |
| --- | --- | --- |
| NM_001010 | RPS6 | Tumor marker |
| NM_002964 | S100A8 | Myeloid marker, MDSC |
| NM_002965 | S100A9 | Myeloid marker, MDSC |
| NM_015474 | SAMHD1 | Lymphocyte infiltrate |
| NM_004168 | SDHA | Housekeeping |
| NM_000655 | SELL | Leukocyte migration |
| NM_002351 | SH2D1A | Lymphocyte activation |
| NM_053282 | SH2D1B | Lymphocyte activation |
| NM_014450 | SIT1 | Lymphocyte infiltrate |
| NM_003930 | SKAP2 | B cell marker |
| NM_021181 | SLAMF7 | Drug target |
| NM_020125 | SLAMF8 | Lymphocyte infiltrate |
| NM_005985 | SNAI1 | Tumor marker, stemness |
| NM_003068 | SNAI2 | Tumor marker, stemness |
| NM_002727 | SRGN | Lymphocyte infiltrate |
| NM_003147 | SSX2 | Tumor antigen |
| NM_007315 | STAT1 | Type II interferon signaling |
| NM_139276 | STAT3 | Drug target |
| NM_003151 | STAT4 | Helper T cells |
| NM_003152 | STAT5A | Cytokine signaling |
| NM_003153 | STAT6 | Helper T cells |
| NM_054114 | TAGAP | Lymphocyte infiltrate |
| NM_000593 | TAP1 | Type II interferon signaling |
| NM_001003806 | TARP | Lymphocyte infiltrate |
| NM_003194 | TBP | Housekeeping |
| NM_013351 | TBX21 | Type II interferon signaling |
| NM_003202 | TCF7 | Tumor marker |
| NM_005651 | TDO2 | Checkpoint pathway |
| NM_001128148 | TFRC | Housekeeping |
| NM_000660 | TGFB1 | Checkpoint pathway |
| NM_173799 | TIGIT | TCR coexpression |
| NM_003265 | TLR3 | Dendridic cell |
| NM_016562 | TLR7 | Innate immune response |
| NM_138636 | TLR8 | Lymphocyte infiltrate |
| NM_017442 | TLR9 | Drug target |
| NM_000594 | TNF | Checkpoint pathway |
| NM_014350 | TNFAIP8 | Lymphocyte infiltrate |
| NM_003820 | TNFRSF14 | Checkpoint pathway |
| NM_001192 | TNFRSF17 | B cell marker |
| NM_004195 | TNFRSF18 | Drug target |
| NM_003327 | TNFRSF4 | Drug target |
| NM_001561 | TNFRSF9 | Drug target |
| NM_003810 | TNFSF10 | Apoptosis |
| NM_006573 | TNFSF13B | B cell marker |
| NM_003807 | TNFSF14 | Checkpoint pathway |
| NM_005092 | TNFSF18 | Checkpoint pathway |
| NM_003326 | TNFSF4 | Checkpoint pathway |
| NM_003811 | TNFSF9 | Cytokine signaling |
| NM_001067 | TOP2A | Proliferation |
| NM_003722 | TP63 | Tumor marker |
| NM_012101 | TRIM29 | Tumor marker |
| NM_178014 | TUBB | Housekeeping |
| NM_000474 | TWIST1 | Tumor marker, stemness |
| NM_198125 | TYROBP | Lymphocyte infiltrate |
| NM_001078 | VCAM1 | Leukocyte migration |
| NM_001171623 | VEGFA | Chemokine signaling |
| NM_024626 | VTCN1 | Checkpoint pathway |
| NM_001097594 | XAGE1B | Tumor antigen |
| NM_001079 | ZAP70 | T cell receptor signaling |
| NM_025224 | ZBTB46 | Dendridic cell |
| NM_001174093 | ZEB1 | Tumor marker, stemness |

In some embodiments, immune response target sequences are selected from immune response genes consisting of the following functions: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, and drug target. In some embodiments, immune response target sequences are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, adhesion/migration, apoptosis, proliferation, tumor antigen, and tumor marker. In some embodiments, immune response target sequences are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, checkpoint pathway, PD-signaling, drug target, adhesion/migration, apoptosis, proliferation, tumor antigen, and tumor marker. In some embodiments, immune response target sequences are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker. In some embodiments, immune response target sequences are selected from immune response genes consisting of the following function: chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker.

In certain embodiments, target immune response sequences are directed to sequences having aberrant expression associated with cancer. In some embodiments, the target sequences or amplified target sequences are directed to sequences having aberrant expression associated with one or more solid tumor cancers selected from the group consisting of head and neck cancers (e.g., HNSCC, nasopharyngeal, salivary gland), brain cancer (e.g., glioblastoma, glioma, gliosarcoma, glioblastoma multiforme, neuroblastoma), breast cancer (e.g., TNBC, trastuzumab resistant HER2+ breast cancer, ER+/HER− breast cancer), gynecological (e.g., uterine, ovarian cancer, cervical cancer, endometrial cancer, fallopian cancer), colorectal cancer, gallbladder cancer, esophageal cancer, gastrointestinal cancer, gastric cancer, bladder cancer, prostate cancer, testicular cancer, urothelial cancer, liver cancer (e.g., hepatocellular, HCC), lung cancer (e.g., non-small cell lung, small cell lung), kidney (renal cell) cancer, pancreatic cancer (e.g., adenocarcinoma, ductal), thyroid cancer, bile duct cancer, pituitary tumor, wilms tumor, kaposi sarcoma, hairy cell carcinoma, osteosarcoma, thymus cancer, skin cancer, melanoma, heart cancer, oral and larynx cancer, neuroblastoma, mesothelioma, and other solid tumors (thymic, bone, soft tissue, oral SCC, myelofibrosis, synovial sarcoma). In one embodiment, the mutations can include substitutions, insertions, inversions, point mutations, deletions, mismatches and translocations. In some embodiments, the target sequences or amplified target sequences are directed to sequences having aberrant expression associated with one or more blood/hematologic cancers selected from the group consisting of multiple myeloma, diffuse large B cell lymphoma (DLBCL), lymphoma, Hodgkins lymphoma, non-Hodgkins lymphoma, follicular lymphoma, leukemia, acute myeloid leukemia (AML), chronic lymphocytic leukemia (CLL), myelodisplastic syndrome. In one embodiment, the aberrant expression associated with cancer are located in at least one of the genes provided in Table 1.

In some embodiments, one or more aberrant expression immune response sequences are located in at least one of the genes selected from CD63, CD69, CXCL1, KLRD1, HLA-DOB, CXCR5, IL12B, PTK7, CEACAM1, CXCL9, IL13, NT5E, VEGFA, ABCF1, CD38, JAML, S100A8, MYC, IRF1, CCL22, CXCR2, IFIT1, IFIT2, CD68, M6PR, SH2D1A, ISG20, GBP1, TBP, STAT6, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R, TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMP3, TNFAIP8, FOXP3, IL12A, SAMHD1, SIT1, CD3E, ICOSLG, HGF, MELK, IGSF6, GNLY, TDO2, KRT7, HLA-E, HLA-DM, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBI3, EFNA4, PVR, BUB1, SKAP2, PRF1, CCL20, TNFRSF18, CTSS, NKG7, ISG15, PDCD1, SNAI1, CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DR, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, IL1A, FCGR3A, IFNA17, EGR2, TOP2A, C10orf54, FOXM1, AXL, MS4A1, IFI6, CD3D, GPR18, CD3G, ZAP70, HMBS, IL7, IFIT3, RB1, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MX1, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDO1, IL18, TNFRSF9, HIF1A, HLA-DPB1, FOXO1, CD33, S100A9, HLA-DMB, HLA-A, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAG3, TNFRSF4, CD2, CCL4, BAGE, LEXM, CCR6, CD70, CDK1, CTAG1B, CTAG2, CX3CR1, CX3CR1, CX3CR1, CX3CR1, GAGE1, GAGE12I, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CEACAM8, CXCR3, FCGR1A, FCGR3B, FYB, HLA-C, HLA-DQA2, IFNG, KIR2DL1, KRT5, LMNA, and PTPN11. In some embodiments the one or more aberrant expression sequences indicate cancer activity.

In some embodiments the one or more aberrant expression sequences indicate a patient's likelihood to response to a therapeutic agent. In some embodiments, the one or more aberrant expression sequences indication a patient's likelihood to not be responsive to a therapeutic agent. In certain embodiments, relevant therapeutic agents can be immunotherapies including but not limited to checkpoint blockades, T cell therapies, and therapeutic vaccines. In some embodiments a therapeutic agent may modify an immune response gene selected from PD1 (e.g., nivolumab, pembrolizumab, AMP-244, MEDI0680, AMP-514, pidlizumab), CTLA4 (e.g., ipilimumab, tremelimumab), PD-L1 (e.g., atezolizumab, MDX1105-01, MEDI4736, avelumab), KIR (e.g., lirilumab, NCC0141-0000-0100), CD9/NKG2A (e.g., IPH2201), LAG3 (e.g., BMS986016), GITR (e.g., TRX518), OX40 (e.g., MEDI6383, MEDI6489, MOXR0916), IDO (e.g., indoximod (NLG8189), INCB024360, F001287, NLG919), TGFbeta (e.g., sotaracept, fresolumimab, trabedersen, lucanix), TGFbetaR (e.g., LY2157299, ACE536), CD137 (e.g., urelumab), CD137/41BB (e.g., pf05082566), CD289/TLR9 (e.g., MGN1703), MUC1/CD227 (e.g., OINT-10, ASN-004), CD27 (e.g., varlilumab), CD27L (e.g., AMG172), SLAMF7/CD1 (e.g., elotuzumab), CD20 (e.g., DI-Leu16-IL2), talimogene laherparepvec, CD70 (e.g., ARGX110), IL10 (e.g., AM0010), PSA (e.g., PROSTVAC), GP100 (e.g., MDX1379), STAT3 (e.g., AZD9150), CVAC, IL12 (e.g., veledimex, INXN2001, MSB0010360N, IMMUNOPULSE, GEN-1, INO-9012; IL2: MSB0010445, RG7813/RO6895882), IL33 (e.g., alarmin IL33), ICT140, CNDO-109, hTERT (e.g., INO-1400), dysplastic tissues (e.g., ADXS-HPV), SMAC-mimetic (e.g., birinapant), ImmTACs (e.g., IMCgp100), and CD40 (e.g., RO7009789. In certain embodiments, relevant therapeutic agent is an immunotherapy selected from checkpoint blockade, T cell therapy, and therapeutic vaccine. In some embodiments a therapeutic agent modifies an immune response gene selected from any of PD1 (e.g., nivolumab, pembrolizumab, AMP-244, MEDI0680, AMP-514, pidlizumab), CTLA4 (e.g., ipilimumab, tremelimumab), PD-L1 (e.g., atezolizumab, MDX1105-01, MEDI4736, avelumab), KIR (e.g., lirilumab, NCC0141-0000-0100), CD9/NKG2A (e.g., IPH2201), LAG3 (e.g., BMS986016), GITR (e.g., TRX518), OX40 (e.g., MEDI6383, MEDI6489, MOXR0916), IDO (e.g., indoximod (NLG8189), INCB024360, F001287, NLG919), TGFbeta (e.g., sotaracept, fresolumimab, trabedersen, lucanix), TGFbetaR (e.g., LY2157299, ACE536), CD137 (e.g., urelumab), CD137/41BB (e.g., pf05082566), CD289/TLR9 (e.g., MGN1703), MUC1/CD227 (e.g., OINT-10, ASN-004), CD27 (e.g., varlilumab), CD27L (e.g., AMG172), SLAMF7/CD1 (e.g., elotuzumab), CD20 (e.g., DI-Leu16-IL2), talimogene laherparepvec, CD70 (e.g., ARGX110), IL10 (e.g., AM0010), PSA (e.g., PROSTVAC), GP100 (e.g., MDX1379), STAT3 (e.g., AZD9150), CVAC, IL12 (e.g., veledimex, INXN2001, MSB0010360N, IMMUNOPULSE, GEN-1, INO-9012; IL2: MSB0010445, RG7813/RO6895882), IL33 (e.g., alarmin IL33), ICT140, CNDO-109, hTERT (e.g., INO-1400), dysplastic tissues (e.g., ADXS-HPV), SMAC-mimetic (e.g., birinapant), ImmTACs (e.g., IMCgp100), and CD40 (e.g., RO7009789).

In some embodiments, target sequences or amplified target sequences are directed to mutations associated with cancer. In some embodiments, the target sequences or amplified target sequences are directed to mutations associated with one or more solid tumor cancers selected from the group consisting of head and neck cancers (e.g., HNSCC, nasopharyngeal, salivary gland), brain cancer (e.g., glioblastoma, glioma, gliosarcoma, glioblastoma multiforme, neuroblastoma), breast cancer (e.g., TNBC, trastuzumab resistant HER2+ breast cancer, ER+/HER− breast cancer), gynecological (e.g., uterine, ovarian cancer, cervical cancer, endometrial cancer, fallopian cancer), colorectal cancer, gallbladder cancer, esophageal cancer, gastrointestinal cancer, gastric cancer, bladder cancer, prostate cancer, testicular cancer, urothelial cancer, liver cancer (e.g., hepatocellular, HCC), lung cancer (e.g., non-small cell lung, small cell lung), kidney (renal cell) cancer, pancreatic cancer (e.g., adenocarcinoma, ductal), thyroid cancer, bile duct cancer, pituitary tumor, wilms tumor, kaposi sarcoma, hairy cell carcinoma, osteosarcoma, thymus cancer, skin cancer, melanoma, heart cancer, oral and larynx cancer, neuroblastoma, mesothelioma, and other solid tumors (thymic, bone, soft tissue, oral SCC, myelofibrosis, synovial sarcoma). In one embodiment, the mutations can include substitutions, insertions, inversions, point mutations, deletions, mismatches and translocations. In one embodiment, the mutations can include variation in copy number. In one embodiment, the mutations can include germline or somatic mutations. In some embodiments, the target sequences or amplified target sequences are directed to sequences having mutations associated with one or more blood/hematologic cancers selected from the group consisting of multiple myeloma, diffuse large B cell lymphoma (DLBCL), lymphoma, Hodgkins lymphoma, non-Hodgkins lymphoma, follicular lymphoma, leukemia, acute myeloid leukemia (AML), chronic lymphocytic leukemia (CLL), myelodisplastic syndrome. In one embodiment, the mutations associated with cancer are located in at least one of the genes provided in Table 1.

In some embodiments, one or more mutations in immune response sequences associated with cancer are located in at least one of the genes selected from CD63, CD69, CXCL1, KLRD1, HLA-DOB, CXCR5, IL12B, PTK7, CEACAM1, CXCL9, IL13, NT5E, VEGFA, ABCF1, CD38, JAML, S100A8, MYC, IRF1, CCL22, CXCR2, IFIT1, IFIT2, CD68, M6PR, SH2D1A, ISG20, GBP1, TBP, STAT6, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R, TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMP3, TNFAIP8, FOXP3, IL12A, SAMHD1, SIT1, CD3E, ICOSLG, HGF, MELK, IGSF6, GNLY, TDO2, KRT7, HLA-E, HLA-DM, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBI3, EFNA4, PVR, BUB1, SKAP2, PRF1, CCL20, TNFRSF18, CTSS, NKG7, ISG15, PDCD1, SNAI1, CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DR, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, IL1A, FCGR3A, IFNA17, EGR2, TOP2A, C10orf54, FOXM1, AXL, MS4A1, IFI6, CD3D, GPR18, CD3G, ZAP70, HMBS, IL7, IFIT3, RB1, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MX1, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDO1, IL18, TNFRSF9, HIF1A, HLA-DPB1, FOXO1, CD33, S100A9, HLA-DMB, HLA-A, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAG3, TNFRSF4, CD2, CCL4, BAGE, LEXM, CCR6, CD70, CDK1, CTAG1B, CTAG2, CX3CR1, CX3CR1, CX3CR1, CX3CR1, GAGE1, GAGE12I, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CEACAM8, CXCR3, FCGR1A, FCGR3B, FYB, HLA-C, HLA-DQA2, IFNG, KIR2DL1, KRT5, LMNA, and PTPN11

In some embodiments, amplified target sequences are directed to any one of more of the genes provided in Table 1. In some embodiments, amplified target sequences comprise any one or more amplicon sequences provided in Table 1. In some embodiments, amplified target sequences consist of any one or more amplicon sequences provided in Table 1. In some embodiments, amplified target sequences include each amplicon sequence provided in Table 1.

In some embodiments, compositions comprise any one or more of the immune response target-specific primer pairs provided in Table 2. In some embodiments, compositions comprise all of the immune response target-specific primer pairs provided in Table 2. In some embodiments, any one or more of the immune response target-specific primer pairs provided in Table 2 can be used to amplify a target sequence present in a sample as disclosed by the methods described herein.

In some embodiments, the immune response target-specific primers from Table 2 can include 2, 3, 4, 5, 6, 7, 8, 9, 10, 20, 40, 60, 80, 100, 150, 200, 250, 300, 350, 398 or more, target-specific primer pairs. In some embodiments, the amplified target sequences can include any one or more of the amplified target sequences provided in Table 1 (e.g., using amplicon ID target-specific primers provided in Table 2). In some embodiments, at least one of the target-specific primers associated with cancer is at least 90% identical to at least one nucleic acid sequence selected from SEQ ID NOs: 399-1194. In some embodiments, at least one of the target-specific primers associated with immune response is complementary across its entire length to at least one target sequence in a sample. In some embodiments, at least one of the target-specific primers associated with immune response includes a non-cleavable nucleotide at the 3' end. In some embodiments, the non-cleavable nucleotide at the 3' end includes the terminal 3' nucleotide. In one embodiment, the amplified target sequences are directed to one or more individual exons having aberrant expression associated with cancer. In one embodiment, the amplified target sequences are directed to individual exons having a mutation associated with cancer. In some embodiments, provided methods comprise selective amplification of more than one target sequences in a sample and the detection and/or identification of mutations associated with cancer. In some embodiments, the amplified target sequences include two or more nucleotide sequences provided in Table 2. In some embodiments, the amplified target sequences can include any one or more the amplified target sequences generated using the target-specific primers provided in Table 2. In one embodiment, the amplified target sequences include 10, 50, 100, 150, 200, 250, 300, 350 or more amplicons from Table 1. In some embodiments, methods comprise detection and optionally, the identification of clinically actionable markers. As defined herein, the term "clinically actionable marker" includes clinically actionable mutations and/or clinically actionable expression patterns that are known or can be associated by one of ordinary skill in the art with, but not limited to, prognosis for the treatment of cancer. In one embodiment, prognosis for the treatment of cancer includes the identification of mutations and/or expression patterns associated with responsiveness or non-responsiveness of a cancer to a drug, drug combination, or treatment regime. In one embodiment, methods comprise amplification of a plurality of target sequences from a population of nucleic acid molecules linked to, or correlated with, the onset, progression or remission of cancer.

In some embodiments, housekeeping genes are comprised in the immune response assay. In certain embodiments, one or more housekeeping gene sequences are included in the assay. In particular embodiments the one or more housekeeping genes are selected from ABCF1, G6PD, GUSB, HMBS, LMNA, LRP1, POLR2A, SDHA, TBP, TFRC, and TUBB.

Provided herein are methods for determining immune response activity in a sample. In some embodiments, the method comprises multiplex amplification of a plurality of target expression sequences from a biological sample, wherein amplifying comprises contacting at least a portion of the sample with a plurality of sets of primer pair reagents directed to the plurality of target sequences, and a polymerase under amplification conditions, to thereby produce amplified target expression sequences. The method further comprises detecting the levels of expression of the target sequences in the sample, wherein a change in the level of expression of one or more immune response markers as compared with a control determines a change in immune response activity in the sample. In some embodiments the target expression sequences of the methods are selected from immune response genes consisting of the following function: checkpoint pathways, T cell related signaling pathways, markers of tumor infiltrating lymphocytes (TILs), tumor markers, and housekeeping genes. In some embodiments, the target genes are selected from immune response genes consisting of the following function: immune checkpoint pathways and targets; T and B cell signaling genes, markers of lymphocyte subsets, interferon signaling genes, cytokine signaling genes; tumor markers, tumor antigens, proliferation markers; and housekeeping genes. In some embodiments, the target genes of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation and TCR coexpression. In some embodiments, the target genes of the methods are selected from immune response genes consisting of the following function: chemokine signaling, cytokine signaling, interferon signaling, Type I interferon signaling, and Type II interferon signaling. In some embodiments, the target genes of the methods are selected from immune response genes consisting of the following function of markers: B cell marker, dendritic cell, dendritic cell/macrophage, helper T cell, macrophage, myeloid, neutrophil, NK activation, NK cell, and T cell differentiation. In some embodiments, the target genes of the methods are selected from immune response genes consisting of the following function of marker: checkpoint pathway, PD-signaling, and drug target. In some embodiments, the target genes of the methods are selected from immune response genes consisting of the following function of markers: adhesion/migration, apoptosis, proliferation, tumor antigen, and tumor marker.

In some embodiments, immune response target sequences of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker.

In some embodiments, immune response target sequences of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, and drug target. In some embodiments, immune response target sequences of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, adhesion/migration, apoptosis, proliferation, tumor antigen, and tumor marker. In some embodiments, immune response target sequences of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, checkpoint pathway, PD-signaling, drug target, adhesion/migration, apoptosis, proliferation, tumor antigen, and tumor marker. In some embodiments, immune response target sequences of the methods are selected from immune response genes consisting of the following function: antigen presentation, antigen processing, innate immune response, leukocyte inhibition, leukocyte migration, lymphocyte activation, lymphocyte development, lymphocyte infiltrate, B cell receptor signaling, T cell receptor signaling, T cell regulation, TCR coexpression, chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker. In some embodiments, immune response target sequences of the methods are selected from immune response genes consisting of the following function: chemokine signaling, cytokine signaling, interferon signaling, Type I interferon signaling, Type II interferon signaling, B cell marker, dendritic cell, dendritic cell/macrophage, helper T cell, macrophage, myeloid, neutrophil, NK activation, NK cell, T cell differentiation, checkpoint pathway, PD-signaling, drug target, adhesion/migration, apoptosis, proliferation, tumor antigen, and tumor marker.

In certain embodiments, target immune response sequences of the methods are directed to sequences having aberrant expression associated with cancer. In some embodiments, the target sequences or amplified target sequences of the methods are directed to sequences having aberrant expression associated with associated with one or more solid tumor cancers selected from the group consisting of head and neck cancers (e.g., HNSCC, nasopharyngeal, salivary gland), brain cancer (e.g., glioblastoma, glioma, gliosarcoma, glioblastoma multiforme, neuroblastoma), breast cancer (e.g., TNBC, trastuzumab resistant HER2+ breast cancer, ER+/HER- breast cancer), gynecological (e.g., uterine, ovarian cancer, cervical cancer, endometrial cancer, fallopian cancer), colorectal cancer, gallbladder cancer, esophageal cancer, gastrointestinal cancer, gastric cancer, bladder cancer, prostate cancer, testicular cancer, urothelial cancer, liver cancer (e.g., hepatocellular, HCC), lung cancer (e.g., non-small cell lung, small cell lung), kidney (renal cell) cancer, pancreatic cancer (e.g., adenocarcinoma, ductal), thyroid cancer, bile duct cancer, pituitary tumor, wilms tumor, kaposi sarcoma, hairy cell carcinoma, osteosarcoma, thymus cancer, skin cancer, melanoma, heart cancer, oral and larynx cancer, neuroblastoma, mesothelioma, and other solid tumors (thymic, bone, soft tissue, oral SCC, myelofibrosis, synovial sarcoma). In certain embodiments, the mutations can include any of substitutions, insertions, inversions, point mutations, deletions, mismatches and translocations. In some embodiments, the target sequences or amplified target sequences are directed to sequences having aberrant expression associated with one or more blood/hematologic cancers selected from the group consisting of multiple myeloma, diffuse large B cell lymphoma (DLBCL), lymphoma, Hodgkins lymphoma, non-Hodgkins lymphoma, follicular lymphoma, leukemia, acute myeloid leukemia (AML), chronic lymphocytic leukemia (CLL), myelodisplastic syndrome. In certain embodiments, aberrant expression associated with cancer involves in at least one of the genes provided in Table 1.

In some embodiments, one or more aberrant expression immune response sequences of the methods are at least one of the genes selected from CD63, CD69, CXCL1, KLRD1, HLA-DOB, CXCR5, IL12B, PTK7, CEACAM1, CXCL9, IL13, NT5E, VEGFA, ABCF1, CD38, JAML, S100A8, MYC, IRF1, CCL22, CXCR2, IFIT1, IFIT2, CD68, M6PR, SH2D1A, ISG20, GBP1, TBP, STATE, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R, TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMP3, TNFAIP8, FOXP3, IL12A, SAMHD1, SIT1, CD3E, ICOSLG, HGF, MELK, IGSF6, GNLY, TDO2, KRT7, HLA-E, HLA-DM, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBI3, EFNA4, PVR, BUB1, SKAP2, PRF1, CCL20, TNFRSF18, CTSS, NKG7, ISG15, PDCD1, SNAI1, CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DR, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, IL1A, FCGR3A, IFNA17, EGR2, TOP2A, C10orf54, FOXM1, AXL, MS4A1, IFI6, CD3D, GPR18, CD3G, ZAP70, HMBS, IL7, IFIT3, RB1, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MX1, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDO1, IL18, TNFRSF9, HIF1A, HLA-DPB1, FOXO1, CD33, S100A9, HLA-DMB, HLA-A, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAG3, TNFRSF4, CD2, CCL4, BAGE, LEXM, CCR6, CD70, CDK1, CTAG1B, CTAG2, CX3CR1, CX3CR1, CX3CR1, CX3CR1, GAGE1, GAGE12I, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CEACAM8, CXCR3, FCGR1A, FCGR3B, FYB, HLA-C, HLA-DQA2, IFNG, KIR2DL1, KRT5, LMNA, and PTPN11. In some embodiments the one or more aberrant expression sequences indicate cancer activity. In some embodiments the one or more aberrant expression sequences indicate a patient's likelihood to response to a therapeutic agent. In some embodiments, the one or more aberrant expression sequences indication a patient's likelihood to not be responsive to a therapeutic agent. In certain embodiments, relevant therapeutic agents can be immunotherapies including but not limited to checkpoint blockades, T cell therapies, and therapeutic vaccines. In some embodiments a therapeutic agent may modify an immune response gene selected from PD1 (e.g., nivolumab, pembrolizumab, AMP-244, MEDI0680, AMP-514, pidlizumab), CTLA4 (e.g., ipilimumab, tremelimumab), PD-L1 (e.g., atezolizumab, MDX1105-01, MEDI4736, avelumab), KIR (e.g., lirilumab, NCC0141-0000-0100), CD9/NKG2A (e.g., IPH2201), LAG3 (e.g., BMS986016), GITR (e.g., TRX518), OX40 (e.g., MEDI6383, MEDI6489, MOXR0916), IDO (e.g., indoximod (NLG8189), INCB024360, F001287, NLG919), TGFbeta (e.g., sotaracept, fresolumimab, trabedersen, lucanix), TGFbetaR (e.g., LY2157299, ACE536), CD137 (e.g., urelumab), CD137/41BB (e.g., pf05082566), CD289/TLR9 (e.g., MGN1703), MUC1/CD227 (e.g., OINT-10, ASN-004), CD27 (e.g., varlilumab), CD27L (e.g., AMG172), SLAMF7/CD1 (e.g., elotuzumab), CD20 (e.g., DI-Leu16-IL2), talimogene laherparepvec, CD70 (e.g., ARGX110), IL10 (e.g., AM0010), PSA (e.g., PROSTVAC), GP100 (e.g., MDX1379), STAT3 (e.g., AZD9150), CVAC, IL12 (e.g., veledimex, INXN2001, MSB0010360N, IMMUNOPULSE, GEN-1, INO-9012; IL2: MSB0010445, RG7813/RO6895882), IL33 (e.g., alarmin IL33), ICT140, CNDO-109, hTERT (e.g., INO-1400), dysplastic tissues (e.g., ADXS-HPV), SMAC-mimetic (e.g., birinapant), ImmTACs (e.g., IMCgp100), and CD40 (e.g., RO7009789). In certain embodiments, relevant therapeutic agent is an immunotherapy selected from checkpoint blockade, T cell therapy, and therapeutic vaccine. In some embodiments a therapeutic agent modifies an immune response gene selected from any of PD1 (e.g., nivolumab, pembrolizumab, AMP-244, MEDI0680, AMP-514, pidlizumab), CTLA4 (e.g., ipilimumab, tremelimumab), PD-L1 (e.g., atezolizumab, MDX1105-01, MEDI4736, avelumab), KIR (e.g., lirilumab, NCC0141-0000-0100), CD9/NKG2A (e.g., IPH2201), LAG3 (e.g., BMS986016), GITR (e.g., TRX518), OX40 (e.g., MEDI6383, MEDI6489, MOXR0916), IDO (e.g., indoximod (NLG8189), INCB024360, F001287, NLG919), TGFbeta (e.g., sotaracept, fresolumimab, trabedersen, lucanix), TGFbetaR (e.g., LY2157299, ACE536), CD137 (e.g., urelumab), CD137/41BB (e.g., pf05082566), CD289/TLR9 (e.g., MGN1703), MUC1/CD227 (e.g., OINT-10, ASN-004), CD27 (e.g., varlilumab), CD27L (e.g., AMG172), SLAMF7/CD1 (e.g., elotuzumab), CD20 (e.g., DI-Leu16-IL2), talimogene laherparepvec, CD70 (e.g., ARGX110), IL10 (e.g., AM0010), PSA (e.g., PROSTVAC), GP100 (e.g., MDX1379), STAT3 (e.g., AZD9150), CVAC, IL12 (e.g., veledimex, INXN2001, MSB0010360N, IMMUNOPULSE, GEN-1, INO-9012; IL2: MSB0010445, RG7813/RO6895882), IL33 (e.g., alarmin IL33), ICT140, CNDO-109, hTERT (e.g., INO-1400), dysplastic tissues (e.g., ADXS-HPV), SMAC-mimetic (e.g., birinapant), ImmTACs (e.g., IMCgp100), and CD40 (e.g., RO7009789).

In some embodiments, target sequences or amplified target sequences of the methods are directed to mutations associated with cancer. In some embodiments, the target sequences or amplified target sequences are directed to mutations associated with one or more solid tumor cancers selected from the group consisting of head and neck cancers (e.g., HNSCC, nasopharyngeal, salivary gland), brain cancer (e.g., glioblastoma, glioma, gliosarcoma, glioblastoma multiforme, neuroblastoma), breast cancer (e.g., TNBC, trastuzumab resistant HER2+ breast cancer, ER+/HER− breast cancer), gynecological (e.g., uterine, ovarian cancer, cervical cancer, endometrial cancer, fallopian cancer), colorectal cancer, gallbladder cancer, esophageal cancer, gastrointestinal cancer, gastric cancer, bladder cancer, prostate cancer, testicular cancer, urothelial cancer, liver cancer (e.g., hepatocellular, HCC), lung cancer (e.g., non-small cell lung, small cell lung), kidney (renal cell) cancer, pancreatic cancer (e.g., adenocarcinoma, ductal), thyroid cancer, bile duct cancer, pituitary tumor, wilms tumor, kaposi sarcoma, hairy cell carcinoma, osteosarcoma, thymus cancer, skin cancer, melanoma, heart cancer, oral and larynx cancer, neuroblastoma, mesothelioma, and other solid tumors (thymic, bone, soft tissue, oral SCC, myelofibrosis, synovial sarcoma). In one embodiment, the mutations can include substitutions, insertions, inversions, point mutations, deletions, mismatches and translocations. In one embodiment, the mutations can include variation in copy number. In one embodiment, mutations can include germline or somatic mutations. In some embodiments, the target sequences or amplified target sequences are directed to sequences having mutations associated with one or more blood/hematologic cancers selected from the group consisting of multiple myeloma, diffuse large B cell lymphoma (DLBCL), lymphoma, Hodgkins lymphoma, non-Hodgkins lymphoma, follicular lymphoma, leukemia, acute myeloid leukemia (AML), chronic lymphocytic leukemia (CLL), myelodisplastic syndrome. In one embodiment, mutations associated with cancer are located in at least one of the genes provided in Table 1.

In some embodiments, one or more mutations in immune response sequences associated with cancer are located in at least one of the genes selected from CD63, CD69, CXCL1, KLRD1, HLA-DOB, CXCR5, IL12B, PTK7, CEACAM1, CXCL9, IL13, NT5E, VEGFA, ABCF1, CD38, JAML, S100A8, MYC, IRF1, CCL22, CXCR2, IFIT1, IFIT2, CD68, M6PR, SH2D1A, ISG20, GBP1, TBP, STAT5, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R, TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMP3, TNFAIP8, FOXP3, IL12A, SAMHD1, SIT1, CD3E, ICOSLG, HGF, MELK, IGSF6, GNLY, TDO2, KRT7, HLA-E, HLA-DM, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBI3, EFNA4, PVR, BUB1, SKAP2, PRF1, CCL20, TNFRSF18, CTSS, NKG7, ISG15, PDCD1, SNAI1, CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DR, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, IL1A, FCGR3A, IFNA17, EGR2, TOP2A, C10orf54, FOXM1, AXL, MS4A1, IFI6, CD3D, GPR18, CD3G, ZAP70, HMBS, IL7, IFIT3, RB1, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MX1, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDO1, IL18, TNFRSF9, HIF1A, HLA-DPB1, FOXO1, CD33, S100A9, HLA-DMB, HLA-A, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAG3, TNFRSF4, CD2, CCL4, BAGE, LEXM, CCR6, CD70, CDK1, CTAG1B, CTAG2, CX3CR1, CX3CR1, CX3CR1, CX3CR1, GAGE1, GAGE12I, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CEACAM8, CXCR3, FCGR1A, FCGR3B, FYB, HLA-DQA2, IFNG, KIR2DL1, KRT5, LMNA, and PTPN11.

In one aspect, compositions and methods of the invention are used to identify biomarkers of response, sensitivity and/or non-response. In some embodiments, provided compositions and methods are used to compare absolute or relative gene expression changes between samples derived from a patients responding to treatment of immunotherapy and samples derived from non-responding patients. Any one or more gene(s) that demonstrate significantly different expression levels (e.g., high in responders group, low in non-responders group) is considered biomarker(s) predictive of drug response. In certain embodiments, such biomarkers of response are used for stratification of patients for immune response therapy. In some embodiments, provided compositions and methods are used to identify biomarkers of immune response monitoring after treatment. In certain embodiments, provided compositions and methods are used to compare absolute or relative gene expression changes correlating with immunohistochemistry readouts of an established clinical makers (e.g., PD-L1, NY-ESO-1, MAGE). In certain embodiments, provided compositions and methods are used to compare absolute or relative gene expression changes correlating with changes in any therapeutic target, pharmacodynamics markers, or immunogenic antigen. Any genes or combination of genes that show correlated up or down expression with these readouts could be considered as predictive markers of drug response. In some embodiments, provided compositions and methods are used to compare absolute or relative gene expression changes correlating with samples containing high level of tumor infiltrating lymphocytes (TIL) and samples containing low level of TIL, as reported by pathology review. Any genes or combination of genes significantly differ in expression between these two groups could be considered predictors of drug response. In some embodiments, provided compositions and methods are used to compare absolute or relative gene expression changes correlating with samples of different molecular subtypes (e.g., examples for colon-rectal cancer include but are not limited to microsatellite instability immune; hypermutated, microsatellite unstable and strong immune activation; epithelial and evident metabolic dysregulation; mesenchymal [www.nature.com/nm/journal/vaop/ncurrent/full/nm.3967]). Any genes or combination of genes significantly differ in expression between any of these groups could be considered predictors of drug response. In certain embodiments, provided compositions and methods are used to compare absolute or relative gene expression changes correlating with samples of different histopathology subtypes (e.g., examples for non-small cell lung include but are not limited to adenocarcinoma, squamous cell carcinoma, not-otherwise specified; examples for colon rectal). Any genes or combination of genes significantly differ in expression between these two groups could be considered predictors of drug response. In certain embodiments, provided compositions and methods are used to evaluate absolute or relative gene expression levels of different pathways and functions such as the T cell signaling pathway between samples derived from patients responding to treatment of immunotherapy and samples derived from non-responders. Any genes that show significantly different expression levels (high in one group, low in the other) could be considered potential biomarkers that are predictive of drug response.

In certain embodiments, provided compositions and methods are used to evaluate absolute or relative gene expression levels of different pathways and functions such as the T cell regulation pathway between samples derived from patients responding to treatment of immunotherapy and samples derived from non-responders. Any genes that show significantly different expression levels (high in one group, low in the other) could be considered potential biomarkers that are predictive of drug response. In certain embodiments, provided compositions and methods are used to evaluate absolute or relative gene expression levels of different pathways and functions such as antigen processing and/or antigen presentation between samples derived from patients responding to treatment of immunotherapy and samples derived from non-responders. Any genes that show significantly different expression levels (high in one group, low in the other) could be considered potential biomarkers that are predictive of drug response. In some embodiments, provided compositions and methods are used to evaluate absolute or relative gene expression levels of different pathways and functions such as the cytokine signaling pathway between samples derived from patients responding to treatment of immunotherapy and samples derived from non-responders. Any genes that show significantly different expression levels (high in one group, low in the other) could be considered potential biomarkers that are predictive of drug response. In some embodiments, provided compositions and methods are used to evaluate absolute or relative gene expression levels of different pathways and functions such as type I or type II interferon pathways between samples derived from patients responding to treatment of immunotherapy and samples derived from non-responders. Any genes that show significantly different expression levels (high in one group, low in the other) could be considered potential biomarkers that are predictive of drug response. In certain embodiments, provided compositions and methods are used to evaluate absolute or relative gene expression levels of different pathways and functions such as lymphocyte development and/or lymphocyte migration between samples derived from patients responding to treatment of immunotherapy and samples derived from non-responders. Any genes that show significantly different expression levels (high in one group, low in the other) could be considered potential biomarkers that are predictive of drug response. In certain embodiments, provided compositions and methods are used to evaluate absolute or relative gene expression levels of different pathways and functions such as the immune checkpoint pathway between samples derived from patients responding to treatment of immunotherapy and samples derived from non-responders. Any genes that show significantly different expression levels (high in one group, low in the other) could be considered potential biomarkers that are predictive of drug response. In certain embodiments, provided compositions and methods are used to evaluate the expression level of any genes contained on the panel or combination thereof (e.g., PD-1, PD-L1, CTLA4, etc.) between samples derived from patients responding to treatment of immunotherapy and samples derived from non-responders. Any genes that show significantly different expression levels (high in one group, low in the other) could be considered potential biomarkers of drug response. In certain embodiments, provided compositions and methods are used to evaluate the expression level of genes or isoforms of antigens (e.g., cancer testis antigens (GAGE), melanoma antigens (MAGE)) between samples derived from patients responding to treatment of immunotherapy and samples derived from non-responders. Any genes that show significantly different expression levels (high in one group, low in the other) could be considered potential biomarkers of drug response. In some embodiments, provided compositions and methods are used to evaluate different mathematical, quantitative or qualitative transformations of raw read count or normalized read count of any genes contained on the panel or combination thereof (for example, PD-1, PD-L1, CTLA4, etc.) between samples derived from patients responding to treatment of immunotherapy and samples derived from non-responders. Any genes that show significantly different expression levels (high in one group, low in the other) could be considered potential biomarkers of drug response. In certain embodiments, provided compositions and methods are used to profile the inflammatory level and abundance of different immune subsets (for example: cytotoxic T cells, helper T cells, macrophages, neutrophils, natural killer cells, myeloid derived suppressor cells) in the tumor micro-environment. Any differences in expression levels of these markers between samples derived responders and non-responders of treatment could be considered biomarkers predictive of response. In certain embodiments, provided compositions and methods are used to determine HLA type and its correlation with antigen presentation, T cell and B cell activation and drug response. In certain embodiments, provided compositions and methods are used to classify tumor samples as likely responder or non-responders to a therapeutic agent based on a classifier defined by another assay. In particular embodiments, provided compositions and methods are used to identify a subset of genes from which another panel can be derived to be used for purposes described herein. In a particular embodiment, additional primer sets could be added to the current panel to create an additional panel which can be used for purposes described herein.

In another aspect, provided compositions and methods are used to evaluate the expression levels of genes up or down regulated by immune checkpoint modulators. See, e.g., www.wikipedia.org/wiki/Immune_checkpoint. The identity of one or more gene(s) modulated by any specific therapeutic agent could be used to elucidate the mechanism of action of that agent. In some embodiments, provided compositions and methods are used to evaluate the expression levels of genes involved in the immune checkpoint pathway (including, e.g., PD-L1 signaling pathway). The identities of one or more genes modulated by any specific therapeutic agent could be used to elucidate the mechanism of action of that agent. In certain embodiments, provided compositions and methods are used to evaluate the expression levels of genes involved chemokine signaling, cytokine signaling, and/or interferon signaling. The identities of one or more genes modulated by any specific therapeutic agent can be used to elucidate the mechanism of action of that agent. In certain embodiments, provided compositions and methods are used to evaluate the expression levels of genes involved tumor cell adhesion, tumor cell migration, tumor cell proliferation or cancer sternness. The pattern of expression associating with each therapeutic agent could be used to infer the mechanism of action of that agent. In particular embodiments, provided compositions and methods are used to detect post-treatment changes in expression of any one or more genes in the panel. The high or low expression levels of such genes would be used to elucidate the mechanism of action of treated agent. In some embodiments, provided compositions and methods are used to detect post-treatment changes in expression of any intracellular or extracellular protein encoding genes contained on the panel. The high or low expression levels of such genes could be used to elucidate the mechanism of action of that agent. In some embodiments, provided compositions and methods are used to study the changed expression of intracellular protein-encoding genes in response to treatment of therapeutic agent or agents modulating extracellular proteins. High or low expression levels of such genes could be used to elucidate the mechanism of action of such agents. In still additional embodiments, provided compositions and methods are used to study the expression of any genes contained on the panel at different time points or treatment conditions. High or low expression levels of such genes could be used to elucidate the mechanism of action of that agent. In particular embodiments, provided compositions and methods are used to study the expression of any genes contained on the panel at different time points or treatment conditions with different therapeutic agents. The patterns of expression that are considered complementary could provide rationales to combine the corresponding agents for greater benefit. In particular embodiments, provided compositions and methods are used to study the expression of any genes contained on the panel at different time points or treatment conditions with different therapeutic agents. Patterns of expression that are considered complementary could provide rationales to combine the corresponding agents for reduced risk of adverse events. In certain embodiments, provided compositions and methods are used to study the expression of any genes modulated by any radiotherapy, chemotherapy, targeted therapy or immunotherapy. Complementary patterns of expression complementary could provide rationales to combine the corresponding agents for greater benefit or reduced risk of adverse events. In still other embodiments, provided compositions and methods are used to study expression of any genes modulated by a T cell therapy and immunosuppressive therapy. Complementary patterns of expression could provide rationales to combine the corresponding agents for greater benefit or reduced risk of adverse events.

In some embodiments, amplified target sequences of the methods are directed to any one of more of the genes provided in Table 1. In some embodiments, amplified target sequences of the methods comprise any one or more amplicon sequences provided in Table 1. In some embodiments, amplified target sequences of the methods consist of any one or more amplicon sequences provided in Table 1. In some embodiments, amplified target sequences of the methods include each amplicon sequence provided in Table 1.

In some embodiments, compositions used in provided methods comprise any one or more of the immune response target-specific primer pairs provided in Table 2. In some embodiments, compositions used in connection with provided methods comprise all of the immune response target-specific primer pairs provided in Table 2. In some embodiments, any one or more of the immune response target-specific primer pairs provided in Table 2 can be used to amplify a target sequence present in a sample as disclosed by the methods described herein.

In some embodiments, the methods utilize immune response target-specific primers from Table 2 and include 2, 3, 4, 5, 6, 7, 8, 9, 10, 20, 40, 60, 80, 100, 150, 200, 250, 300, 350, 398 or more, target-specific primer pairs. In some embodiments, methods include targeting amplified target sequences including one or more of the amplified target sequences generated in Table 1 (e.g., using amplicon target-specific primers provided in Table 2). In some embodiments, methods include use of at least one target-specific primer pair wherein each primer is at least 90% identical to at least one nucleic acid sequence selected from SEQ ID NOs: 399-1194. In some embodiments, methods include use of at least one of the target-specific primers associated with immune response is complementary across its entire length to at least one target sequence in a sample. In some embodiments, methods include use of at least one of the target-specific primers associated with immune response includes a non-cleavable nucleotide at the 3' end. In some embodiments, methods include use of target specific primers wherein non-cleavable nucleotide at the 3' end includes the terminal 3' nucleotide. In one embodiment, methods include use of amplified target sequences directed to one or more individual exons having aberrant expression associated with cancer. In one embodiment, methods include use of amplified target sequences directed to individual exons having a mutation associated with cancer. In some embodiments, provided methods comprise selective amplification of more than one target sequences in a sample and the detection and/or identification of mutations associated with cancer. In some embodiments, methods include use of amplified target sequences including two or more nucleotide sequences provided in Table 2. In some embodiments, methods include use of amplified target sequences including any one or more the amplified target sequences generated using the target-specific primers provided in Table 2. In one embodiment, methods include use of amplified target sequences including 10, 50, 100, 150, 200, 250, 300, 350 or more amplicons from Table 1. In some embodiments, methods comprise detection and optionally, the identification of clinically actionable marker(s). As defined herein, the term "clinically actionable marker" includes clinically actionable mutations and/or clinically actionable expression patterns that are known or can be associated by one of ordinary skill in the art with, but not limited to, prognosis for the treatment of cancer. In one embodiment, prognosis for the treatment of cancer includes the identification of mutations and/or expression patterns associated with responsiveness or non-responsiveness of a cancer to a drug, drug combination, or treatment regime. In one embodiment, methods comprise amplification of a plurality of target sequences from a population of nucleic acid molecules linked to, or correlated with, the onset, progression or remission of cancer.

In some embodiments, provided compositions and methods are used to compare absolute or relative gene expression changes between samples derived from patients with good prognosis (defined by durable response, overall survival or 5-year survival) and those with poor prognosis. For example, gene(s) that show significantly different expression levels (e.g., high in one group, low in the other) could be considered potential prognostic biomarkers. In some embodiments, provided compositions and methods are used to compare absolute or relative gene expression changes correlating with samples containing high level of tumor infiltrating lymphocytes (TIL) and samples containing low level of TIL, as reported by pathology review. For example, gene(s) or combination of genes significantly differ in expression between these two groups could be considered potential prognostic biomarkers. In some embodiments, provided compositions and methods are used to compare absolute or relative gene expression changes correlating with samples of different histopathology subtypes molecular subtypes (examples for breast cancer include luminal A, luminal B, basal-like, HER2 positive). For example, gene(s) or combination of genes that significantly differ in expression between any of these groups could be considered potential prognostic biomarkers. In some embodiments, provided compositions and methods are used to compare absolute or relative gene expression changes correlating with samples of different histopathology subtypes (e.g., for breast cancer include, for example, ER+, PR+, HER2+, triple negative). For example, gene(s) or combination of genes that significantly differ in expression between these two groups could be considered prognostic biomarkers. In some embodiments, provided compositions and methods are used to evaluate absolute or relative gene expression levels of different pathways and functions such as the T cell signaling pathway between samples derived from patients responding to treatment of immunotherapy and samples derived from non-responders. For example, gene(s) that show significantly different expression levels (e.g., high in one group, low in another) could be considered potential prognostic biomarkers. In some embodiments, provided compositions and methods are used to evaluate gene expression levels of different pathways and functions such as the T cell regulation pathway between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate gene expression levels of different pathways and functions such as the expression of genes in antigen processing and/or antigen presentation between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate absolute or relative gene expression levels of different pathways and functions such as the expression of genes in cytokine signaling pathway between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate absolute or relative gene expression levels of different pathways and functions such as type I or type II interferon pathways between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate absolute or relative gene expression levels of different pathways and functions such as lymphocyte development and migration between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate absolute or relative gene expression levels of different pathways and functions such as the immune checkpoint pathway between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate the expression level of any genes contained on the panel or combination thereof (e.g., for example, PD-1, PD-L1, CTLA4, etc.) between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to evaluate different mathematical, quantitative or qualitative transformations of raw read count or normalized read count of any genes contained on the panel or combination thereof (e.g., for example, PD-1, PD-L1, CTLA4, etc.) between samples derived from patients responding to treatment of immunotherapy and samples derived from non-responders. For example, gene(s) that show significantly different expression levels (high in one group, low in the other) could be considered potential prognostic biomarkers. In some embodiments, provided compositions and methods are used to profile the inflammatory level and presence of different immune subsets (for example: cytotoxic T cells, helper T cells, macrophages, neutrophils, natural killer cells, myeloid derived suppressor cells) in the tumor micro-environment. Any differences in expression levels of these markers between samples derived responder and non-responder of treatment could be considered potential prognostic biomarkers.

In some embodiments, housekeeping genes are utilized in conjunction with provided methods in the immune response assay. In certain embodiments, one or more housekeeping gene sequences are included in the assay methods. In particular method embodiments the one or more housekeeping genes are selected from ABCF1, G6PD, GUSB, HMBS, LMNA, LRP1, POLR2A, SDHA, TBP, TFRC, and TUBB.

In some embodiments, the disclosure provides for amplification of multiple target-specific sequences from a population of expressed nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the digesting includes partial digesting of one or more of the target-specific primers from the amplified target sequence. In some embodiments, the amplified target sequences can be ligated to one or more adapters. In some embodiments, adapters can include one or more DNA barcodes or tagging sequences. In some embodiments, amplified target sequences once ligated to an adapter can undergo a nick translation reaction and/or further amplification to generate a library of adapter-ligated amplified target sequences.

In some embodiments, provided methods comprise preparation and formation of multiple immune response target-specific amplicons. In some embodiments, the method comprises hybridizing one or more target-specific primer pairs to a nucleic acid molecule, extending a first primer of the primer, pair, denaturing the extended first primer from the nucleic acid molecule, hybridizing to the extended first primer product, a second primer of the primer pair and extending the second primer, digesting the target-specific primer pairs to generate a plurality of target-specific amplicons. In some embodiments, adapters can be ligated to the ends of the target-specific amplicons prior to performing a nick translation reaction to generate a plurality of target-specific amplicons suitable for nucleic acid sequencing. In some embodiments, the one or more target specific amplicons can be amplified using bridge amplification or emPCR to generate a plurality of clonal templates suitable for nucleic acid sequencing. In some embodiments, the disclosure provides methods for preparing a target-specific amplicon library, for use in a variety of downstream processes or assays such as nucleic acid sequencing or clonal amplification. In one embodiment, the disclosure provides a method of performing target-specific multiplex PCR on a nucleic acid sample having a plurality of expressed target sequences using primers having a cleavable group.

In certain embodiments, library and/or template preparation to be sequenced can be prepared automatically from a population of nucleic acid samples using the compositions provided herein using an automated systems, e.g., the Ion Chef™ system.

In one embodiment, nucleic acid templates to be sequenced using the Ion Torrent PGM 318™ or Ion Torrent S5 520™ or Ion Torrent S5 530™ system can be prepared from a population of nucleic acid molecules using the target-specific amplification techniques as outlined herein. Optionally, following target-specific amplification a secondary and/or tertiary amplification process including, but not limited to, a library amplification step and/or a clonal amplification step such as emPCR can be performed.

In some embodiments, provided are compositions comprising a plurality of target-specific primer pairs, each containing a forward primer and a reverse primer having at least one cleavable group located at either a) the 3' end or the 5' end, and/or b) at about the central nucleotide position of the target-specific primer, and wherein the target-specific primer pairs can be substantially non-complementary to other primer pairs in the composition. In some embodiments, the composition comprises at least 50, 100, 150, 200, 250, 300, 350, 398, or more target-specific primer pairs. In some embodiments, the target-specific primer pairs comprise about 15 nucleotides to about 40 nucleotides in length, wherein at least one nucleotide is replaced with a cleavable group. In some embodiments the cleavable group can be a uridine nucleotide. In some embodiments, the target-specific primer sets are designed to amplify an exon, gene, exome or region of the genome associated with a clinical or pathological condition, e.g., the amplification of one or more expressed sequences associated with cancer, wherein an increase and/or decrease in expression is associated with a change in immune response. In some embodiments, the target-specific primer sets are designed to amplify an exon, gene, exome or region of the genome associated with a change in immune response wherein an increase and/or decrease in expression is indicative of a cancer patient's likelihood to respond to one or more therapeutic agent(s). In some embodiments, the target-specific primer sets are designed to amplify an exon, gene, exome or region of the genome associated with a clinical or pathological condition, e.g., the amplification of one or more mutations associated with cancer. In some embodiments, the target-specific primer pairs when hybridized to a target sequence and amplified as outlined herein can generate a library of adapter-ligated amplified target sequences that are about 100 to about 500 base pairs in length. In some embodiments, no one adapter-ligated amplified target sequence is overexpressed in the library by more than 30% as compared to the remainder of the adapter-ligated amplified target sequences in the library. In some embodiments, the adapter-ligated amplified target sequence library is substantially homogenous with respect to GC content, amplified target sequence length or melting temperature (Tm).

In some embodiments, a kit is provided for performing multiplex PCR comprising a plurality of target-specific primers having a cleavable group, a DNA polymerase, an adapter, dATP, dCTP, dGTP and dTTP. In some embodiments, the cleavable group can be a uracil nucleotide. The kit can further include one or more antibodies, nucleic acid barcodes, purification solutions or columns.

In some embodiments, provided is a kit for generating a target-specific amplicon library comprising a plurality of target-specific primers having a cleavable group, a DNA polymerase, an adapter, dATP, dCTP, dGTP, dTTP, and a cleaving reagent. In some embodiments, the kit further comprises one or more antibodies, nucleic acid barcodes, purification solutions or columns.

In one embodiment, methods are provided for amplification of multiple target-specific sequences from a single nucleic acid source or sample. In another embodiment, methods are provided for target-specific amplification of two or more target sequences from two or more nucleic acid sources, samples or species. For example, it is envisioned by the disclosure that a single nucleic acid sample can include expressed RNA or fixed-formalin paraffin-embedded (FFPE) RNA. It is also envisioned that the sample can be from a single individual, a collection of nucleic acid samples from genetically related members, multiple nucleic acid samples from genetically unrelated members, multiple nucleic acid samples (matched) from a single individual such as a tumor sample and normal tissue sample, or genetic material from a single source that contains two distinct forms of genetic material such as maternal and fetal RNA obtained from a maternal subject, or the presence of contaminating bacteria RNA in a sample that contains plant or animal nucleic acid. In some embodiments, the source of nucleic acid material can include nucleic acids obtained from a newborn, for example as typically procured as a blood sample for newborn screening.

The nucleic acid sample can include high molecular weight material such as expressed RNA or cDNA. The sample can include low molecular weight material such as nucleic acid molecules obtained from FFPE or archived RNA samples. In another embodiment, low molecular weight material includes enzymatically or mechanically sheared nucleic acid sample. The sample can include cell-free circulating RNA such as material obtained from a maternal subject. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

In some embodiments, provided methods comprise selective amplification of at least one target sequence in a normal or diseased containing tissue, biopsy, core, tumor, fine needle aspirate, fine needle biopsy, tumor microenvironment, blood, serum, or other sample. In some embodiments, provided methods comprise selective amplification of at least one target sequence and the detection and/or identification of mutations in the diseased tissue, biopsy, core, tumor, fine needle aspirate, fine needle biopsy, tumor microenvironment, blood, serum, or other sample. In some embodiments, the diseased or normal sample can include whole transcriptomic RNA, formalin-fixed paraffin-embedded tissue (FFPE), sheared or enzymatically treated RNA. In some embodiments, the disclosure is directed to the selective amplification of at least one target sequence and detection and/or identification of clinically actionable mutations or expression patterns. In some embodiments, the disclosure is directed to the detection and/or identification of mutations or expression associated with drug resistance or drug susceptibility.

In some embodiments, provided methods comprise selective amplification of at least one target sequence in cell-free circulating RNA. In some embodiments, the selective amplification of at least one target sequence in a sample includes a mixture of different nucleic acid molecules. The selective amplification can optionally be accompanied by detection and/or identification of mutations observed in circulating RNA. In some embodiments, selective amplification can optionally be accompanied by detection and/or identification of mutations associated with cancer or an inherited disease such as metabolic, neuromuscular, developmental, cardiovascular, autoimmune or other inherited disorder.

In some embodiments, the target-specific primers and primer pairs are target-specific sequences that can amplify specific regions of a nucleic acid molecule. In some embodiments, the target-specific primers can amplify expressed RNA or cDNA. In some embodiments, the target-specific primers can amplify mammalian RNA, such as human RNA or cDNA prepared therefrom. In some embodiments, the amount of RNA required for selective amplification can be from about 1 ng to 1 microgram. In some embodiments, the amount of RNA required for selective amplification of one or more target sequences can be about 1 ng, about 5 ng or about 10 ng. In some embodiments, the amount of RNA required for selective amplification of target sequence is about 10 ng to about 200 ng.

In some embodiments, selective amplification of at least one target sequence further includes nucleic acid sequencing of the amplified target sequence. Optionally, the method further includes detecting and/or identifying mutations present in the sample identified through nucleic acid sequencing of the amplified target sequence.

In one embodiment, a sample containing one or more target sequences can be amplified using any one or more of the target-specific primers disclosed herein. In another embodiment, amplified target sequences obtained using the methods (and associated compositions, systems, apparatuses and kits) disclosed herein, can be coupled to a downstream process, such as but not limited to, nucleic acid sequencing. For example, once the nucleic acid sequence of an amplified target sequence is known, the nucleic acid sequence can be compared to one or more reference samples such as Hg19 genome. The Hg19 genome is commonly used in the genomics field as a reference genome sample for humans.

It is envisaged that one of ordinary skill in the art can readily prepare one or more target-specific primers using the primer criteria disclosed herein without undue experimentation. It is also envisaged that one of ordinary skill in the art can readily prepare one or more target-specific primers using the criteria disclosed herein, to identify at least one medically relevant polymorphism. In some instances, a medically relevant polymorphism can be used in forensic or human identification purposes. A medically relevant mutation includes a mutation that is associated with at least one disease state in multiple populations (e.g., a European Caucasian population). In some embodiments, a medically relevant polymorphism includes any one or more of the polymorphisms outlined below.

In some embodiments, provided are methods (and associated compositions, systems, apparatuses and kits) for reducing the formation of amplification artifacts in a multiplex PCR. In some embodiments, primer-dimers or non-specific amplification products are obtained in lower number or yield as compared to standard multiplex PCR of the prior art. In some embodiments, the reduction in amplification artifacts is in part, governed by the use of target-specific primer pairs in the multiplex PCR reaction. In one embodiment, the number of target-specific primer pairs in the multiplex PCR reaction can be greater than 50, 100, 150, 200, 250, 300 or more. In some embodiments, provided are methods (and associated compositions, systems, apparatuses and kits) for performing multiplex PCR using target-specific primers that contain a cleavable group. In one embodiment, target-specific primers containing a cleavable group can include one or more cleavable moieties per primer of each primer pair. In some embodiments, a target-specific primer containing a cleavable group includes a nucleotide neither normally present in a non-diseased sample nor native to the population of nucleic acids undergoing multiplex PCR. For example, a target-specific primer can include one or more non-native nucleic acid molecules such as, but not limited to thymine dimers, 8-oxo-2'-deoxyguanosine, inosine, deoxyuridine, bromodeoxyuridine, apurinic nucleotides, and the like.

In some embodiments, provided methods (and associated compositions, systems, etc.,) involve performing a primary amplification of target sequences from a population of nucleic acids, optionally using target-specific primers. In some embodiments, provided methods involve amplifying target sequences using target-specific forward and reverse primer pairs. The target-specific forward and reverse primer pairs can optionally include one or more intron-specific and/or exon specific forward and reverse primer pairs. In some embodiments, each primer pair is directed to a single or discrete exon. In some embodiments, provided methods involve amplifying target sequences using exon-specific forward and reverse primer pairs containing at least one cleavable group. In some embodiments, the target-specific forward and reverse primer pairs contain a uracil nucleotide as the one or more cleavable groups. In one embodiment, a target-specific primer pair can include a uracil nucleotide in each of the forward and reverse primers of each primer pair. In one embodiment, a target-specific forward or reverse primer contains one, two, three or more uracil nucleotides. In some embodiments, provided methods involve amplifying at least 10, 50, 100, 150, 200, 250, 300, 350, 398 or more, target sequences from a population of nucleic acids having a plurality of target sequences using target-specific forward and reverse primer pairs containing at least two uracil nucleotides.

In some embodiments, target-specific primers (including but not limited to intron-specific and exon-specific primers, which can be forward and/or reverse primers) can be designed de novo using algorithms that generate oligonucleotide sequences according to specified design criteria. For example, the primers may be selected according to any one or more of criteria specified herein. In some embodiments, one or more of the target-specific primers are selected or designed to satisfy any one or more of the following criteria: (1) inclusion of two or more modified nucleotides within the primer sequence, at least one of which is included near or at the termini of the primer and at least one of which is included at, or about the center nucleotide position of the primer sequence; (2) primer length of about 15 to about 40 bases in length; (3) $T_m$ of from about 60° C. to about 70° C.; (4) low cross-reactivity with non-target sequences present in the target genome or sample of interest; (5) for each primer in a given reaction, the sequence of at least the first four nucleotides (going from 3' to 5' direction) are not complementary to any sequence within any other primer present in the same reaction; and (6) no amplicon includes any consecutive stretch of at least 5 nucleotides that is complementary to any sequence within any other amplicon.

In some embodiments, the target-specific primers include one or more primer pairs designed to amplify target sequences from the sample that are about 100 base pairs to about 500 base pairs in length. In some embodiments, the target-specific primers include a plurality of primer pairs designed to amplify target sequences, where the amplified target sequences are predicted to vary in length from each other by no more than 50%, typically no more than 25%, even more typically by no more than 10%, or 5%. For example, if one target-specific primer pair is selected or predicted to amplify a product that is 100 nucleotides in length, then other primer pairs are selected or predicted to amplify products that are between 50-150 nucleotides in length, typically between 75-125 nucleotides in length, even more typically between 90-110 nucleotides, or 95-105 nucleotides, or 99-101 nucleotides in length.

In some embodiments, at least one primer pair in the amplification reaction is not designed de novo according to any predetermined selection criteria. For example, at least one primer pair can be an oligonucleotide sequence selected or generated at random, or previously selected or generated for other applications. In one exemplary embodiment, the amplification reaction can include at least one primer pair selected from the TaqMan® probe reagents (Roche Molecular Systems). The TaqMan® reagents include labeled probes and can be useful, inter alia, for measuring the amount of target sequence present in the sample, optionally in real time. Some examples of TaqMan technology are disclosed in U.S. Pat. Nos. 5,210,015, 5,487,972, 5,804,375, 6,214,979, 7,141,377 and 7,445,900, hereby incorporated by reference in their entireties.

In some embodiments, at least one primer within the amplification reaction can be labeled, for example with an optically detectable label, to facilitate a particular application of interest. For example, labeling may facilitate quantification of target template and/or amplification product, isolation of the target template and/or amplification, product, and the like.

In some embodiments, one or more of the primers within the amplification reaction can be useful in genotyping of a nucleic acid sample.

In some embodiments, the target-specific primers can be provided as a set of target-specific primer pairs in a single amplification vessel. In some embodiments, the target-specific primers can be provided in one or more aliquots of target-specific primer pairs that can be pooled prior to performing the multiplex PCR reaction in a single amplification vessel or reaction chamber. In one embodiment, the target-specific primers can be provided as a pool of target-specific forward primers and a separate pool of target-specific reverse primers. In another embodiment, target-specific primer pairs can be pooled into subsets such as non-overlapping target-specific primer pairs. In some embodiments, the pool of target-specific primer pairs can be provided in a single reaction chamber or microwell, for example on a PCR plate to perform multiplex PCR using a thermocycler. In some embodiments, the target-specific forward and reverse primer pairs can be substantially complementary to the target sequences.

In some embodiments, the method of performing multiplex PCR amplification includes contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules. In some embodiments, the steps of the amplification PCR method can be performed in any order. In some instances, the methods disclosed herein can be further optimized to remove one or more steps and still obtain sufficient amplified target sequences to be used in a variety of downstream processes. For example, the number of purification or clean-up steps can be modified to include more or less steps than disclose herein, providing the amplified target sequences are generated in sufficient yield.

In some embodiments, the target-specific primer pairs do not contain a common extension (tail) at the 3' or 5' end of the primer. In another embodiment, the target-specific primers do not contain a Tag or universal sequence. In some embodiments, the target-specific primer pairs are designed to eliminate or reduce interactions that promote the formation of non-specific amplification.

In one embodiment, the target-specific primer pairs comprise at least one cleavable group per forward and reverse target-specific primer. In one embodiment, the cleavable group can be a uracil nucleotide. In one embodiment, the target-specific primer pairs are partially or substantially removed after generation of the amplified target sequence. In one embodiment, the removal can include enzymatic, heat or alkali treatment of the target-specific primer pairs as part of the amplified target sequence. In some embodiments, the amplified target sequences are further treated to form blunt-ended amplification products, referred to herein as, blunt-ended amplified target sequences.

There is a need for new methods, computer readable media, and systems for identifying or designing products or kits that use PCR to enrich one or more genomic regions of interest (which may be, for example, cumulative regions of 1 kb to 1 Mb) for subsequent sequencing.

There is a need for new methods, computer readable media, and systems for identifying or designing products or kits including primers or assays that maximize coverage of one or more genomic regions or targets of interest while minimizing one or more of off-target hybridization, a number of primers, and a number of primer pools.

In accordance with the teachings and principles embodied in this application, new methods, computer readable media, and systems are provided that identify or design products or kits that use PCR to enrich one or more genomic regions or targets of interest for subsequent sequencing and/or that include primers or assays that maximize coverage of one or more genomic regions or targets of interest while minimizing one or more of off-target hybridization, a number of primers, and a number of primer pools.

According to an exemplary embodiment, there is provided a method comprising: (1) receiving or providing as inputs a genomic target region and a set of candidate amplicons for the genomic target region; (2) generating a graph comprising a source vertex, a set of amplicon vertices arranged in correspondence with the set of candidate amplicons, and a sink vertex; (3) determining a cost associated with one or more paths across the graph from the source vertex to the sink vertex via amplicon vertices; and (4) extracting the amplicon vertices from the one of the one or more paths across the graph having a least cost associated therewith.

In various embodiments, the one or more paths may comprise a sequence of amplicons wherein an ending portion of an insert of a first amplicon in the sequence of amplicons overlaps a beginning portion of an insert of a second amplicon in the sequence of amplicons. An ending portion of an insert of the second amplicon in the sequence of amplicons may overlap a beginning portion of an insert of a third amplicon in the sequence of amplicons. An ending portion of an insert of the third amplicon in the sequence of amplicons may overlap a beginning portion of an insert of a fourth amplicon in the sequence of amplicons.

In various embodiments, the one or more paths may comprise a sequence of N amplicons, N being a positive integer, wherein an ending portion of an insert of an amplicon amp in the sequence of amplicons overlaps a beginning portion of an insert of an amplicon amp+1 in the sequence of amplicons, wherein amp is an integer taking values 1, . . . , N−1. The one or more paths may comprise a sequence of L=N+M amplicons, N and M being positive integers, wherein an ending portion of an insert of an amplicon amp in the sequence of amplicons overlaps (which may include merely touching) a beginning portion of an insert of an amplicon amp+1 in the sequence of amplicons where amp is an integer taking values 1, . . . , N−1; wherein an ending portion of an insert of an amplicon amp in the sequence of amplicons overlaps (which may include merely touching) a beginning portion of an insert of an amplicon amp+1 in the sequence of amplicons where amp is an integer taking values N+1, . . . , N+M−1; and wherein there is a gap between an ending portion of an insert of amplicon amp=N and a beginning portion of an insert of amplicon amp=N+1.

In various embodiments, the cost associated with each of the one or more paths may be a sum of the cost of every edge of the path linking two amplicon vertices. The cost associated with every edge of the path linking two amplicon vertices may be a sum of a first term related to the cost of the edge's destination amplicon vertex and a second term related to the cost of an overlap between an insert of the edge's destination amplicon and an insert of the edge's origin amplicon. The first term and the second term may be weighed by a blending factor such that the first term is multiplied by the blending factor or a function thereof and the second term is multiplied by one minus the blending factor or a function thereof. The cost of an amplicon vertex may be a numerical value along a scale between a first value representing a lower level of one or more undesirable characteristics selected from a group comprising at least a level of off-target amplification and a level of primer-dimer propensity and a second value representing a higher level of the one or more undesirable characteristics. The cost of an overlap between an insert of the edge's destination amplicon and an insert of the edge's origin amplicon may be determined based on a redundancy introduced by overlapping inserts. The cost of an overlap between an insert of the edge's destination amplicon and an insert of the edge's origin amplicon may be a function of a quotient between a number of base pairs in an overlap between the insert of the edge's destination amplicon and the insert of the edge's origin amplicon and a number of base pairs in a union of the insert of the edge's destination amplicon and the insert of the edge's origin amplicon.

According to an exemplary embodiment, there is provided a non-transitory machine-readable storage medium comprising instructions which, when executed by a processor, cause the processor to perform a method comprising: (1) receiving or providing as inputs a genomic target region and a set of candidate amplicons for the genomic target region; (2) generating a graph comprising a source vertex, a set of amplicon vertices arranged in correspondence with the set of candidate amplicons, and a sink vertex; (3) determining a cost associated with one or more paths across the graph from the source vertex to the sink vertex via amplicon vertices; and (4) extracting the amplicon vertices from the one of the one or more paths across the graph having a least cost associated therewith. In some embodiments, such a method may be extended to a method for pooling amplicons across a plurality of pools by using as input the amplicons corresponding to the extracted vertices.

According to an exemplary embodiment, there is provided a system, comprising: (1) a machine-readable memory; and (2) a processor configured to execute machine-readable instructions, which, when executed by the processor, cause the system to perform steps including: (a) receiving or providing as inputs a genomic target region and a set of candidate amplicons for the genomic target region; (b) generating a graph comprising a source vertex, a set of amplicon vertices arranged in correspondence with the set of candidate amplicons, and a sink vertex; (c) determining a cost associated with one or more paths across the graph from the source vertex to the sink vertex via amplicon vertices; and (d) extracting the amplicon vertices from the one of the one or more paths across the graph having a least cost associated therewith. In some embodiments, such a system may be extended to a system for pooling amplicons across a plurality of pools by using as input the amplicons corresponding to the extracted vertices.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

In some embodiments, the amplified target sequences generated by the methods disclosed herein represent at least 60%, 70%, 80%, 90%, or more, of one or more exons amplified from the plurality of target sequences. In one embodiment, amplified target sequences of the present invention are about 90 to about 140 base pairs in length, about 100 to about 200 base pairs in length, about 100 to about 300 base pairs in length, or about 100 to about 400 base pairs in length. In one embodiment, the amplified target sequence includes the length of the forward primer and the length of the complementary reverse primer for each primer pair. In another embodiment, the amplified target sequence length includes the length of the reverse primer and the length of the complementary forward primer. In some embodiments, the length of the amplified target sequence minus the forward and reverse primer lengths is about 40 base pairs to about 350 base pairs. In some embodiments, the length of the amplified target sequences generated in the multiplex PCR reaction is substantially the same. As defined herein, "substantially the same" with respect to length of amplified target sequences generated via the methods disclosed herein refers to no more than 30% deviation in nucleotide length across the total number of amplified target sequences. In one embodiment, the percent GC content of an amplicon is less than 85%, less than 75%, less than 65%, less than 60%, or less than 50%. In one embodiment, substantially all amplified target sequences within a reaction contain between 30% and less than 85% GC content. In one embodiment, where the nucleic acid molecules are obtained from an archived or FFPE RNA sample, the length of the amplified target sequence is typically about 100 to about 200 base pairs in length. In one embodiment, if the nucleic acid sample is derived or obtained from expressed RNA or cDNA, the length of the amplified target sequence can be about 100 to about 500 base pairs in length.

In some embodiments, the amplified target sequences of provided methods can be used in various downstream analysis or assays with, or without, further purification or manipulation. For example, the amplified target sequences can be clonally amplified by techniques known in the art, such a bridge amplification or emPCR to generate a template library that can be used in next generation sequencing. In some embodiments, the amplified target sequences of provided methods or the resulting template libraries can be used for single nucleotide polymorphism (SNP) analysis, genotyping or epigenetic analysis, copy number variation analysis, gene expression analysis, analysis of gene mutations including but not limited to detection, prognosis and/or diagnosis, detection and analysis of rare or low frequency allele mutations, nucleic acid sequencing including but not limited to de novo sequencing, targeted resequencing and synthetic assembly analysis. In one embodiment, amplified target sequences can be used to detect mutations at less than 5% allele frequency. In some embodiments, the methods disclosed herein can be used to detect mutations in a population of nucleic acids at less than 4%, 3%, 2% or at about 1% allele frequency. In another embodiment, amplified target sequences prepared as described herein can be sequenced to detect and/or identify germline or somatic mutations from a population of nucleic acid molecules.

In some embodiments, the forward and/or reverse target-specific primers in the target-specific primer pairs can be "complementary" or "substantially complementary" to the population of nucleic acid molecules. As termed herein "substantially complementary to the population of nucleic acid molecules" refers to percentage complementarity between the primer and the nucleic acid molecule to which the primer will hybridize. The term "substantially complementary" as used herein refers to at least 70% complementarity. Therefore, substantially complementary refers to a range of complementarity of at least 70% but less than 100% complementarity between the primer and the nucleic acid molecule. A complementary primer is one that possesses 100% complementarity to the nucleic acid molecule. In one embodiment, each target-specific primer pair is designed to minimize cross-hybridization to another primer (or primer pair) in the same multiple PCR reaction (i.e., reduce the prevalence of primer-dimers). In another embodiment, each target-specific primer pair is designed to minimize cross-hybridization to non-specific nucleic acid sequences in the population of nucleic acid molecules (i.e., minimize off-target hybridization). In one embodiment, each target-specific primer is designed to minimize self-complementarity, formation of hairpin structures or other secondary structures.

In some embodiments, the amplified target sequences are formed via polymerase chain reaction. Extension of target-specific primers can be accomplished using one or more DNA polymerases. In one embodiment, the polymerase can be any Family A DNA polymerase (also known as pol I family) or any Family B DNA polymerase. In some embodiments, the DNA polymerase can be a recombinant form capable of extending target-specific primers with superior accuracy and yield as compared to a non-recombinant DNA polymerase. For example, the polymerase can include a high-fidelity polymerase or thermostable polymerase. In some embodiments, conditions for extension of target-specific primers can include 'Hot Start' conditions, for example Hot Start polymerases, such as Amplitaq Gold® DNA polymerase (Applied Biosciences), Platinum® Taq DNA Polymerase High Fidelity (Invitrogen) or KOD Hot Start DNA polymerase (EMD Biosciences). A 'Hot Start' polymerase includes a thermostable polymerase and one or more antibodies that inhibit DNA polymerase and 3'-5' exonuclease activities at ambient temperature. In some instances, 'Hot Start' conditions can include an aptamer.

In some embodiments, the polymerase can be an enzyme such as Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentaq™ (New England Biolabs), Platinum® Taq DNA Polymerase High Fidelity (Invitrogen), Platinum® Pfx (Invitrogen), Accuprime™ Pfx (Invitrogen), or Accuprime™ Taq DNA Polymerase High Fidelity (Invitrogen).

In some embodiments, the DNA polymerase can be a thermostable DNA polymerase. In some embodiments, the mixture of dNTPs can be applied concurrently, or sequentially, in a random or defined order. In some embodiments, the amount of DNA polymerase present in the multiplex reaction is significantly higher than the amount of DNA polymerase used in a corresponding single plex PCR reaction. As defined herein, the term "significantly higher" refers to an at least 3-fold greater concentration of DNA polymerase present in the multiplex PCR reaction as compared to a corresponding single plex PCR reaction.

In some embodiments, the amplification reaction does not include a circularization of amplification product, for example as disclosed by rolling circle amplification.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently. In one example, amplified target nucleic acid molecules prepared by provided methods can be ligated to Ion Torrent™ Sequencing Adapters (A and P1 adapters, sold as a component of the Ion Fragment Library Kit, Life Technologies, Part No. 4466464) or Ion Torrent™ DNA Barcodes (Life Technologies, Part No. 4468654).

The methods disclosed herein are directed to the amplification of multiple target sequences via polymerase chain reaction (PCR). In some embodiments the multiplex PCR comprises hybridizing one or more target-specific primer pairs to a nucleic acid molecule, extending the primers of the target-specific primer pairs via template dependent synthesis in the presence of a DNA polymerase and dNTPs; repeating the hybridization and extension steps for sufficient time and sufficient temperature there generating a plurality of amplified target sequences. In some embodiments, the steps of the multiplex amplification reaction method can be performed in any order.

The amount of nucleic acid material required for successful multiplex amplification can be about 1 ng. In some embodiments, the amount of nucleic acid material can be about 10 ng to about 50 ng, about 10 ng to about 100 ng, or about 1 ng to about 200 ng of nucleic acid material. Higher amounts of input material can be used, however one aspect of the disclosure is to selectively amplify a plurality of target sequence from a low (ng) about of starting material.

The multiplex PCR amplification reactions disclosed herein can include a plurality of "cycles" typically performed on a thermocycler. Each cycle includes at least one annealing step and at least one extension step. In one embodiment, a multiplex PCR amplification reaction is performed wherein target-specific primer pairs are hybridized to a target sequence; the hybridized primers are extended generating an extended primer product/nucleic acid duplex; the extended primer product/nucleic acid duplex is denatured allowing the complementary primer to hybridize to the extended primer product, wherein the complementary primer is extended to generate a plurality of amplified target sequences. In one embodiment, the methods disclosed herein have about 5 to about 18 cycles per pre-amplification reaction. The annealing temperature and/or annealing duration per cycle can be identical; can include incremental increases or decreases, or a combination of both. The extension temperature and/or extension duration per cycle can be identical; can include incremental increases or decreases, or a combination of both. For example, the annealing temperature or extension temperature can remain constant per cycle. In some embodiments, the annealing temperature can remain constant each cycle and the extension duration can incrementally increase per cycle. In some embodiments, increases or decreases in duration can occur in 15 second, 30 second, 1 minute, 2 minute or 4 minute increments. In some embodiments, increases or decrease in temperature can occur as 0.5, 1, 2, 3, or 4 Celsius deviations.

In some embodiments, the amplification reaction can be conducted using hot-start PCR techniques. These techniques include the use of a heating step (>60° C.) before polymerization begins to reduce the formation of undesired PCR products. Other techniques such as the reversible inactivation or physical separation of one or more critical reagents of the reaction, for example the magnesium or DNA polymerase can be sequestered in a wax bead, which melts as the reaction is heated during the denaturation step, releasing the reagent only at higher temperatures. The DNA polymerase can also be kept in an active state by binding to an aptamer or an antibody. This binding is disrupted at higher temperatures, releasing the functional DNA polymerase that can proceed with the PCR unhindered.

In some embodiments, the disclosed methods can optionally include destroying one or more primer-containing amplification artifacts, e.g., primer-dimers, dimer-dimers or superamplicons. In some embodiments, the destroying can optionally include treating the primer and/or amplification product so as to cleave specific cleavable groups present in the primer and/or amplification product. In some embodiments, the treating can include partial or complete digestion of one or more target-specific primers. In one embodiment, the treating can include removing at least 40% of the target specific primer from the amplification product. The cleavble treatment can include enzymatic, acid, alkali, thermal, photo or chemical activity. The cleavable treatment can result in the cleavage or other destruction of the linkages between one or more nucleotides of the primer, or between one or more nucleotides of the amplification product. The primer and/or the amplification product can optionally include one or more modified nucleotides or nucleobases. In some embodiments, the cleavage can selectively occur at these sites, or adjacent to the modified nucleotides or nucleobases. In some embodiments, the cleavage or treatment of the amplified target sequence can result in the formation of a phosphorylated amplified target sequence. In some embodiments, the amplified target sequence is phosphorylated at the 5' terminus.

In some embodiments, the template, primer and/or amplification product includes nucleotides or nucleobases that can be recognized by specific enzymes. In some embodiments, the nucleotides or nucleobases can be bound by specific enzymes. Optionally, the specific enzymes can also cleave the template, primer and/or amplification product at one or more sites. In some embodiments, such cleavage can occur at specific nucleotides within the template, primer and/or amplification product. For example, the template, primer and/or amplification product can include one or more nucleotides or nucleobases including uracil, which can be recognized and/or cleaved by enzymes such as uracil DNA glycosylase (UDG, also referred to as UNG) or formamidopyrimidine DNA glycosylase (Fpg). The template, primer and/or amplification product can include one or more nucleotides or nucleobases including RNA-specific bases, which can be recognized and/or cleaved by enzymes such as RNAseH. In some embodiments, the template, primer and/or amplification product can include one or more abasic sites, which can be recognized and/or cleaved using various proofreading polymerases or apyrase treatments. In some embodiments, the template, primer and/or amplification product can include 7,8-dihydro-8-oxoguanine (8-oxoG) nucleobases, which can be recognized or cleaved by enzymes such as Fpg. In some embodiments, one or more amplified target sequences can be partially digested by a FuPa reagent.

In some embodiments, the primer and/or amplification product includes one or more modified nucleotides including bases that bind, e.g., base pair, with other nucleotides, for example nucleotides in a complementary nucleic acid strand, via chemical linkages. In some embodiments, the chemical linkages are subject to specific chemical attack that selectively cleaves the modified nucleotides (or selectively cleaves one or more covalent linkages between the modified nucleotides and adjacent nucleotides within the primer and/or amplification product) but leaves the other nucleotides unaffected. For example, in some embodiments modified nucleotides can form disulfite linkages with other nucleotides in a complementary strand. Such disulfite linkages can be oxidized via suitable treatments. Similarly, certain modified nucleotides can base pair with other nucleotides in a complementary nucleic acid strand through linkages that can be selectively disrupted via alkali treatment. In some embodiments, the primer and/or amplification product includes one or more modified nucleotides that bind, e.g., base pair, with other nucleotides in a complementary nucleic acid strand through linkages exhibiting decreased thermal stability relative to typical base pairing linkages formed between natural bases. Such reduced-thermal stability linkages can be selectively disrupted through exposure of the primer and/or amplification product to elevated temperatures following amplification.

In an exemplary embodiment amplification primers are bisulfite in design, with either a 5' universal forward amplification sequence linked to a 3' target-specific forward primer, or a 5' universal reverse amplification sequence linked to a 3' target-specific reverse primer. Both primers contain modified nucleotides.

In some embodiments, primers are synthesized that are complementary to, and can hybridize with, discrete segments of a nucleic acid template strand, including: a primer that can hybridize to the 5' region of the template, which encompasses a sequence that is complementary to either the forward or reverse amplification primer. In some embodiments, the forward primers, reverse primers, or both, share no common nucleic acid sequence, such that they hybridize to distinct nucleic acid sequences. For example, target-specific forward and reverse primers can be prepared that do not compete with other primer pairs within the primer pool to amplify the same nucleic acid sequence. In this example, primer pairs that do not compete with other primer pairs in the primer pool assist in the reduction of non-specific or spurious amplification products. In some embodiments, the forward and reverse primers of each primer pair are unique, in that the nucleotide sequence for each primer is non-complementary and non-identical to the other primer in the primer pair. In some embodiments, the primer pair can differ by at least 10%, at least 20%, at least 30%, at least 40%, at least 50%, at least 60%, at least 70%, at least 75%, at least 80%, at least 85%, or at least 90% nucleotide identity. In some embodiments, the forward and reverse primers in each primer pair are non-complementary or non-identical to other primer pairs in the primer pool or multiplex reaction. For example, the primer pairs within a primer pool or multiplex reaction can differ by at least 5%, at least 10%, at least 20%, at least 30%, at least 40%, at least 50%, at least 60%, or at least 70% nucleotide identity to other primer pairs within the primer pool or multiplex reaction. Primers are designed to minimize the formation of primer-dimers, dimer-dimers or other non-specific amplification products. Typically, primers are optimized to reduce GC bias and low melting temperatures ($T_m$) during the amplification reaction. In some embodiments, the primers are designed to possess a $T_m$ of about 55° C. to about 72° C. In some embodiments, the primers of a primer pool can possess a $T_m$ of about 59° C. to about 70° C., 60° C. to about 68° C., or 60° C. to about 65° C. In some embodiments, the primer pool can possess a $T_m$ that does not deviate by more than 5° C.

In some embodiments, the target-specific primers do not contain a carbon-spacer or terminal linker. In some embodiments, the target-specific primers or amplified target sequences do not contain an enzymatic, magnetic, optical or fluorescent label.

The template can include a 3' region that contains the sequence for either the upstream or downstream regions surrounding a particular gene or region of interest, such that the region of interest is bracketed by a forward amplification/upstream gene-specific fusion, and a reverse amplification/downstream region of interest fusion primer. In some embodiments, an internal separator sequence can separate the template regions that can hybridize to the amplification and gene-specific primers, and this may act as a key or barcode for subsequent downstream applications such as sequencing, etc. In some embodiments, a barcode or key can be incorporated into each of the amplification products to assist with data analysis and for example, cataloging. In some embodiments, the barcodes can be Ion Torrent™ DNA barcodes (Life Technologies).

In some embodiments, the primer includes a sufficient number of modified nucleotides to allow functionally complete degradation of the primer by the cleavage treatment, but not so many as to interfere with the primer's specificity or functionality prior to such cleavage treatment, for example in the amplification reaction. In some embodiments, the primer includes at least one modified nucleotide, but no greater than 75% of nucleotides of the primer are modified.

In some embodiments, multiple different primers including at least one modified nucleotide can be used in a single amplification reaction. For example, multiplexed primers including modified nucleotides can be added to the amplification reaction mixture, where each primer (or set of primers) selectively hybridizes to, and promotes amplification of different target nucleic acid molecules within the nucleic acid population. In some embodiments, different primer combinations can be added to the amplification reaction at plexy of at least about 12-plex, 24-plex, 48-plex, 74-plex, 96-plex, 120-plex, 144-plex, 168-plex, 192-plex, 216-plex, 240-plex, 264-plex, 288-plex, 312-plex, 336-plex, 360-plex, 384-plex, or 398-plex. In some embodiments, the modified primers contain at least one modified nucleotide near or at the termini of the primer. In some embodiments, the modified primers contain two or more modified nucleotides within the primer sequence. In an exemplary embodiment, the primer sequence contains a uracil near, or at, the termini of the primer sequence. For the purposes of this disclosure "near" or "at the termini" of the primer sequences refers up to 10 nucleotides from the termini of the primer sequence. In some embodiments, the primer sequence contains a uracil located at, or about, the center nucleotide position of the primer sequence. For the purposes of this disclosure "at, or about the center nucleotide position of the primer sequence" refers to the incorporation of a uracil moiety at the center nucleotide of the primer sequence or within eight nucleotides, in either a 3' or 5' direction flanking the center nucleotide. In one embodiment, the target-specific primer sequence can contain a modified nucleobase at or about the center nucleotide position and contain a modified nucleobase at the 3' and/or 5' terminus. In some embodiments, the length of the forward or reverse primer sequence can be about 15 to about 40 bases in length. In some embodiments, the $T_m$ of the primer sequence used in the multiplex reaction can be about 55° C. to about 72° C. In some embodiments, the primer pairs are designed to amplify sequences from the target nucleic acid molecules or amplicons that are about 100 base pairs to about 500 base pairs in length.

In some embodiments, the amplification reactions are conducted in parallel within a single reaction phase (for example, within the same amplification reaction mixture within a single tube). In some instances, an amplification reaction can generate a mixture of products including both the intended amplicon product as well as unintended, unwanted, nonspecific amplification artifacts such as primer-dimers. Post amplification, the reactions are then treated with any suitable agent that will selectively cleave or otherwise selectively destroy the nucleotide linkages of the modified nucleotides within the excess unincorporated primers and the amplification artifacts without cleaving or destroying the specification amplification products. For example, the primers can include uracil-containing nucleobases that can be selectively cleaved using UNG/UDG (optionally with heat and/or alkali). In some embodiments, the primers can include uracil-containing nucleotides that can be selectively cleaved using UNG and Fpg. In some embodiments, the cleavage treatment includes exposure to oxidizing conditions for selective cleavage of dithiols, treatment with RNAseH for selective cleavage of modified nucleotides including RNA-specific moieties (e.g., ribose sugars, etc.), and the like. This cleavage treatment can effectively fragment the original amplification primers and non-specific amplification products into small nucleic acid fragments that include relatively few nucleotides each. Such fragments are typically incapable of promoting further amplification at elevated temperatures. Such fragments can also be removed relatively easily from the reaction pool through the various post-amplification cleanup procedures known in the art (e.g., spin columns, NaEtOH precipitation, etc).

In some embodiments, amplification products following cleavage or other selective destruction of the nucleotide linkages of the modified nucleotides are optionally treated to generate amplification products that possess a phosphorylation at the 5' termini. In some embodiments, the phosphorylation treatment includes enzymatic manipulation to produce 5' phosphorylated amplification products. In one embodiment, enzymes such as polymerases can be used to generate 5' phosphorylated amplification products. For example, T4 polymerase can be used to prepare 5' phosphorylated amplicon products. Klenow can be used in conjunction with one or more other enzymes to produce amplification products with a 5' phosphate. In some embodiments, other enzymes known in the art can be used to prepare amplification products with a 5' phosphate group. For example, incubation of uracil nucleotide containing amplification products with the enzyme UDG, Fpg and T4 polymerase can be used to generate amplification products with a phosphate at the 5' termini. It will be apparent to one of skill in the art that other techniques, other than those specifically described herein, can be applied to generate phosphorylated amplicons. It is understood that such variations and modifications that are applied to practice the methods, systems, kits, compositions and apparatuses disclosed herein, without resorting to undue experimentation are considered within the scope of the disclosure.

In some embodiments, primers that are incorporated in the intended (specific) amplification products, these primers are similarly cleaved or destroyed, resulting in the formation of "sticky ends" (e.g., 5' or 3' overhangs) within the specific amplification products. Such "sticky ends" can be addressed in several ways. For example, if the specific amplification products are to be cloned, the overhang regions can be designed to complement overhangs introduced into the cloning vector, thereby enabling sticky ended ligations that are more rapid and efficient than blunt ended ligations. Alternatively, the overhangs may need to be repaired (as with several next-generation sequencing methods). Such repair can be accomplished either through secondary amplification reactions using only forward and reverse amplification primers (e.g., correspond to A and P1 primers) comprised of only natural bases. In this manner, subsequent rounds of amplification rebuild the double-stranded templates, with nascent copies of the amplicon possessing the complete sequence of the original strands prior to primer destruction. Alternatively, the sticky ends can be removed using some forms of fill-in and ligation processing, wherein the forward and reverse primers are annealed to the templates. A polymerase can then be employed to extend the primers, and then a ligase, optionally a thermostable ligase, can be utilized to connect the resulting nucleic acid strands. This could obviously be also accomplished through various other reaction pathways, such as cyclical extend-ligation, etc. In some embodiments, the ligation step can be performed using one or more DNA ligases.

In some embodiments, provided are methods for single-tube multiplex PCR. In some embodiments, the method for single-tube multiplex PCR can include target-specific or exon-specific primers. In some embodiments, the exon-specific or target-specific primers can include at least one uracil nucleotide. In some embodiments, single-tube multiplex PCR can include selective amplification of at least 10, 50, 100, 150, 200, 250, 300, 350, 398 or more target nucleic acid molecules using target-specific or exon-specific uracil based primers.

In some embodiments, provided are methods for generating a target-specific or exon-specific amplicon library. In some embodiments, the amplicon library generated using target-specific or exon-specific primers can be associated with aberrant expression in human cancers. In some embodiments, the amplicon library generated using target-specific or exon-specific primers can be associated with mutations of human cancers. In some embodiments, the amplicon library can be generated from expressed RNA or cDNA or formalin-fixed, paraffin-embedded (FFPE) tissue. In some embodiments, the amplicons of the amplicon library prepared using the methods disclosed herein can be about 100 to about 300 base pairs in length, about 100 to about 250 base pairs in length, about 120 to about 220 base pairs in length or about 135 to about 205 base pairs in length. In some embodiments, the amplicon library can be prepared using primer pairs that are targeted to cancer specific mutations. In some embodiments, the primer pairs can be used to generate amplicons that once sequenced by any sequencing platform, including semi-conductor sequencing technology can be used to detect genetic mutations such as inversion, deletions, point mutations and variations in copy number.

In some embodiments, the primer pairs used to produce an amplicon library can result in the amplification of target-specific nucleic acid molecules possessing one or more of the following metrics: greater than 97% target coverage at 20× if normalized to 100× average coverage depth; greater than 97% of bases with greater than 0.2× mean; greater than 90% base without strand bias; greater than 95% of all reads on target; greater than 99% of bases with greater than 0.01× mean; and greater than 99.5% per base accuracy.

In some embodiments, the amplicon library can be used to detect and/or identify known mutations or de novo mutations in a sample.

In some embodiments, the amplicon library prepared using target-specific primer pairs can be used in downstream enrichment applications such as emulsion PCR or bridge PCR. In some embodiments, the amplicon library can be used in an enrichment application and a sequencing application. For example, an amplicon library can be sequenced using any suitable DNA sequencing platform. In some embodiments, an amplicon library can be sequenced using an Ion Torrent PGM Sequencer (Life Technologies). In some embodiments, a PGM sequencer can be coupled to server that applies parameters or software to determine the sequence of the amplified target nucleic acid molecules. In some embodiments, the amplicon library can be prepared, enriched and sequenced in less than 24 hours. In some embodiments, the amplicon library can be prepared, enriched and sequenced in approximately 9 hours. In some embodiments, an amplicon library can be a paired library, that is, a library that contains amplicons from a tumor sample and amplicons from a non-diseased sample. Each pair can be aligned, to detect and/or identify mutations present in the target nucleic acid molecules.

In some embodiments, methods for generating an amplicon library can include: amplifying RNA expression or cDNA targets using exon-specific or target-specific primers to generate amplicons; purifying the amplicons from the input RNA or cDNA and primers; phosphorylating the amplicons; ligating adapters to the phosphorylated amplicons; purifying the ligated amplicons; nick-translating the amplified amplicons; and purifying the nick-translated amplicons to generate the amplicon library. In some embodiments, additional amplicon library manipulations can be conducted following the step of amplification of RNA expression targets to generate the amplicons. In some embodiments, any combination of additional reactions can be conducted in any order, and can include: purifying; phosphorylating; ligating adapters; nick-translating; amplification and/or sequencing. In some embodiments, any of these reactions can be omitted or can be repeated. It will be readily apparent to one of skill in the art that the method can repeat or omit any one or more of the above steps. It will also be apparent to one of skill in the art that the order and combination of steps may be modified to generate the required amplicon library, and is not therefore limited to the exemplary methods provided.

A phosphorylated amplicon can be joined to an adapter to conduct a nick translation reaction, subsequent downstream amplification (e.g., template preparation), or for attachment to particles (e.g., beads), or both. For example, an adapter that is joined to a phosphorylated amplicon can anneal to an oligonucleotide capture primer which is attached to a particle, and a primer extension reaction can be conducted to generate a complementary copy of the amplicon attached to the particle or surface, thereby attaching an amplicon to a surface or particle. Adapters can have one or more amplification primer hybridization sites, sequencing primer hybridization sites, barcode sequences, and combinations thereof. In some embodiments, amplicons prepared by the methods disclosed herein can be joined to one or more Ion Torrent™ compatible adapters to construct an amplicon library. Amplicons generated by such methods can be joined to one or more adapters for library construction to be compatible with a next generation sequencing platform. For example, the amplicons produced by the teachings of the present disclosure can be attached to adapters provided in the Ion Fragment Library Kit (Life Technologies, Catalog No. 4466464).

In some embodiments, amplification of expressed RNA targets or FFPE samples can be conducted using a 2× AmpliSeq Hi Fi Master Mix. In some embodiments, the AmpliSeq Hi Fi Master Mix can include glycerol, dNTPs, and a DNA polymerase, such as Platinum® Taq DNA polymerase High Fidelity. In some embodiments, the 2× AmpliSeq Hi Fi Master Mix can further include at least one of the following: a preservative, magnesium sulfate, tris-sulfate and/or ammonium sulfate.

In some embodiments, amplification of expressed RNA targets or FFPE samples can be conducted using a 5× Ion AmpliSeq Hi Fi Master Mix. In some embodiments, the 5× Ion AmpliSeq Hi Fi Master Mix can include glycerol, dNTPs, and a DNA polymerase such as Platinum® Taq DNA polymerase High Fidelity. In some embodiments, the 5× Ion AmpliSeq Hi Fi Master Mix can further include at least one of the following: a preservative, magnesium chloride, magnesium sulfate, tris-sulfate and/or ammonium sulfate.

In some embodiments, phosphorylation of the amplicons can be conducted using a FuPa reagent. In some embodiments, the FuPa reagent can include a DNA polymerase, a DNA ligase, at least one uracil cleaving or modifying enzyme, and/or a storage buffer. In some embodiments, the FuP reagent can further include at least one of the following: a preservative and/or a detergent.

In some embodiments, phosphorylation of the amplicons can be conducted using a FuPa reagent. In some embodiments, the FuPa reagent can include a DNA polymerase, at least one uracil cleaving or modifying enzyme, an antibody and/or a storage buffer. In some embodiments, the FuPa reagent can further include at least one of the following: a preservative and/or a detergent. In some embodiments, the antibody is provided to inhibit the DNA polymerase and 3'-5' exonuclease activities at ambient temperature.

In some embodiments, the amplicon library produced by the teachings of the present disclosure are sufficient in yield to be used in a variety of downstream applications including the Ion Xpress™ Template Kit using an Ion Torrent™ PGM system (e.g., PCR-mediated addition of the nucleic acid fragment library onto Ion Sphere™ Particles)(Life Technologies, Part No. 4467389). For example, instructions to prepare a template library from the amplicon library can be found in the Ion Xpress Template Kit User Guide (Thermo Fisher Scientific). Instructions for loading the subsequent template library onto the Ion Torrent™ Chip for nucleic acid sequencing are described in the Ion Sequencing User Guide (Thermo Fisher Scientific). In some embodiments, the amplicon library produced by the teachings of the present disclosure can be used in paired end sequencing (e.g., paired-end sequencing on the Ion Torrent™ PGM system (Thermo Fisher Scientific).

It will be apparent to one of ordinary skill in the art that numerous other techniques, platforms or methods for clonal amplification such as wildfire PCR and bridge amplification can be used in conjunction with the amplified target sequences of the present disclosure. It is also envisaged that one of ordinary skill in art upon further refinement or optimization of the conditions provided herein can proceed directly to nucleic acid sequencing (for example using the Ion Torrent PGM™ or Proton™ sequencers, Life Technologies) without performing a clonal amplification step.

In some embodiments, at least one of the amplified targets sequences to be clonally amplified can be attached to a support or particle. The support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety.

In some embodiments, nucleic acid sequencing of the amplified target sequences produced by the teachings of this disclosure include de novo sequencing or targeted resequencing. In some embodiments, nucleic acid sequencing further includes comparing the nucleic acid sequencing results of the amplified target sequences against a reference nucleic acid sample. In some embodiments, the reference sample can be normal tissue or well documented tumor sample. In some embodiments, nucleic acid sequencing of the amplified target sequences further includes determining the presence or absence of a mutation within the nucleic acid sequence. In some embodiments, the method further includes correlating the presence of a mutation with drug susceptibly, prognosis of treatment and/or organ rejection. In some embodiments, nucleic acid sequencing includes the identification of genetic markers associated with cancer. In some embodiments, nucleic acid sequencing includes the identification of copy number variation in a sample under investigation.

In some embodiments, a kit is provided for amplifying multiple immune response target expression sequences from a population of nucleic acid molecules in a single reaction. In some embodiments, the kit includes a plurality of target-specific primer pairs containing one or more cleavable groups, one or more DNA polymerases, a mixture of dNTPs and at least one cleaving reagent. In one embodiment, the cleavable group can be 8-oxo-deoxyguanosine, deoxyuridine or bromodeoxyuridine. In some embodiments, the at least one cleaving reagent includes RNaseH, uracil DNA glycosylase, Fpg or alkali. In one embodiment, the cleaving reagent can be uracil DNA glycosylase. In some embodiments, the kit is provided to perform multiplex PCR in a single reaction chamber or vessel. In some embodiments, the kit includes at least one DNA polymerase, which can be a thermostable DNA polymerase. In some embodiments, the concentration of the one or more DNA polymerases is present in a 3-fold excess as compared to a single PCR reaction. In some embodiments, the final concentration of each target-specific primer pair is present at about 25 nM to about 50 nM. In one embodiment, the final concentration of each target-specific primer pair can be present at a concentration that is 50% lower than conventional single-plex PCR reactions. In some embodiments, the kit provides amplification of at least 100, 150, 200, 250, 300, 350, 398, or more, target immune response expression sequences from a population of nucleic acid molecules in a single reaction chamber. In particular embodiments, a provided kit of the invention is a test kit.

In some embodiments, the kit further comprises one or more adapters, barcodes, and/or antibodies.

A common concern in study of RNA expression analyses is determination of how gene expression changes between different samples. Current methodology for RNA sequencing typically requires an amplification step followed by sequence analysis of select amplified products (e.g., transcripts) to a fixed number of reads. In particular, with the provided methods of the invention, expression of each gene can be inferred by amplifying an amplicon that represents a transcript (e.g., an amplicon crosses a selected exon/exon junction). Due to the selected amplification, there is a dependency between the number of reads associated with a particular gene transcript and the number of reads produced by all other genes. Such interdependency means an apparent identical fold-change can be induced by two distinct biological processes: an increase in the ration of expression of a particular gene, or a decrease in the expression ration of all other genes measured. To accurately measure which of the two scenarios takes place, number of reads should be correctly normalized within each sample before cross comparison of samples takes place. Normalization has been studies for full transcriptome RNA sequencing analyses. Among such studies, log RPM (read counts per million) has been widely accepted to provide an interpretable measure of gene expression that robustly reflects the difference in expression between samples. The accuracy of this measure, however, depends on the underlying assumption that the majority of the genes measured are not differentially expressed. This assumption tends to hold true for transcriptomic studies, where more than 20,000 genes of the same tissues are typically profiled. However, such an assumption is unlikely to always hold for smaller gene panels, for panels comprising very low expression genes, or for panels that focus on similar biological processes, such as, for example, the methods and compositions provided herein. As a simple illustration, consider a targeted panel of 20 genes made up of 2 functional categories, one with 16 and the other with 4 genes, where each gene of a function is perfectly correlated to the others. In this example, the actual number of RNA molecules in sample 1 and sample 2 is known, and can sequence an exact of proportion of reads. When a standard RPM computation is applied to measure the expression of each gene and calculate the fold change using our estimated expression, there is 2-fold increase in the smaller category, the fold change estimate maintains a fairly accurate estimate of true fold change (FIG. 8, left panel). However, if the number of molecules in the larger category of 16 genes increases 2-fold, the estimated fold change based on RPM, suggests that instead of an increase of 16 genes, we have decrease in 4 genes (FIG. 8, middle panel). Thus, on a targeted panel with a small number of total genes and strong correlation structure of most genes, standard RPM normalization provides inaccurate fold change estimation. However, if we assume that a smaller category is a set of standard endogenous controls, e.g., housekeeping (HK) genes, and are comparable across samples, this set of genes as a reference point to accurately measure the expression the target functional set of 16 genes. Using the latter strategy provides an accurate fold change result (FIG. 8, right panel). Knowing how correlated the genes are to each other provides some guidelines for whether or not standard expression measurements will be biased on small, targeted RNA-seq panels.

Thus, in conjunction with the compositions and methods of the invention, provided compositions include primer pairs and methods for determination of expression of a set of housekeeping genes for use of one or more as endogenous controls and an effective means for normalization of expression levels and determination of expression changes across samples.

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

Exemplification

Materials and Methods

Provided immune response assay compositions include reagents directed to 395 immune response markers designed for library preparation technology of expressed target sequences. Generally, RNAs extracted from samples (e.g., tumor samples, e.g., fresh, frozen, FFPE, of various types, e.g., lung tumor, NSCLC) were reverse transcribed; libraries were generated, template prepared, e.g., using Ion Chef™ or Ion OneTouch™ 2 System, then prepared samples were sequenced using next generation sequencing technology, e.g., an Ion S5™, an Ion PGM™ System.

Total RNA was extracted from samples, 10 ng of total RNA was first reverse transcribed to and used as template to amplify targets (e.g., target expression sequences in Table 1) with the immune response assay comprising primer pairs in Table 2. Manual library prep was performed with the Ion AmpliSeq™ Library Kit 2.0 which was then templated with either the Ion OneTouch™ 2 System or Ion Chef™ instrument. Automated library prep and templating was performed with the Ion AmpliSeq™ Kit for Chef DL8 and Ion Chef™ Instrument. Sequencing was performed on either the Ion S5™ System or the Ion PGM™ System. Gene expression was quantified with the Ion Torrent Suite™ software.

HL-60 and human normal lung (AM7968) were purchased from ATCC and Ambion, respectively. De-identified melanoma and NSCLC FFPE samples were procured from Asterand and Research Dx respectively.

TABLE 1 genes and amplicon insert sequences of the immune response assay

| Gene/Accession | Amplicon Sequence | SEQ ID NO: |
| --- | --- | --- |
| CD63/NM_001780 | CCCGACTCCTGCTGCATTAATGTTACTGTGGGCTGTGGGATTAATTTCAACGA GAAGGCGATCCATAAGGAGGGCTGTGTGGAGAAGATTGGGGGCTGGCTGAGGA AA | 1 |
| CD69/NM_001781 | GTTCCTGTCCTGTGTGCTGTAATGAATGTGGTCTTCATCACCATTTTAATCAT AGCTCTCATTGCCTTATCAGTGGGCCAATACAATTGTCCAGGCCAATACACAT TC | 2 |
| CXCL1/NM_001511 | TAAGAAAATCATCGAAAAGATGCTGAACAGTGACAAATCCAACTGACCAGAAG GGAGGAGGAAGCTCACTGGTGGCTGTTCCTGAAGGAGGCCCTGCCCTTA | 3 |
| KLRD1/NM_002262 | CGGCATCTCTGTGCTTCTCAGAAATCCAGCCTGCTTCAGCTTCAAAACACAGA TGAACTGGATTTTATGAGCTCCAGTCAACAATTTTACTGGATTGGACTCTC | 4 |
| HLA-DOB/NM_002120 | CTCCAGAAGATTTTGTGATTCAGGCAAAGGCTGACTGTTACTTCACCAACGGG ACAGAAAAGGTGCAGTTTGTGGTCAGATTCATCTTTAACTTGGAGGAGTATGT AC | 5 |
| CXCR5/NM_001716 | GGTGACTCACAGCCGGCACAGCCATGAACTACCCGCTAACGCTGGAAATGGAC CTCGAGAACCTGGAGGACCTGTTCTGGGAACTGGACAGATTGGACA | 6 |
| IL12B/NM_002187 | CAAAGGAGGCGAGGTTCTAAGCCATTCGCTCCTGCTGCTTCACAAAAAGGAAG ATGGAATTTGGTCCACTGATATTTTAAAGGACCAGAAAGAACCCAAAAATAAG AC | 7 |
| PTK7/NM_002821 | TTGCCTGACCCAGGCCACACCAAAACCTACAGTTGTCTGGTACAGAAACCAGA TGCTCATCTCAGAGGACTCACGGTTCGAGGTCTTCAAGAATGGGACCTTGCGC ATC | 8 |
| CEACAM1/NM_001712 | GTCACTGGCTGCAACAGGACCACAGTCAAGACGATCATAGTCACTGAGCTAAG TCCAGTAGTAGCAAAGCCCCAAATCAAAGCCAGCAAGACCACAGTCACAGGAG AT | 9 |
| CXCL9/NM_002416 | CCAAGGGACTATCCACCTACAATCCTTGAAAGACCTTAAACAATTTGCCCCAA GCCCTTCCTGCGAGAAAATTGAAATCATTGCTACACTGAAGAATGGAG | 10 |
| IL13/NM_002188 | CAACGTGTCAGGCTGCAGTGCCATCGAGAAGACCCAGAGGATGCTGAGCGGAT TCTGCCCGCACAAGGTCTCAGCTGGGCAGTTTTCCAGCTTGCATGTCCGAGAC ACCA | 11 |
| NT5E/NM_002526 | TGAGGGGTGTGGACGTCGTGGTGGGAGGACACTCCAACACATTTCTTTACACA GGCAATCCACCTTCCAAAGAGGTGCCTGCTGGGAAGTACCCATTCATAG | 12 |
| VEGFA/NM_001171623 | CAGATGTGACAAGCCGAGGCGGTGAGCCGGGCAGGAGGAAGGAGCCTCCCTCA GGGTTTCGGGAACCAGATCTCTCACCAGGAAAGACTGATACAGAACGATCGA | 13 |
| ABCF1/NM_001025091 | TGATGTGTTGCTGTGTGAGCAGGAGGTGGTAGCAGATGAGACACCAGCAGTCC AGGCTGTTCTTCGAGCTGACACCAAGCGATTGAAGCTGCTGGAAGAGGAGCGG CGG | 14 |

TABLE 1-continued genes and amplicon insert sequences of the immune response assay

| Gene/Accession | Amplicon Sequence | SEQ ID NO: |
|---|---|---|
| CD38/NM_001775 | TCCAGCGGGACATGTTCACCCTGGAGGACACGCTGCTAGGCTACCTTGCTGAT GACCTCACATGGTGTGGTGAATTCAACACTTCCAAAATAAACTATCAATCTTG CCC | 15 |
| JAML/NM_001098526 | CTTTCAGTTGAGCTTGGGGACTGCAGCTGTGGGGAGATTTCAGTGCATTGCCT CCCCTGGGTGCTCTTCATCTTGGATTTGAAAGTTGAGAGCAGCATGTTTTGCC CACT | 16 |
| S100A8/NM_002964 | GGGAATTTCCATGCCGTCTACAGGGATGACCTGAAGAAATTGCTAGAGACCGA GTGTCCTCAGTATATCAGGAAAAAGGGTGCAGACGTCTGGTT | 17 |
| MYC/NM_002467 | GCAGCTGCTTAGACGCTGGATTTTTTTCGGGTAGTGGAAAACCAGCAGCCTCC CGCGACGATGCCCCTCAACGTTAGCTTCACCAACAGGAACTATGACCTCGACT ACG | 18 |
| IRF1/NM_002198 | GGAGGTGGAGCAGGCCCTGACTCCAGCACTGTCGCCATGTGCTGTCAGCAGCA CTCTCCCCGACTGGCACATCCCAGTGGAAGTTGTGCCGGACAGCACCAGTGAT CTG | 19 |
| CCL22/NM_002990 | GCTGTGGCGCTTCAAGCAACTGAGGCAGGCCCCTACGGCGCCAACATGGAAGA CAGCGTCTGCTGCCGTGATTACGTCCGTTACCGTCTGCCCCTGCGCGTGGTGA | 20 |
| CXCR2/NM_001557 | AGCCCAGCGACCCAGTCAGGATTTAAGTTTACCTCAAAAATGGAAGATTTTAA CATGGAGAGTGACAGCTTTGAAGATTTCTGGAAAGGTGAAGATCTTAGTAATT A | 21 |
| IFIT1/NM_001548 | ACAGCAACCATGAGTACAAATGGTGATGATCATCAGGTCAAGGATAGTCTGGA GCAATTGAGATGTCACTTTACATGGGAGTTATCCATTGATGACGATGA | 22 |
| IFIT2/NM_001547 | GCAGCTGCCTGAACCGAGCCCTGCCGAACAGCTGAGAATTGCACTGCAACCAT GAGTGAGAACAATAAGAATTCCTTGGAGAGCAGCCTACGGCAACTAA | 23 |
| CD68/NM_001251 | TGGGTGAGGCGGTTCAGCCATGAGGCTGGCTGTGCTTTTCTCGGGGGCCCTGC TGGGGCTACTGGCAGCCCAGGGGACAGGGAATGACTGTCCTCACAAAAAATCA GC | 24 |
| M6PR/NM_002355 | TCACTGGGGATTCTGAGCTTTGGCTACTCCAGTTTCCCACGACACGATGTTCC CTTTCTACAGCTGCTGGAGGACTGGACTGCTACTACTACTCCTGGCTGTGGCA G | 25 |
| SH2D1A/NM_002351 | AACAGGTTCTTGGAGTGCTGAGACAGCACCTGGGGTACATAAAAGATATTTCC GGAAAATAAAAAATCTCATTTCAGCATTTCAGAAGCCAGATCAAGGCAT | 26 |
| ISG20/NM_002201 | GGCGTGAGGCCAAGCTGGACCACTGCAGGCGTGTCTCCCTGCGGGTGCTGAGT GAGCGCCTCCTGCACAAGAGCATCCAGAACAGCCTGCTTGGACACAGCTCGGT GG | 27 |
| GBP1/NM_002053 | TTTCTCCCTGGACTTGGAAGCAGATGGACAACCCCTCACACCAGATGAGTACC TGACATACTCCCTGAAGCTGAAGAAAGGTACCAGTCAAAAAGATGAAA | 28 |
| TBP/NM_003194 | CCAAGAAGAAAGTGAACATCATGGATCAGAACAACAGCCTGCCACCTTACGCT CAGGGCTTGGCCTCCCCTCAGGGTGCCATGACTCCCGGAATCCCTATCTTTAG TC | 29 |
| STAT6/NM_003153 | GGGGCCTGGAAGTGCCCGCTGAGAAAGGGAGAAGACAGCAGAGGGGTTGCCGA GGCAACCTCCAAGTCCCAGATCATGTCTCTGTGGGTCTGGTCTCCAAGATGC CC | 30 |
| ID3/NM_002167 | ATCCTACAGCGCGTCATCGACTACATTCTCGACCTGCAGGTAGTCCTGGCCGA GCCAGCCCCTGGACCCCCTGATGGCCCCCACCTTCCCATCCAGACAGCCGAGC | 31 |
| CX3CL1/NM_002996 | AAGATACCTGTAGCTTTGCTCATCCACTATCAACAGAACCAGGCATCATGCGG CAAACGCGCAATCATCTTGGAGACGAGACAGCACAGGCTGTTCTGTGCCGACC CG | 32 |
| KLRB1/NM_002258 | TTGCCCTGAAACTTAGCTGTGCTGGGATTATTCTCCTTGTCTTGGTTGTTACT GGGTTGAGTGTTTCAGTGACATCCTTAATACAGAAATCATCAATAGAAAAATG C | 33 |
| TNFSF4/NM_003326 | ACAATTTACCGAATATAAGAAGGAGAAAGGTTTCATCCTCACTTCCCAAAAGG AGGATGAAATCATGAAGGTGCAGAACAACTCAGTCATCA | 34 |

TABLE 1-continued genes and amplicon insert sequences of the immune response assay

| Gene/Accession | Amplicon Sequence | SEQ ID NO: |
|---|---|---|
| CD52/NM_001803 | CCAAGACAGCCACGAAGATCCTACCAAAATGAAGCGCTTCCTCTTCCTCCTAC TCACCATCAGCCTCCTGGTTATGGTACAGATACAAACTGGACTCTCAGGACA | 35 |
| IL10RA/NM_001558 | TCCACCACATCCTCCACTGGACACCCATCCCAAATCAGTCTGAAAGTACCTGC TATGAAGTGGCGCTCCTGAGGTATGGAATAGAGTCCTGGAACTCCATCTCC | 36 |
| HLA-DOA/NM_002119 | TGATTAAAGCACCAGAGTGTAATGGCCCTCAGAGCAGGGCTGGTCCTGGGGTT CCACACCCTGATGACCCTCCTGAGCCCGCAGGAGGCAGGGGCCACCAAGGCTG AC | 37 |
| IFNB1/NM_002176 | GTGGAAATCCTAAGGAACTTTTACTTCATTAACAGACTTACAGGTTACCTCCG AAACTGAAGATCTCCTAGCCTGTGCCTCTGGGACTGGACAATTGCTTCAAGCA T | 38 |
| CCR5/NM_001100168 | CGTTCCCCTACAAGAAACTCTCCCCGGGTGGAACAAGATGGATTATCAAGTGT CAAGTCCAATCTATGACATCAATTATTATACATCGGAGCCCTGCCAAAAAATC AA | 39 |
| IKZF3/NM_012481 | GTGTGGATTATCCTGCATCAGCTTCAATGTCTTAATGGTTCATAAGCGAAGCC ATACTGGTGAACGCCCATTCCAGTGTAATCAGTGTGGGGCATCTTTTACTCAG A | 40 |
| STAT1/NM_007315 | AGTGCTGAGTTGGCAGTTTTCTTCTGTCACCAAAAGAGGTCTCAATGTGGACC AGCTGAACATGTTGGGAGAGAAGCTTCTTGGTCCTAACGCCAGCCCCGATGGT CTC | 41 |
| CD6/NM_006725 | GCAGGTTCCAGATGCCACCCTTGGAGGAAGGACTTGAAGAGTTGCATGCCTCC CACATCCCAACTGCCAACCCTGGACACTGCATTACAGACCCGCCATCCCTGGG CCC | 42 |
| BRCA1/NM_007300 | CTGAGTGACAAGGAATTGGTTTCAGATGATGAAGAAAGAGGAACGGGCTTGGA AGAAAATAATCAAGAAGAGCAAAGCATGGATTCAAACTTAGGTGAAGCAGC | 43 |
| CORO1A/NM_007074 | GGCCCTGATCTGTGAGGCCAGCGGGGGAGGGGCCTTCCTGGTGCTGCCCCTGG GCAAGACTGGACGTGTGGACAAGAATGCGCCCACGGTCTGTGGCCACACAGCC | 44 |
| TBX21/NM_013351 | TTTGGGAAACTAAAGCTCACAAACAACAAGGGGGCGTCCAACAATGTGACCCA GATGATTGTGCTCCAGTCCCTCCATAAGTACCAGCCCCGGCTGCATATCGTTG AGGTG | 45 |
| KLRK1/NM_007360 | CTCACCCAACCTACTAACAATAATTGAAATGCAGAAGGGAGACTGTGCACTCT ATGCCTCGAGCTTTAAAGGCTATATAGAAAACTGTTCAACTCCAAATACGTAC | 46 |
| CXCR6/NM_006564 | GCATCTCTGCTGGTGTTCATCAGAACAGACACCATGGCAGAGCATGATTACCA TGAAGACTATGGGTTCAGCAGTTTCAATGACAGCAGCCAGGAGGAGCATCAA | 47 |
| PTEN/NM_000314 | TATCTAGTACTTACTTTAACAAAAAATGATCTTGACAAAGCAAATAAAGACAA AGCCAACCGATACTTTTCTCCAAATTTTAAGGTGAAGCTGTACTTCACAAAA | 48 |
| PMEL/NM_006928 | CCAGAGTGGACAGAAGCCCAGAGACTTGACTGCTGGAGAGGTGGTCAAGTGTC CCTCAAGGTCAGTAATGATGGGCCTACACTGATTGGTGCAAATGCCTCCTTCT | 49 |
| DMBT1/NM_007329 | AGCACCAACCTGCTCTGTCTGCCAAATCACATGCAAGCCAGTGTGAGCAGGAG CTATCTCCAATCCTTGGGCTTTTCTGCCAGTGACCTTGTCATTTCCACCTGGA | 50 |
| IFI44L/NM_006820 | CTTCAAGACAACTTTTTAAACATGAGTAGATCTATGACTTCTCAAAGCCGGGT CATGAATGTCCATAAAATGCTAGGCATTCCTATTTCCAATATTTTG | 51 |
| LAPTM5/NM_006762 | CATGGAAGTGCCCACCTATCTCAACTTCAAGTCCATGAACCACATGAATTACC TCCCCAGCCAGGAGGATATGCCTCATAACCAGTTCATCAAGATGATGATCATC TTT | 52 |
| CD226/NM_006566 | GTCACAGTCTCAGACTCGGGGCTTTACCGCTGCTACTTGCAGGCCAGCGCAGG AGAAAACGAAACCTTCGTGATGAGATTGACTGTAGCCGAGGGTAAAACCGA | 53 |
| TNFSF13B/NM_006573 | CTCAGCTTTAAAAGGGGAAGTGCCCTAGAAGAAAAAGAGAATAAAATATTGGT CAAAGAAACTGGTTACTTTTTTATATATGGTCAGGTTTTATATACTGATAAG | 54 |
| ICOS/NM_012092 | TATTACTTCTGCAACCTATCAATTTTTGATCCTCCTCCTTTTAAAGTAACTCT TACAGGAGGATATTTGCATATTTATGAATCACAACTTTGTTGCCAGCTGAAG | 55 |
| CD160/NM_007053 | CTGGGCCTGCTGACAGCGTGCAGGATGCTGTTGGAACCCGGCAGAGGCTGCTG TGCCCTGGCCATCCTGCTGGCAATTGTGGACATCCAGTCTGGTGGATGCATTA | 56 |

TABLE 1-continued genes and amplicon insert sequences of the immune response assay

| Gene/Accession | Amplicon Sequence | SEQ ID NO: |
|---|---|---|
| TRIM29/NM_012101 | GAATCATAGCACCGTGACAGTGGAGGAGGCCAAGGCCGAGAAGGAGACGGAGC TGTCATTGCAAAAGGAGCAGCTGCAGCTCAAGATCATTGAGATTGAGGATGAA GC | 57 |
| LST1/NM_007161 | CCAGCCCCTGATCATTTCGCCTAAAAGAGCAAGGACTAGAGTTCCTGACCTCC AGGCCAGTCCCTGATCCCTGACCTAATGTTATCGCGGAATGATGA | 58 |
| ZBTB46/NM_025224 | GCCTGCTGTCGCTGAAGGCCGACGTGCTGGGGGATGACGGCTCCCTGCTGTTC GAGTACCTGCCCAGAGGGGCCCACTCGCTGTCCCTGAATGAGTTCACGGTG | 59 |
| VTCN1/NM_024626 | GGCAGCGGCAGCTCCACTCAGCCAGTACCCAGATACGCTGGGAACCTTCCCCA GCCATGGCTTCCCTGGGGCAGATCCTCTTCTGGAGCATAATTAGCATCATCAT TA | 60 |
| KREMEN1/NM_032045 | AAGATACTTCTGCACGTCACATTCAAATCCCATCGTGTTCCTGCTTCAGGGGA CCTTAGGGATTGTCATCAACCAGGGACTTCGGGGGAAATCTGGAGCATTT | 61 |
| PDCD1LG2/NM_025239 | CACCAGATAGCAGCTTTATTCACAGTGACAGTCCCTAAGGAACTGTACATAAT AGAGCATGGCAGCAATGTGACCCTGGAATGCAACTTTGACACTGGAAGTCATG TG | 62 |
| TUBB/NM_178014 | TGGCCAGATCTTTAGACCAGACAACTTTGTATTTGGTCAGTCTGGGGCAGGTA ACAACTGGGCCAAAGGCCACTACACAGAGGGCGCCGAGCTGGTTGATTCTGTC CTGG | 63 |
| CLEC4C/NM_130441 | TGACCCTGCATGGTGTGCGGTGCCCTCCTGCCTCAGGCCGCGAAGAAGGATCT AAGGGCTTGGCTTGTTTGAAAGAACCACACCCCGAAAGTAACATCTTTGGAGA A | 64 |
| CD86/NM_175862 | TGTGATGGCCTTCCTGCTCTCTGGTGCTGCTCCTCTGAAGATTCAAGCTTATT TCAATGAGACTGCAGACCTGCCATGCCAATTTGCAAACTCTCAAA | 65 |
| HAVCR2/NM_032782 | TCCCAGGCATAATGAATGATGAAAAATTTAACCTGAAGTTGGTCATCAAACCA GCCAAGGTCACCCCTGCACCGACTCGGCAGAGAGACTTCACTGCAGCCTTTCC AAGGA | 66 |
| GZMH/NM_033423 | GAGAAGAGTCGGAAGAGGTGTGGCGGCATCCTAGTGAGAAAGGACTTTGTGCT GACAGCTGCTCACTGCCAGGGAAGCTCCATAAATGTCACCTTGGGGGCCCACA | 67 |
| NFATC1/NM_172387 | GCGAGAGCCTGAAGAGTTGGACCAGTTGTACCTGGATGACGTAAATGAAATAA TACGAAATGACCTCTCCAGCACGAGCACCCACTCCTAGTTGCCACATTGGAGC A | 68 |
| CD8B/NM_172213 | CTGCATGATCGTCGGGAGCCCCGAGCTGACCTTCGGGAAGGGAACTCAGCTGA GTGTGGTTGATTTCCTTCCCACCACTGCCCAGCCCACCAAGAAGTCCACCCTC A | 69 |
| BCL2/NM_000633 | GGCACCTGCACACCTGGATCCAGGATAACGGAGGCTGGGATGCCTTTGTGGAA CTGTACGGCCCCAGCATGCGGCCTCTGTTTGATTTCTCCTGGCTGTCTCTG | 70 |
| GADD45GIP1/NM_052850 | GGCGACCATGCAGGAGTCGCTGCGGGTGAAGCAGCTGGCCGAAGAGCAGAAGC GTCGGGAGAGGGAGCAGCACATCGCAGAGTGCATGGCCAAGATGCCA | 71 |
| CBLB/NM_170662 | CGGCGCCGAAAGAACTAAAATTCCAGATGGCAAACTCAATGAATGGCAGAAAC CCTGGTGGTCGAGGAGGAAATCCCCGAAAAGGTCGAATTTTGGGTATTATTGA TGCTA | 72 |
| ITGA1/NM_181501 | GACACAGCAAGAAAGGAGGCATTCACGGAAGCCCGGGGTGCCCGAAGAGGAGT TAAAAAAGTCATGGTTATTGTGACAGATGGAGAGTCTCATGACAATC | 73 |
| CD8A/NM_171827 | GTCCCCGGCCTGTGGTCAAATCGGGAGACAAGCCCAGCCTTTCGGCGAGATAC GTCTAACCCTGTGCAACAGCCACTACATTACTTCAAACTGAGATCCTTCCT | 74 |
| IL2RA/NM_000417 | TGGGGACTGCTCACGTTCATCATGGTGCCTGGCTGCCAGGCAGAGCTCTGTGA CGATGACCCGCCAGAGATCCCACACGCCACATTCAAAGCCATGGC | 75 |
| EIF2AK2/NM_001135651 | CCACACTTCCGTGATTATCTGCGTGCATTTTGGACAAAGCTTCCAACCAGGAT ACGGGAAGAAGAAATGGCTGGTGATCTTTCAGCAGGTTTCTTCATGG | 76 |
| MADCAM1/NM_130760 | CAACAGGCTCGTCCAAACCTGCGGGTGACCAGCTGCCCGCGGCTCTGTGGACC AGCAGTGCGGTGCTGGGACTGCTGCTCCTGGCCTTGCCCACC | 77 |

TABLE 1-continued genes and amplicon insert sequences of the immune response assay

| Gene/Accession | Amplicon Sequence | SEQ ID NO: |
|---|---|---|
| PTPN6/NM_080548 | CTATCCCCCAGCCATGAAGAATGCCCATGCCAAGGCCTCCCGCACCTCGTCCA AACACAAGGAGGATGTGTATGAGAACCTGCACACTAAGAACAAGAGGGAGGAG AAAG | 78 |
| LRG1/NM_052972 | GCAGACAGCGACCAAAAAGCCCAGGGGGCATTCAACCCCATGTTTCTAGAACT CTGTTCCTGCTGCTGCTGTTGGCAGCCTCAGCCTGGGGGGTCACCCTGAGCCC C | 79 |
| ADGRE5/NM_078481 | TCTTCGACGATCGGAGCTTGGTGCTGACCTATGTGTTTACCATCCTCAACTGC CTGCAGGGCGCCTTCCTCTACCTGCTGCACTGCCTGCTCAACAAGAAGGTTCG GGA | 80 |
| SH2D1B/NM_053282 | TTGCTGCTCAAGGAAGGGGTGGATGGCAACTTTCTTTTAAGAGACAGCGAGTC GATACCAGGAGTCCTGTGCCTCTGTGTCTCGTTTAAAAATATTGTCTAC | 81 |
| ITGB2/NM_000211 | TGACCGTGCAGGTTCTTCCCCAGTGTGAGTGCCGGTGCCGGGACCAGAGCAGA GACCGCAGCCTCTGCCATGGCAAGGGCTTCTTGGAGTGCGGCATCTGCAGGTG | 82 |
| HLA-DPA1/NM_033554 | TCCATATCAGAGCTGTGATCTTGAGAGCCCTCTCCTTGGCTTTCCTGCTGAGT CTCCGAGGAGCTGGGGCCATCAAGGCGGACCATGTGTCAACTTATGCCGCGTT TG | 83 |
| DGAT2/NM_032564 | AGGTCCAAGGTGGAAAAGCAGCTACAGGTCATCTCAGTGCTCCAGTGGGTCCT GTCCTTCCTTGTACTGGGAGTGGCCTGCAGTGCCATCCTCATGTACATATTCT GCA | 84 |
| IGF1R/NM_000875 | CATGCCTTGGTCTCCTTGTCCTTCCTAAAAAAACCTTCGCCTCATCCTAGGAGA GGAGCAGCTAGAAGGGAATTACTCCTTCTACGTCCTCGACAACCAGAACTTGC AGC | 85 |
| TAGAP/NM_054114 | TGCTCACCCTGGAGAATGACCAGAGCCTGTCATTTGAAGCCCAGAAGGACCTG AACAACAAGGTGAAGACACTGGTGGAATTCCTCATTGATAACTGCTTTGAAAT A | 86 |
| LMNA/NM_170707 | AAGGAGCTGAAAGCGCGCAATACCAAGAAGGAGGGTGACCTGATAGCTGCTCA GGCTCGGCTGAAGGACCTGGAGGCTCTGCTGAACTCCAAGGAGGCCGCACTGA GC | 87 |
| NCAM1/NM_181351 | CTGAACAAGTGTGGCCTGTTCATGTGCATTGCGGTCAACCTGTGTGGAAAAGC CGGGCCCGGGGCCAAGGGCAAGGACATGGAGGAGGGCAAGGCCGCCTTCTCGA AA | 88 |
| TIGIT/NM_173799 | CAGGGGAGTACTTCTGCATCTATCACACCTACCCTGATGGGACGTACACTGGG AGAATCTTCCTGGAGGTCCTAGAAAGCTCAGTGGCTGAGCACGGTGCCAGGTT CC | 89 |
| IL17F/NM_052872 | AAGAGCTTCCTGCACAAAGTAAGCCACCAGCGCAACATGACAGTGAAGACCCT GCATGGCCCAGCCATGGTCAAGTACTTGCTGCTGTCGATATTGGGGCTTGC | 90 |
| HLA-F-AS1/NR_026972 | CTGCAGCTGTGCTCACACCTGGAGGAAACCTCAATGGTCACATCCTCTTTCCT GTGTCAAGAAGCATCGTCCGGGGAGGTGAGAAGAAGACAGTCCTCCCTAGAAT TG | 91 |
| CD247/NM_198053 | GGAAGGCGCTTTTCACCGCGGCCATCCTGCAGGCACAGTTGCCGATTACAGAG GCACAGAGCTTTGGCCTGCTGGATCCCAAACTCTGCTACCTGCTGGA | 92 |
| CD79B/NM_001039933 | CCAGGGCTGCGGCACAGAGCTGCGAGTCATGGGATTCAGCACCTTGGCACAGC TGAAGCAGAGGAACACGCTGAAGGATGGTATCATCATGATCCAGACGCTGCTG | 93 |
| IDO2/NM_194294 | CAAGCTCATGTGGACAAGATGCCCCTGCTGAGCTGCCAGTTCCTGAAGGGTCA CCGGGAGCAGCGCCTGGCCCACCTGGTCCTGAGCTTCCTCACCATGGGTTA | 94 |
| IL4/NM_000589 | TTCCTGAAACGGCTCGACAGGAACCTCTGGGGCCTGGCGGGCTTGAATTCCTG TCCTGTGAAGGAAGCCAACCAGAGTACGTTGGAAAACTTCTTGG | 95 |
| TYROBP/NM_198125 | TCAGGAGCTCCAGGGTCAGAGGTCGGATGTCTACAGCGACCTCAACACACAGA GGCCGTATTACAAATGAGCCCGAATCATGACAGTCAGCAACATGATACCTGG | 96 |
| BTLA/NM_181780 | GGAACTGGGAAATTATTTTGGGTCTTCTTCTTAATCCCATATCTGGACATCTG GAACATCCATGGGAAAGAATCATGTGATGTACAGCTTTATATAAAGAGACAAT C | 97 |

TABLE 1-continued genes and amplicon insert sequences of the immune response assay

| Gene/ Accession | Amplicon Sequence | SEQ ID NO: |
|---|---|---|
| AKT1/ NM_001014431 | GTGAAGGAGGGTTGGCTGCACAAACGAGGGGAGTACATCAAGACCTGGCGGCC ACGCTACTTCCTCCTCAAGAATGATGGCACCTTCATTGGCTACAAGGAGCGGC CGC | 98 |
| IL2RG/NM_000206 | ATCTCTGTTGGCTCCATGGGATTGATTATCAGCCTTCTCTGTGTGTATTTCTG GCTGGAACGGACGATGCCCCGAATTCCCACCCTGAAGAACCTAGAGGATCT | 99 |
| POLR2A/NM_000937 | TCTTCCTGCGCTGCATCGAGTCCAACATGCTGACAGATATGACCCTGCAGGGC ATCGAGCAGATCAGCAAGGTGTACATGCACTTGCCACAGACAGACAAC | 100 |
| ITGAX/NM_000887 | GTTCTAAGAACCTGCTTGGGAGCCGTGACCTCCAAAGCTCTGTGACCTTGGAC CTGGCCCTCGACCCTGGCCGCCTGAGTCCCCGTGCCACCTTCCAGGAAAC | 101 |
| IL1B/NM_000576 | TGATAAGCCCACTCTACAGCTGGAGAGTGTAGATCCCAAAAATTACCCAAAGA AGAAGATGGAAAAGCGATTTGTCTTCAACAAGATAGAAATCAATAACAAGCTG G | 102 |
| CSF2RB/NM_000395 | GGCAGAGAAACACATAAAGAGCTCAGTGAACATCCAGATGGCCCCTCCATCCC TCAACGTGACCAAGGATGGAGACAGCTACAGCCTGCGCTGGGAAACAATGA | 103 |
| DDX58/NM_014314 | CTGAATGTTTAATTAATCAGGAATGTGAAGAAATTCTACAGATTTGCTCTACT AAGGGGATGATGGCAGGTGCAGAGAAATTGGTGGAATGCCTTCTCAGATC | 104 |
| KIAA0101/ NM_014736 | AAGGAATTGGAGAATTCTTTAGGTTGTCCCCTAAAGATTCTGAAAAAGAGAAT CAGATTCCTGAAGAGGCAGGAAGCAGTGGCTTAGGAAAAGCAAAGAGAAAAGC A | 105 |
| CD274/NM_014143 | TGGTGGTGCCGACTACAAGCGAATTACTGTGAAAGTCAATGCCCCATACAACA AAATCAACCAAAGAATTTTGGTTGTGGATCCAGTCACCTCTGAACATGAACTG AC | 106 |
| LAMP3/NM_014398 | AGTGCGTGAGTGAACAGAGCCTCCAGTTGTCAGCCCACCTGCAGGTGAAAACA ACCGATGTCCAACTTCAAGCCTTTGATTTTGAAGATGACCACTTTGGAAATGT GG | 107 |
| TNFAIP8/ NM_014350 | TTATGCACTCCGAAGCAGAAGAATCCAAGGAAGTGGCCACAGATGTCTTTAAT TCCAAAAACCTGGCCGTTCAGGCACAAAAGAAGATCTTGGGTAAAATGGTGTC C | 108 |
| FOXP3/NM_014009 | GAAGGGCAGGGCACAATGTCTCCTCCAGAGAGAGATGGTACAGTCTCTGGAGC AGCAGCTGGTGCTGGAGAAGGAGAAGCTGAGTGCCATGCAGGCCCACCTGGCT GGGA | 109 |
| IL12A/NM_000882 | GACCATGAATGCAAAGCTTCTGATGGATCCTAAGAGGCAGATCTTTCTAGATC AAAACATGCTGGCAGTTATTGATGAGCTGATGCAGGCCCTGAATTTCAAC | 110 |
| SAMHD1/NM_015474 | ATATTTTGTTCAGTGGTGTGCAGACAGAAATTTCACCAAGCCGCAGGATGGCG ATGTTATAGCCCCACTCATAACACCTCAAAAAAAGGAATGGAACGACAGTACT | 111 |
| SIT1/NM_014450 | TCTGCAGCCATGAGCAGAGGCGACAACTGCACGGATCTACTCGCACTGGGAAT CCCCTCCATAACCCAGGCCTGGGGACTGTGGGTCCTCTTAGGGGCTGTGACGC | 112 |
| CD3E/NM_000733 | CTGGGGGCTTGCTGCTGCTGGTTTACTACTGGAGCAAGAATAGAAAGGCCAAG GCCAAGCCTGTGACACGAGGAGCGGGTGCTGGCGGCAGGCAAAGGGGACA | 113 |
| ICOSLG/NM_015259 | GCCAATCCCTGGGATTCCAGGAGGTTTTGAGCGTTGAGGTTACACTGCATGTG GCAGCAAACTTCAGCGTGCCCGTCGTCAGCGCCCCCACAGCCCCTCCCAGG | 114 |
| HGF/NM_000601 | GAACATGGAAGACTTACATCGTCATATCTTCTGGGAACCAGATGCAAGTAAGC TGAATGAGAATTACTGCCGAAATCCAGATGATGATGCTCATGGACCCTGG | 115 |
| MELK/NM_014791 | AAAAATCATGGATAAAAACACACTAGGGAGTGATTTGCCCCGGATCAAACGG AGATTGAGGCCTTGAAGAACCTGAGACATCAGCATATATGTCAACTCT | 116 |
| IGSF6/NM_005849 | TTGAGTTCCACATGCAGAGCAGATGCGACAGCTAGAAGTGAGTAGGGCCCAGA CCCTGGCCCAGGAAGATCCACTAAAGGAGGCCATCCTTCCGCCTTCTTCTGCA GGAGTCAGGATGGAAAGGCAGATGTAAAGTCCCTCATGGCGAAATATAACACG GGGGGCAACCCGACAGAGGATGTCTCAGTCAATAGCCGACCCTTCAGAGTCAC AGGGCCAAACTCATCTTCAGGAATACAAGCAAGAAAGAACTTATTCAACAACC AAGGAAATGCCAGCCCTCCTGCAGGACCCAGCAATGTACCTAAGTTTGGGTCC CCAAAGCCACCTGTGGCAGTCAAACCTTCTTCTGAGGAAAAGCCTGACAAGGA ACCCAAGCCCCCGTTTCTAAAGCCCACTGGAGCAGGCCAAAGATTCGGAACAC CAGCCAGCTTGACCACCAGAGACCCCGAGGCGAAAGTGGGATTTCTGAAACCT | 117 |

TABLE 1-continued genes and amplicon insert sequences of the immune response assay

| Gene/Accession | Amplicon Sequence | SEQ ID NO: |
|---|---|---|
| | GTAGGCCCCAAGCCCATCAACTTGCCCAAAGAAGATTCCAAACCTACATTTCC<br>CTGGCCTCCTGGAAACAAGCCATCTCTTCACAGTGTAAACCAAGACCATGACT<br>TAAAGCCACTAGGCCCGAAATCTGGGCCTACTCCTCCAACCTCAGAAAATGAA<br>CAGAAGCAAGCGTTTCCCAAATTGACTGGGGTTAAAGGGAAATTTATGTCAGC<br>ATCACAAGATCTTGAACCCAAGCCCCTCTTCCCCAAACCCGCCTTTGGCCAGA<br>AGCCGCCCCTAAGTACCGAGAACTCCCATGAAGACGAAAGCCCCATGAAGAAT<br>GTGTCTTCATCAAAAGGGTCCCCAGCTCCCCTGGGAGTCAGGTCCAAAAGCGG<br>CCCTTTAAAACCAGCAAGGGAAGACTCAGAAAATAAAGACCATGCAGGGGAGA<br>TTTCAAGTTTGCCCTTTCCTGGAGTGGTTTTGAAACCTGCTGCGAGCAGGGGA<br>GGCCCAGGTCTCTCCAAAAATGGTGAAGAAAAAAGGAAGATAGGAAGATAGA<br>TGCTGCTAAGAACACCTTCCAGAGCAAAATAAATCAGGAAGAGTTGGCCTCAG<br>GGACTCCTCCTGCCAGGTTCCCTAAGGCCCCTTCTAAGCTGACAGTGGGGGGG<br>CCATGGGGCCAAAGTCAGGAAAAGGAAAAGGGAGACAAGAATTCAGCCACCCC<br>GAAACAGAAGCCATTGCCTCCCTTGTTTACCTTGGGTCCACCTCCACCAAAC<br>CCAACAGACCACCAAATGTTGACCTGACGAAATTCCACAAAACCTCTTCTGGA<br>AACAGTACTAGCAAAGGCCAGACGTCTTACTCAACAACTTCCCTGCCACCACC<br>TCCACCATCCCATCCGGCCAGCCAACCACCATTGCCAGCATCTCAC | |
| GNLY/NM_006433 | TCCTGCCCGTGCCTGGCCCAGGAGGGCCCCCAGGGTGACCTGTTGACCAAAAC<br>ACAGGAGCTGGGCCGTGACTACAGGACCTGTCTGACGATAGTCCAAAAACTGA | 118 |
| TDO2/NM_005651 | GCCTTTTCACCATGAGTGGGTGCCCATTTTTAGGAAACAACTTTGGATATACT<br>TTTAAAAAACTCCCCGTAGAAGGCAGCGAAGAAGACAAATCACAAACTGGTGT<br>G | 119 |
| KRT7/NM_005556 | TCATCGACAAGGTGCGGTTCCTGGAGCAGCAGAACAAGGTTCTGGACACCAAG<br>TGGACCCTGCTGCAGGAGCAGGGCACCAAGACTGTGAGGCAGAACCTGGAGCC<br>GTTGTTCGAGCAGTACATCAACAACCTCAGGAGGCAGCTGGACAGCATCGTGG<br>GGGAACGGGCCGCCTGGACTCAGAGCTGAGAAACATGCAGGACCTGGTGGAA<br>GACTTCAAGAACAAGTATGAGGATGAAATCAACAAGCGTACCACTGCTGAGAA<br>TGAGTTTGTGATGCTGAAGAAGGATGTAGATGCTGCCTACATGAACAAGGTGG<br>AGCTGGAGGCCAAGGTTGATGCACTGATGGATGAGATTAACTTCATGAAGATG<br>TTCTTTGATGCGGAGCTGTCCCAGATGCAGACGCATGTCTCTGACACCTCAGT<br>GGTCCTCTCCATGGACAACAACCGCAACCTGGAC | 120 |
| HLA-E/NM_005516 | TCTGAGGCGGAGCACCAGAGAGCCTACCTGGAAGACACATGCGTGGAGTGGCT<br>CCACAAATACCTGGAGAAGGGGAAGGAGACGCTGCTTCACCTGGAGCCCCCAA<br>AG | 121 |
| HLA-DMA/NM_006120 | CTGCTGGAGAATGTGCTGTGTGGCGTGGCCTTTGGCCTGGGTGTGCTGGGCAT<br>CATCGTGGGCATTGTTCTCATCATCTACTTCCGGAAGCCTTGCTCAGGTGAC | 122 |
| LAMP1/NM_005561 | ATGGTGAAAAATGGCAACGGGACCGCGTGCATAATGGCCAACTTCTCTGCTGC<br>CTTCTCAGTGAACTACGACACCAAGAGTGGCCCTAAGAACATGACCTTTGACC<br>TGCCA | 123 |
| NTN3/NM_006181 | CCCTGGCCGTGCCCTGAGTGACCGTCGGGCTTGCAGGGCCTGCGACTGTCACC<br>CGGTTGGTGCTGCTGGCAAGACCTGCAACCAGACCACAGGCC | 124 |
| CD28/NM_006139 | AGAGCAATGGAACCATTATCCATGTGAAAGGGAAACACCTTTGTCCAAGTCCC<br>CTATTTCCCGGACCTTCTAAGCCCTTTTGGGTGCTGGTGGTGGTTGGTGG | 125 |
| TARP/NM_001003806 | CAATTGTTCAAAAGATGCAAATGATACACTACTGCTGCAGCTCACAAACACCT<br>CTGCATATTACATGTACCTCCTCCTGCTCCTCAAGAGTGTGGTCTATT | 126 |
| EGFR/NM_005228 | GGCCCGAGACCCCCAGCGCTACCTTGTCATTCAGGGGGATGAAAGAATGCATT<br>TGCCAAGTCCTACAGACTCCAACTTCTACCGTGCCCTGATGGATGAAGAA | 127 |
| CCR4/NM_005508 | GCCTCACAGACCTTCCTCAGAGCCGCTTTCAGAAAAGCAAGCTGCTTCTGGTT<br>GGGCCCAGACCTGCCTTGAGGAGCCTGTAGAGTTAAAAAATGAACCCCACGGA | 128 |
| MAGEA3/NM_005362 | CGGCCTGACGTCGGTGGAGGGAAGCAGGCGCAGGCTCCGTGAGGAGGCAAGGT<br>TCTGAGGAGACAGGCCCCGGAGCAGCACTAGCTCCTGCCCACACTCCTACC | 129 |
| BATF/NM_006399 | CAGCCATGCCTCACAGCTCCGACAGCAGTGACTCCAGCTTCAGCCGCTCTCCT<br>CCCCCTGGCAAACAGGACTCATCTGATGATGTGAGAAGAGTTCAGAGGAGGGA<br>GA | 130 |
| KLRG1/NM_005810 | GGTCTGAGGAACAATTCTGGCTGGAGGTGGGAAGATGGATCACCTCTAAACTT<br>CTCAAGGATTTCTTCTAATAGCTTTGTGCAGACATGCGGTGCCATCAACAAAA<br>AT | 131 |
| IRS1/NM_005544 | TAAGCGCCTATGCCAGCATCAGTTTCCAGAAGCAGCCAGAGGACCGTCAGTAG<br>CTCAACTGGACATCACAGCAGAATGAAGACCTAAATGACCTCAGCAA | 132 |

TABLE 1-continued genes and amplicon insert sequences of the immune response assay

| Gene/Accession | Amplicon Sequence | SEQ ID NO: |
|---|---|---|
| CSF1R/NM_005211 | AGGGCAACAGTTATACTTTCATCGACCCCACGCAGCTGCCTTACAACGAGAAG<br>TGGGAGTTCCCCCGGAACAACCTGCAGTTTGGTAAGACCCTCGGAGCTGGAGC | 133 |
| CTLA4/NM_005214 | GGCAACGGAACCCAGATTTATGTAATTGATCCAGAACCGTGCCCAGATTCTGA<br>CTTCCTCCTCTGGATCCTTGCAGCAGTTAGTTCGGGGTTGTTTTTTTATAGC | 134 |
| TNFSF18/<br>NM_005092 | GATCATCCTGGAAGCTGTGGCTCTTTTGCTCAATAGTTATGTTGCTATTTCTT<br>TGCTCCTTCAGTTGGCTAATCTTTATTTTTCTCCAATTAGAGACTGC | 135 |
| POU2AF1/<br>NM_006235 | AAAAGGCAACATCCTGTCACAGGCCATGCTCTGGCAAAAACCCACAGCTCCGG<br>AGCAAGCCCCAGCCCCGGCCCGGCCATACCAGGGCGTCCGTGTGAAGGAGCCA<br>G | 136 |
| GZMA/NM_006144 | GGTCCTACTTAGTCTTGACAGAAAAACCATCTGTGCTGGGGCTTTGATTGCAA<br>AAGACTGGGTGTTGACTGCAGCTCACTGTAACTTGAACAAAAGGTCC | 137 |
| PIK3CA/<br>NM_006218 | AAGAGTACCTTGTTCCAATCCCAGGTGGAATGAATGGCTGAATTATGATATAT<br>ACATTCCTGATCTTCCTCGTGCTGCTCGACTTTGCCTTTCCATTTGCTCTGTT | 138 |
| ITK/NM_005546 | CTGAAGACAACAGGCGACCACTTTGGGAACCTGAAGAAACTGTGGTCATTGCC<br>TTATATGACTACCAAACCAATGATCCTCAGGAACTCGCACTGCGGCGCAACGA | 139 |
| IFI27/NM_005532 | CACATTCTCAGGAACTCTCCTTCTTTGGGTCTGGCTGAAGTTGAGGATCTCTT<br>ACTCTCTAGGCCACGGAATTAACCCGAGCAGGCATGGAGGCCTCTGCTCTCAC | 140 |
| EOMES/NM_005442 | AATGTGTTCGTAGAGGTGGTGCTGGCGGACCCCAACCACTGGCGCTTCCAGGG<br>GGGCAAATGGGTGACCTGTGGCAAAGCCGACAATAACATGCAGGGCAACAAA | 141 |
| LCN2/NM_005564 | GATCCCAGCCCCACCTCTGAGCAAGGTCCCTCTGCAGCAGAACTTCCAGGACA<br>ACCAATTCCAGGGGAAGTGGTATGTGGTAGGCCTGGCAGGGAATGCAATTCTC | 142 |
| CD80/NM_005191 | GCTCTTGGTGCTGGCTGGTCTTTCTCACTTCTGTTCAGGTGTTATCCACGTGA<br>CCAAGGAAGTGAAAGAAGTGGCAACGCTGTCCTGTGGTCACAATGTT | 143 |
| CD83/NM_004233 | CTCGGGGACATACAGGTGCACTCTGCAGGACCCGGATGGGCAGAGAAACCTAA<br>GTGGCAAGGTGATCTTGAGAGTGACAGGATGCCCTGCACAGCGTAAA | 144 |
| CXCL13/NM_006419 | TTATCCCTAGACGCTTCATTGATCGAATTCAAATCTTGCCCCGTGGGAATGGT<br>TGTCCAAGAAAAGAAATCATAGTCTGGAAGAAGAACAAGTCAATTGTGTGTG | 145 |
| MTOR/NM_004958 | TTGGGGAAAGGAACGTGAAAGGCATGTTTGAGGTGCTGGAGCCCTTGCATGCT<br>ATGATGGAACGGGGCCCCCAGACTCTGAAGGAAACATCCTTTAATCAGG | 146 |
| FCER1G/NM_004106 | CCAGCAGTGGTCTTGCTCTTACTCCTTTTGGTTGAACAAGCAGCGGCCCTGGG<br>AGAGCCTCAGCTCTGCTATATCCTGGATGCCATCCTGTTTCTGTATGGAATTG<br>T | 147 |
| TFRC/NM_001128148 | CAATCACACTCAGTTTCCACCATCTCGGTCATCAGGATTGCCTAATATACCTG<br>TCCAGACAATCTCCAGAGCTGCTGCAGAAAAGCTGTTTGGGAATATGGAAGGA<br>G | 148 |
| RORC/NM_005060 | TGTGCCGGGCCTACAATGCTGACAACCGCACGGTCTTTTTTGAAGGCAAATAC<br>GGTGGCATGGAGCTGTTCCGAGCCTTGGGCTGCAGCGAGCTCATCAGCTCCAT | 149 |
| MMP9/NM_004994 | GGCTTCTGCCCGGACCAAGGATACAGTTTGTTCCTCGTGGCGGCGCATGAGTT<br>CGGCCACGCGCTGGGCTTAGATCATTCCTCAGTGCCGGAGGCGCTCATGTACC<br>CTA | 150 |
| BST2/NM_004335 | GCAACAAGAGCTGACCGAGGCCCAGAAGGGCTTTCAGGATGTGGAGGCCCAGG<br>CCGCCACCTGCAACCACACTGTGATGGCCCTAATGGCTTCCCTGGATGCAG | 151 |
| PIK3CD/NM_005026 | GGCTCCTTCGCCATCAAGTCGCTGCGGAAACTGACGGACGATGAGCTGTTCCA<br>GTACCTGCTGCAGCTGGTGCAGGTGCTCAAGTACGAGTCCTACCTGGACTGCG<br>AGCTG | 152 |
| FCGR2B/NM_004001 | GGGGATCATTGTGGCTGTGGTCACTGGGATTGCTGTAGCGGCCATTGTTGCTG<br>CTGTAGTGGCCTTGATCTACTGCAGGAAAAAGCGGATTTCAGCTCTCCCAGGA<br>TACCC | 153 |
| TNFRSF14/NM_003820 | CCAAGTGCAGCTGGCTGGTGACGAAGGCCGGAGCTGGGACCAGCAGCTCCCAC<br>TGGGTATGGTGGTTTCTCTCAGGGAGCCTCGTCATCGTCATTGTTTGCTCC | 154 |

TABLE 1-continued genes and amplicon insert sequences of the immune response assay

| Gene/Accession | Amplicon Sequence | SEQ ID NO: |
|---|---|---|
| OAS3/NM_006187 | TTCGCCCAGCCAAGTTGAAGAACCTAATCTTGCTGGTGAAGCACTGGTACCAC CAGGTGTGCCTACAGGGGTTGTGGAAGGAGACGCTGCCCCCGGTCTATGCCCT GGA | 155 |
| GRAP2/NM_004810 | TGATTTCACTGCTTCAGGTGAGGATGAACTGAGCTTTCACACTGGAGATGTTT TGAAGATTTTAAGTAACCAAGAGGAGTGGTTTAAGGCGGAGCTTGGGAGCC | 156 |
| CCNB2/NM_004701 | ACTTCTTAAGGCGAGCATCAAAAGCCGGGGAGGTTGATGTTGAACAGCACACT TTAGCCAAGTATTTGATGGAGCTGACTCTCATCGACTATGATATGGTGCATTA TCA | 157 |
| MLANA/NM_005511 | TCCTGGGAGTCTTACTGCTCATCGGCTGTTGGTATTGTAGAAGACGAAATGGA TACAGAGCCTTGATGGATAAAAGTCTTCATGTTGGCACTCAATGTGCCTTAAC | 158 |
| MAGEA12/NM_005367 | CGGCCTGACGTCGGTGGAGGGAAGCAGGCGCAGGCTCCGTGAGGAGGCAAGGT TCTGAGGAGACAGGCCCCGGAGCAGCACTAGCTCCTGCCCACACTCCTACC | 159 |
| VCAM1/NM_001078 | AATGGATTCTGTGCCCACAGTAAGGCAGGCTGTAAAAGAATTGCAAGTCTACA TATCACCCAAGAATACAGTTATTTCTGTGAATCCATCCACAAAGCTGCAAG | 160 |
| CDKN3/NM_005192 | AATCGCAGATGGAGGGACTCCTGACATAGCCAGCTGCTGTGAAATAATGGAAG AGCTTACAACCTGCCTTAAAAATTACCGAAAAACCTTAATACACTGC | 161 |
| NCR1/NM_004829 | GACGGGACTCCAGAAAGACCATGCCCTCTGGGATCACACTGCCCAGAATCTCC TTCGGATGGGCCTGGCCTTTCTAGTCCTGGTGGCTCTAGTGTGGTTCCTGGTT G | 162 |
| FAS/NM_000043 | CAGTTGAGACTCAGAACTTGGAAGGCCTGCATCATGATGGCCAATTCTGCCAT AAGCCCTGTCCTCCAGGTGAAAGGAAAGCTAGGGACTGCACAGTCAATG | 163 |
| GZMB/NM_004131 | GTGCGAATCTGACTTACGCCATTATTACGACAGTACCATTGAGTTGTGCGTGG GGGACCCAGAGATTAAAAAGACTTCCTTTAAGGGGGACTCTGGAGGCCCTCTT G | 164 |
| IRF9/NM_006084 | CTTATCACAGTGAAGATGGAGCAGGCCTTTGCCCGATACTTGCTGGAGCAGAC TCCAGAGCAGCAGGCAGCCATTCTGTCCCTGGTGTAGAGCCTGGGGGACC | 165 |
| IFITM2/NM_006435 | CGCCTACTCCGTGAAGTCTAGGGACAGGAAGATGGTTGGCGACGTGACCGGGG CCCAGGCCTATGCCTCCACCGCCAAGTGCCTGAACATCTGGGCCCTGATTCTG | 166 |
| TNFSF14/NM_003807 | GAAGGGAAAGCTGGGGGCTCCCCACTGCACTTGCCACCTGAGTCACATTTTCA GAAGCCTCTGGAAAGTCGTGCACAGCCCAGGAGTGTTGAGCAATTTCGGTTTC CTCT | 167 |
| HLA-B/NM_005514 | CTGGAGAACGGGAAGGACAAGCTGGAGCGCGCTGACCCCCCAAAGACACACGT GACCCACCACCCCATCTCTGACCATGAGGCCACCCTGAGGTGCTGGGCCCTGG G | 168 |
| SDHA/NM_004168 | ACATCGGAACTGCGACTCAGCATGCAGAAGTCAATGCAAAATCATGCTGCCGT GTTCCGTGTGGGAAGCGTGTTGCAAGAAGGTTGTGGGAAAATCAGC | 169 |
| NRP1/NM_003873 | TCCTACCGAGAGTGGATACAGGTAGACTTGGGCCTTCTGCGCTTTGTCACGGC TGTCGGGACACAGGGCGCCATTTCAAAAGAAACCAAGAAGAAATATTATGTC | 170 |
| EBI3/NM_005755 | GCTGCGCGCTTCCACCGGGTGGGGCCCATTGAAGCCACGTCCTTCATCCTCAG GGCTGTGCGGCCCCGAGCCAGGTACTACGTCCAAGTGGCGGCTCAGGACCTCA CAG | 171 |
| EFNA4/NM_005227 | GGAGAGGAAGTCTGAGTCAGCCCATCCTGTTGGGAGCCCTGGAGAGAGTGGCA CATCAGGGTGGCGAGGGGGGACACTCCCAGCCCCCTCGTCTCTTGC | 172 |
| PVR/NM_006505 | CCTGCAAGGTGGAGCACGAGAGCTTTGAGAAGCCTCAGCTGCTGACTGTGAAC CTCACCGTGTACTACCCCCCAGAGGTATCCATCTCTGGCTATGATAACAACTG G | 173 |
| BUB1/NM_004336 | TATCTTCAGCTTGTGATAAAGAGTCAAATATGGAACGAAGAGTGATCACGATT TCTAAATCAGAATATTCTGTGCACTCATCTTTGGCATCCAAAGTTGATG | 174 |
| SKAP2/NM_003930 | ATGAATAACACTCTAAGAAAGGATGGAAAGAAAGATTGCTGTTTTGAAATCTC TGCTCCTGATAAACGTATATATCAGTTTACAGCAGCTTCTCCCAAAGATG | 175 |
| PRF1/NM_005041 | AGTTTCCATGTGGTACACACTCCCCCGCTGCACCCTGACTTCAAGAGGGCCCT CGGGGACCTGCCCCCACCACTTCAACGCCTCCACCCAGCCCGCCTACCTCAGGC | 176 |

TABLE 1-continued genes and amplicon insert sequences of the immune response assay

| Gene/Accession | Amplicon Sequence | SEQ ID NO: |
|---|---|---|
| CCL20/NM_004591 | TCCAAAACAGACTTGGGTGAAATATATTGTGCGTCTCCTCAGTAAAAAAGTCA AGAACATGTAAAAACTGTGGCTTTTCTGGAATGGAATTGGACATAGCCCAAGA | 177 |
| TNFRSF18/NM_004195 | GACTGCATGTGTGTCCAGCCTGAATTCCACTGCGGAGACCCTTGCTGCACGAC CTGCCGGCACCACCCTTGTCCCCCAGGCCAGGGGGTACAGTCCCAGGGGAAAT TC | 178 |
| CTSS/NM_004079 | GAAAACCTATGGCAAACAATACAAGGAAAAGAATGAAGAAGCAGTACGACGTC TCATCTGGGAAAAGAATCTAAAGTTTGTGATGCTTCACAACCTGGAGCATT | 179 |
| NKG7/NM_005601 | CTCCTGGTCCTTCTACCTGGGCTGGGTCTCAGCTATCCTCTTGCTCTGTACAG GTGCCCTGAGCCTGGGTGCTCACTGTGGCGGTCCCCGTCCTGGCTATGAAACC T | 180 |
| ISG15/NM_005101 | CAGGAGCTTGTGCCGTGGCCCACAGCCCACAGCCCACAGCCATGGGCTGGAC CTGACGGTGAAGATGCTGGCGGGCAACGAATTCCAGGTGTCCCTGAGCAGCTC C | 181 |
| PDCD1/NM_005018 | GACTCCCCAGACAGGCCCTGGAACCCCCCCACCTTCTCCCCAGCCCTGCTCGT GGTGACCGAAGGGGACAACGCCACCTTCACCTGCAGCTTCTCCAACAC | 182 |
| SNAI1/NM_005985 | TACAGCGAGCTGCAGGACTCTAATCCAGAGTTTACCTTCCAGCAGCCCTACGA CCAGGCCCACCTGCTGGCAGCCATCCCACCTCCGGAGATCCTCAACCCCACCG CC | 183 |
| CXCL11/NM_005409 | GTTGTTCAAGGCTTCCCCATGTTCAAAAGAGGACGCTGTCTTTGCATAGGCCC TGGGGTAAAAGCAGTGAAAGTGGCAGATATTGAGAAAGCCTCCATAA | 184 |
| CIITA/NM_000246 | GGACCTGGCTGGAGAAGAAGAGATTGAGCTCTACTCAGAACCCGACACAGACA CCATCAACTGCGACCAGTTCAGCAGGCTGTTGTGTGACATGGAAGGTGAT | 185 |
| IFI35/NM_005533 | TAGTTTCCAATTTGCGGATCCACTGCCCTCTGCTTGCGGGCTCTGCTCTGATC ACCTTTGATGACCCCAAAGTGGCTGAGCAGGTGCTGCAACAAAAGGAGCACAC G | 186 |
| TNFSF9/NM_003811 | GGCCCAAAATGTTCTGCTGATCGATGGGCCCCTGAGCTGGTACAGTGACCCAG GCCTGGCAGGCGTGTCCCTGACGGGGGGCCTGAG | 187 |
| TNFSF10/NM_003810 | GCAGATGCAGGACAAGTACTCCAAAAGTGGCATTGCTTGTTTCTTAAAAGAAG ATGACAGTTATTGGGACCCCAATGACGAAGAGAGTATGAACAGCCCCTGCTGG | 188 |
| MMP2/NM_004530 | TGAGAAGGATGGCAAGTACGGCTTCTGTCCCCATGAAGCCCTGTTCACCATGG GCGGCAACGCTGAAGGACAGCCCTGCAAGTTTCCATTCCGCTTCCAGGGCACA TC | 189 |
| EGR3/NM_004430 | CCAACTGCCTGACAATCTGTACCCCGAGGAGATCCCCAGCGCGCTCAACCTCT TCTCCGGCAGCAGCGACTCGGTAGTCCATTACAATCAGATGGCTACAGAGAA | 190 |
| MAGEA1/NM_004988 | CTGAGGGACGGCGTAGAGTTCGGCCGAAGGAACCTGACCCAGGCTCTGTGAGG AGGCAAGGTTTTCAGGGACAGGCCAACCCAGAGGACAGGATTCCCTGGAGGC CACAG | 191 |
| CD163/NM_004244 | GTCCTTCAGAGCAAGTGGCCTCTGTAATCTGCTCAGGAAACCAGTCCCAAACA CTGTCCTCGTGCAATTCATCGTCTTTGGGCCCAACAAGGCCTACCATTCC | 192 |
| IL6/NM_000600 | AGTGAGGAACAAGCCAGAGCTGTGCAGATGAGTACAAAAGTCCTGATCCAGTT CCTGCAGAAAAAGGCAAAGAATCTAGATGCAATAACCACCCCTGACCCAACC | 193 |
| KLRF1/NM_016523 | GAATATCTGGAACCGTGAATGGTATTCTCACTTTGACTTTGATCTCCTTGATC CTGTTGGTTTCTCAGGGAGTATTGCTAAAATGCCAAAAAGGAAG | 194 |
| B3GAT1/NM_018644 | CCAGTTGGGCCGGACTCTCCAAACCTGCTTCCGCAATGGGTGGGTTGTGAGTG CTGGTAATGAGGAGCCGTGGGTGCAGCCAGCCTTGGAGATGCCGAAGAGACGG GACA | 195 |
| C1QA/NM_015991 | ACAGGAGGCAGAGGCATCATGGAGGGTCCCCGGGGATGGCTGGTGCTCTGTGT GCTGGCCATATCGCTGGCCTCTATGGTGACCGAGGACTTGTGCCGAGCACC | 196 |
| OAS1/NM_016816 | AATTGTAAGAAGAAGCTTGGGAAGCTGCCACCTCAGTATGCCCTGGAGCTCCT GACGGTCTATGCTTGGGAGCGAGGGAGCATGAAAACACATTTCAACACAGCCC AG | 197 |

TABLE 1-continued genes and amplicon insert sequences of the immune response assay

| Gene/Accession | Amplicon Sequence | SEQ ID NO: |
|---|---|---|
| IKZF2/NM_016260 | GCCCAATGTGCTTATGGTACATAAAAGGAGTCACACTGGTGAACGCCCCTTCC ACTGTAACCAGTGTGGAGCTTCTTTTACTCAGAAGGGCAACCTTCTGAG | 198 |
| TLR9/NM_017442 | CCCCTGCCCCCAGCATGGGTTTCTGCCGCAGCGCCCTGCACCCGCTGTCTCT CCTGGTGCAGGCCATCATGCTGGCCATGACCCTGGCCCTGGGTACCTTGCCTG CC | 199 |
| KLF2/NM_016270 | CGCGGGCTGCGGCAAGACCTACACCAAGAGTTCGCATCTGAAGGCGCATCTGC GCACGCACACAGGTGAGAAGCCCTACCACTGCAACTGGGACGGCTGCGGCTGG | 200 |
| GUSB/NM_000181 | TTGCAGGGTTTCACCAGGATCCACCTCTGATGTTCACTGAAGAGTACCAGAAA AGTCTGCTAGAGCAGTACCATCTGGGTCTGGATCAAAAACGCAGAAAATACG | 201 |
| NFKBIA/NM_020529 | GTCAATGCTCAGGAGCCCTGTAATGGCCGGACTGCCCTTCACCTCGCAGTGGA CCTGCAAAATCCTGACCTGGTGTCACTCCTGTTGAAGTGTGGGGCTGATGTCA | 202 |
| IL23A/NM_016584 | GAGATGGCTGTGACCCCCAAGGACTCAGGGACAACAGTCAGTTCTGCTTGCAA AGGATCCACCAGGGTCTGATTTTTTATGAGAAGCTGCTAGGATCGGATATTT | 203 |
| HERC6/NM_017912 | CTGTGTGTGAAATGAGTAAACAATCTTTGCAAGTCCTAAAGAAGTGTTGGGCA TTTTTGCAAGAATCTTCTCTGAATCCGCTGATCCAGATGCTTAAAGCAGCC | 204 |
| SLAMF8/NM_020125 | ATGTGCTGCTGGTGGTGGTGCCTGTCTCGCTGCTCCTGATGCTGGTTACTCTC TTCTCTGCCTGGCACTGGTGCCCCTGCTCAGGGAAAAAGAAAAAGGATGTCCA TGC | 205 |
| IL15/NM_000585 | CACTGCCTTCGAAGTCCGGCGCCCCCGGGAGGGAACTGGGTGGCCGCACCCT CCCGGCTGCGGTGGCTGTCGCCCCCACCCTGCAGCCAGGACTCGATGGAGAA | 206 |
| TLR7/NM_016562 | CAACCAGACCTCTACATTCCATTTTGGAAGAAGACTAAAAATGGTGTTTCCAA TGTGGACACTGAAGAGACAAATTCTTATCCTTTTTAACATAATCCTAATTTCC A | 207 |
| OAS2/NM_016817 | AATGCACTGGGTCAGCTGAGTTCTGGCTCCACACCCAGCCCCGAGGTTTATGC AGGGCTCATTGATCTGTATAAATCCTCGGACCTCCCGGGAGGAGAGTTTTCTA CCT | 208 |
| HLA-DRA/NM_019111 | CAAAGAAGAACATGTGATCATCCAGGCCGAGTTCTATCTGAATCCTGACCAAT CAGGCGAGTTTATGTTTGACTTTGATGGTGATGAGATTTTCCATGTGGATATG GC | 209 |
| CRTAM/NM_019604 | GTAAGCACAAAGGAAGTGAAAGTGATTGTGCTGGCAACTCCTTTCAAGCCAAT CCTGGAAGCTTCAGTTATCAGAAAGCAAAATGGAGAAGAACATGTTGTACTC | 210 |
| MAGEC2/NM_016249 | GCAGAGGAGGCCCAGGCAGTGCCAGGAGTCAAGGCCTGTTGGATCTCATCATC CATATCCCTGTTGATACGTTTACCTGCTGCTCCTGAAGAAGTCGTCATGCCTC CCG | 211 |
| ICAM1/NM_000201 | GCCCTGATGGGCAGTCAACAGCTAAAACCTTCCTCACCGTGTACTGGACTCCA GAACGGGTGGAACTGGCACCCCTCCCCTCTTGGCAGCCAGTGGGCAAGAACCT | 212 |
| CD4/NM_000616 | CGCCTGTTTGAGAAGCAGCGGGCAAGAAAGACGCAAGCCCAGAGGCCCTGCCA TTTCTGTGGGCTCAGGTCCCTACTGGCTCAGGCCCCTGCCTCCCTCGGCAAGG CC | 213 |
| MAPK14/NM_139012 | TTGCTCAGTACCACGATCCTGATGATGAACCAGTGGCCGATCCTTATGATCAG TCCTTTGAAAGCAGGGACCTCCTTATAGATGAGTGGAAAAGCCTGACCTATGA TG | 214 |
| C1QB/NM_000491 | CCAGGAGGCGTCTGACACAGTATGATGATGAAGATCCCATGGGGCAGCATCCC AGTACTGATGTTGCTCCTGCTCCTGGGCCTAATCG | 215 |
| NOTCH3/NM_000435 | CTGTGCCTGTCTTCCTGGGTTTGAGGGTCAGAATTGTGAAGTGAACGTGGACG ACTGTCCAGGACACCGATGTCTCAATGGGGGACATGCGTGGATGGCGTCAAC ACC | 216 |
| NCR3/NM_147130 | TCCCCTTCGCCAACTGGGACATCTTCCGACATGGCCTGGATGCTGTTGCTCAT CTTGATCATGGTCCATCCAGGATCCTGTGCTCTCTGGGTGTCCCAGCCCCCTG AG | 217 |
| STAT3/NM_139276 | GGCCGAGGTCCTGAGCTGGCAGTTCTCCTCCACCACCAAGCGAGGACTGAGCA TCGAGCAGCTGACTACACTGGCAGAGAAACTCTTGGGACCTGGTGTGAATTA | 218 |

TABLE 1-continued genes and amplicon insert sequences of the immune response assay

| Gene/ Accession | Amplicon Sequence | SEQ ID NO: |
|---|---|---|
| TLR8/NM_138636 | CCATTCTGCGCTGCTGCAAGTTACGGAATGAAAAATTAGAACAACAGAAACAT GGAAAACATGTTCCTTCAGTCGTCAATGCTGACCTGCATTTTCCTGCT | 219 |
| CYBB/NM_000397 | TGCAGATCTGCTGCAACTGCTGGAGAGCCAGATGCAGGAAAGGAACAATGCCG GCTTCCTCAGCTACAACATCTACCTCACTGGCTGGGATGAGTCTCAGGCCAAT C | 220 |
| IKZF4/NM_022465 | TAATGGAATCTTTATTTTGTGAAAGTAGCGGGGACTCATCTCTGGAGAAGGAG TTCCTCGGGGCCCCAGTGGGGCCCTCGGTGAGCACCCCCAACAGCCAGCACTC | 221 |
| IFIH1/NM_022168 | TGCCATTGCAGATGCAACCAGAGAAGATCCATTTAAAGAGAAACTTCTAGAAA TAATGACAAGGATTCAAACTTATTGTCAAATGAGTCCAATGTCAGATTTTGGA | 222 |
| LCK/NM_001042771 | GGGGATCCCAGGATCTCACAATCTCAGGGACCATGGGCTGTGGCTGCAGCTCA CACCCGGAAGATGACTGGATGGAAAACATCGATGTGTGTGAGAACTGCCA | 223 |
| BCL2L11/NM_138621 | CAAATCAACACAAACCCCAAGTCCTCCTTGCCAGGCCTTCAACCACTATCTCA GTGCAATGGCTTCCATGAGGCAGGCTGAACCTGCAGATATGCGCCCAGAGATA TGG | 224 |
| ITGAM/NM_001145808 | GGAGCGCTTGCCCTCTCACTCCGACTTTCTGGCTGAGCTTCGGAAGGCCCCCG TGGTGAACTGCTCCATCGCTGTCTGCCAGAGAATCCAGTGTGACATCCCGTTC | 225 |
| ITGB7/NM_000889 | GAGAAGGAGCAGCAACAACTCAACTGGAAGCAGGACAGTAATCCTCTCTACAA AAGTGCCATCACGACCACCATCAATCCTCGCTTTCAAGAGGCAGACAGTCCCA CTCT | 226 |
| JCHAIN/NM_144646 | AGTCAAGATGAAGAACCATTTGCTTTTCTGGGGAGTCCTGGCCGGTTTTTATTA AGGCTGTTCATGTGAAAGCCCAAGAAGATGAAAGGATTGTTCTTGTTGACA | 227 |
| CD209/NM_021155 | GAAGTAACCGCTTCACCTGGATGGGACTTTCAGATCTAAATCAGGAAGGCACG TGGCAATGGGTGGACGGCTCACCTCTGTTGCCCAGCTTCAAGCAGTATTGGAA CAG | 228 |
| SLAMF7/NM_021181 | ATACGGTTTACTCCACTGTGGAAATACCGAAAAAGATGGAAAATCCCCACTCA CTGCTCACGATGCCAGACACACCAAGGCTATTTGCCTATGAGAATGTTATC | 229 |
| IL10/NM_000572 | GCCTTTAATAAGCTCCAAGAGAAAGGCATCTACAAAGCCATGAGTGAGTTTGA CATCTTCATCAACTACATAGAAGCCTACATGACAATGAAGATACGAAACTGAG A | 230 |
| IL1A/NM_000575 | GAAGCAGTGAAATTTGACATGGGTGCTTATAAGTCATCAAAGGATGATGCTAA AATTACCGTGATTCTAAGAATCTCAAAAACTCAATTGTATGTGACTGCCC | 231 |
| FCGR3A/NM_000569 | CCCTCAGTGACCCGGTGCAGCTAGAAGTCCATATCGGCTGGCTGTTGCTCCAG GCCCCTCGGTGGGTGTTCAAGGAGGAAGACCCTATTCACCTGAGGTGTCACAG CTGGAAGAACACTGCTCTGCATAAGGTCACATATTTACAGAATGGCAAAGGCA GGAAGTATTTTCATCATAATTCTGACTTCTACATTCCAAAAGCCACACTCAAA GACAGCGGCTCCTACTTCTGCAGGGGCTTTTTGGGAGTAAAAATGTGTCTTC AGAGACTGTGAACATCACCATCACTCAAGGTTTGGCAGTGTCAACCATCTCA | 232 |
| IFNA17/NM_021268 | CAAAGACTCACTTCTATAACCACCACGAGTTGAATCAAAATTTTCAAATGTTT TCAGCAGTGTAAAGAAGCGTCGTGTATACCTGTGCAGGCACTAG | 233 |
| EGR2/NM_000399 | CCCAATGCCGAACTGGGAGGCCCCTTTGACCAGATGAACGGAGTGGCCGGAGA TGGCATGATCAACATTGACATGACTGGAGAGAAGAGGTCGTTGGATCTCCCA | 234 |
| TOP2A/NM_001067 | CCAACTTTGATGTGCGTGAAATTGTAAATAACATCAGGCGTTTGATGGATGGA GAAGAACCTTTGCCAATGCTTCCAAGTTACAAGAACTTCAAGGGTACTAT | 235 |
| C10orf54/NM_022153 | GCGGCCTCTACTGCTGCCTGGTGGTGGAGATCAGGCACCACCACTCGGAGCAC AGGGTCCATGGTGCCATGGAGCTGCAGGTGCAGACAGGCAAAGATGCACCATC CAAC | 236 |
| FOXM1/NM_021953 | CTTTGAAAGACATCTATACGTGGATTGAGGACCACTTTCCCTACTTTAAGCAC ATTGCCAAGCCAGGCTGGAAGAACTCCATCCGCCACAACCTTTCCCTGCACGA CATGT | 237 |
| AXL/NM_021913 | TCGCCTGAAGCAGCCTGCGGACTGTCTGGATGGACTGTATGCCTTGATGTCGC GGTGCTGGGAGCTAAATCCCCAGGACCGGCCAAGTTTTACAGAGCTGCGGGAA GAT | 238 |
| MS4A1/NM_021950 | GGAGACTCAGGAGTTTTGAGAGCAAAATGACAACACCCAGAAATTCAGTAAAT GGGACTTTCCCGGCAGAGCCAATGAAAGGCCCTATTGCTATGCAATCTGGTC | 239 |

TABLE 1-continued genes and amplicon insert sequences of the immune response assay

| Gene/Accession | Amplicon Sequence | SEQ ID NO: |
|---|---|---|
| IFI6/NM_022873 | CAGCAGGCTCCGGGCTGAAGATTGCTTCTCTTCTCTCCTCCAAGGTCTAGTGA CGGAGCCCGCGCGCGGCGCCACCATGCGGCAGAAGGCGGTATCGCTTTTCTTG TGC | 240 |
| CD3D/NM_000732 | TCATTATCGAATGTGCCAGAGCTGTGTGGAGCTGGATCCAGCCACCGTGGCTG GCATCATTGTCACTGATGTCATTGCCACTCTGCTCCTTGCTTTGGGAGTC | 241 |
| GPR18/NM_001098200 | ATGCTCATCTCTCACACAGACTTTTGATGGACAGGAGTTTCTAAGTATCATGC CTACCAACAAGCTGTAAAATGATCACCCTGAACAATCAAGATCAACCTG | 242 |
| CD3G/NM_000073 | GAGGAGGAATTGAACTCAGGACTCAGAGTAGTCCAGGTGTTCTCCTCCTATTC AGTTCCCAGAATCAAAGCAATGCATTTTGGAAAGCTCCTAGCAGAGAG | 243 |
| ZAP70/NM_001079 | CGGCCCACGAGCGGATGCCCTGGTACCACAGCAGCCTGACGCGTGAGGAGGCC GAGCGCAAACTTTACTCTGGGGCGCAGACCGACGGCAAGTTCCTGCTGAGGCC GC | 244 |
| HMBS/NM_000190 | GCTGTGGGCCAGGGGGCCTTGGGCGTGGAAGTGCGAGCCAAGGACCAGGACAT CTTGGATCTGGTGGGTGTGCTGCACGATCCCGAGACTCTGCTTCGCTGCATCG CT | 245 |
| IL7/NM_000880 | GAGCTTGCTCCTGCTCCAGTTGCGGTCATCATGACTACGCCCGCCTCCCGCAG ACCATGTTCCATGTTTCTTTTAGGTATATCTTTGGACTTCCTCCCCTGATCCT T | 246 |
| IFIT3/NM_001031683 | GGAATCAGTAAGCTAAAAACAAAATCAACCGGGACCCCAGCTTTTCAGAACTG CAGGGAAACAGCCATCATGAGTGAGGTCACCAAGAATTCCCTGGAGAAA | 247 |
| RB1/NM_000321 | AAACAAATATTTTGCAGTATGCTTCCACCAGGCCCCCTACCTTGTCACCAATA CCTCACATTCCTCGAAGCCCTTACAAGTTTCCTAGTTCACCCTTACGG | 248 |
| PTGS2/NM_000963 | AGTCTTTTAATGAGTACCGCAAACGCTTTATGCTGAAGCCCTATGAATCATTT GAAGAACTTACAGGAGAAAAGGAAATGTCTGCAGAGTTGGAAGCACTCTATGG T | 249 |
| TGFB1/NM_000660 | AAAGTGGAGCAGCACGTGGAGCTGTACCAGAAATACAGCAACAATTCCTGGCG ATACCTCAGCAACCGGCTGCTGGCACCCAGCGACTCGCCAGAGTGGTTATCTT | 250 |
| NCF1/NM_000265 | GTACCGCGACAGACATCACCGGCCCCATCATCCTGCAGACGTACCGCGCCATT GCCAACTACGAGAAGACCTCGGGCTCCGAGATGGCTCTGTCCACGGGGACGT GG | 251 |
| TWIST1/NM_000474 | GGGGGCCTGGTCCATGTCCGCGTCCCACTAGCAGGCGGAGCCCCCCACCCCCT CAGCAGGGCCGGAGACCTAGATGTCATTGTTTCCAGAGAAGGAGAAAATGG | 252 |
| CA4/NM_000717 | CCAGGCCAAACAGTTGCACCTGCACTGGTCCGACTTGCCATATAAGGGCTCGG AGCACAGCCTCGATGGGGAGCACTTTGCCATGGAGATGCACATAGTACATGAG AAAG | 253 |
| SELL/NM_000655 | ACCCTTGTGCTAAGTCAAGAGGCTCAATGGGCTGCAGAAGAACTAGAGAAGGA CCAAGCAAAGCCATGATATTTCCATGGAAATGTCAGAGCACCCAGAGGGACTT | 254 |
| LILRB1/NM_001081637 | GGCCGTCATCCTACTGCTCCTCCTCCTCCTCCTCTTCCTCATCCTCCGAC ATCGACGTCAGGGCAAACACTGGACATCGACCCAGAGAAAGGCTG | 255 |
| CD14/NM_000591 | GCACTTCCAGAGCCTGTCCGGAGCTCAGAGGTTCGGAAGACTTATCGACCATG GAGCGCGCGTCCTGCTTGTTGCTGCTGCTGCTGCCGCTGGTGCACGTCTCTGC | 256 |
| ALOX15B/NM_001141 | CACCCTGCACATCAACACACTCGCCCGGGAGCTGCTTATCGTGCCAGGGCAGG TGGTGGACAGGTCCACAGGCATCGGCATTGAAGGCTTCTCTGAGTTGATACAG | 257 |
| PECAM1/NM_000442 | TCCAGCCATGGCTGCCATTACCTGACCAGCGCCACAGCCGGTCTCTCTGCAGG CGCCGGGAGAAGTGACCAGAGCAATTTCTGCTTTTCACAGGGCGGGTTTCTCA ACGG | 258 |
| NOS2/NM_000625 | GGGACTGGGCAGTTCTAGACAGTCCCGAAGTTCTCAAGGCACAGGTCTCTTCC TGGTTTGACTGTCCTTACCCCGGGGAGGCAGTGCAGCCAGCTGCAAGCCCC | 259 |
| FASLG/NM_000639 | TTTCATGGTTCTGGTTGCCTTGGTAGGATTGGGCCTGGGGATGTTTCAGCTCT TCCACCTACAGAAGGAGCTGGCAGAACTCCGAGAGTCTACCAGCCAGATGC | 260 |

TABLE 1-continued genes and amplicon insert sequences of the immune response assay

| Gene/Accession | Amplicon Sequence | SEQ ID NO: |
|---|---|---|
| CD44/NM_000610 | CTTTTACACCTTTTCTACTGTACACCCCATCCCAGACGAAGACAGTCCCTGGATCACCGACAGCACAGACAGAATCCCTGCTACCACTTTGATGAGCACTAGTGCTAC | 261 |
| ENTPD1/NM_001098175 | TGGCCAAGAGGAAGGTGCCTATGGCTGGATTACTATCAACTATCTGCTGGGCAAATTCAGTCAGAAAACAAGGTGGTTCAGCATAGTCCCATATGAAACCAATAATC | 262 |
| CMKLR1/NM_001142345 | GGAGACATGGAGGAGGAAGAGGCTGAGGGGAAGATGGAAGAAGGAGGGAAGGAAGGAGAAATCTTTGCTTTTGGGTAATCAGGTGTTTCTAGCTGTGTACAGGGACT | 263 |
| CD53/NM_001040033 | GGTCTTGAAGGACACTGGGATCCTGTAACACAGCCCCGGATATCTGTGTTACCAGCCTTGTCTCGGCCACCTCAAGGATAATCACTAAATTCTGCCGAAAGGACT | 264 |
| TNF/NM_000594 | TGTAGCAAACCCTCAAGCTGAGGGGCAGCTCCAGTGGCTGAACCGCCGGGCCAATGCCCTCCTGGCCAATGGCGTGGAGCTGAGAGATAACCAGCTGGTGGTGCC | 265 |
| CXCL8/NM_000584 | TTCTGCAGCTCTGTGTGAAGGTGCAGTTTTGCCAAGGAGTGCTAAAGAACTTAGATGTCAGTGCATAAAGACATACTCCAAACCTTTCCACCCCAAATTTATCAA | 266 |
| CD40LG/NM_000074 | TGTGTTACAGTGGGCTGAAAAAGGATACTACACCATGAGCAACAACTTGGTAACCCTGGAAAATGGGAAACAGCTGACCGTTAAAAGACAAGGACTCTAT | 267 |
| HLA-F/NM_001098479 | TCCCAGACGCGGAGGTTGGGGTCATGGCGCCCCGAAGCCTCCTCCTGCTGCTCTCAGGGGCCCTGGCCCTGACCGATACTTGGGCGGGCTCCCACTCCTTGAG | 268 |
| GATA3/NM_001002295 | CTGTGCAACGCCTGCGGGCTCTATCACAAAATGAACGGACAGAACCGGCCCCTCATTAAGCCCAAGCGAAGGCTGTCTGCAGCCAGGAGAGCAGGGACGTCCTGTGCG | 269 |
| LYZ/NM_000239 | AAGGTGTGAGTTGGCCAGAACTCTGAAAAGATTGGGAATGGATGGCTACAGGGGAATCAGCCTAGCAAACTGGATGTGTTTGGCCAAATGGGAGAGTGGTTA | 270 |
| ARG1/NM_000045 | AAAGGCTGGTCTGCTTGAGAAACTTAAAGAACAAGAGTGTGATGTGAAGGATTATGGGGACCTGCCCTTTGCTGACATCCCTAATGACAGTCCCTTTCAAATTG | 271 |
| IL2RB/NM_000878 | CCCAGCTGAGCTCAGAGCATGGAGGAGACGTCCAGAAGTGGCTCTCTTCGCCCTTCCCCTCATCGTCCTTCAGCCCTGGCGGCCTGGCACCTGAGATCTCGCCACTAG | 272 |
| NECTIN2/NM_001042724 | TGCCGTGGGCATGGGCCGCGCTGAGCAGGTCATCTTTGTCCGAGAGACCCCCAACACAGCAGGCGCAGGGGCCACAGGCGGCATCATCGGGGGCATCATCGCCGCCAT | 273 |
| MPO/NM_000250 | GCCCGGAAGATCGTGGGGGCCATGGTCCAGATCATCACTTACCGGGACTACCTGCCCCTGGTGCTGGGGCCAACGGCCATGAGGAAGTACCTGCCCACGTACCGTTCC | 274 |
| CCR2/NM_001123396 | TGCTGAGAAGCCTGACATACCAGGACTGCCTGAGACAAGCCACAAGCTGAACAGAGAAAGTGGATTGAACAAGGACGCATTTCCCCAGTACATCCACA | 275 |
| BRCA2/NM_000059 | CTGTACTTCAGGGCCGTACACTGCTCAAATCATTCCTGGTACAGGAAACAAGCTTCTGATGTCTTCTCCTAATTGTGAGATATATTATCAAAGTCCTTTATCACT | 276 |
| ADORA2A/NM_000675 | GCCATCCGCATCCCGCTCCGGTACAATGGCTTGGTGACCGGCACGAGGGCTAAGGGCATCATTGCCATCTGCTGGGTGCTGTCGTTTGCCATCGGCCTGACT | 277 |
| G6PD/NM_000402 | GACGTCCGTGATGAGAAGGTCAAGGTGTTGAAATGCATCTCAGAGGTGCAGGCCAACAATGTGGTCCTGGGCCAGTACGTGGGGAACCCCGATGGAGAGGGCGAGGCCAC | 278 |
| TAP1/NM_000593 | CTGGACCACTAGTATTTCAGGTATGCTGCTGAAAGTGGGAATCCTCTACATTGGTGGGCAGCTGGTGACCAGTGGGCTGTAAGCAGTGGGAACCTTGTCACATT | 279 |
| MX1/NM_001178046 | CGAAGTGGACATCGCAAAAGCTGATCCAGCTGCTGCATCCCACCCTCTATTACTGAATGGAGATGCTACTGTGGCCCAGAAAAATCCAGGCTCGGTGGCTGAGA | 280 |
| HLA-DQB2/NM_001198858 | GCTGAGCACCCCAGTGGCTGAGGCCAGAGACTTTCCCAAGGATTTCTTGGTCCAGTTTAAGGGCATGTGCTACTTCACCAACGGGACAGAGCGCGTGCGCG | 281 |

TABLE 1-continued genes and amplicon insert sequences of the immune response assay

| Gene/Accession | Amplicon Sequence | SEQ ID NO: |
|---|---|---|
| CD27/NM_001242 | CCGGGGGTCTCCTTCTCTCCTGACCACCACACCCGGCCCCACTGTGAGAGCTG TCGGCACTGTAACTCTGGTCTTCTCGTTCGCAACTGCACCATCACTGCCAATG CT | 282 |
| CD276/NM_001024736 | CATCCCTGAGGCTGCAGCGCGTGCGTGTGGCGGACGAGGGCAGCTTCACCTGC TTCGTGAGCATCCGGGATTTCGGCAGCGCTGCCGTCAGCCTGCAGGTGGCCGC TCC | 283 |
| STAT4/NM_003151 | GGGACTGTGAGGGGCGCTTCTGACTTTGGACTTGAGCACTGCCTGGGACCTGT GCTGAGAGAGCGCTAGCATGTCTCAGTGGAATCAAGTCCAACAGTTAGAAATC A | 284 |
| PTPN7/NM_001199797 | TCTGCGCACTGCTGGACACCCCCTTACCCGCTGGGCCCTTCAGCGCCAGCCAC CCAGCCCCAAGCAACTGGAAGAAGAATTCTTGAAGATCCCTTCAAACTTTGTC AGCC | 285 |
| PTPRC/NM_002838 | GACAACCACCCTCAGCCTTGCACACCACAGCTCTGCTGCCTTACCTGCACGCA CCTCCAACACCACCATCACAGCGAACACCTCAGATGCCTACCTTAATGCCTCT G | 286 |
| PSMB9/NM_002800 | ATCAGCTATAAATATCGAGAGGACTTGTCTGCACATCTCATGGTAGCTGGCTG GGACCAACGTGAAGGAGGTCAGGTATATGGAACCCTGGGAGGAATGCTGACTC G | 287 |
| CD244/NM_001166663 | CTCAGGACTGTCAGAATGCCCATCAGGAATTCAGATTTTGGCCGTTTTTGGTG ATCATCGTGATTCTAAGCGCACTGTTCCTTGGCACCCTTGCCTGCTTCTGTG | 288 |
| CXCR4/NM_003467 | GGGGATCAGTATATACACTTCAGATAACTACACCGAGGAAATGGGCTCAGGGG ACTATGACTCCATGAAGGAACCCTGTTTCCGTGAAGAAAATGCTAATTTCAAT AA | 289 |
| MAPK1/NM_002745 | TTTGTCAGGACAAGGGCTCAGAGGACTGGACGTGCTCAGACATCGGTGTTCTT CTTCCCAGTTCTTGACCCCTGGTCCTGTCTCCAGCCCGTCTTGGCTTA | 290 |
| TP63/NM_003722 | ATCCAGCGTTTCGTAGAAACCCCAGCTCATTTCTCTTGGAAAGAAAGTTATTA CCGATCCACCATGTCCCAGAGCACACAGACAAATGAATTCCTCAGTCCAG | 291 |
| IRF4/NM_002460 | TATGCTTGTGCCCCACCTGAGTCCCAGGCTCCCGGAGTCCCCACAGAGCCAAG CATAAGGTCTGCCGAAGCCTTGGCGTTCTCAGACTGCCGGCTGCACATCTGCC TGT | 292 |
| CCL3/NM_002983 | TCATAGCTGACTACTTTGAGACGAGCAGCCAGTGCTCCAAGCCCGGTGTCATC TTCCTAACCAAGCGAAGCCGGCAGGTCTGTGCTGACCCCAGTGAGGAGTGGG | 293 |
| CCL18/NM_002988 | TATTCTGAAACCAGCCCCCAGTGCCCCAAGCCAGGTGTCATCCTCCTAACCAA GAGAGGCCGGCAGATCTGTGCTGACCCCAATAAGAAGTGGGTCCA | 294 |
| IL7R/NM_002185 | TTAATACATCACACTTGCAAAAGAAGTATGTAAAAGTTTTAATGCACGATGTA GCTTACCGCCAGGAAAAGGATGAAAACAAATGGACGCATGTGAATTTATCCAG C | 295 |
| HLA-DRB1/NM_0021424 | ACAGGATTCCTGAGCTGAAATGCAGATGACCACATTCAAGGAAGAACTTTCTG CCCCGGCTTTGCAGGATGAAAAGCTTTCCTGCTTGGCAGTTATTCTTCCACA | 296 |
| CEACAM8/NM_001816 | GTGAAATACAGAACCCAGCGAGTGCAAACTTCAGTGACCCAGTCACCCTGAAT GTCCTCTATGGCCCAGATGCCCCCACCATTTCCCCTTCAGACACCTATT | 297 |
| CXCL10/NM_001565 | AATTTACTGAAAGCAGTTAGCAAGGAAAGGTCTAAAAGATCTCCTTAAAACCA GAGGGGAGCAAAATCGATGCAGTGCTTCCAAGGATGGACCACACAGAGGCTG | 298 |
| CCL2/NM_002982 | GCAAGTGTCCCAAAGAAGCTGTGATCTTCAAGACCATTGTGGCCAAGGAGATC TGTGCTGACCCCAAGCAGAAGTGGGTTCAGGATTCCATGGACCACCTGGAC | 299 |
| SRGN/NM_002727 | TGCCTTGAAGAAAAAGGACCAATGTTCGAACTACTTCAGGTGAATCCAACAA GATCCCCCGTCTGAGGACTGACCTTTTTCCAAAGACGAGAATCCA | 300 |
| CD19/NM_001178098 | TGGGGGGCTTCTACCTGTGCCAGCCGGGGCCCCCCTCTGAGAAGGCCTGGCAG CCTGGCTGGACAGTCAATGTGGAGGGCAGCGGGGAGCTGTTCCGGTGGAATGT TTCGGACCTAGGTGGCCTGGGCTGTGGCCTGAAGAACAGGTCCTCAGAGGGCC CCAGCTCCCCTTCCGGGAAGCTCATGAGCCCCAAGCTGTATGTGTGGGCCAAA GACCGCCCTGAGATCTGGGAGGGAGAGCCTCCGTGTCTCCCACCGAGGGACAG CCTGAACCAGAGCCTCAGCCAGGACCTCACCATGGCCCCTGGCTCCACACTCT | 301 |

TABLE 1-continued genes and amplicon insert sequences of the immune response assay

| Gene/Accession | Amplicon Sequence | SEQ ID NO: |
|---|---|---|
| | GGCTGTCCTGTGGGGTACCCCCTGACTCTGTGTCCAGGGGCCCCCTCTCCTGG<br>ACCCATGTGCACCCCAAGGGGCCTAAGTCATTGCTGAGCCTAGAGCTGAAGGA<br>CGATCGCCCGGCCAGAGATATGTGGGTAATGGAGACGGGTCTGTTGTTGCCCC<br>GGGCCACAGCTCAAGACGCTGGAAAGTATTATTGTCACCGTGGCAACCTGACC<br>ATGTCATTCCACCTGGAGATCACTGCTCGGCCAGTACTATGGCACTGGCTGCT<br>GAGGACTGGTGGCTGGAAGGTCTCAGCTGTGACTTTGGCTTATCTGATCTTCT<br>GCCTGTGTTCCCTTGTGGGCATTCTTCATCTTCAAAGAGCCCTGGTCCTGAGG<br>AGGAAAAGAAAGCGAATGACTGACCCCACCAGGAGATTCTTCAAAGTGACGCC<br>TCCCCAGGAAGCGGGCCCCAGAACCAGTACGGGAACGTGCTGTCTCTCCCCA<br>CACCCACCTCAGGCCTCGGACGCGCCCAGCGTTGGGCCGCAGGCCTGGGGGGC<br>ACTGCCCCGTCTTATGGAAACCGAGCAGCGACGTCCAGGCGGATGGAGCCTT<br>GGGGTCCCGGAGCCCGCCGGGAGTGGGCCCAGAAGAAGAGGAAGGGGAGGGCT<br>ATGAGGAACCTGACAGTGAGGAGGACTCCG | |
| ITGB1/NM_002211 | CTCAATGAAAGACGATTTGGAGAATGTAAAAAGTCTTGGAACAGATCTGATGA<br>ATGAAATGAGGAGGATTACTTCGGACTTCAGAATTGGATTTGGCT | 302 |
| IFITM1/NM_003641 | CGTGAAGTCTAGGGACAGGAAGATGGTTGGCGACGTGACCGGGGCCCAGGCCT<br>ATGCCTCCACCGCCAAGTGCCTGAACATCTGGGCCCTGATTCTGGGC | 303 |
| CCL21/NM_002989 | AAGGGCTCCAAAGGCTGCAAGAGGACTGAGCGGTCACAGACCCCTAAAGGGCC<br>ATAGCCCAGTGAGCAGCCTGGAGCCCTGGAGACCCCACCAGCCTCACCAGCGC<br>T | 304 |
| MRC1/NM_002438 | GGAACCACAGACAATCTGTGCTCCAGAGGTTATGAAGCCATGTATACGCTACT<br>AGGCAATGCCAATGGAGCAACCTGTGCATTCCCGTTCAAGTTTGAAAACAAG | 305 |
| PGF/NM_002632 | GCCCATCCTGTGTCTCCCTGCTGCGCTGCACCGGCTGCTGCGGCGATGAGAAT<br>CTGCACTGTGTGCCGGTGGAGACGGCCAATGTCACCATGCAGCTCCT | 306 |
| ITGAL/NM_002209 | CCAGAACACCTATCTGAGTGGCCTGTGTTACCTCTTCCGCCAGAATCTGCAGG<br>GTCCCATGCTGCAGGGGCGCCCTGGTTTTCAGGAATGTATCAAGGGCAAC | 307 |
| ID2/NM_002166 | TGTGGCTGAATAAGCGGTGTTCATGATTTCTTTTATTCTTTGCACAACAACAA<br>CAACAACAAATTCACGGAATCTTTTAAGTGCTGAACTTATTTTTCAA | 308 |
| CD22/NM_001771 | CGTGGGCCCGGGAAGGTCGGAAGAAGTGTTCCTGCAAGTGCAGTATGCCCCGG<br>AACCTTCCACGGTTCAGATCCTCCACTCACCGGCTGTGGAGGGAAGTCAAGTC<br>G | 309 |
| CCL17/NM_002987 | TCTGAGGACTGCTCCAGGGATGCCATCGTTTTTGTAACTGTGCAGGGCAGGGC<br>CATCTGTTCGGACCCCAACAACAAGAGAGTGAAGAATGCAGTTAAATACCTGC | 310 |
| ITGAE/NM_002208 | ATATCTTTCAACAAATCTCTATATGAGGGACTGAATGCAGAGAACCACAGAAC<br>TAAGATCACTGTCGTCTTCCTGAAAGATGAGAAGTACCATTCTTTGCCTATCA | 311 |
| IL3RA/NM_002183 | GACCTGGGACCTTAACAGAAATGTGACCGATATCGAGTGTGTTAAAGACGCCG<br>ACTATTCTATGCCGGCAGTGAACAATAGCTATTGCCAGTTTGGAGCA | 312 |
| CCR7/NM_001838 | AGGTATGCCTGTGTCAAGATGAGGTCACGGACGATTACATCGGAGACAACACC<br>ACAGTGGACTACACTTTGTTCGAGTCTTTGTGCTCCAAGAAGGACGTGCGG | 313 |
| CD1C/NM_001765 | TATGGTTTAAGAAGCACTGCTCATATCAGGACATCCTGTGAGACTCTTCCCCC<br>TGACTCCCCCATTGTGTTAAGAACCCAGCAACCCAGGAGCCTAGTACAATA | 314 |
| MAD2L1/NM_002358 | TCCCTGGCCATGGCGCTGCAGCTCTCCCGGGAGCAGGGAATCACCCTGCGCGG<br>GAGCGCCGAAATCGTGGCCGAGTTCTTCTCATTCGGCATCAACAGCATTTTAT | 315 |
| PYGL/NM_002863 | GCAGCCTATGGATACGGCATTCGGTATGAATATGGGATTTTCAATCAGAAGAT<br>CCGAGATGGATGGCAGGTAGAAGAAGCAGATGATTGGCTCAGATATGGAAACC<br>CTTGG | 316 |
| CD40/NM_001250 | CACACTGCCACCAGCACAAATACTGCGACCCCAACCTAGGGCTTCGGGTCCAG<br>CAGAAGGGCACCTCAGAAACAGACACCATCTGCACCTGTGAAGAAGGCTGGCA<br>C | 317 |
| LY9/NM_002348 | ATCACCCCAACCTCACATGCACAGCCAGCAACCCTGTCAGCAGGAGTTCCCAC<br>CAGTTTCTTTCTGAGAACATCTGTTCAGGACCTGAGAGAAACACAAAG | 318 |
| HLA-G/NM_002127 | GCAGACCCTGCGCGGCTACTACAACCAGAGCGAGGCCAGTTCTCACACCCTCC<br>AGTGGATGATTGGCTGCGACCTGGGGTCCGACGGACGCCTCCTCCGCGGGTAT<br>GAACAGTATGCCTACGATGGCAAGGATTACCTCGCCCTGAACGAGGACCTGCG<br>CTCCTGGACCGCAGCGGACACTGCGGCTCAGATCTCCAAGCGCAAGTGTGAGG<br>CGGCCAATGTGGCTGAACAAAGGAGAGCCTACCTGGAGGGCACGTGCGTGGAG | 319 |

TABLE 1-continued genes and amplicon insert sequences of the immune response assay

| Gene/ Accession | Amplicon Sequence | SEQ ID NO: |
|---|---|---|
| | TGGCTCCACAGATACCTGGAGAACGGGAAGGAGATGCTGCAGCGCGCGGACCC CCCCAAG | |
| TLR3/NM_003265 | TTGAACTAGAAGCAATTGTTAACAGCATCAAAAGAAGCAGAAAAATTATTTTT GTTATAACACACCATCTATTAAAAGACCCATTATGCAAAAGATTCAAGG | 320 |
| CD48/NM_001778 | GCAGCAAGAATGGCACGGTCTGCCTCAGTCCACCCTGTACCCTGGCCCGGTCC TTTGGAGTAGAATGGATTGCAAGTTGGCTAGTGGTCACGGTGCCCACCAT | 321 |
| STAT5A/NM_003152 | GGAGTACCACCAAGCCACGGGCACCCTCAGTGCCCACTTCAGGAACATGTCAC TGAAGAGGATCAAGCGTGCTGACCGGCGGGGTGCAGAGTCCGTGACAGAGG | 322 |
| FCRLA/NM_001184866 | CAAAAGGCAGACAGCGGGCACTACCACTGCAGTGGCATCTTCCAGAGCCCTGG TCCTGGGATCCCAGAAACAGCATCTGTTGTGGCTATCACAGTCCAAGAACTG | 323 |
| BCL6/NM_001706 | CACTCTGGAGAGAAGCCCTACAAATGCGAAACCTGCGGGAGCCAGATTTGTACA GGTGGCCCACCTCCGTGCCCATGTGCTTATCCACACTGGTGAGAAGCCCTATC C | 324 |
| ZEB1/NM_001174093 | CCCCAGGTGTAAGCGCAGAAAGCAGGCGAACCCGCGGCGCAATAACGTTACAA ATTATAATACTGTGGTAGAAACAAATTCAGATTCAGATGATGAAGACA | 325 |
| CCL5/NM_002985 | ACTGCCCTCTGCGCTCCTGCATCTGCCTCCCCATATTCCTCGGACACCACACC CTGCTGCTTTGCCTACATTGCCCGCCCACTGCCCCGTGCCCACATCAAGGAGT ATT | 326 |
| IDO1/NM_002164 | CTGGCCAGCTTCGAGAAAGAGTTGAGAAGTTAAACATGCTCAGCATTGATCAT CTCACAGACCACAAGTCACAGCGCCTTGCACGTCTAGTTCTGGGATGC | 327 |
| IL18/NM_001562 | CAGCTTCGGGAAGAGGAAAGGAACCTCAGACCTTCCAGATCGCTTCCTCTCGC AACAAACTATTTGTCGCAGGAATAAAGATGGCTGCTGAACCAGTAGAAGACAA | 328 |
| TNFRSF9/NM_001561 | GTTGTTAAACGGGGCAGAAAGAAACTCCTGTATATATTCAAACAACCATTTAT GAGACCAGTACAAACTACTCAAGAGGAAGATGGCTGTAGCTGCCGATTTCC | 329 |
| HIF1A/NM_001530 | GGTGGATATGTCTGGGTTGAAACTCAAGCAACTGTCATATATAACACCAAGAA TTCTCAACCACAGTGCATTGTATGTGTGAATTACGTTGTGAGTGGTATT | 330 |
| HLA-DPB1/NM_002121 | GGTGCTGCTCACATCTGTGGTCCAGGGCAGGGCCACTCCAGAGAATTACCTTT TCCAGGGACGGCAGGAATGCTACGCGTTTAATGGGACACAGCGCTTCCTGGA | 331 |
| FOXO1/NM_002015 | AAGGATAAGGGTGACAGCAACAGCTCGGCGGGCTGGAAGAATTCAATTCGTCA TAATCTGTCCCTACACAGCAAGTTCATTCGTGTGCAGAATGAAGGAACTGGA | 332 |
| CD33/NM_001772 | CTTCTTTCGGATGGAGAGAGGAAGTACCAAATACAGTTACAAATCTCCCCAGC TCTCTGTGCATGTGACAGACTTGACCCACAGGCCCAAAATCCTCATCCCTGGC | 333 |
| S100A9/NM_002965 | TCTGCAAAATTTTCTCAAGAAGGAGAATAAGAATGAAAAGGTCATAGAACACA TCATGGAGGACCTGGACACAAATGCAGACAAGCAGCTGAGCTTCGAGGAGTTC | 334 |
| HLA-DMB/NM_002118 | GGGGCTCCTGAGCCCATCCTTCGGGACTGGACACCTGGGCTGTCCCCATGCA GACCCTGAAGGTTTCTGTGTCTGCAGTGACTCTGGGCCTGGGCCTCATCATCT TC | 335 |
| HLA-A/NM_002116 | ACACGGAATGTGAAGGCCCAGTCACAGACTGACCGAGTGGACCTGGGGACCCT GCGCGGCTACTACAACCAGAGCGAGGCCGGTTCTCACACCATCCAGA | 336 |
| SNAI2/NM_003068 | TACCTTGTGTTTGCAAGATCTGCGGCAAGGCGTTTTCCAGACCCTGGTTGCTT CAAGGACACATTAGAACTCACACGGGGAGAAGCCTTTTTCTTGCCCTCACTG | 337 |
| TNFRSF17/NM_001192 | TATTTTGACAGTTTGTTGCATGCTTGCATACCTTGTCAACTTCGATGTTCTTC TAATACTCCTCCTCTAACATGTCAGCGTTATTGTAATGCAAGTGTGACCAAT | 338 |
| LRP1/NM_002332 | GGCCCAATGGGCTAAGCCTGGACATCCCGGCTGGGCGCCTCTACTGGGTGGAT GCCTTCTACGACCGCATCGAGACGATACTGCTCAATGGCACAGACCGGAAGAT | 339 |
| MAGEA4/NM_001011548 | CGCAGCTTGAGACTGCGGAGGGAAGCCCGCCCAGGCTCTATAAGGAGACAAG GTTCTGAGCAGACAGGCCAACCGGAGGACAGGATTCCCTGGAGGCCACAGAGG AGCACCAAGGAGAAGATCTGCCTGTGGGTCCCCATTGCCCAGCTTTTGCCTGC ACTCTTGCC | 340 |
| HLA-DQA1/NM_002122 | TTCCTCCCTTCTGCTGATGAGATTTATGACTGCAAGGTGGAGCACTGGGGCCT GGACCAGCCTCTTCTGAAACACTGGGAGCCTGAGATTCCAGCCCCTATGTCAG AGCTCACAGAGACTGTGGTCTGTGCCCTGGGGTTGTCTGTGGGCCTCATGGGC | 341 |

TABLE 1-continued genes and amplicon insert sequences of the immune response assay

| Gene/Accession | Amplicon Sequence | SEQ ID NO: |
|---|---|---|
| | ATTGTGGTGGGCACTGTCTTCATCATCCAAGGCCTGCGTTCAGTTGGTGCTTC CAGACACCAAGGGCCATTGTGAATCCCATCCTGGAAGGGAAGGTGCATCGCCA TCTACAGGAGCAGAAGAATGGACTTGCTAAATGACCTAGCACTATTCTCTGGC CCGATTTATCATATCCCTTTTCTCCTC | |
| CD1D/NM_001766 | GGCCTCCTTGAGTCAGGGAAGTCGGAACTGAAGAAGCAAGTGAAGCCCAAGGC CTGGCTGTCCCGTGGCCCCAGTCCTGGCCCTGGCCGTCTGCTGCTGGTGTGCC A | 342 |
| RPS6/NM_001010 | ATGAGAAGCGTATGGCCACAGAAGTTGCTGCTGACGCTCTGGGTGAAGAATGG AAGGGTTATGTGGTCCGAATCAGTGGTGGGAACGACAAACAAGGTTTCCCCA | 343 |
| MKI67/NM_002417 | CTCTTCTGACCCTGATGAGAAAGCTCAAGATTCCAAGGCCTATTCAAAAATCA CTGAAGGAAAAGTTTCAGGAAATCCTCAGGTACATATCAAGAATGTCAAAGA | 344 |
| GZMK/NM_002104 | GTATGGCGGACATCACGTTTGTGGAGGTGTTCTGATTGATCCACAGTGGGTGC TGACAGCAGCCCACTGCCAATATCGGTTTACCAAAGGCCAGTCTCCCACTGTG GT | 345 |
| CD79A/NM_001783 | GATGCCTGGGGGTCCAGGAGTCCTCCAAGCTCTGCCTGCCACCATCTTCCTCC TCTTCCTGCTGTCTGCTGTCTACCTGGGCCCTGGGTGCCAGGCCCTGTGGATG | 346 |
| CD37/NM_001774 | ACCATCCAAAAGTACGGCACCAACCCCGAGGAGACCGCGGCCGAGGAGAGCTG GGACTATGTGCAGTTCCAGCTGCGCTGCTGCGGCTGGCACTACCCGCAGGACT GGT | 347 |
| FUT4/NM_002033 | GCAGTGGTATAGCATATCCTCACATTTCTAGTGCCCTTGAGACTGTGCTATGG AACCAATCTTGAACATACATGCATTGACTTGACAAGTTACTGAGTAAGCAGCA TA | 348 |
| AIF1/NM_001623 | TGACTTTCTCAGGATGATGCTGGGCAAGAGATCTGCCATCCTAAAAATGATCC TGATGTATGAGGAAAAAGCGAGAGAAAAGGAAAAGCCAACAGGCCCCCCAGCC | 349 |
| CCR1/NM_001295 | ACCAGAGAGAAGCCGGGATGGAAACTCCAAACACCACAGAGGACTATGACACG ACCACAGAGTTTGACTATGGGGATGCAACTCCGTGCCAGAAG | 350 |
| PRDM1/NM_001198 | CAAGGAATCTGCTTTTCAAGTATGCCACCAACAGTGAAGAGGTTATTGGAGTG ATGAGTAAAGAATACATACCAAAGGGCACACGTTTTGGACCCCTAATAGGT | 351 |
| CD47/NM_001777 | CTACAGGGATATTAATATTACTTCACTACTATGTGTTTAGTACAGCGATTGGA TTAACCTCCTTCGTCATTGCCATATTGGTTATTCAGGTGATAGCCTATATCC | 352 |
| CD74/NM_001025159 | AAGCCCACTGACGCTCCACCGAAAGTACTGACCAAGTGCCAGGAAGAGGTCAG CCACATCCCTGCTGTCCACCCGGGTTCATTCAGGCCCAAGTGCGACGAGAACG GCA | 353 |
| LAG3/NM_002286 | GGATGTGAGCCAGGCCCAGGCTGGGACCTACACCTGCCATATCCATCTGCAGG AACAGCAGCTCAATGCCACTGTCACATTGGCAATCATCACAGTGACTCCCAAA TC | 354 |
| TNFRSF4/NM_003327 | CCTCAGAAGTGGGAGTGAGCGGAAGCAGCTGTGCACGGCCACACAGGACACAG TCTGCCGCTGCCGGGCGGGCACCCAGCCCCTG | 355 |
| CD2/NM_001767 | TCAATATATGATACAAAAGGAAAAAATGTGTTGGAAAAAATATTTGATTTGAA GATTCAAGAGAGGGTCTCAAAACCAAAGATCTCCTGGACTTGTATCAAC | 356 |
| CCL4/NM_002984 | GCTGCCTTCTGCTCTCCAGCGCTCTCAGCACCAATGGGCTCAGACCCTCCCAC CGCCTGCTGCTTTTCTTACACTGCGAGGAAGCTTCCTCGCAACTTT | 357 |
| BAGE/NM_182482 | GGCCTGAGCGGTAGGAGTGGGGCTGGAGCAGTAAGATGGCGGCCAGAGCGGTT TTTCTGGCATTGTCTGCCCAGCTGCTCCAAGCCAGGCTGATGAAGGAGGAGTC CCCTGTGGTGA | 358 |
| LEXM/NM_001110533 | CTCCAAGGGGTCAGGTGCAAAGGCCTGCCAGATGATTATGGGAAGCTGGAACC CAGTAGGTGTGGGCCGCTACCTCAACACCTGGCTGATGGAGACAAAGG | 359 |
| CCR6/NM_004367 | TTTCTACAACCAGCTTGCATTTTTTCTGCCCACAATGAGCGGGGAATCAATGA ATTTCAGCGATGTTTTCGACTCCAGTGAAGATTATTTTG | 360 |
| CD70/NM_001252 | GCATCCAGCGCTTCGCACAGGCTCAGCAGCAGCTGCCGCTCGAGTCACTTGGG TGGGACGTAGCTGAGCTGCAGCTGAATCACACAGGACCTCAGCAGGACCCC | 361 |
| CDK1/NM_001786 | GGTGACTGATGATCTAAGTTTCCCGAGGTTTCTCAGAGCCTCTCTGGTTCTTT CACTGGTGACCAGCCAGCCCCTCCTCTTTCTTCCTCCGGTGCTGGCGGAAGAG CCCCC | 362 |
| CTAG1B/NM_001327 | GCTGCAGATGCGGGGCCAGGGGGCCGGAGAGCCGCCTGCTTGAGTTCTACCTC GCCATGCCTTTCGCGACACCCATGGAAGCAGAGCTGGCCCGCAGGAGCCTGGC | 363 |

TABLE 1-continued genes and amplicon insert sequences of the immune response assay

| Gene/Accession | Amplicon Sequence | SEQ ID NO: |
|---|---|---|
| | CCAGGATGCCCCACCGCTTCCCGTGCCAGGGGTGCTTCTGAAGGAGTTCACTG TGTCCGGCAACATACTGACTATCCGACTGACTGCTGCAGACCACCGCCAACTG CAGCTCTCCATCAGCTCCTGTCTCCAGCAGCTTTC | |
| CTAG2/NM_020994 | CTCTCCCCCGACCAGGGGCGGTTCTGAAGGACTTCACCGTGTCCGGCAACCTA CTGTTTATGTCAGTTCGGGACCAGGACAGGGAAGGCGCTGGGCGGATGAGGGT GGTGGGTTGGGGGCTGGGATCCGCCTCCCCGGAGGGGCAGAAAGCTAGAGATC TCAGAACACCCAAACACAAGGTCTCAGAACAGAGACCTGGTACACCAGGCCCG CCGCCACCCGAGGGAGCCCAGGGAGATGGGTGCAGAGGTGTCGCCTTTAATGT GATGTTCTCTGCCCCTCACATTTAGCCGACTGACTGCTGCAGACCACCGCCAA CTGCAGCTCTCCATCAGCTCCTGTCTCCAGCAGCTTTC | 364 |
| CX3CR1/NM_001171174 | GCTGACTGCAGGGCCTGCTCCCTGCCCCCCACCTCCAGGTTGGGGCCTTCACC ATGGATCAGTTCCCTGAATCAGTGACAGAAAACTTTGAGTACGATGATTTGG | 365 |
| CX3CR1/ENST00000541347 | GTGGCTGACTGGCAGATCCAGAGGTTCCCTTGGCAGTCCACGCCAGGCCTTCA CCATGGATCAGTTCCCTGAATCAGTGACAGAAAACTTTGAGTACGATGATTTG G | 366 |
| CX3CR1/ENST00000435290 | GCGTTTAAGTTGGCAGACTTGGATTTCAGGAAGAGCTCTCTGGCTTCTGGGTG GAGAATGGCCAGTGGGGCCTTCACCATGGATCAGTTCCCTGAATCAGTGACAG AAAACTTTGAGTACGATGATTTGG | 367 |
| CX3CR1/ENST00000399220 | CTCGGAACACCACAGCGACTAGAGGCCTTCACCATGGATCAGTTCCCTGAATC AGTGACAGAAAACTTTGAGTACGATGATTTGG | 368 |
| GAGE1,GAGE12I,GAGE12F/NM_001040663 | ACCTATTATCGGCCTAGACCAAGACGCTACGTAGAGCCTCCTGAAATGATTGG GCCTATGCGGCCCGAGCAGTTCAGTGATGAAGTGGAACCAGCAACACCTGAAG AAGGGGAACC | 369 |
| GAGE12J/NM_001098406 | ACCTATTATCGGCCTAGACCAAGACGCTACGTAGAGCCTCCTGAAATGATTGG GCCTATGCGGCCCGAGCAGTTCAGTGATGAAGTGGAACCAGCAACACCTGAAG AAGGGGAACC | 370 |
| GAGE2C,GAGE2A,GAGE2E/NM_001472 | ACCTATTATCGGCCTAGACCAAGACGCTACGTAGAGCCTCCTGAAATGATTGG GCCTATGCGGCCCGAGCAGTTCAGTGATGAAGTGGAACCAGCAACACCTGAAG AAGGGGAACC | 371 |
| GAGE10/NM_001098413 | ACCTATTATCGGCCTAGACCAAGACGCTACGTAGAGCCTCCTGAAATGATTGG GCCTATGCGGCCCGAGCAGTTCAGTGATGAAGTGGAACCAGCAACACCTGAAG AAGGGGAACC | 372 |
| GAGE13/NM_001098412 | ACCTATTATCGGCCTAGACCAAGACGCTACGTAGAGCCTCCTGAAATGATTGG GCCTATGCGGCCCGAGCAGTTCAGTGATGAAGTGGAACCAGCAACACCTGAAG AAGGGGAACC | 373 |
| IKZE1/NM_006060 | GACATGTCCCAAGTTTCAGGGAAGGAAAGCCCCCCTGTAAGCGATACTCCAGA TGAGGGCGATGAGCCCATGCCGATCCCCGAGGACCTCTCCACCACCTCGGGAG GACAGC | 374 |
| IL17A/NM_002190 | CTCAGATTACTACAACCGATCCACCTCACCTTGGAATCTCCACCGCAATGAGG ACCCTGAGAGATATCCCTCTGTGATCTGGGAGGC | 375 |
| IL2/NM_000586 | CTTAATCAGCAATATCAACGTAATAGTTCTGGAACTAAAGGGATCTGAAACAA CATTCATGTGTGAATATGCTGATGAGACAGCA | 376 |
| IL21/NM_021803 | CTTCCACAAATGCAGGGAGAAGACAGAAACACAGACTAACATGCCCTTCATGT GATTCTTATGAGAAAAAACCACCCAAAGA | 377 |
| IL22/NM_020525 | GACGTTCGTCTCATTGGGGAGAAACTGTTCCACGGAGTCAGTATGAGTGAGCG CTGCTATCTGATGAAGCAGGTGCTGAACTTCAC | 378 |
| KIR2DL2/ENST00000344867 | CCATGTCGCTCATGGTCGTCAGCATGGCGTGTGTTGGGTTCTTCTTGCTGCAG GGGGCCTGGCCACATGAGGGAGTCCACAGAAAACCTTCCCTCCTGGCCCACCC AGGTCCCCTGGTGAAATCAGAAGAGACAGTCATCCTGCAATGTTGGTCAGATG TCAGGTTTGAGCACTTCCTTCTGCACAGAGAGGGGAAGTATAAGGACACTTTG CACCTCATTGGAGAGCACCATGATGGGGTCTCCAAGGCCAACTTCTCCATCGG TCCCATGATGCAAGACCTTGCAGGGACCTACAGATGCTACGGTTCTGTTACTC ACTCCCCCTATCAGTTGTCAGCTCCCAGTGACCCTCTGGACATCGTCATCACA GGTCTATATGAGAAACCTTCTCTCTCAGCCCAGCCGGGCCCCACGGTTTTGGC AGGAGAGAGCGTGACCTTGTCCTGCAGCTCCCGGAGCTCCTATGACATGTACC ATCTATCCAGGGAGGGGGAGGCCCATGAACGTAGGTTCTCTGCAGGGCCCAAG GTCAACGGAACATTCCAGGCCGACTTTCCTCTGGGCCCTGCCACCCACGGAGG AACCTACAGATGCTTCGGCTCTTTCCGTGACTCTCCCTATGAGTGGTCAAACT | 379 |

TABLE 1-continued genes and amplicon insert sequences of the immune response assay

| Gene/ Accession | Amplicon Sequence | SEQ ID NO: |
|---|---|---|
| | CGAGTGACCCACTGCTTGTTTCTGTCACAGGAAACCCTTCAAATAGTTGGCCT TCACCCACTGAACCAAGCTCCAAAACCGGTAAC | |
| KIR2DL3/NM_015868 | CTATGAGTGGTCAAACTCGAGTGACCCACTGCTTGTTTCTGTCACAGGAAACC CTTCAAATAGTTGGCCTTCACCCACTGAACCAAGCTCCAAAACCGGTAAC | 380 |
| MAGEA10/NM_021048 | TGGGACACCACAGAGCAGCACTGAAGGAGAAGACCTGCCTGTGGGTCCCCATC GCCCAAGTCCTGCCCACACTCCCACC | 381 |
| MIF/NM_002415 | TCCGAGCTCACCCAGCAGCTGGCGCAGGCCACCGGCAAGCCCCCCCAGTACAT CGCGGTGCACGTGGTCCCGGACCAGCTCATGGCCTTCGGCGGCTCCAGCGAGC CGTGCGC | 382 |
| PTPRCAP/ ENST00000326294 | TCACTTCTCGCTCGACACAGCCAGAGCTGGAGGTGGGTGCCCGGCACGGAGGG GCCTGCGGACCAATGGCTCTGCCCTGCACCTTAGGGCTCGGGATGCTGCTGGC CCTGCCAGGGGCCTTGGGCTCGGGTGG | 383 |
| SSX2/NM_003147 | CTCGGAGAAAATCTTCTATGTGTATATGAAGAGAAAGTATGAGGCTATGACTA AACTAGGTTTCAAGGCCACCCTCCCACCTTTCATGTGTAATAAACGGGCCGAA GACTTCCAGG | 384 |
| TCF7/NM_003202 | CTCTCTACGAACATTTCAACAGCCCACATCCCACCCCTGCACCTGCGGACATC AGCCAGAAGCAAGTTCACAGGCCTCTGCAGACCCCTGACCTCTCTGGCTTCTA CTCCCTGACCTCAGGC | 385 |
| XAGE1B/NM_001097594 | AGATAATACCTAAAGAGGAACACTGTAAAATGCCAGAAGCAGGTGAAGAGCAA CCACAAGTTTAAATGAAGACAAGCT | 386 |
| CEACAM8/NM_001816 | GTGAAATACAGAACCCAGCGAGTGCAAACTTCAGTGACCCAGTCACCCTGAAT GTCCTCTATGGCCCAGATGCCCCCACCATTTCCCCTTCAGACACCTATT | 387 |
| CXCR3/NM_001504 | CACCAAAGCAGAGGGGCAGGCAGCACACCACCCAGCAGCCAGAGCACCAGCCC AGCCATGGTCCTTGAGGTGAGTGACCACCAAGTGCTAAATGACGCCGAGGTTG CCGCCCTCCTGGAGAACTTCA | 388 |
| FCGR1A/NM_000566 | CCATTGCTCAGGCATGGGAAAGCATCGCTACACATCAGCAGGAATATCTGTCA CTGTGAAAGAGCTATTTCCAGCTCCAGTGCTGAATGCATCTGTGACATCCCC | 389 |
| FCGR3B/NM_000570 | AGCGGCTCCTACTTCTGCAGGGGGCTTGTTGGGAGTAAAAATGTGTCTTCAGA GACTGTGAACATCACCATCACTCAAGGTTTGGCAGTGTCAACCATCTCA | 390 |
| FYB/NM_001465 | CTGGAAACAGTACTAGCAAAGGCCAGACGTCTTACTCAACAACTTCCCTGCCA CCACCTCCACCATCCCATCCGGCCAGCCAACCACCATTGCCAGCATCTCAC | 391 |
| HLA-C/NM_002117 | GCAGCACGAGGGGCTGCAAGAGCCCCTCACCCTGAGCTGGGAGCCATCTTCCC AGCCCACCATCCCCATCATGGGCATCGTTGCTGGCCTGGCTGTCCTGGTTG | 392 |
| HLA-DQA2NM_020056 | AGGAAGGTGCATCACCATCTACAGGAGAAGAAGAATGGACTTGCTAAATGACC TAGCACTATTCTCTGGCCTGATTTATCATATCCCTTTTCTCCTC | 393 |
| IFNG/NM_000619 | GTGTGGAGACCATCAAGGAAGACATGAATGTCAAGTTTTTCAATAGCAACAAA AAGAAACGAGATGACTTCGAAAAGCTGACTAATTATTCGGTAACTGA | 394 |
| KIR2DL1/NM_014218 | CGCGGCTGCCTGTCTGCTCCGGCAGCACCATGTCGCTCTTGGTCGTCAGCATG GCGTGTGTTGGGTTCTTCTTGCTGCAGGGGGCCTGGCCACATGAGGGAGTCCA CAGAAAACCTTCCCTCCTGGCCCACCC | 395 |
| KRT5/NM_000424 | AACTTCATGAAGATGTTCTTTGATGCGGAGCTGTCCCAGATGCAGACGCATGT CTCTGACACCTCAGTGGTCCTCTCCATGGACAACAACCGCAACCTGGAC | 396 |
| LMNA/NM_170707 | AAGGAGCTGAAAGCGCGCAATACCAAGAAGGAGGGTGACCTGATAGCTGCTCA GGCTCGGCTGAAGGACCTGGAGGCTCTGCTGAACTCCAAGGAGGCCGCACTGA GC | 397 |
| PTPN11/NM_002834 | CTCCCGAGTGATTGTCATGACAACGAAAGAAGTGGAGAGAGGAAAGAGTAAAT GTGTCAAATACTGGCCTGATGAGTATGCTCTAAAAGAATATGGCGTCATGCGT G | 398 |

TABLE 2

| Gene/Accession | PRIMER1 | SEQ ID NO: | PRIMER2 | SEQ ID NO: |
|---|---|---|---|---|
| CD63/ NM_001780 | TTCCATGUCGAAGAACCGAGUC | 399 | GCAGCUACCACCAGCACAUT | 400 |
| CD69/ NM_001781 | CGTCAUGAAGGGTCCTUCCAA | 401 | ATGGCTGTCUGATGGCATUGA | 402 |
| CXCL1 NM_001511 | CAATCCTGCAUCCCCCAUAGT | 403 | TGTCTCTCTTTCCUCTTCTGTTCCUA | 404 |
| KLRD1 NM_002262 | GUGAACAGAAAACTGGAACGAAAGT | 405 | CGGTGTGCUCCTCACTGUAA | 406 |
| HLA-DOB NM_002120 | CCAUGACUCAAGGCACAGACT | 407 | TCCCCACAUCACTGUCGAAAC | 408 |
| CXCR5 NM_001716 | TCTCAACAUAAGACAGTGACCAGUCT | 409 | ACCAGGGAGGUGTCGTTAUAGT | 410 |
| IL12B NM_002187 | CTGGCCAGUACACCTGUCA | 411 | TCTTGGCCUCGCATCTUAGAAAG | 412 |
| PTK7 NM_002821 | GCAAACCCGGCUACTUGGA | 413 | CATCATACACCUCCACGCTGUT | 414 |
| CEACAM1 NM_001712 | TGTGGAATTAUCACCCATCATCAUCC | 415 | ACAAGATCUCCCAAGTCCTCCAUA | 416 |
| CXCL9 NM_002416 | TGUTCCTGCAUCAGCACCAA | 417 | GCTGAATCTGGGUTTAGACATGTTUGAA | 418 |
| IL13 NM_002188 | CAGCCCUGGAATCCCUGAT | 419 | AAACTGGGCCACCUCGATUT | 420 |
| NT5E NM_002526 | GAAATGGAUAAACTCATCGCUCAGAAAG | 421 | CCGCCCAUCATCAGAAGUGA | 422 |
| VEGFA NM_001171623 | CAGCTTGAGTUAAACGAACGTACTUG | 423 | CGGCAGCGUGGTTTCTGUA | 424 |
| ABCF1 NM_001025091 | CTGAGCAUCCCUCCCAACAT | 425 | TTGTTCCAGCUGTCCCUGAAG | 426 |
| CD38 NM_001775 | GGCCCAUCAGTUCACACAGG | 427 | CTGCAGTCCUUTCTCCAGUCT | 428 |
| JAML NM_001098526 | CUAGAGTGCUCGCAGCAGT | 429 | ACTGGCAGCAGGAUGAGUUC | 430 |
| S100A8 NM_002964 | GTCTACCACAAGUACTCCCTGAUAAAG | 431 | ACCATCAGTGUUGATATCCAACTCTTUG | 432 |
| MYC NM_002467 | GCTTCTCUGAAAGGCTCTCCUT | 433 | AAAUACGGCUGCACCGAGT | 434 |
| IRF1 NM_002198 | CCAGGCTACAUGCAGGACUT | 435 | GGGTGACACCUGGAAGTTGUA | 436 |
| CCL22 NM_002990 | TGGTTGTCCUCGTCCTCCUT | 437 | AGTCTGAGGUCCAGTAGAAGTGUT | 438 |
| CXCR2 NM_001557 | TGGAGGTGUCCTACAGGUGAAA | 439 | GGCAGGGUAGAGCTGTAACUG | 440 |
| IFIT1 NM_001548 | TGCAGAACGGCUGCCTAATUT | 441 | CAAGACTCTGTTUTCTAAATCAGGCAUT | 442 |
| IFIT2 NM_001547 | GCAGAAGAGGAAGAUUCUGAAGAGT | 443 | TCAAGTTCCAGGUGAAATGGCAUT | 444 |
| CD68 NM_001251 | CAGACAGCCUAGCTGGACUT | 445 | CGTGAAGGAUGGCAGCAAAGUA | 446 |
| M6PR NM_002355 | CTCCCAUCCCCAGAAGGGUAT | 447 | TCTGTCUGCCAGGATTCUCUCA | 448 |

TABLE 2-continued primer pair sequences of the immune response assay

| Gene/Accession | PRIMER1 | SEQ ID NO: | PRIMER2 | SEQ ID NO: |
|---|---|---|---|---|
| SH2D1A NM_002351 | ACCGAGUGUCCCAGACAGA | 449 | TCAACTGGATACUGCAGAGG TATUACA | 450 |
| ISG20 NM_002201 | GTCCACUGACAGGCTGTUGT | 451 | ATCGTTGCCCUCGCATCUT | 452 |
| GBP1 NM_002053 | GACTTTGUGTGGACACUGAGAGA | 453 | ATACAGAGTCUGGGCAGGTU AAAAG | 454 |
| TBP NM_003194 | GCGCAAGGGUTTCTGGTTUG | 455 | CCAGTGCCAUAAGGCATCAT UG | 456 |
| STAT6 NM_003153 | GCTGGACAGAGCUACAGACCUAT | 457 | GCCGCUGCACTTTTTCUGG | 458 |
| ID3 NM_002167 | CTCAGCTUAGCCAGGUGGAA | 459 | GAGATGACAAGUTCCGGAGU GA | 460 |
| CX3CL1 NM_002996 | ACGTGCAGCAAGAUGACAUCA | 461 | GTCCTTGACCCAUTGCTCCU T | 462 |
| KLRB1 NM_002258 | AGGGTUCACCTTGGCAUCAAT | 463 | TGCTCUGTTGAATGUCCACA CT | 464 |
| TNFSF4 NM_003326 | CGGTATCCUCGAATTCAAAGTA UCAAAGT | 465 | GAGATGAGAUAAAACCCATC ACAGTUGA | 466 |
| CD52 NM_001803 | CCTGAGATCACCUAAAAAGCTG CUA | 467 | TGGTTTGGCUGGTGTCGTUT | 468 |
| IL10RA NM_001558 | GTCTGTGTGGUTTGAAGCAGAA TTUT | 469 | GACAGGGTCUGGCTACAGUT | 470 |
| HLA-DOA NM_002119 | ACCACACGGACUGAGACTGAUT | 471 | GTCCGUAGGAGCCCATGUG | 472 |
| IFNB1 NM_002176 | TGTGCCUGGACCATAGUCAGA | 473 | AACAGCAUCTGCTGGTUGAA GA | 474 |
| CCR5 NM_001100168 | GGCCAGAAGAGCUGAGACAUC | 475 | GGCTGCGAUTTGCTUCACA | 476 |
| IKZF3 NM_012481 | AGTGGAAAGAUGAACTGCGAUGT | 477 | TGGCGGAGGAGGUTACCUT | 478 |
| STAT1 NM_007315 | CGATGGGCUCAGCTTUCAGA | 479 | ACAAAACCUCGUCCACGGAA T | 480 |
| CD6 NM_006725 | CAGAUGAGGAGGUCCAGCAAA | 481 | TGCTCCUCGGGTGATACUGA | 482 |
| BRCA1 NM_007300 | CUGAAAGCCAGGGAGTUGGT | 483 | CUTGTTTCACTCUCACACCC AGAT | 484 |
| CORO1A NM_007074 | TGTGCTGUCAACCCTAAGTTUG T | 485 | CAGGCGAUGTCUAGCACAGG | 486 |
| TBX21 NM_013351 | GGAUGCGCCAGGAAGTTCA | 487 | CTCTGGCUCTCCGTCGUT | 488 |
| KLRK1 NM_007360 | GTGGGAAGAUGGCTCCATUCT | 489 | ACACAGUCCTTTGCAUGCAG AT | 490 |
| CXCR6 NM_006564 | TCATCTCUGGAACAAACUGGCA AA | 491 | CTTGCTGAACUGCAGGAAGU C | 492 |
| PTEN NM_000314 | AGCGUGCAGATAAUGACAAGGA A | 493 | GATTTGACGGCUCCTCTACU GT | 494 |
| PMEL NM_006928 | CCUGGAACAGGCAGCTGUAT | 495 | TTCCAGGGAAGUTCAAGGCA AUAG | 496 |

TABLE 2-continued primer pair sequences of the immune response assay

| Gene/Accession | PRIMER1 | SEQ ID NO: | PRIMER2 | SEQ ID NO: |
|---|---|---|---|---|
| DMBT1 NM_007329 | ACTACTCCAGUCCCTCCAAUGAC | 497 | GCCGACACUCGTAGTAUCCAT | 498 |
| IFI44L NM_006820 | AAGTGGATGATUGCAGTGAGGUT | 499 | CAAATCUGAAGCATAGTTUCCAACCAT | 500 |
| LAPTM5 NM_006762 | TGACCCTCUGCAGCTCCUA | 501 | GACAGTGAUGAAGGCGAUGGA | 502 |
| CD226 NM_006566 | CGUCATCGTCAUCCCCGAT | 503 | CAGCCACAAAGAGGGUATATTGGTUA | 504 |
| TNFSF13B NM_006573 | GATCTTACACATUTGTTCCATGGCUT | 505 | GATGTCCCAUGGCGUAGGT | 506 |
| ICOS NM_012092 | CTTGGACCAUTCTCAUGCCAAC | 507 | GCACAUCCTATGGGUAACCAGAA | 508 |
| CD160 NM_007053 | AGAGCCAACAUTTGCTTCAAGTUC | 509 | GGAAGCUGAGCTGGTGAUGT | 510 |
| TRIM29 NM_012101 | TGCAUGTCCAGGAGCACAA | 511 | CTTCTCCTTCUGCCACTTCUCA | 512 |
| LST1 NM_007161 | ATGAGGAACUGAGGCAAGUCA | 513 | CCAGGCCCCGUAGATACATAUA | 514 |
| ZBTB46 NM_025224 | CGGCGCUCATGAGUAAGAACA | 515 | CGGACACUGAACTTCTTCCUGAT | 516 |
| VTCN1 NM_024626 | CUGGTTGTGAGUCACCAAGGAA | 517 | TGCAAUGCUCCAGCCAGAA | 518 |
| KREMEN1 NM_032045 | ACAGUCACAGCCATTGUAGCA | 519 | GGAAATTGAAGUGGAAGGCTTGUAAA | 520 |
| PDCD1LG2 NM_025239 | TGAGCCUGGAATTGCAGCUT | 521 | TGGCTGTTATUGCTCCAAGGUT | 522 |
| TUBB NM_178014 | CTCTGTTCGCUCAGGTCCTUT | 523 | GCCTCCUTCCGUACCACAT | 524 |
| CLEC4C NM_130441 | TCCCAAGUGCAACCTCTGUC | 525 | GGTGCAGAAGCUCTTGTAUCACT | 526 |
| CD86 NM_175862 | CACTATGGGACUGAGTAACATTCTCUT | 527 | CTAGCTCACUCAGGCTTGGT | 528 |
| HAVCR2 NM_032782 | CTACTGCUGCCGGAUCCAAA | 529 | TGTCCCCUGGTGGUAAGCA | 530 |
| GZMH NM_033423 | GGCCTTTGUTCAGTTTCUGCAA | 531 | GTCCGCTCCUGTTCCTTGAUAT | 532 |
| NFATC1 NM_172387 | CCCCTATUCCTGTAACGGUCAA | 533 | GCATACCCCUGCTGAACUGAG | 534 |
| CD8B NM_172213 | CGGAAGACAGUGGCATCTACUT | 535 | GTAACCGGCACACUCTCTUCT | 536 |
| BCL2 NM_000633 | GTGGATGACUGAGTACCUGAACC | 537 | GGCCAAACUGAGCAGAGTCUT | 538 |
| GADD45GIP1 NM_052850 | CGAAUGGUACCCGAGCCT | 539 | GCTGCCAGUCACAATCATCUG | 540 |
| CBLB NM_170662 | GCGTGTCUCTGGACAGCUA | 541 | GGGTCCAACUGCATCCUGAA | 542 |
| ITGA1 NM_181501 | CCAGACTAUGACAGCTCTTGGAAUA | 543 | CTTGGATGACCUTCTTCAGUCGAT | 544 |

TABLE 2-continued primer pair sequences of the immune response assay

| Gene/ Accession | PRIMER1 | SEQ ID NO: | PRIMER2 | SEQ ID NO: |
|---|---|---|---|---|
| CD8A NM_171827 | GAACCGAAGACGUGTTUGCAAAT | 545 | GGAAGGACUTGCTCCCUCAAA | 546 |
| IL2RA NM_000417 | GGAAGATGGAUCATACCTGCTGAUG | 547 | AGTTCAACATGGUTCCTTCCTTGUAG | 548 |
| EIF2AK2 NM_001135651 | TGGCGGUCTTCAGAAUCAACAT | 549 | GCTTCTGACGGUATGTATTAAGTUCCT | 550 |
| MADCAM1 NM_130760 | CACGCAGGGAGAAGUGAUCC | 551 | GCAGCGTTUCCAGAGGTGAUA | 552 |
| PTPN6 NM_080548 | GTCGGAGUACGGGAACAUCAC | 553 | GCTGACCGCUGCTTCTUCA | 554 |
| LRG1 NM_052972 | AGAGCTACCAUGTCCTCTUGGA | 555 | CGGAACACCUGGCAGTCTUT | 556 |
| ADGRE5 NM_078481 | CTGGGTCTUTGGCCTGTUCA | 557 | GGCCCACUTCCGGTATUCT | 558 |
| SH2D1B NM_053282 | ACCAAGCAAGACUGUGAGACC | 559 | GTGTTTCTCUGAAGATTCGGTAUGT | 560 |
| ITGB2 NM_000211 | GCTGGGCUTCACGGACAUAG | 561 | TTTTCCCAATGUAGCCAGTGUCA | 562 |
| HLA-DPA1 NM_033554 | GCGCCCUGAAGACAGAAUGT | 563 | CCTGTTGGTCUATGCGTCTGUA | 564 |
| DGAT2 NM_032564 | CTTCTCTGUCACCTGGCUCAAT | 565 | GCGAUGAGCCAGCAAUCAG | 566 |
| IGF1R NM_000875 | CTACGTGAAGAUCCGCCAUCT | 567 | TGGTCCCAGUCCCACAGUT | 568 |
| TAGAP NM_054114 | CCAUCTGCATGGACCCAACA | 569 | GCACUGGAATGTTCUCCCCAAA | 570 |
| LMNA NM_170707 | TGAACTCTCCCUATGTGTGGTCUT | 571 | CCGACAUCAGAGACACACUGG | 572 |
| NCAM1 NM_181351 | TGTGGACAUCACCTGCTACTUC | 573 | ATGGGCTCCUTGGACTCAUC | 574 |
| TIGIT NM_173799 | GTCGCUGACCGTGAACGAUA | 575 | ATGGCUCCAAGCAATGGAAUCT | 576 |
| IL17F NM_052872 | GCAUACACAGGAAGATACAUCACAGA | 577 | TGCCGCCUCACUCAGAAAG | 578 |
| HLA-F-AS1 NR_026972 | ACUGAAGCGACAAGGTGUGT | 579 | CATCTGGTTCUCCCTGGTTCUT | 580 |
| CD247 NM_198053 | CUGAGGGAAAGGACAAGAUGAAGT | 581 | TGACACCATAGAUGAAGAGGATUCCA | 582 |
| CD79B NM_001039933 | CAACAACACCUCGGAGGTCUA | 583 | GGCACGAUGATGAAGAGGAUGAT | 584 |
| IDO2 NM_194294 | CAATTGATTGAUGCTCACCAGCUT | 585 | CCUCTCCTTCCUGCCAGACA | 586 |
| IL4 NM_000589 | GCACAAGCAGCUGAUCCGA | 587 | CTCTCTCATGAUCGTCTTTAGCCTUT | 588 |
| TYROBP NM_198125 | ACTGAGACCGAGUCGCCUA | 589 | GGCUCAGGAATGGCUGGAT | 590 |
| BTLA NM_181780 | GACATTGCCUGCCATGCUT | 591 | TCTCCTGCUAAGATGGAGTGTUCA | 592 |

TABLE 2-continued primer pair sequences of the immune response assay

| Gene/ Accession | PRIMER1 | SEQ ID NO: | PRIMER2 | SEQ ID NO: |
|---|---|---|---|---|
| AKT1 NM_001014431 | CCATGAGCGACGUGGCTAUT | 593 | CTCACGTUGGTCCACAUCCT | 594 |
| IL2RG NM_000206 | TGCAUGGAAGCCGTGGUT | 595 | AAAAGTTCCCGUGGTATTCA GUAACA | 596 |
| POLR2A NM_000937 | TGGTGGACAAGAUGGATGATGA UG | 597 | CCTCCGTGAUGATGATCTTC TTCUT | 598 |
| ITGAX NM_000887 | CCAACATCUGCCTTTACATUGA CAAAC | 599 | GGCTCAGACUCCGGTTCTUT | 600 |
| IL1B NM_000576 | CCTGTCCUGCGTGTUGAAAGA | 601 | GGGAACUGGGCAGACTCAAA UT | 602 |
| CSF2RB NM_000395 | CGUCTCTGTUCAGCCAAGGAG | 603 | TGGTCTATGTGUCGTATCG CATUT | 604 |
| DDX58 NM_014314 | CCCAACCGAUATCATTTCTGAT CUGT | 605 | TTGGGCCAGUTTTCCTTGUC T | 606 |
| KIAA0101 NM_014736 | CCCAACUCCCAAGUGGCAAA | 607 | TGUGATCAGGTUGCAAAGGA CA | 608 |
| CD274 NM_014143 | GTACCGCUGCATGATCAGCUA | 609 | GTAGCCCUCAGCCUGACAT | 610 |
| LAMP3 NM_014398 | GCAGUCGGGCATTCCTUCA | 611 | GTGTAGUCAGACGAGCACUC AT | 612 |
| TNFAIP8 NM_014350 | CTGCAGCUGGTTATCCUGACA | 613 | AAGGTGGUGGCGATGGATUT | 614 |
| FOXP3 NM_014009 | GCGGACCAUCTTCTGGAUGA | 615 | AGCCTTGGUCAGTGCCATUT | 616 |
| IL12A NM_000882 | GAAGATGUACCAGGTGGAGTUC AA | 617 | GATTTTTGUGGCACAGTCUC ACT | 618 |
| SAMHD1 NM_015474 | AGAGUTTGTAUGCCGCAAGACA | 619 | GGCGAGTUGGATTTTGGACU GA | 620 |
| SIT1 NM_014450 | GTGTGCUGTGGACTCUCACA | 621 | GCCAGCGAGAUGAGAAAUAG CA | 622 |
| CD3E NM_000733 | AATTGTCATAGUGGACATCTGC AUCA | 623 | GTGGTGGCCUCTCCTTGTUT | 624 |
| ICOSLG NM_015259 | AGTTTCACUGCCTGGTGTUGA | 625 | GTACACGUGAAGGTGAGCUC AT | 626 |
| HGF NM_000601 | GGACTAACAUGTTCAATGUGGG ACAA | 627 | GAGTGGATUTCCCGTGUAGC A | 628 |
| MELK NM_014791 | CATATCCTTACUGGAGAGATGG TAGCUAT | 629 | GGCTGTCUCTAGCACAUGGT | 630 |
| IGSF6 NM_005849 | AGAGTGACTUCAAATGACAGUG CAA | 631 | TCAGGAAGCUCCGCAGUC | 632 |
| GNLY NM_006433 | CACCUGCGTGAUGAGGAGAAA | 633 | GTGGGCTUAUCCACCATCTU CT | 634 |
| TDO2 NM_005651 | CTCCGUGCTTCUCAGACAGT | 635 | GACCTCCTTUGCTGGCTCTA UT | 636 |
| KRT7 NM_005556 | CCTCAACAACAAGUTTGCCUCC T | 637 | AGCAATCUGGGCCTCAAAGA UG | 638 |
| HLA-E NM_005516 | CCGAGCAAAAGUCAAATGAUGC C | 639 | GGTGGTGAGUCACGTGUGT | 640 |

TABLE 2-continued primer pair sequences of the immune response assay

| Gene/Accession | PRIMER1 | SEQ ID NO: | PRIMER2 | SEQ ID NO: |
|---|---|---|---|---|
| HLA-DMA NM_006120 | GAACGCACUGCCCUCAGAT | 641 | CATCAAACTCUGGTCTGGAA GAAUCA | 642 |
| LAMP1 NM_005561 | GTGCGUCAGCAGCAATGTUT | 643 | GCACCACUGTGGCATCUGA | 644 |
| NTN3 NM_006181 | CGGGAGGGCUTCTAUCGAGA | 645 | CCAUCCTUGCAGGGACACT | 646 |
| CD28 NM_006139 | CCTCCTCCUTACCTAGACAAUG AGA | 647 | CAAGCUAUAGCAAGCCAGGA CT | 648 |
| TARP NM_001003806 | ATGTCAUCACAATGGAUCCCAA AGA | 649 | ACAGCAGGUGATGAUGGCAA | 650 |
| EGFR NM_005228 | GTGAGTTGAUCATCGAATTCUC CAAAAT | 651 | CCACCACGUCGTCCATGUC | 652 |
| CCR4 NM_005508 | CCTGAGCAAGCCUGGCAUT | 653 | ATCGAGGGUGGTGTCTGCTA UA | 654 |
| MAGEA3 NM_005362 | GAGATTCUCGCCCUGAGCAA | 655 | AGATCTTCUCCTTCAGTGCU CCT | 656 |
| BATF NM_006399 | GTGUGAGAGCCCGGAAGATUT | 657 | TCTGGGCGGCAAUACGATTU T | 658 |
| KLRG1 NM_005810 | AGTGAGGCCUTTTGCTGGAUT | 659 | ACAGCUTGAGGCTUGAAGAC C | 660 |
| IRS1 NM_005544 | CGCCGCUCAAGTGAGGAUT | 661 | GGGUACCCATGAGTUAGAAG AGGAT | 662 |
| CSF1R NM_005211 | GCTGGAAGAUCATCGAGAGCTA UG | 663 | CCUCCACCACCTUCCCAAAG | 664 |
| CTLA4 NM_005214 | CGCCATACUACCTGGGCAUA | 665 | TCAAAGAAACAGCUGUGAGG AGAAA | 666 |
| TNFSF18 NM_005092 | CATTCAAGAACUCAAGGAGCUC AGA | 667 | ACTTAGCCAUACAGGGCTCC TUA | 668 |
| POU2AF1 NM_006235 | CCAAACUGTCGGCUCAAAGAG | 669 | TCCTCCUCAGCAGTTCCTUC A | 670 |
| GZMA NM_006144 | AGTAACTCCUCAUCAAGACCC UACAT | 671 | TGAGCCCCAAGAAUGACCUG | 672 |
| PIK3CA NM_006218 | CCCUTATGUGACAATGTGAACA CUCA | 673 | AGCACCCUTTCGGCCTUT | 674 |
| ITK NM_005546 | CAAAGAAGCCUCTTCCTCCTAC UC | 675 | TGUCCAGCAGGCAGTACUCT | 676 |
| IFI27 NM_005532 | CTTAAGACGGUGAGGTCAGCUT | 677 | ACACTGGUCACTGCTGAUGA G | 678 |
| EOMES NM_005442 | CTCAATCCCACUGCCCACUAC | 679 | AGGAGACTCUGGGTGAACAU ACAT | 680 |
| LCN2 NM_005564 | CAGGACUCCACCUCAGACCT | 681 | TTTTGCGGGUCTTTGTCTTC UCT | 682 |
| CD80 NM_005191 | CCAAGTGTCCAUACCTCAATTT CTTUCA | 683 | TTGUGCCAGCTCUUCAACAG A | 684 |
| CD83 NM_004233 | CCGAAACAUACCAGCUGCAA | 685 | TCCGCTCTGTATUTCTTAAA AGTCTCTUC | 686 |
| CXCL13 NM_006419 | TGTGUCCAAGAGAGCTCAGUCT | 687 | CCATTCAGCUTGAGGGUCCA | 688 |
| MTOR NM_004958 | GGAAGAGGCAUCTCGTTTGUAC T | 689 | GCCTCCAUAAATCTCGACC AUAGG | 690 |

TABLE 2-continued primer pair sequences of the immune response assay

| Gene/Accession | PRIMER1 | SEQ ID NO: | PRIMER2 | SEQ ID NO: |
|---|---|---|---|---|
| FCER1G NM_004106 | CGATCUCCAGCCCAAGATGAUT | 691 | CGACAGUAGAGGAGGGUGAGG | 692 |
| TFRC NM_001128148 | CACACCTGGAUTCCCTTCCUT | 693 | GUTTTCCAGUCAGAGGGACAGT | 694 |
| RORC NM_005060 | GGAAGTGGUGCTGGTUAGGA | 695 | CTTAGGGAGUGGGAGAAGUCAAAG | 696 |
| MMP9 NM_004994 | CTTUGACAGCGACAAGAAGUGG | 697 | CCCTCAGUGAAGCGGUACA | 698 |
| BST2 NM_004335 | CGCAATGUCACCCATCUCCT | 699 | TTTCTTTTGTCCUTGGGCCTUCT | 700 |
| PIK3CD NM_005026 | CTTCCCCGAUTGCCACGUA | 701 | CGGUCCAGCAGGAATTGGT | 702 |
| FCGR2B NM_004001 | CTCCCAGCUCTUCACCGAT | 703 | CTCCCATTUCCCTGCACUCA | 704 |
| TNFRSF14 NM_003820 | GGAGGAAUGUCAGCACCAGA | 705 | TCACACAUAUGAUTAGGCCAACUGT | 706 |
| OAS3 NM_006187 | TGCGGAGGAACUTTGUGAACA | 707 | AGGCGAAGAUGGUCAGCAAT | 708 |
| GRAP2 NM_004810 | CATGGAAGCUGTTGCCAAGUT | 709 | AAATTCTUGGGCACATATCCTUCCT | 710 |
| CCNB2 NM_004701 | GGTCGACCCUTGCCACUAC | 711 | AGCTGCUGCTACCTUAGAAGGA | 712 |
| MLANA NM_005511 | GATCGGCAUCCTGACAGUGA | 713 | CCCTTCTTGUGGGCATCTTCUT | 714 |
| MAGEA12 NM_005367 | GAGATTCUCGCCCUGAGCAA | 715 | TGGUCAGGGCAGCAGGUA | 716 |
| VCAM1 NM_001078 | TGCCGAGCUAAATTACACATTGAUGA | 717 | CATGGUCACAGAGCCACCUT | 718 |
| CDKN3 NM_005192 | GTGGCCCUGTAGGACCTUC | 719 | CGATGUCGCACGGTACCUG | 720 |
| NCR1 NM_004829 | GGCACCUACCTTTUAACCACAGA | 721 | CTTCCTGCUGAGCCAGTCUT | 722 |
| FAS NM_000043 | GGATTGGAATUGAGGAAGACTGTTACUA | 723 | ACGCAGUCTGGTTCAUCCC | 724 |
| GZMB NM_004131 | ATGACAGUGCAGGAAGAUCGAAA | 725 | CTGGGCCACCUTGTUACACA | 726 |
| IRF9 NM_006084 | CTCCAGCCAUACUCCACAGAAT | 727 | AACAAAGAGGUGAGGTGGAAGAUG | 728 |
| IFITM2 NM_006435 | TGCCTGGGCUCTCATAGCAUT | 729 | GCAGAATGGUCATGAAGAUGCC | 730 |
| TNFSF14 NM_003807 | CCAAGCGAAUGAAGCAUCCAA | 731 | GCCTGGGUCCTTCAACCUC | 732 |
| HLA-B NM_005514 | GGAGTGGCUCCGCAGAUAC | 733 | GTGATCUCCGCAGGGUAGAAA | 734 |
| SDHA NM_004168 | TTGAGATTTGCUGATGGAAGCAUAAGA | 735 | GTGCTTTAGGUCTCCATAGAGCUT | 736 |
| NRP1 NM_003873 | GUGGACUCCCGGAGAGGAT | 737 | GAGCTAACGUCGATCTTGTAAGTCUT | 738 |

TABLE 2-continued primer pair sequences of the immune response assay

| Gene/ Accession | PRIMER1 | SEQ ID NO: | PRIMER2 | SEQ ID NO: |
|---|---|---|---|---|
| EBI3 NM_005755 | CCGUACAAGCGUCAGGGA | 739 | AGTCACTCAGUTCCCCGUAGT | 740 |
| EFNA4 NM_005227 | CAGGTGUCTGTCTGCUGCAA | 741 | GACGAAGAAUCAGAAGCAGCAGTAAUA | 742 |
| PVR NM_006505 | GGUGGACGGCAAGAATGUGA | 743 | GCCTCATTCUGGCCAAGGUA | 744 |
| BUB1 NM_004336 | GGTTCAGAGCUTTCTGGAGUGA | 745 | CTTGCAATACAUAACAACCTGCUCAA | 746 |
| SKAP2 NM_003930 | GCAATAGAUGGCTACAGTGUCAGA | 747 | AGCTGCTGUACCCATTCTUCAG | 748 |
| PRF1 NM_005041 | GGTGGAGUGCCGCTTCUAC | 749 | GGGTGCCGUAGTTGGAGAUAA | 750 |
| CCL20 NM_004591 | AAAAGTUGTCTGTGUGCGCAAA | 751 | CCCCAGCAAGGUCTTTCUGT | 752 |
| TNFRSF18 NM_004195 | GGAGTGCUGTTCCGAGUGG | 753 | TCGAUACACUGGAAGCCAAAACT | 754 |
| CTSS NM_004079 | CACCACUGGCATCTCUGGAA | 755 | AGATCGTATGAGUGCATTCCCATUG | 756 |
| NKG7 NM_005601 | CCCCCAGAUCCAGACCTTCUT | 757 | GCTCTUGCCTTCTGCUCACA | 758 |
| ISG15 NM_005101 | AGCGAACTCAUCTTTGCCAGUA | 759 | CUTCAGCTCUGACACCGACAT | 760 |
| PDCD1 NM_005018 | GCGGCCAGGAUGGTTCTUA | 761 | GTTUAGCACGAAGCTCUCCGAT | 762 |
| SNAI1 NM_005985 | ACCCCAAUCGGAAGCCUAAC | 763 | AGAUGAGCATGGCAGCGA | 764 |
| CXCL11 NM_005409 | TTGGCTGTGAUATTGTGTGCUACA | 765 | TTTGTCACAGTUGTTACTTGGGUACA | 766 |
| CIITA NM_000246 | GCCTCUACCACTTCTAUGACCAGAT | 767 | CATAAGCCUCCCTGGTCTCTUC | 768 |
| IFI35 NM_005533 | CCCGGAAGUGCCTAAGTCUT | 769 | CGGCACUCCTCCATGTUGAT | 770 |
| TNFSF9 NM_003811 | CATGTTUGCGCAGCUGGT | 771 | GCTCCTTCGUGTCCTCTTTGUAG | 772 |
| TNFSF10 NM_003810 | CGTGTACTUUACCAACGAGCUGAA | 773 | CGGAGTUGCCACTTGACTUG | 774 |
| MMP2 NM_004530 | GTGCUCCACCACCTACAACUT | 775 | TCAGTGGUGCAGCTGTCAUAG | 776 |
| EGR3 NM_004430 | GTGACCAUGAGCAGTTTGCUAAA | 777 | GGTCAGACCGAUGTCCAUACA | 778 |
| MAGEA1 NM_004988 | AGAGAGAAGCGAGGUUCCAUT | 779 | TCTCCTTGGUGCTCCTCUGT | 780 |
| CD163 NM_004244 | CTGTAACTGCTCUAGGTGCTTCATUAT | 781 | AGGCCACAGCACUUCTUCT | 782 |
| IL6 NM_000600 | AGTACCUCCAGAACAGATTUGAGAGT | 783 | TCAGCAGGCUGGCATTUGT | 784 |
| KLRF1 NM_016523 | CGTTGCACTGGUATAAAATCTTACUGG | 785 | CCTCATACUGAGTGGCATTUGAACAA | 786 |
| B3GAT1 NM_018644 | AGCGACCCCUCUCAGACT | 787 | CGATGAGGACGAUCGCUAGGA | 788 |

TABLE 2-continued primer pair sequences of the immune response assay

| Gene/Accession | PRIMER1 | SEQ ID NO: | PRIMER2 | SEQ ID NO: |
|---|---|---|---|---|
| C1QA NM_015991 | GAGCATCCAGUTGGAGTUGACA | 789 | CCTCCCCUTTCTTCCCGUCT | 790 |
| OAS1 NM_016816 | CCTAGUCAAGCACTGGUACCAA | 791 | TCCAAGACCGUCCGAAAUCC | 792 |
| IKZF2 NM_016260 | TGTGGCAUGGTTTGCAUGG | 793 | CTTCTCTCCAGAGUGTAACTTTATGUGT | 794 |
| TLR9 NM_017442 | GCCAGACCCUCUGGAGAAG | 795 | TGGAGCUCACAGGGUAGGAA | 796 |
| KLF2 NM_016270 | CCACTCACACCUGCAGCUA | 797 | GTCUGAGCGCGCAAACUT | 798 |
| GUSB NM_000181 | GCGAGUAUGGAGCAGAAACGA | 799 | AATTCCAAAUGAGCTCUCCAACCA | 800 |
| NFKBIA NM_020529 | GGTGTCCUTGGGTGCUGAT | 801 | AATAGCCCTGGUAGGTAACTCUGT | 802 |
| IL23A NM_016584 | AATGATGTTCCCCAUATCCAGTGUG | 803 | AGAGAAGGCUCCCCTGUGA | 804 |
| HERC6 NM_017912 | CTGGTGGUTCCATTUGCAAAGG | 805 | CTGATGAAGCAGCUGAGAGAUGAT | 806 |
| SLAMF8 NM_020125 | CAGGGAAGGCCUCCUACAAAG | 807 | TCTCUGGACCCACTCTGUCA | 808 |
| IL15 NM_000585 | GAATCCCAGCUGACUCGCT | 809 | CCACATGGCCAUATATTGGAAUGGA | 810 |
| TLR7 NM_016562 | ACCTCTCATGCUCTGCTCTCUT | 811 | ACCATCUAGCCCCAAGGAGUT | 812 |
| OAS2 NM_016817 | CTTTGATGTGCUTCCTGCCTUT | 813 | CGCUGCAGGACTGUGAAAC | 814 |
| HLA-DPA NM_019111 | CGCTCAGGAAUCATGGGCUAT | 815 | GCCAGACCGUCUCCUUCUUT | 816 |
| CRTAM NM_019604 | AAGTGCTTACAUTACAGCGACUCT | 817 | GCUTCTCATGGUGGAGCACAT | 818 |
| MAGEC2 NM_016249 | ACACAGCCUAAAGUCAGCACA | 819 | CGGAAUGGAACGCCUGGAA | 820 |
| ICAM1 NM_000201 | GCCAACCAAUGTGCTATUCAAACT | 821 | ACCTGGCAGCGUAGGGUA | 822 |
| CD4 NM_000616 | AGCTCCAAGUCCTCACACAGAUA | 823 | GGACUCCCCGGTTCAUGT | 824 |
| MAPK14 NM_139012 | GCCCTUGCACATGCCUACT | 825 | GTGGCACAAAGCUGATGACUT | 826 |
| C1QB NM_000491 | CCUCACAGGACACCAGCUUC | 827 | AGCTGGGCCUGGGAGAUAT | 828 |
| NOTCH3 NM_000435 | GTGGCGACCUCACTUACGA | 829 | AGGAGGGCACUGGCAGTUAA | 830 |
| NCR3 NM_147130 | CCCAGACCUCACTGCUCAGA | 831 | AGGATCCUTCCAGGGUACGAAT | 832 |
| STAT3 NM_139276 | CCAATGGAACCUGGGAUCAAGT | 833 | CCATGTGAUCTGACACCCUGAA | 834 |
| TLR8 NM_138636 | CCACCTCCUGCATAGAGGGUA | 835 | CGCATAACUCACAGGAACCAGATAUT | 836 |

TABLE 2-continued primer pair sequences of the immune response assay

| Gene/Accession | PRIMER1 | SEQ ID NO: | PRIMER2 | SEQ ID NO: |
|---|---|---|---|---|
| CYBB NM_000397 | ACACACATGCCUTTGAGTGGUT | 837 | CAUCATGGUGCACAGCAAAGT | 838 |
| IKZF4 NM_022465 | GGCCCAAGACUCCAACCATTTUA | 839 | TGAGUGAGCGGCUAGGAGAA | 840 |
| IFIH1 NM_022168 | ACAGGAGCCAUGCAAGAAGUT | 841 | GCCCATTGUTCATAGGGTUGAGT | 842 |
| LCK NM_001042771 | AGCTTTTCUGTGGCTGGUGAAT | 843 | CCATCCAGUGGGACTATGGGAUAA | 844 |
| BCL2L11 NM_138621 | CCAGCACCCAUGAGTTGUGA | 845 | CCGCAACUCUGGGCGAT | 846 |
| ITGAM NM_001145808 | CGAGUACGUGCCACACCAA | 847 | CATTGAATTCUTCCTGGAUGCCAAA | 848 |
| ITGB7 NM_000889 | GCCGGGAAUACAGTCGCTUT | 849 | AGTGTCCCUCCCTCCTUCAG | 850 |
| JCHAIN NM_144646 | TGCTCCAGTTUTTCAGAAGAAGUGA | 851 | TCCGGGCACACUTACATTUGT | 852 |
| CD209 NM_021155 | CCTACAGCUGCAGTCTUCCA | 853 | AACGTTGTUGGGCTCUCCT | 854 |
| SLAMF7 NM_021181 | AACAAUCCUAAAGGAAGAUCCAGCAA | 855 | GGGAGTGCACUGCTGTCUA | 856 |
| IL10 NM_000572 | CCGUGGAGCAGGUGAAGAAT | 857 | TCTATAGAGUCGCCACCCUGAUG | 858 |
| IL1A NM_000575 | GGCTGCUGCATTACATAATCUGGAT | 859 | AGCACTGGUUGGTCTTCAUCUT | 860 |
| FCGR3A NM_000569 | GUGCCAGACAAACCTCUCCA | 861 | TTATGCAGAGCAGUGTTCUCCA | 862 |
| IFNA17 NM_021268 | TCACACTTTCAUGAGTTCCUCCATUT | 863 | GACATCAGCAUGGTCATCUGTAAAGUA | 864 |
| EGR2 NM_000399 | CCACGTCGGUGACCATCUUT | 865 | GGAGCAAAGCUGCTGGGAUA | 866 |
| TOP2A NM_001067 | TGGGTGGUCCTGCAAAAUCC | 867 | ACATATTGATTUGGAGCCAGTTCTUCA | 868 |
| C10orf54 NM_022153 | CAACCTGACCCUGCTGGAUA | 869 | GAGGAUGGGUACACCACACA | 870 |
| FOXM1 NM_021953 | CACUGAGAGGAAGCGCAUGA | 871 | CAGACGUCUCCCGGACAA | 872 |
| AXL NM_021913 | GACUAUCUGCGCCAGGGAAA | 873 | GGCCUUCAGTGTGTTCUCCAA | 874 |
| MS4A1 NM_021950 | GCCCTTGAGAUUTGAGGCCUT | 875 | ACATCCTCCUGAAGAGTGGTTTUG | 876 |
| IFI6 NM_022873 | CGCTGCUGUGCCCATCUAT | 877 | GCAAGUGAAGAGCAGCAGGUA | 878 |
| CD3D NM_000732 | GGACAAAGAAUCTACCGUGCAAGT | 879 | TCUCATGUCCAGCAAAGCAGAA | 880 |
| GPR18 NM_001098200 | CGACAGAAGUGGAAGTGCUGAAAA | 881 | CTGGATGUGAGCTGTUAAAAGGGA | 882 |
| CD3G NM_000073 | GCCACCUUCAAGGAAACCAGUT | 883 | CTTGAGUCUAGATTTAGGGCUGAAAGT | 884 |

TABLE 2-continued primer pair sequences of the immune response assay

| Gene/Accession | PRIMER1 | SEQ ID NO: | PRIMER2 | SEQ ID NO: |
|---|---|---|---|---|
| ZAP70 NM_001079 | GTGGAGAAGCUCATTGCUACGA | 885 | GTATGTGCCCUGCTCCTUCC | 886 |
| HMBS NM_000190 | GCACCCUGAGGAATGCATGUAT | 887 | GCCUCAGGAAGGCCCTTUC | 888 |
| IL7 NM_000880 | GAGTGACTAUGGGCGGUGA | 889 | AGAUGATGCTACUGGCAACAGAAC | 890 |
| IFIT3 NM_001031683 | GGAAACCTCTUCAGCATTTGCUT | 891 | GGCAUTTCAGCTGUGGAAGGAT | 892 |
| RB1 NM_000321 | CGGTCTTCAUGCAGAGACUGA | 893 | GTGAAATAUAGATGTTCCCUCCAGGAAT | 894 |
| PTGS2 NM_000963 | CCAGAGCAGGCAGAUGAAAUACC | 895 | AGCTCCACAGCAUCGATGUC | 896 |
| TGFB1 NM_000660 | CGTCTGCUGAGGCTCAAGTUA | 897 | GCACAACUCCGGTGACAUCAA | 898 |
| NCF1 NM_000265 | TGAUGCCCAAAGAUGGCAAGA | 899 | CGCTCTTCUCTACGACCUCCA | 900 |
| TWIST1 NM_000474 | TTCTCGGUCTGGAGGAUGGA | 901 | CAGCTCCAGAGUCTCTAGACUGT | 902 |
| CA4 NM_000717 | AGGACTGCCUGCCCCAUA | 903 | ACATTCCTCGAUGTCCCCUCT | 904 |
| SELL NM_000655 | CCTTUGGGCAAGGACCUGAG | 905 | CCCCACAACUTGAAGATGUCCAT | 906 |
| LILRB1 NM_001081637 | GGTTGTGAUCGGCATCTUGGT | 907 | CCCCUGCAGGATGTUGGAAAT | 908 |
| CD14 NM_000591 | CCGCTGTGUAGGAAAGAAGCUAAA | 909 | ACAAGGTTCUGGCGTGGUC | 910 |
| ALOX15B NM_001141 | GAUCCCGCACACCCGAUA | 911 | AATAGTTCAGCTGCTTCATGTUCCT | 912 |
| PECAM1 NM_000442 | GCCCCAUGTTCCCGGUT | 913 | GGCACUGCCCACAAGUCA | 914 |
| NOS2 NM_000625 | TCTCGGCCACCUTTGAUGAG | 915 | ATTTGAGCTCAGAUGTTCTTCACUGT | 916 |
| FASLG NM_000639 | GCCTGTGTCUCCTTGTGATGUT | 917 | GCTTCTCCAAAGAUGATGCTGUGT | 918 |
| CD44 NM_000610 | GCAGCACTUCAGGAGGTUACAT | 919 | TGGTTGCUGTCTCAGTUGCT | 920 |
| ENTPD1 NM_001098175 | CCAGGGUGCCAGGATCAUAC | 921 | TCCAAAGCUCCAAAGGTTUCCT | 922 |
| CMKLR1 NM_001142345 | CUGTGATTCUGCCCACGGAA | 923 | CCAATGTGAGUCCTCAGCCAAUC | 924 |
| CD53 NM_001040033 | GACAGACUGAAGAAACAUCCAAGGT | 925 | TTTCCAGGCACCGUTCCUC | 926 |
| TNF NM_000594 | GACAAGCCUGTAGCCCAUGT | 927 | ATGAGGUACAGGCCCTCUGAT | 928 |
| CXCL8 NM_000584 | CTCTUGGCAGCCTTCCUGAT | 929 | TCCACTCTCAAUCACTCTCAGTUCT | 930 |
| CD40LG NM_000074 | GAGGCCAGCAGUAAAACAACAUC | 931 | ACAGAAGGTGACUTGGGCATAGAUAUA | 932 |

TABLE 2-continued primer pair sequences of the immune response assay

| Gene/Accession | PRIMER1 | SEQ ID NO: | PRIMER2 | SEQ ID NO: |
|---|---|---|---|---|
| HLA-F NM_001098479 | CCCCGCGGGACUCATATTUT | 933 | GACACAGCGGUGCTGAAAUAC | 934 |
| GATA3 NM_001002295 | GAGAUGGCACGGGACACUAC | 935 | GGTTGTGGUGGTCTGACAGUT | 936 |
| LYZ NM_000239 | GTCCAGGGCAAGGUCTTUGA | 937 | CATTGTAGTTTGUAGCTCGTGTGTUG | 938 |
| ARG1 NM_000045 | GGAAGAAGGCCCUACAGTATUGAG | 939 | CCCACAGACCUTGGATTCTUCA | 940 |
| IL2RB NM_000878 | CCAGACCCCUCGAAGTTCTTUT | 941 | CTTGTCCCUCTCCAGCACUT | 942 |
| NECTIN2 NM_001042724 | TTCGTCUGCACAGUCACCAA | 943 | CAGCCACAGCAGUAGCAAUG | 944 |
| MPO NM_000250 | GGGAGAGGCUCUACCAGGAA | 945 | GTGGGTCCACUGAGTCATTGUA | 946 |
| CCR2 NM_001123396 | TTCTACCTCUAGATCTGTTTGGTUCAGT | 947 | AACGAGATGUGGACAGCAUGT | 948 |
| BRCA2 NM_000059 | GTGGUCCACCCCAACUAAAGA | 949 | ACAGACTTCCUTTTGGCCAUACAA | 950 |
| ADORA2A NM_000675 | TCGCCAUUGACCGCTACAUT | 951 | AGTTGTUCCAACCTAGCAUGGG | 952 |
| G6PD NM_000402 | CGCCUCCACCAACUCAGAT | 953 | GGTCGUCCAGGTACCCTTUG | 954 |
| TAP1 NM_000593 | TGTGGCCUAUGCAGTCAACUC | 955 | GTGAACUGCATCTGGUAGAGAACA | 956 |
| MX1 NM_001178046 | TTGCAAAGAAGGAAGAUGGTTGTTUC | 957 | ATACTGGCUGCACAGGTUGT | 958 |
| HLA-DQB2 NM_001198858 | GTGACCGUGATGCTGGUGAT | 959 | CGGTUATAGATGTATCGGCCACAC | 960 |
| CD27 NM_001242 | CTGCTCAGTGUGATCCTTGCAUA | 961 | CATUGCGACAGGCACACUC | 962 |
| CD276 NM_001024736 | CTGCUGGCACAAGGCAAUG | 963 | TCATGCUGGGCTTCGAGUAG | 964 |
| STAT4 NM_003151 | CGTCAGCGGCUTTCTCCUA | 965 | TTGAUCCACCTGCUCCAAAAACT | 966 |
| PTPN7 NM_001199797 | CGGGAGGUCACCCTACACUT | 967 | GGGATGUCCAGGTCTUCGG | 968 |
| PTPRC NM_002838 | CTACAGACCCAGUTCCCCAUT | 969 | AAGGGCUCAGAGTGGTTGTUT | 970 |
| PSMB9 NM_002800 | CTGCUGCAAATGTGGUGAGAAAT | 971 | CACCAAUGGCAAAAGGCUGT | 972 |
| CD244 NM_001166663 | GAAAGCCACACCCUGAATCUCA | 973 | TCCTTCCUCTTTCTCCUCCACA | 974 |
| CXCR4 NM_003467 | GAACCAGCGGUTACCAUGGA | 975 | GTAGATGGUGGGCAGGAAGAUT | 976 |
| MAPK1 NM_002745 | GATTCCAGCCAGGAUACAGATCTUAAA | 977 | GGCTCAAAGGAGUCAAAGUGGA | 978 |
| TP63 NM_003722 | CAGTACTGCCCUGACCCUAC | 979 | AAAATCCCAGAUATGCUGGAAAACCT | 980 |

TABLE 2-continued primer pair sequences of the immune response assay

| Gene/Accession | PRIMER1 | SEQ ID NO: | PRIMER2 | SEQ ID NO: |
|---|---|---|---|---|
| IRF4 NM_002460 | GCCAGGUGACAGGAACCTUT | 981 | TCACGAGGAUUTCCCGGUAGT | 982 |
| CCL3 NM_002983 | CCCGGCAGAUUCCACAGAAUT | 983 | CAGGTCGCUGACATATTTCUGGA | 984 |
| CCL18 NM_002988 | GCAGATUCCACAAAAGTTCATAGTUGAC | 985 | AGCTTCAGGUCGCTGATGTATTUC | 986 |
| IL7R NM_002185 | AGCCAAUGACTTTGTGGUGACAT | 987 | TGCAGGAGUGTCAGCTTUGT | 988 |
| HLA-DRB1 NM_002124 | GACACUCTGGACTUCAGCCA | 989 | GGTCCUGAGAAAGCCCTCUCT | 990 |
| CEACAM8 NM_001816 | CCUGCCACGCCAATAACUCA | 991 | AGGTCAGGTUCACAGAGTCCUT | 992 |
| CXCL10 NM_001565 | TCCAGAAUCGAAGGCCAUCAAG | 993 | TGUAGGGAAGTGAUGGGAGAGG | 994 |
| CCL2 NM_002982 | CGAGCUATAGAAGAAUCACCAGCA | 995 | TCTTCGGAGUTGGGTTTGCUT | 996 |
| SRGN NM_002727 | GCAAUCCAGACAGTAATTCUGCAAAC | 997 | AAAGTGGGAAGAUACGATTCAAGUCC | 998 |
| CD19 NM_001178098 | CACUGCCCCGTCTTAUGGAAA | 999 | AGGTTGGAGUCGTTCTCAUAGAACT | 1000 |
| ITGB1 NM_002211 | CCTCTACTACCTUATGGACCTGTCTUA | 1001 | GGCATCACAGUCTTTTCCACAAAUG | 1002 |
| IFITM1 NM_003641 | GGCTTCATAGCAUTCGCCTACUC | 1003 | GGATGAAUCCAATGGTCAUGAGGAT | 1004 |
| CCL21 NM_002989 | CUCCAAGACUGGCAAGAAAGGA | 1005 | GCATCTTGGGUTCAGGCTUCA | 1006 |
| MRC1 NM_002438 | GTTTATGGAGCAGGUGGAAGATCUAT | 1007 | TCGTGCAAUCTGCGUACCA | 1008 |
| PGF NM_002632 | CGAGGUGGAGCACATGTUCA | 1009 | GGUCCCCAGAACGGATCTUT | 1010 |
| ITGAL NM_002209 | GGCTGTCUCGAACGTGUGA | 1011 | AACCATCAAACAGAAAUACCAGGTCUAC | 1012 |
| ID2 NM_002166 | ATGTCAAAUGACAGCAAAGCACUG | 1013 | CAACTTGTCCUCCTTGTGAAAUGG | 1014 |
| CD22 NM_001771 | CTGCTGUCAGGTCTCCAAUGA | 1015 | GCCAGUGACAUGCAAAGAAACT | 1016 |
| CCL17 NM_002987 | CTGAAGACGUGGUACCAGACA | 1017 | GCTTCAAGACCUCTCAAGGCTUT | 1018 |
| ITGAE NM_002208 | CTGAACTGCAGAUCCTTGGUGAA | 1019 | CACCAACGCUGCCTTTAAUGA | 1020 |
| IL3RA NM_002183 | GAAAGCAAAGGCUCAGCAGUT | 1021 | TGTAGTTGGUCACTTCACAUAAGGAAAT | 1022 |
| CCR7 NM_001838 | GTGGCTCUCCTTGTCATTTUCC | 1023 | GGGAGGAACCAGGCUTAAAGUT | 1024 |
| CD1C NM_001765 | CCTTGGTGATUCTAATAGTCCTTGUGT | 1025 | CGACGGGAUGGCATCACUA | 1026 |
| MAD2L1 NM_002358 | GCGCGUGCTTTTGTTTGUG | 1027 | CAGATGGATAUATGCCACGCUGAT | 1028 |

TABLE 2-continued primer pair sequences of the immune response assay

| Gene/Accession | PRIMER1 | SEQ ID NO: | PRIMER2 | SEQ ID NO: |
|---|---|---|---|---|
| PYGL NM_002863 | CATGGCAACCCUGGGACUT | 1029 | AATTCUGGGCGGGACTTCUC | 1030 |
| CD40 NM_001250 | CCUAGACACCUGGAACAGAGAGA | 1031 | TCACAGGCCUCACTCGUACA | 1032 |
| LY9 NM_002348 | AATGTCTCAUGGAGAAGCAGUGAAA | 1033 | CAUCAGGAACAACCCAAUCCAAAG | 1034 |
| HLA-G NM_002127 | GCACAGACUGACAGAAUGAACCT | 1035 | GCCATCGUAGGCATACTGTTCAUAC | 1036 |
| TLR3 NM_003265 | GGACTTUGAGGCGGGTGTUT | 1037 | TCAATAGCTTGTUGAACTGCATGATGUA | 1038 |
| CD48 NM_001778 | TGCCAAGUCAGCAATTCTGUGA | 1039 | TCUCAGGTAAGUAACAGGCCAAGA | 1040 |
| STAT5A NM_003152 | CTGAACAACUGCTGCGUGAT | 1041 | GACTCAAACAGGACUGTGAACTUCT | 1042 |
| FCRLA NM_001184866 | GGAATTCTCCAUCACCGTGGUA | 1043 | TCTGAGAAUGGCGCUGGAAA | 1044 |
| BCL6 NM_001706 | ACCTGAAAACCCACACUCGAAUT | 1045 | GGGUGCCACAGATTUCACAG | 1046 |
| ZEB1 NM_001174093 | GAGAGGAUCATGGCGGAUGG | 1047 | ACACTTTCTTCTUCCACAATATGCAGUT | 1048 |
| CCL5 NM_002985 | CTCGCTGUCATCCTCATUGCT | 1049 | GCACTUGCCACTGGTGUAGA | 1050 |
| IDO1 NM_002164 | CTAAACATCUGCCTGATCTCAUAGAGT | 1051 | CCCACACAUATGCCATGGUGAT | 1052 |
| IL18 NM_001562 | CCACCTGCUGCAGTCUACA | 1053 | TTCATUGCCACAAAGTTGAUGCAA | 1054 |
| TNFRSF9 NM_001561 | CCTCACGCUCCGTTTCUCT | 1055 | AGTTCACATCCUCCTTCTTCTTCTUCT | 1056 |
| HIF1A NM_001530 | AGTACAGGAUGCTUGCCAAAAGA | 1057 | GGAGAAAAUCAAGTCGTGCUGAAT | 1059 |
| HLA-DPB1 NM_002121 | GCTCUGACGGCGTTACUGAT | 1059 | TCCTCCCGGUTGTAGATGTATCUC | 1060 |
| FOX01 NM_002015 | TCAAGAGCGUGCCCTACTUC | 1061 | GATTGAGCAUCCACCAAGAACTTUT | 1062 |
| CD33 NM_001772 | CCAGGAGGAGGGAUAATGGTTCAUA | 1063 | AGUGGCCGGGTTCUAGAGT | 1064 |
| S100A9 NM_002965 | TCAAAGAGCUGGUGCGAAAAGA | 1065 | GCCTCGCCAUCAGCAUGAT | 1066 |
| HLA-DMB NM_002118 | CCUGTGTGGUAGAGCACACT | 1067 | CCAGCUGAUCACACCAAGAGA | 1068 |
| HLA-A NM_002116 | CGGAGUAUGGGACCAGGAG | 1069 | CCACGUCGCAGCCATACAUA | 1070 |
| SNAI2 NM_003068 | AUGCATATUCGGACCCACACAT | 1071 | CCTGTCTGCAAAUGCTCTGTUG | 1072 |
| TNFRSF17 NM_001192 | GGCAGTGCUCCCAAAAUGAA | 1073 | TCGCATTCGUCCTTTCACUGA | 1074 |
| LRP1 NM_002332 | TCACCUCCAAGACAGTGCTUT | 1075 | TCAGCUCAGGACCTTCAUACACA | 1076 |

TABLE 2-continued primer pair sequences of the immune response assay

| Gene/ Accession | PRIMER1 | SEQ ID NO: | PRIMER2 | SEQ ID NO: |
|---|---|---|---|---|
| MAGEA4 NM_001011548 | CGAGCTUCTGCGTCUGACT | 1077 | AGATCTTCUCCTTGGTGCUCCT | 1078 |
| HLA-DQA1 NM_002122 | CCTTCTTCAAGAUCAGTTACCUCACC | 1079 | ACAGTCTCUGTGAGCTCUGACAT | 1080 |
| CD1D NM_001766 | CCUGCCCCCAATTTGUCAGT | 1081 | GCTTTGGGUAGAATCCUGAGACA | 1082 |
| RPS6 NM_001010 | GATGAACGCAAACUTCGTACTTUCT | 1083 | GGTCAAGACACCCUGCTUCA | 1084 |
| MKI67 NM_002417 | CGTCGTGTCUCAAGATCTAGCUT | 1085 | TGAGTCATCUGCGGTACTGUCT | 1086 |
| GZMK NM_002104 | GCCATTTAUGGCCTCCAUCCA | 1087 | GAGAGAGAGUGTGCGCCUAAA | 1088 |
| CD79A NM_001783 | ACUAACCAACCCACUGGGAGAA | 1089 | TCAATGATGCUGGGACCTTGUG | 1090 |
| CD37 NM_001774 | GCGGGACGUCGUAGAGAAA | 1091 | CCTCTCAGGAUGAGGACTUGGA | 1092 |
| FUT4 NM_002033 | CAGGTUCCCCTCACAGUCAAT | 1093 | CATGTAGUGGCACCTGCUGAA | 1094 |
| AIF1 NM_001623 | GGGAGACGUCAGCUACCC | 1095 | GGGCAACUCAGAGATAGCTTTCUT | 1096 |
| CCR1 NM_001295 | CACGGACAAAGUCCCTUGGA | 1097 | CCAAAGGCCCUCTCGTUCAC | 1098 |
| PRDM1 NM_001198 | CAGGCGGAGGCAUCCTUAC | 1099 | AGGAACTGTGUCATTGGTGTAGATTUC | 1100 |
| CD47 NM_001777 | ACTGGCCTTGGUUAATTGTGACUT | 1101 | CUCAGUCCAACCACAGCGA | 1102 |
| CD74 NM_001025159 | CAGGCACUCCTGGAGCAA | 1103 | GCACTGGAGUGGCAGAUAGT | 1104 |
| LAG3 NM_002286 | GCGACTUACCCTTCGACUAGA | 1105 | GGGAUCCAGGUGACCCAAAG | 1106 |
| TNFRSF4 NM_003327 | GCCCUGCACGTGGTGUAA | 1107 | CAACTCCAGGCUTGTAGCTGUC | 1108 |
| CD2 NM_001767 | GACCGATGAUCAGGATATCTACAAGGUA | 1109 | ACCTCACAGGUCAGGGTUGT | 1110 |
| CCL4 NM_002984 | GTCCTGTCTCUCCTCATGCTAGUA | 1111 | CTGCTGGTCUCATAGTAATCUACCAC | 1112 |
| BAGE NM_182482 | CAGGCUCCAACCUCCAGC | 1113 | AGCUGGAGTGTUAGGAGGGC | 1114 |
| LEXM NM_001110533 | AGCCCCCAUTCCTGTUGAC | 1115 | GATATCGCUGCCGCCUGT | 1116 |
| CCR6 NM_004367 | GGGCTGAACCAUACACTCCUT | 1117 | AATCAACTGAGTAAUATGAAGTATTGACUGACA | 1118 |
| CD70 NM_001252 | CCCCCUGCCAGTAUAGCCT | 1119 | GTGATCUGCCTCGTGGUGT | 1120 |
| CDK1 NM_001786 | GAAGTGUGGCCAGAAGUGGA | 1121 | TCGTTTGGCTGGAUCATAGATTAACAUT | 1122 |
| CTAG1B NM_001327 | CATCCUGGGCCAGGCUC | 1123 | GGCUUCAGGGCTGAAUGGAT | 1124 |

TABLE 2-continued primer pair sequences of the immune response assay

| Gene/Accession | PRIMER1 | SEQ ID NO: | PRIMER2 | SEQ ID NO: |
|---|---|---|---|---|
| CTAG2 NM_020994 | TGCGTGAUCCACAUCAACAGG | 1125 | GUCCCGGGAUGCCGCAC | 1126 |
| CX3CR1 NM_001171174 | ATAACAGGCCUCAGCCAAAUCAT | 1127 | GGUAAAGTCUGAGCAGGACAGG | 1128 |
| CX3CR1 ENST00000541347 | AATATAACAGGCCUCAGCCAAAUCAT | 1129 | AGCTGACTGUGCTGTGCTUT | 1130 |
| CX3CR1 ENST00000435290 | GTCCCCAAUATAACAGGCCUCAG | 1131 | ACAGAGCACCCGCUGUC | 1132 |
| CX3CR1 ENST00000399220 | CCCCAATAUAACAGGCCUCAGC | 1133 | AGGAUGAGAGAACCCCUGGAG | 1134 |
| GAGE1, GAGE12I, GAGE12F NM_001040663 | TATGAGTUGGCGAGGAAGAUCG | 1135 | GGATCCUGACGTTGAGTUGCT | 1136 |
| GAGE12J NM_001098406 | TATGAGTUGGCGAGGAAGAUCG | 1137 | GGATCCUGACGTTGAGTUGCT | 1138 |
| GAGE2C, GAGE2A, GAGE2E NM_001472 | TATGAGTUGGCGAGGAAGAUCG | 1139 | GGATCCUGACGTTGAGTUGCT | 1140 |
| GAGE10 NM_001098413 | TATGAGTUGGCGAGGAAGAUCG | 1141 | GGATCCUGACGTTGAGTUGCT | 1142 |
| GAGE13 NM_001098412 | TATGAGTUGGCGAGGAAGAUCG | 1143 | GGATCCUGACGTTGAGTUGCT | 1144 |
| IKZF1 NM_006060 | CATGGATGCUGATGAGGGUCAA | 1145 | GACTCTGTCACUCTTGGAGCTUT | 1146 |
| IL17A NM_002190 | GAATACCAATACCAAUCCCAAAAGGUC | 1147 | CCAAGUGGCGGCACTUT | 1148 |
| IL2 NM_000586 | AATCCATCTGTUCAGAAATTCTACAAUGGT | 1149 | AAAAACUTTCACTUAAGACCCAGGGA | 1150 |
| IL21 NM_021803 | TTTGGAGAAGUGATTTGAATCTTTCUAGGAAT | 1151 | TCAAUTAAAAAGCUGAAGAGGAAACCAC | 1152 |
| IL22 NM_020525 | AGGGAACAGCACUTCTUCAAGG | 1153 | GCTAGCUTGGCTGAUAACAACACA | 1154 |
| KIR2DL2 ENST00000344867 | CCUGTCUGCACAGACAGCA | 1155 | CAGGCGACCUGGGUGGG | 1156 |
| KIR2DL3 NM_015868 | GGCTCTTUCCGTGACTCUCC | 1157 | GAACAUGCAGGTGTCUGGG | 1158 |
| MAGEA10 NM_021048 | ATGATGACTCUGATCAGGGUAGCA | 1159 | GAGAGCAAGAGGUCAAGAGCUG | 1160 |
| MIF NM_002415 | TGCCGGACGGGUUCCUC | 1161 | TGUGCAGGCUGCAGAGC | 1162 |
| PTPRCAP ENST00000326294 | CGCTGTCCUCCGCGCUG | 1163 | CUGCAGACGAGCACUGAGC | 1164 |
| SSX2 NM_003147 | CGGTTAGGGUCATTATCCAAATCATUCC | 1165 | AGGAAGAGUGGGAAAAGAUGAAAGC | 1166 |
| TCF7 NM_003202 | ACGGTGUCCCCCAACUCT | 1167 | GGGAGCUGCCCCAUGCT | 1168 |
| XAGE1B NM_001097594 | GTTCCGGCGUCAAGGUGA | 1169 | ATCTAATATAAAACCAGCUTGCGTTGTTUC | 1170 |
| CEACAM8 NM_001816 | AGGAATGACGUAGGACCCUAUGAAT | 1171 | GTTGAGATTUACCCCTGCAUGGT | 1172 |

TABLE 2-continued primer pair sequences of the immune response assay

| Gene/Accession | PRIMER1 | SEQ ID NO: | PRIMER2 | SEQ ID NO: |
|---|---|---|---|---|
| CXCR3 NM_001504 | CGTTTTCUCCATAGTCAUAGGAAGAGC | 1173 | CUGCAGGTTUCCAACCACAAG | 1174 |
| FCGR1A NM_000566 | CCAACATAAGUCACAATGGCACCUA | 1175 | CCAGAUTCCCCUCCAGGAGT | 1176 |
| FCGR3B NM_000570 | CATUCCAAAAGCCACACUCAAAGAT | 1177 | GGTACCCAGGUGGAGAGAAUGA | 1178 |
| FYB NM_001465 | CTGACGAAATUCCACAAAACCTCUT | 1179 | GGGACTGGUGGTTGTGAUGG | 1180 |
| HLA-C NM_002117 | GAGCAGAGAUACACGTGCCAUAT | 1181 | AGCUCCAAGGACAGCUAGGA | 1182 |
| HLA-DQA2 NM_020056 | GGCTCTTAUGAATCCCATCCUGAAA | 1183 | AGAGAAGAGGUGAGAGAAGAAACATTUG | 1184 |
| IFNG NM_000619 | TTTAAAGAUGACCAGAGCAUCCAAAAGA | 1185 | TGCTTTGCGUTGGACATUCAAG | 1186 |
| KIR2DL1 NM_014218 | GCTGAGCUGAGCUCGGT | 1187 | CUGATTUCACCAGGCGACCT | 1188 |
| KRT5 NM_000424 | GGTTGATGCACUGATGGATGAGAUT | 1189 | CCTCAGCGAUGATGCTAUCCAG | 1190 |
| LMNA NM_170707 | AGCAAAGTGCGUGAGGAGTUT | 1191 | CGCUCTCACUGAGAGCAGT | 1192 |
| PTPN11 NM_002834 | GCGGAUGGTGTUCCAAGAAAA | 1193 | GCGCTTTCTUTGACGTTCCUAA | 1194 |

RNA and cDNA Preparation

Total RNA was extracted from samples with the Recov-erAll™ Total Nucleic Acid Isolation Kit (Ambion, Inc.), according to the manufacturer instructions, and quantified, e.g., using the Qubit™ RNA HS Assay Kit (Thermo Fisher) for quantifying RNA. A total of 10 ng of total RNA was first reverse transcribed to cDNA with SuperScript® VILO™ cDNA Synthesis Kit (Thermo Fisher, Cat. No. 11754050) according to manufacturer instructions. Prepared template was used to amplify targets with the immune response assay comprising primer pairs in Table 2.

PCR Amplify RNA Targets

A multiplex polymerase chain reaction was performed to amplify 398 individual amplicons across a RNA expression sample. A list of genes and the resulting amplicon sequences generated are provided in Table 1. Primer pairs are presented in Table 2. To a single well of a 96-well PCR plate was added 4 microliters of immune response primer pool containing 398 primer pairs at a concentration of 15 µM in TE, 10 microliters prepared cDNA and 4 microliters of an amplification reaction mixture (5× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free Water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperate profile to generate the preamplified amplicon library.

An initial holding stage was performed at 99° C. for 2 minutes, followed by 19 cycles of denaturing at 99° C. for 15 seconds and an annealing and extending stage at 60° C. for 4 minutes. After cycling, the preamplified amplicon library was held at 10° C. until proceeding.

Partially Digest Amplicons

The sample was briefly centrifuged to collect contents before proceeding. To the preamplified amplicon library (~20 microliters), 2 microliters of FuPa reagent was added. The reaction mixture was sealed, mixed thoroughly to ensure uniformity and incubated at 50° C. for 10 minutes, 55° C. for 10 minutes, 60° C. for 20 minutes, then held at 10° C. for up to 1 hour. The sample was briefly centrifuged to collect contents before proceeding.

Ligate Adapters to Amplicons and Purify

After incubation, the reaction mixture proceeded directly to a ligation step. Here, the reaction mixture now containing the phosphorylated amplicon library was combined with 2 microliters of A/P1 Adapters (sold as a component of the Ion Fragment Library Kit, Thermo Fisher), 4 microliters of Switch Solution (sold as a component of the Fragment Library Kit, Thermo Fisher) and 2 microliters of DNA ligase, added last (sold as a component of the Ion Fragment Library Kit, Thermo Fisher), then incubated at the following: 22° C. for 30 minutes, 72° C. for 10 minutes, then held at 10° C. for up to 1 hour. The sample was briefly centrifuged to collect contents before proceeding.

After the incubation step, 45 microliters (1.5× sample volume) of room temperature AgenCourt® AMPure® Reagent (Beckman Coulter, Calif.) was added to ligated DNA. The mixture was pipetted thoroughly to mix the bead suspension with the ligated DNA. The mixture was pulse-spin and incubated at room temperature for 5 minutes. Samples underwent another pulse-spin and were placed on a magnetic rack such as a DynaMag™-2 spin magnet (Life Technologies, CA, Part No. 123-21D) for two minutes. After the solution had cleared, the supernatant was discarded. Without removing the tube from the magnetic rack, 150 microliters of freshly prepared 70% ethanol was introduced into the sample, and incubated while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

The pellet was resuspended in 20 microliters of DNase/RNase Free Water (Life Technologies, CA, Part No. 600004) and vortexed to ensure the sample was mixed thoroughly. The sample was pulse-spin and placed on the magnetic rack for two minutes. After the solution cleared, the supernatant containing the ligated DNA was transferred to a new Eppendorf LoBind™ tube for long-term storage. After quantification, determine the dilution factor that results in a concentration of ~100 pM, which is suitable for template preparation using an Ion template kit.

Quantify the Library

Ligated library was quantified, using a Qubit™ 2.0 or 3.0 Fluorometer and/or by qPCR using the Ion Library TaqMan® Quantitation Kit (Cat. No. 4468802), according to manufacturer instructions.

Amplify and Purify the Library

The ligated preamplified library (~20 microliters) was combined with 50 microliters of Platinum® PCR SuperMix High Fidelity (Thermo Fisher, sold as a component of the Ion Fragment Library Kit) and 2 microliters of Library Amplification Primer Mix (sold as a component of the Ion Fragment Library Kit). The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library: hold at 98° C. for 2 minutes, followed by 5 cycles of denaturing at 98° C. for 15 seconds and an annealing and extending stage at 64° C. for 1 minute. After cycling, the final amplicon library was held at 4° C. until proceeding to the final purification step outlined below.

A two-round purification of the final library was carried out. 25 µL (0.5× sample volume) of Agencourt™ AMPure™ XP Reagent was added to each plate well containing ~50 µL, of sample. The bead suspension was pipetted up and down to thoroughly mix the bead suspension with the final amplicon library. The sample was then pulse-spun and incubated for 5 minutes at room temperature. The plate containing the final amplicon library was placed on a magnetic rack such as a DynaMag™-side magnet (Thermo Fisher) for 5 minutes to capture the beads. Once the solution cleared, the supernatant was carefully transferred without disturbing the bead pellet. A second round of purification was carried out, adding 60 microliters (1.2× sample volume) of Agencourt™ AMPure™ XP Reagent was added to each plate well containing sample. The bead suspension was pipetted up and down to thoroughly mix the bead suspension and incubated for 5 minutes at room temperature. The plate containing the final amplicon library was placed on a magnetic rack for 3 minutes to capture the beads. Without removing the plate from the magnetic rack, 150 microliters of freshly prepared 70% ethanol was introduced into the beads containing sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 50 microliters of Low TE was added (Thermo Fisher), pipetted and vortexed to ensure the sample was mixed thoroughly. The sample was pulse-spin and placed on the magnetic rack for two minutes. After the solution cleared, the supernatant containing the final amplicon library was analyzed using Qubit™ Fluorometer and Qubit™ dsDNA HS Assay Kit according to manufacturer instructions to quantify the library and calculate the dilution factor for template preparation and sequencing. Library was diluted to ~50 pM for use in template preparation or stored in 1.5-mL Eppendorf LoBind™ tube for long-term storage.

Template Preparation and Sequencing

An aliquot of the final library was used in template preparation with either Ion OneTouch™ 2 System or Ion Chef™ instrument according to the manufacturer's instructions.

Sequencing was performed on either the Ion S5™ System or the Ion PGM™ System. According to manufacturer instructions, and gene expression was quantified with the Ion Torrent Suite™ software subjected to analysis and sequencing according to manufacturer instructions.

Automated Processes

Alternatively, automated library prep and templating can be performed using cDNA prepared as described above in conjunction with the Ion AmpliSeq™ Kit for Chef DL8 and Ion Chef™ Instrument according to manufacturer instructions and described in the Ion AmpliSeq Library Preparation on the Ion Chef System (Thermo Fisher Scientific publication number MAN0013432), hereby incorporated by reference.

Multiple Library Preparation

When sequencing multiple libraries, a different barcode will be ligated to each library. DNA and RNA libraries from the same sample also require different barcodes. IonCode Adapters are provided at the appropriate concentration and include forward and reverse adapters in a single well. For each barcode selected, prepare a mix of Ion P1 adapter and IonXpress Barcode X (Thermo Fisher) at a final dilution of 1:4 for each adapter. Substitute 2 uL of this barcode adapter mix for the Ion AmpliSeq Adapters in ligation reactions above; and scale volumes as necessary. Multiple barcoded libraries can be sequenced on a single chip by combining equal volumes of each library before template preparation. The manufacturer recommends up to eight libraries for the following chips: Ion 318 Chip v2 (up to 4), Ion 520 Chip (up to 4), Ion 530 Chip (up to 8). A combined library is prepared by diluting all individual libraries to 50 pM concentration; combining 10 uL of each library in a single tube (preferably Eppendorf LoBind tube). After combining the last library, mix thoroughly by pipetting up and down 5 times, then centrifuge briefly to collect in the bottom of the tube. Proceed to templating and sequencing as desired.

Data Analysis

Gene expression level quantification is performed using the Torrent Suite™ RNA plugin that produces gene transcript quantification from sequence read data. The plugin utilizes target region .bed file and an associated reference library .fasta file, and optionally accepts a second .bed file that specifies a subset of target genes allowing sample clustering. Resulting report includes gene expression counts (number of aligned reads to a given target sequence), data analysis summary, and QC plots. Normalized gene level count data can be determined using the Affymetrix Transcriptome Analysis Console (TAC) 3.1 software (Thermo Fisher Scientific). CHP files generated from Torrent Suite™ plugin can be used directly with Transcriptome Analysis Console (TAC$^3$ software for differential gene expression analysis. Affymetrix® Transcriptome Analysis Console (TAC) Software is freely available, www.affymetrix.com.

Normalization of Expression

To observe how expression profiles among the selected target immune response genes vary within a large cohort of samples, we downloaded and processed more than 9,600 patient samples across 18 cancer studies from the ICGC database [Zhang et al., 2011]. To ensure high-quality RNA profiles, we excluded all samples with a library size less than 20 million reads mapped to the transcriptome and ended up with 9,148 full transcriptome datasets. For this study, we used the log 2 CPM full transcriptome (FT) expression of each gene as the 'true' expression value and the total number of reads mapping to genes as the 'true' normalizing constant for each sample in the cohort.

Results

Total RNA extracted from, samples e.g., NSCLC FFPE samples, were reverse transcribed. Libraries were generated, templated on Ion Chef™ or Ion OneTouch™ 2 System and sequenced on the Ion S5™ or Ion PGM™ System. With an input requirement as low as 10 ng of total RNA, we were able to measure robust expression, including for low expressing transcripts (e.g., IFN, IL2, IL21, IL10, IL23) from samples, e.g., NSCLC FFPE samples, CRC samples. Results show high sensitivity and specificity, with broad dynamic range and great reproducibility. Technical replicates were highly reproducible (see FIG. 1), consistent among various sample types (See FIG. 4), and the assay results were highly specific, with negligible background when tested with gDNA and water control samples in parallel. Dynamic range of the assay was determined, for example, the expression profiles of HL-60 and human lung total RNA were measured individually and mixed at 4 different ratios to evaluate dynamic range (see FIG. 2). Fold changes between pure and mixed samples were correlated, and rank order of fold change correlations between pure and mixed samples were compared. Expected fold change was calculated from pure samples and observed fold change was derived from fitting a line to the mixed samples (see TABLE 3). Ability to reliably detect low expressing markers of the panel was confirmed in replicate experiments carried out in automated and manual workflows, demonstrating consistent results even for very low expressing genes (e.g., IL2, IL21, IL2B, IL13, IL23A, IL10) and higher expressing interleukins (e.g., IL1A, IL12A, IL15, IL6, IL7, IL2RB). Data not shown. Sequencing data from the provided immune response assay also showed high concordance with results from parallel samples using quantitative real-time PCR evaluation (see FIG. 3). A larger concordance study examining results over fifty genes using reference RNA generated similar concordance. Data not shown.

TABLE 3

Sensitivity and specificity for 2-fold and 4-fold differential expression

| q_value | Observed fold change | Expected fold change | Sensitivity | Specificity |
|---|---|---|---|---|
| 0.05 | 2 | 2 | 77.5% | 98.5% |
| 0.05 | 4 | 4 | 89.4% | 99.1% |

Analysis report files include, for example, a sample summary report (table listing each sample, total reads, aligned reads, percent aligned); absolute read count data (absolute reads for genes of each sample), RPM data (normalized by total read count for each sample), mean housekeeping scaled log 2 RPM data (for each sample), CHP files normalized by RPM, CHP files normalized by mean housekeeping genes, and expression data for genomic DNA and water samples. See FIG. 5 and FIG. 6. The analysis output generated data demonstrating distribution of genes showing frequency of genes having similar and differential read counts. See FIG. 5A. Curves are plotted on the same axis scale; and count data is fitted to a Gaussian kernel using the default R 'density' function. Expression of housekeeping genes across samples demonstrated similar levels of expression independent of sample type. See FIG. 5B. A heatmap correlation for r-values comparing log 2 RPM reads pair correlation samples, demonstrates correlation across entire expression assay among samples. Sample reads demonstrate correlations across each of the targets for samples. See FIG. 5C. and FIG. 6 (upper panels show Pearson correlation r-values for the regression line; diagonal panels show frequency density plot for the individual log (RPM+1) values for each sample; and lower panels show log 2 RPM+1 values plotted for each barcode pair of the entire panel, with linear least squares regression line overlaid and line slope is reported). Expression levels as measured by read count can also be depicted as a heatmap, depicting the most variation in representation across barcodes as measured by coefficient variation of normalized read counts for genes that have at least one sample with at least 100 RPM reads. For the plot, samples are eliminated if they have less than $10^5$ reads total. An exemplary heatmap analysis demonstrating high and low expression genes across the entire panel is shown in FIG. 7.

Thus, we verified a linear and unbiased estimate of fold change in our assays across mixing concentrations of a cell-line titration experiment. FIG. 2. By achieving a high correlation (r>0.99) of technical replicates, along with robust expression estimation even at low input amounts (10 ng RNA), our assay offers a valuable solution for biomarker research in cancer immunotherapy.

Using endogenous controls accurately estimates fold change. When most genes do not change between the samples, the fold change estimate has negligible error. When most genes do change, the fold change estimate is wildly inaccurate. See FIG. 8. Thus, when using endogenous controls, we accurately measure fold change. In silico analysis of gene expression across 9148 samples across cancer types was assessed. See Table 4. Standard CPM normalization was applied to measure the expression of each gene and calculate the resulting fold change. Full transcriptome profiling provides a true estimate of expression presumably because, over the total, only a small number of the 20,000+ genes are expected to be differentially expressed. We assessed both full transcriptome expression data as well as the immune response assay expression data. Although the relative number of genes within the immune response assay subcategory vary, no single category uses a majority of the genes on the entire assay, and multiple gene categories have to change to dominate the proportion of genes of the assay. Although the immune response assay is not as large as the full transcriptome, the relative diversity of uncorrelated gene categories requires differential expression among samples to bias expression estimates. Thus, housekeeping gene normalization provides an effective optimization approach for effective estimates of targeted expression fold change estimates in cases where uncorrelated gene categories are differentially expressed among samples.

To first understand how assaying only genes from a common function can affect estimate of expression, an assay was made comprising only the 5 genes associated with the Leukocyte Migration category (ITGAL, ITGAM, ITGB7, SELL, VCAM1). Assaying only those genes does not provide an accurate expression estimate. Expanding the assay by 2 Leukocyte Inhibition and 19 TCR co-expression genes (CCR7, CD247, CD3D, CD3E, CD3G, CD6, CD8A, CD8B, CRTAM, GPR18, GRAP2, IKZF3, IL2RB, IL7R, ITK, LAMP3, LCK, PTPRCAP, TIGIT) does not increase the correlation. However, assaying 27 genes from the unrelated Tumor Marker category (AKT1, BRCA1, BRCA2, CDKN2A, EFNA4, EGFR, EGR3, IRS1, KRT5, KRT7, MAPK1, MMP2, MMP9, MYC, NOTCH3, PGF, PTGS2, PTK7, RB1, RPS6, SNAIL SNAI2, TCF7, TP63, TRIM29, TWIST1, ZEB1) or 11 housekeeping (HK) genes (ABCF1, G6PD, GUSB, HMBS, LMNA, LRP1, POLR2A, SDHA, TBP, TFRC, TUBB) improves the correlation with true expression values. See FIG. 9A. HK genes are uncorrelated with each other, however, unlike tumor markers (that are also uncorrelated with each other), HK genes provide low-variance and are able to be measured with high precision. For example, when we compared performance and robustness of various metrics for accurate fold change estimates, we found the geometric mean of housekeeping genes provides a more accurate fold change estimate than a standard CPM calculation (with or without housekeeping genes. See FIG. 9B. Housekeeping genes alone can solely correct expression estimates in small panel assays. Using uncorrelated gene categories also has similar effect to normalization. Furthermore, using the inverse of the sum of only the HK genes as the normalizing factor provides an even stronger correlation than using the sum of all genes on the panel.

TABLE 4

Distribution of samples across cancer types

| Study ID | Cancer Type | Sample Size |
| --- | --- | --- |
| BLCA-US | Bladder Urothelial Cancer | 318 |
| BRCA-US | Breast Cancer | 1195 |
| CESC-US | Cervical Squamous Cell Carcinoma | 264 |
| COAD-US | Colon Adenocarcinoma | 516 |
| HNSC-US | Head and Neck Squamous Cell Carcinoma | 524 |
| KIRC-US | Kidney Renal Clear Cell Carcinoma | 598 |
| KIRP-US | Kidney Renal Papillary Cell Carcinoma | 254 |
| LIHC-US | Liver Hepatocellular carcinoma | 345 |
| LUAD-US | Lung Adenocarcinoma | 543 |
| LUSC-US | Lung Squamous Cell Carcinoma | 473 |
| OV-US | Ovarian Serous Cystadenocarcinoma | 530 |
| PAAD-US | Pancreatic Cancer | 145 |
| PRAD-US | Prostate Adenocarcinoma | 870 |
| READ-US | Rectum Adenocarcinoma | 163 |
| SKCM-US | Skin Cutaneous melanoma | 868 |
| STAD-US | Gastric Adenocarcinoma | 900 |
| THCA-US | Head and Neck Thyroid Carcinoma | 566 |
| UCEC-US | Uterine Corpus Endometrial Carcinoma | 541 |

Thus, we also found that normalization using endogenous controls (housekeeping genes) provides accurate fold change estimates for small panel assays with highly-correlated genes. Uncorrelated gene categories can have the same effect as house-keeping genes on normalization, however, close cases where uncorrelated gene categories are differentially expressed between samples will bias expression estimates when not using housekeeping genes. The method of housekeeping gene normalization provided herein can improve correlation with true values of expression assays. In particular, housekeeping gene normalization may improve assessment of expression in sub-panels of the provided immune response assay, and may be useful in connection with the relatively large immune response assay provided herein.

From the previous analysis, it is clear that normalization using housekeeping genes in conjunction with compositions and methods of the invention are necessary for accurately estimating fold change expression. It is also clear that using only the housekeeping genes to calculated a normalizing constant is a preferred way to estimate gene expression for accurate fold change estimation. An important factor to using housekeeping genes for calculating normalizing constant is to determine which is metric of the gene counts provides the most accurate fold change estimates. We thus compared 6 metrics across 18 cancer studies; for each study we calculate the log 10 of the total counts and determine the correlation to the following metrics: log 10 of the sum of housekeeping counts (analogous to RPM normalization), log 10 of the geometric mean of the housekeeping counts, the median of the log 10 of housekeeping counts, the $75^{th}$ quantile of the log 10 of housekeeping counts, and the trimmed mean (15% and 25% of the log 10 of HK counts). Interestingly, the sum of housekeeping counts does not provide an optimal correlation value, instead the geometric mean provides the highest average correlation and number of cancers where the R-squared is greater than 0.5 (data not shown). Of the more robust measures, the 15% trimmed mean provides the highest average R-squared. To further estimate which metric is most robust, we simulate a dropout of a random housekeeping genes for every sample by setting a random housekeeping gene of each sample to have 0 reads. We then reproduce the same analysis to compare the various metrics using dropout samples. Interestingly, the geometric mean still provides the highest correlation with the full transcriptome normalizing constant even in the dropout samples, while the 15% trimmed mean also shows high performances (data not shown). This suggests that the geometric mean is an optimal metric due to its high correlation with the true normalizing constant values and its robustness to dropouts. Additionally, we carried out analysis of normalizing constant, correlations and drop out correlation among various cancer types of interest and confirmed even across various sample types the housekeeping set of genes provided in the instant compositions and methods performed consistently across populations of interest.

Housekeeping (HK) Constant:
  Let x be a vector of counts for every gene on the immune response assay and let HKgenes be the set of housekeeping genes; add a pseudocount 1 to every entry in the vector x, creating a new vector y.
  Find the geometric mean of the counts of housekeeping genes, calculated as 10^mean (log 10(y_HKgenes)), where y_HKgenes is a subset of the y vector to only include the counts associated with the housekeeping genes. This geometric mean value will be denoted as HKnorm.

Multiply each entry of y by the (10^6/HKnorm), creating a new vector z.

Finally take the log 2 value of each entry in z and add, creating the final housekeeping gene normalized expression estimate.

Once established, an HKnorm constant was calculated by taking the geometric mean of our 11 housekeeping genes and comparing our normalizing strategy to a standard RNA-seq RPM measurement using the 398 genes of the provided immune response assay. Since this assay is made up of a relatively large number of genes that are on average uncorrelated to each other, one could make a valid argument that housekeeping genes are unnecessary to the assay and do not provide additional information. To address this concern, we compared the HKnorm constant against the standard RPM constant and the RPM constant when housekeeping genes are removed from the assay. We first evaluated how these normalizing strategies compare to the full transcriptome constant across all samples, where we found that removing housekeeping genes led to decrease in the correlation of the RPM constant compared to a standard RPM calculation, however, even the standard RPM calculation under-performs when compared to HKnorm. (data not shown). We then examined which normalizing strategy would be optimal for each cancer study that we evaluated, and found that HKnorm largely outperforms the RPM strategies across all studies except for LIHC-US, where no normalization strategy does particularly well and all the strategies produce equivalent results. When looking at the performance each strategy across target genes on the immune response assay of the invention, we see that HKnorm outperforms the RPM strategies in all genes, as expected. Interestingly, genes with smaller variance have a smaller correlation to their FT values than those with higher variance. See FIG. 9B. Furthermore, genes with low expression and those with high average expression also have smaller correlation values than those closer to the mean of average expression values (data not shown).

REFERENCES

Schalper K A, et al. Objective measurement and clinical significance of TILs in non-small cell lung cancer. J Natl Cancer Inst. 2015 Feb. 3; 107(3).

Padmanee S, et al. Immune Checkpoint Targeting in Cancer Therapy: Toward Combination Strategies with Curative Potential. Cell 2015 April 161(2):205-214.

Love M, Huber W, Anders S. *Moderated estimation of fold change and dispersion for RNA-seq data with DESeq2*. Genome Biology, 2014.

Law C, Chen Y, Shi W, Smyth G. *voom: precision weights unlock linear model analysis tools for RNA-seq read counts*. Genome Biology, 2014.

Hansen K, Irizarry R. *Removing technical variability in RNA-seq data using conditional quantile normalization*. Biostatistics, 2011.

Risso D, Schwartz K, Sherlock G and Dudoit S. *GC-Content Normalization for RNA-Seq Data*. BMC Bioinformatics, 2011.

Zhang, J., Baran, J., Cros, A., Guberman, J. M., Haider, S., Hsu, J. Kasprzyk, A. (2011). *International Cancer Genome Consortium Data Portal a one—stop shop for cancer genomics data*. Database: The Journal of Biological Databases and Curation, 2011.

What is claimed:

1. A composition for a single stream multiplex determination of an immune response in a sample, comprising a plurality of sets of primer pair reagents directed to a sequence of one or more housekeeping genes and a plurality of immune response target sequences to measure the expression levels of the targets in the sample, wherein the plurality of immune response target genes are selected from the group consisting of the following function: checkpoint pathways, T cell related signaling pathways, markers of tumor infiltrating lymphocytes (TILs), and tumor markers, and wherein the plurality of primer pairs includes SEQ ID NO: 399-SEQ ID NO: 1194.

2. The composition of claim 1 wherein target genes are selected from the group consisting of immune checkpoint pathways and targets; T and B cell signaling genes, markers of lymphocyte subsets, interferon signaling genes, cytokine signaling genes; tumor markers, tumor antigens, proliferation markers; and housekeeping genes.

3. The composition of claim 1 wherein the target genes are selected from the genes of CD63, CD69, CXCL1, KLRD1, HLA-DOB, CXCR5, IL12B, PTK7, CEACAM1, CXCL9, IL13, NT5E, VEGFA, ABCF1, D38, JAML, S100A8, MYC, IRF1, CCL22, CXCR2, IFIT1, IFIT2, CD68, M6PR, SH2D1A, ISG20, GBP1, TBP, STAT6, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMPS, TNFAIP8, FOXP3, IL12A, SAMHD1, SIT1, CD3E, ICOSLG, HGF, MELK, IGSF6, GNLY, TDO2, KRT7, HLA-E, HLA-DMA, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBB, EFNA4, PVR BUB1, SKAP2, PRF1, CCL20, TNFRSF18, CTSS, NKG7, ISG15, PDCD1, SNAIL CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DRA, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, ILIA, FCGR3A, IFNA17, EGR2, TOP2A, C10orf54, FOXM1, AXL, MS4A1, IFI6, CD3D, GPR18, CD3G, ZAP70, HMBS, IL7, IFIT3, RBI, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MXI, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDOL IL18, TNFRSF9, HIF1A, HLA-DPB1, FOXO1, CD33, S100A9, HLA-DMB, HLAA, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAGS, TNFRSF4, CD2, CCL4, BAGE, LEXM, CCR6, CD70, CDK1, CTAG1B, CTAG2, CX3CR1, GAGE1, GAGE121, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CXCR3, FCGR1A, FCGR3B, FYB, HLA-C, HLA-DQA2, IFNG, KIR2DL1, KRT5, and PTPN11.

4. The composition of claim 1 wherein the target genes consist of the genes of CD63, CD69, CXCL1, KLRD1, HLA-DOB, CXCR5, IL12B, PTK7, CEACAM1, CXCL9, IL13, NT5E, VEGFA, ABCF1, D38, JAML, S100A8, MYC, IRF1, CCL22, CXCR2, IFIT1, IFIT2, CD68, M6PR, SH2D1A, ISG20, GBP1, TBP, STAT6, ID3, CX3CL1, KLRB1, TNFSF4, CD52, IL10RA, HLA-DOA, IFNB1, CCR5, IKZF3, STAT1, CD6, BRCA1, CORO1A, TBX21, KLRK1, CXCR6, PTEN, PMEL, DMBT1, IFI44L, LAPTM5, CD226, TNFSF13B, ICOS, CD160, TRIM29, LST1, ZBTB46, VTCN1, KREMEN1, PDCD1LG2, TUBB, CLEC4C, CD86, HAVCR2, GZMH, NFATC1, CD8B, BCL2, GADD45GIP1, CBLB, ITGA1, CD8A, IL2RA, EIF2AK2, MADCAM1, PTPN6, LRG1, ADGRE5, SH2D1B, ITGB2, HLA-DPA1, DGAT2, IGF1R TAGAP, LMNA, NCAM1, TIGIT, IL17F, HLA-F-AS1, CD247, CD79B, IDO2, IL4, TYROBP, BTLA, AKT1, IL2RG, POLR2A, ITGAX, IL1B, CSF2RB, DDX58, KIAA0101, CD274, LAMP3, TNFAIP8, FOXP3, IL12A, SAMHD1, SIT1, CD3E, ICOSLG, HGF, MELK, IGSF6, GNLY, TDO2, KRT7, HLA-E, HLADMA, LAMP1, NTN3, CD28, TARP, EGFR, CCR4, MAGEA3, BATF, KLRG1, IRS1, CSF1R, CTLA4, TNFSF18, POU2AF1, GZMA, PIK3CA, ITK, IFI27, EOMES, LCN2, CD80, CD83, CXCL13, MTOR, FCER1G, TFRC, RORC, MMP9, BST2, PIK3CD, FCGR2B, TNFRSF14, OAS3, GRAP2, CCNB2, MLANA, MAGEA12, VCAM1, CDKN3, NCR1, FAS, GZMB, IRF9, IFITM2, TNFSF14, HLA-B, SDHA, NRP1, EBB, EFNA4, PVR BUB1, SKAP2, PRF1, CCL20, TNFRSF18, CTSS, NKG7, ISG15, PDCD1, SNAIL CXCL11, CIITA, IFI35, TNFSF9, TNFSF10, MMP2, EGR3, MAGEA1, CD163, IL6, KLRF1, B3GAT1, C1QA, OAS1, IKZF2, TLR9, KLF2, GUSB, NFKBIA, IL23A, HERC6, SLAMF8, IL15, TLR7, OAS2, HLA-DRA, CRTAM, MAGEC2, ICAM1, CD4, MAPK14, C1QB, NOTCH3, NCR3, STAT3, TLR8, CYBB, IKZF4, IFIH1, LCK, BCL2L11, ITGAM, ITGB7, JCHAIN, CD209, SLAMF7, IL10, ILIA, FCGR3A, IFNA17, EGR2, TOP2A, C10orf54, FOXM1, AXL, MS4A1, IFI6, CD3D, GPR18, CD3G, ZAP70, HMBS, IL7, IFIT3, RBI, PTGS2, TGFB1, NCF1, TWIST1, CA4, SELL, LILRB1, CD14, ALOX15B, PECAM1, NOS2, FASLG, CD44, ENTPD1, CMKLR1, CD53, TNF, CXCL8, CD40LG, HLA-F, GATA3, LYZ, ARG1, IL2RB, NECTIN2, MPO, CCR2, BRCA2, ADORA2A, G6PD, TAP1, MXI, HLA-DQB2, CD27, CD276, STAT4, PTPN7, PTPRC, PSMB9, CD244, CXCR4, MAPK1, TP63, IRF4, CCL3, CCL18, IL7R, HLA-DRB1, CEACAM8, CXCL10, CCL2, SRGN, CD19, ITGB1, IFITM1, CCL21, MRC1, PGF, ITGAL, ID2, CD22, CCL17, ITGAE, IL3RA, CCR7, CD1C, MAD2L1, PYGL, CD40, LY9, HLA-G, TLR3, CD48, STAT5A, FCRLA, BCL6, ZEB1, CCL5, IDOL IL18, TNFRSF9, HIF1A, HLA-DPB1, FOXO1, CD33, S100A9, HLA-DMB, HLAA, SNAI2, TNFRSF17, LRP1, MAGEA4, HLA-DQA1, CD1D, RPS6, MKI67, GZMK, CD79A, CD37, FUT4, AIF1, CCR1, PRDM1, CD47, CD74, LAGS, TNFRSF4, CD2, CCL4, BAGE, LEXM, CCR6, CD70, CDK1, CTAG1B, CTAG2, CX3CR1, GAGE1, GAGE121, GAGE12F, GAGE12J, GAGE2C, GAGE2A, GAGE2E, GAGE10, GAGE13, IKZF1, IL17A, IL2, IL21, IL22, KIR2DL2, KIR2DL3, MAGEA10, MIF, PTPRCAP, SSX2, TCF7, XAGE1B, CXCR3, FCGR1A, FCGR3B, FYB, HLA-C, HLA-DQA2, IFNG, KIR2DL1, KRT5, and PTPN11.

5. The composition of claim 1 wherein the plurality of target sequences comprise the amplicon sequences selected from SEQ ID NOS: 1-398.

6. The composition of claim 1 wherein the plurality of target sequences include each of the amplicon sequences of SEQ ID NOS: 1-398.

7. The composition of claim 1 wherein the plurality of primer pair reagents consist of each of the primer pairs of SEQ ID NO: 399 SEQ ID NO: 1194.

8. The composition of claim 1 wherein the one or more housekeeping genes are selected from ABCF1, G6PD, GUSB, HMBS, LMNA, LRP1, POLR2A, SDHA, TBP, TFRC, and TUBB.

* * * * *